(12) United States Patent
Xiang et al.

(10) Patent No.: US 7,632,838 B2
(45) Date of Patent: Dec. 15, 2009

(54) 11-BETA HSD1 INHIBITORS

(75) Inventors: Jason Shaoyun Xiang, Winchester, MA (US); Eddine Saiah, Brookline, MA (US); Steve Y. Tam, Wellesley, MA (US); John C. Mckew, Arlington, MA (US); Lihren Chen, Bedford, MA (US); Manus Ipek, Watertown, MA (US); Huan-Qiu Li, Brighton, MA (US); Jianchang Li, Carlisle, MA (US); Wei Li, Acton, MA (US); Tarek Suhayl Mansour, New City, NY (US); Vipin Suri, Waltham, MA (US); Yuchuan Wu, Acton, MA (US); Zhao-Kui Wan, Arlington, MA (US); Jinbo Lee, Andover, MA (US); Eva Binnun, Boston, MA (US); Douglas P. Wilson, Ayer, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/703,522

(22) Filed: Feb. 7, 2007

(65) Prior Publication Data

US 2007/0219198 A1 Sep. 20, 2007

Related U.S. Application Data

(60) Provisional application No. 60/771,262, filed on Feb. 7, 2006.

(51) Int. Cl.
*A61K 31/4965* (2006.01)
*C07D 241/04* (2006.01)
*C07D 295/00* (2006.01)

(52) U.S. Cl. ................. 514/255.03; 544/383

(58) Field of Classification Search ............... 544/383; 514/255.03
See application file for complete search history.

(56) References Cited

U.S. PATENT DOCUMENTS

| | | | | |
|---|---|---|---|---|
| 2,875,205 | A | * | 2/1959 | Ruschig ............... 544/391 |
| 4,760,062 | A | * | 7/1988 | Roger et al. ........... 514/218 |
| 4,857,644 | A | | 8/1989 | Abou-Gharbia |
| 5,464,788 | A | | 11/1995 | Bock et al. |
| 5,756,504 | A | | 5/1998 | Bock et al. |
| 6,063,930 | A | | 5/2000 | Dinsmore et al. |
| 6,297,239 | B1 | | 10/2001 | deSolms et al. |
| 6,465,468 | B1 | * | 10/2002 | Baxter et al. ......... 514/252.12 |
| 6,673,799 | B1 | | 1/2004 | Taniguchi et al. |
| 6,953,857 | B2 | | 10/2005 | Nazare et al. |
| 6,984,663 | B2 | | 1/2006 | Churcher et al. |
| 7,067,665 | B2 | | 6/2006 | Nazare et al. |
| 7,179,912 | B2 | | 2/2007 | Halbrook et al. |
| 7,304,094 | B2 | | 12/2007 | Churcher et al. |
| 7,402,704 | B2 | | 7/2008 | Fan et al. |
| 2002/0165218 | A1 | | 11/2002 | Halbrook et al. |
| 2002/0198195 | A1 | | 12/2002 | Nazare et al. |
| 2003/0114496 | A1 | | 6/2003 | Churcher et al. |
| 2004/0116404 | A1 | | 6/2004 | Pineiro et al. |
| 2005/0124625 | A1 | | 6/2005 | Salvati et al. |
| 2005/0165058 | A1 | | 7/2005 | Nazare et al. |
| 2005/0234046 | A1 | | 10/2005 | Zhao et al. |
| 2005/0277665 | A1 | | 12/2005 | Fan et al. |
| 2005/0288308 | A1 | | 12/2005 | Amrien et al. |
| 2006/0025445 | A1 | | 2/2006 | Xiang et al. |
| 2006/0025455 | A1 | | 2/2006 | Amrien et al. |
| 2006/0035884 | A1 | | 2/2006 | Neitzel et al. |
| 2006/0040936 | A1 | | 2/2006 | Josien et al. |
| 2006/0041020 | A1 | | 2/2006 | Churcher et al. |
| 2006/0223829 | A1 | | 10/2006 | Aertgeerts et al. |
| 2007/0167435 | A1 | | 7/2007 | Mutahi et al. |
| 2007/0173494 | A1 | | 7/2007 | Powers et al. |
| 2007/0213329 | A1 | | 9/2007 | Castro Pineiro et al. |
| 2007/0219187 | A1 | | 9/2007 | Bessis et al. |
| 2007/0299110 | A1 | | 12/2007 | Gagliardi et al. |
| 2008/0045533 | A1 | | 2/2008 | Churcher et al. |
| 2008/0090782 | A1 | | 4/2008 | Halbrook et al. |

FOREIGN PATENT DOCUMENTS

| | | | |
|---|---|---|---|
| EP | 0042731 | * | 12/1981 |
| EP | 138720 | A2 | 10/1984 |
| EP | 138720 | A3 | 10/1984 |
| EP | 0661266 | A1 | 7/1995 |
| EP | 751773 | A1 | 9/1995 |
| EP | 891334 | A1 | 10/1997 |
| EP | 934270 | A1 | 12/1997 |
| EP | 973396 | A1 | 10/1998 |
| EP | 1021188 | A1 | 4/1999 |
| EP | 1351946 | A2 | 3/2002 |
| EP | 1217000 | A1 | 6/2002 |
| EP | 1349847 | A1 | 7/2002 |

(Continued)

OTHER PUBLICATIONS

Lee, Jae W., et al., Nitrophenol Resins for Facile Amide and Sulfonamide Library Synthesis, Journal of Combinatorial Chemistry (2003), 5(3), 330-335.*
Fontanella, L., et al., New thioxanthenes active on the central nervous system, Farmaco, Edizione Scientifica (1971), 26(6), 489-511.*
U.S. Appl. No. 60/900,261, filed Feb. 7, 2007, Saiah et al.
Barf, Tjeerd et al., "Arylsulfonamidothiazoles as a New Class of Potential Antidiabetic Drugs. Discovery of Potent and Selective Inhibitors of the 11β-Hydroxysteroid Dehydrogenase Type I", *Journal of Medicinal Chemistry*, vol. 45, No. 18, pp. 3814-3816, (2002).

(Continued)

*Primary Examiner*—James O Wilson
*Assistant Examiner*—Erich A Leeser
(74) *Attorney, Agent, or Firm*—Fish & Richardson P.C.

(57) ABSTRACT

This invention relates to inhibiting 11βHSD1.

69 Claims, No Drawings

FOREIGN PATENT DOCUMENTS

| | | |
|---|---|---|
| EP | 1379498 A1 | 10/2002 |
| EP | 1421062 A1 | 3/2003 |
| EP | 1685105 A1 | 5/2005 |
| EP | 1744751 A2 | 9/2005 |
| EP | 1735275 A2 | 11/2005 |
| EP | 1735280 A1 | 12/2005 |
| EP | 1758884 A2 | 12/2005 |
| EP | 1789404 A2 | 1/2006 |
| EP | 1809620 A1 | 5/2006 |
| EP | 1866298 A2 | 10/2006 |
| EP | 952842 A2 | 10/2007 |
| EP | 1122242 B1 | 1/2008 |
| JP | 60081168 A * | 5/1985 |
| JP | 2001261657 | 9/2001 |
| JP | 2001328938 | 11/2001 |
| WO | WO 93/12086 * | 12/1992 |
| WO | WO95/25443 | 9/1995 |
| WO | WO97/36876 | 10/1997 |
| WO | WO97/38664 | 10/1997 |
| WO | WO97/45412 | 12/1997 |
| WO | WO98/44797 | 10/1998 |
| WO | WO99/17777 | 4/1999 |
| WO | WO00/17163 | 3/2000 |
| WO | WO00/25789 | 5/2000 |
| WO | WO01/66534 | 9/2001 |
| WO | WO02/20500 | 3/2002 |
| WO | WO02/051831 | 7/2002 |
| WO | WO02/081435 | 10/2002 |
| WO | WO03/018543 | 3/2003 |
| WO | WO03/044000 | 5/2003 |
| WO | WO03/044009 | 5/2003 |
| WO | WO03/076422 | 9/2003 |
| WO | WO 2005/115983 | 12/2003 |
| WO | WO2004/011410 | 2/2004 |
| WO | WO2004/033427 | 4/2004 |
| WO | WO2004/041264 | 5/2004 |
| WO | WO2004/065351 | 8/2004 |
| WO | WO 2004/089416 | 10/2004 |
| WO | WO2004/089471 | 10/2004 |
| WO | WO2004/092117 | 10/2004 |
| WO | WO2005/011654 | 2/2005 |
| WO | WO2005/011656 | 2/2005 |
| WO | WO2005/011657 | 2/2005 |
| WO | WO2005/040136 | 5/2005 |
| WO | WO2005/044797 | 5/2005 |
| WO | WO2005/063247 | 7/2005 |
| WO | WO2005/073200 | 8/2005 |
| WO | WO2005/089502 | 9/2005 |
| WO | WO2005/110980 | 11/2005 |
| WO | WO2005/110992 | 11/2005 |
| WO | WO2005/113542 | 12/2005 |
| WO | WO2005/115983 | 12/2005 |
| WO | WO2005/118538 | 12/2005 |
| WO | WO2006/002349 | 1/2006 |
| WO | WO2006/002350 | 1/2006 |
| WO | WO2006/002361 | 1/2006 |
| WO | WO2006/004880 | 1/2006 |
| WO | WO2006/012173 | 2/2006 |
| WO | WO2006/012226 | 2/2006 |
| WO | WO2006/012227 | 2/2006 |
| WO | WO2006/020598 | 2/2006 |
| WO | WO2006/034441 | 3/2006 |
| WO | WO2006/034446 | 3/2006 |
| WO | WO2006/048771 | 5/2006 |
| WO | WO2006/086445 | 8/2006 |
| WO | WO2006/105127 | 10/2006 |
| WO | WO 2007/055942 * | 5/2007 |
| WO | WO 2007/070506 * | 6/2007 |
| WO | WO2007/075629 | 7/2007 |
| WO | WO2007/092435 | 8/2007 |
| WO | WO2008/011072 | 1/2008 |

OTHER PUBLICATIONS

Coppola, Gary M. et al., "Perhydroquinolylbenzamides as Novel Inhibitors of of 11β-hydroxysteroid dehydrogenase type 1", *Journal of Medicinal Chemistry*, vol. 48, No. 21, pp. 6696-6712, (2005).

Olson, Steven et al., "Adamantyl triazoles as selective inhibitors of 11β-hydroxysteroid dehydrogenase type 1", *Bioorganic & Medicinal Chemistry Letters 15*, pp. 4359-4362, (2005).

Tomlinson, Jeremy W. et al., "11β-hydroxysteroid Dehydrogenase Type 1: A Tissue-Specific Regulator of Glucocorticoid Response", *Endocrine Reviews*, vol. 25, No. 5, pp. 831-866, (2004).

Xiang, Jason et al., "Synthesis and biological evaluation of sulfonamidooxazoles and β-keto sulfones: selective inhibitors of 11β-hydroxysteroid dehydrogenase type I", *Bioorganic & Medicinal Chemistry Letters 15*, pp. 2865-2869, (2005).

Fenster, Michael D.B. et al., "Construction of azaspirocyclic ketones through alpha-hydroxyiminium ion or alpha-siloxy epoxide semipinacol rearrangements," *Organic Letters*, 3(13):2109-2112 (2001).

Fraser, Robert R. et al., "Stereoselectivity in the reactions of Nitrosopiperidine carbanions steric vs. stereoelectronic control," *Canadian Journal of Chemistry*, 53:2473-2480 (1975).

Tamaru, Yoshinao et al., "Synthesis of five- and six- membered nitrogen heterocycles via a palladium(II)-catalyzed cyclization of unsaturated amides," *Journal of Organic Chemistry*, 51:4089-4090 (1986).

Gless, Richard D. & Rapoport, Henry, "6,7-Benzomorophans. Stereospecific synthesis of 2,9alpha-and 2, 9beta dimethyl-2'-methoxy-6,7-benzomorphans," *Journal of Organic Chemistry*, 44(8):1324-1336 (1979).

* cited by examiner

11-BETA HSD1 INHIBITORS

CROSS REFERENCE TO RELATED APPLICATIONS

This application claims the benefit of U.S. Provisional Application No. 60/771,262, filed on Feb. 7, 2006, which is incorporated herein by reference in its entirety.

TECHNICAL FIELD

This invention relates to inhibiting 11βHSD1.

BACKGROUND

Diabetes is generally characterized by relatively high levels of plasma glucose (hyperglycemia) in the fasting state. Patients having type 2 diabetes (non-insulin dependent diabetes mellitus (NIDDM)) produce insulin (and even exhibit hyperinsulinemia), whilst demonstrating hyperglycemia.

Type 2 diabetics can often develop insulin resistance, in which the effect of insulin in stimulating glucose and lipid metabolism is diminished. Further, patients having insulin resistance, but have not developed type 2 diabetes, are also at risk of developing Syndrome X (metabolic syndrome). Syndrome X is characterized by insulin resistance, along with obesity (e.g., abdominal obesity), hyperinsulinemia, high blood pressure, relatively low HDL and relatively high VLDL.

Glucocorticoids (e.g., cortisol in humans, corticosterone in rodents) are counter regulatory hormones that oppose the action of insulin. It is established that glucocorticoid activity is controlled at the tissue level by intracellular interconversion of active cortisol and inactive cortisone by the 11-beta hydroxysteroid dehydrogenases, 11βHSD1, which activates cortisone and 11βHSD2, which inactivates cortisol. Excess levels of glucocorticoids (e.g., cortisol) can cause metabolic complications. For example, excess cortisol is associated with disorders including NIDDM, obesity, dyslipidemia, insulin resistance, and hypertension.

It is believed that inhibition of 11βHSD1 can reduce the effects of excessive amounts of 11β-hydroxysteroids, e.g., cortisol, and therefore can be useful for the treatment and control of diseases mediated by abnormally high levels of cortisol and other 11β-hydroxysteroids, e.g., NIDDM, obesity, dyslipidemia, and hypertension.

SUMMARY

In one aspect, this invention relates to a compound of formula (I):

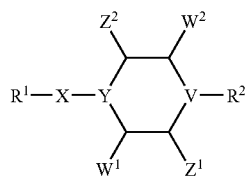

in which:

$R^1$ is:

(i) $C_6$-$C_{18}$ aryl or heteroaryl including 5-20 atoms, each of which is optionally substituted with from 1-10 $R^a$; or (ii) $C_7$-$C_{20}$ aralkyl; $C_3$-$C_{16}$ cycloalkyl; ($C_1$-$C_{12}$ alkyl)-($C_3$-$C_{16}$ cycloalkyl); heteroaralkyl including 6-20 atoms; arylheterocyclyl including 8-20 atoms; arylcycloalkenyl including 8-20 atoms; arylheterocycloalkenyl including 8-20 atoms (e.g., arylheterocyclyl including 8-20 atoms or arylheterocycloalkenyl including 8-20 atoms); $C_3$-$C_{16}$ cycloalkenyl; heterocyclyl including 3-16 atoms; or heterocycloalkenyl including 3-16 atoms; each of which is optionally substituted with from 1-10 $R^b$;

$R^2$ is:

(i) $C_6$-$C_{18}$ aryl or heteroaryl including 5-20 atoms, each of which is optionally substituted with from 1-10 $R^c$; or (ii) $C_3$-$C_{16}$ cycloalkyl; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) $OR^1$; $SR^1$; or $NR^3R^4$, wherein $R^3$ and $R^4$ are each, independently, hydrogen or $R^1$; or (iv) $C(O)R^5$, wherein $R^5$ is $C_1$-$C_{20}$ alkyl or $C_7$-$C_{20}$ aralkoxy;

X is CO, $S(O)_n$, or $S(O)_nNR^6$, wherein n is 1 or 2, and $R^6$ is hydrogen, $C_1$-$C_{12}$ alkyl, or $C_3$-$C_{16}$ cycloalkyl;

each of V and Y is, independently, $CR^7$ or N, wherein $R^7$ is hydrogen or $C_1$-$C_{12}$ alkyl, provided that Y and V cannot both be $CR^7$;

each of $W^1$, $Z^1$, $W^2$, and $Z^2$ is, independently:

(i) hydrogen; or (ii) oxo; or (iii) $C_1$-$C_{12}$ alkyl; or (iv) $C_6$-$C_{18}$ aryl or heteroaryl including 5-20 atoms, each of which is optionally substituted with from 1-10 $R^a$; or (ii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$;

$R^a$ at each occurrence is, independently:

(i) halo; $NR^dR^e$; nitro; azido; hydroxy; $C_1$-$C_{12}$ alkoxy or $C_1$-$C_{12}$ thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^{a'}$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; $C_1$-$C_3$ alkylenedioxy; —C(O)$R^g$, —C(O)O$R^g$; —OC(O)$R^g$; —C(O)S$R^g$; —SC(O)$R^g$; —C(S)SR; —SC(S)$R^g$; —C(O)NR$^d$R$^e$; —NR$^h$C(O)R$^i$; —OC(O)NR$^d$R$^e$; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^{a'}$;

$R^{a'}$ at each occurrence is, independently, $C_1$-$C_{12}$ alkyl, $C_1$-$C_{12}$ haloalkyl, $C_2$-$C_{12}$ alkenyl; $C_2$-$C_{12}$ alkynyl; $C_3$-$C_{16}$ cycloalkyl; $C_3$-$C_{16}$ cycloalkenyl, heterocyclyl including 3-16 atoms, heterocycloalkenyl including 3-16 atoms; $C_7$-$C_{20}$ aralkyl; $C_6$-$C_{16}$ aryl; heteroaryl including 5-16 atoms; halo; $NR^dR^eC$; nitro; azido, hydroxy; $C_1$-$C_{12}$ alkoxy; $C_1$-$C_{12}$ thioalkoxy; $C_1$-$C_{12}$ haloalkoxy; $C_6$-$C_{16}$ aryloxy, $C_6$-$C_{16}$ thioaryloxy; heteroaryloxy including 5-20 atoms; thioaryloxy including 5-20 atoms; $C_2$-$C_{12}$ alkenyloxy; $C_2$-$C_{12}$ alkynyloxy; $C_3$-$C_{16}$ cycloalkyloxy; $C_3$-$C_{16}$ cycloalkenyloxy; heterocyclyloxy including 3-16 atoms; heterocycloalkenyloxy including 3-16 atoms; $C_7$-$C_{20}$ aralkoxy; heteroaralkoxy including 6-20 atoms; mercapto; cyano; $C_1$-$C_3$ alkylenedioxy; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^d R^e$; —N$R^h$C(O)$R^i$; or —OC(O)N$R^d R^e$;

$R^b$ at each occurrence is, independently:

(i) halo; N$R^d R^e$; nitro; azido; hydroxy; oxo, thioxo, =N$R^k$, $C_1$-$C_{12}$ alkoxy or $C_1$-$C_{12}$ thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^a$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; $C_1$-$C_3$ alkylenedioxy; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^d R^e$; —N$R^h$C(O)$R^i$; —OC(O)N$R^d R^e$; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

$R^c$ at each occurrence is, independently:

(i) halo; nitro; hydroxy; $C_1$-$C_{12}$ alkoxy optionally substituted with 1-5 $R^f$; $C_1$-$C_{12}$ haloalkoxy; cyano; $C_1$-$C_3$ alkylenedioxy; or SO$_2 R^m$; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

each of $R^d$, $R^e$, $R^g$, $R^h$, and $R^k$, at each occurrence is, independently:

(i) hydrogen; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

$R^f$ is N$R^d R^e$; nitro; azido; hydroxy; oxo, thioxo, =N$R^k$, $C_1$-$C_{12}$ alkoxy or $C_1$-$C_{12}$ thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^{a'}$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; $C_1$-$C_3$ alkylenedioxy; —C(O)$R^g$, —OC(O)$R^g$; —C(O)S$R^g$; —SC(O)$R^g$; —C(S)S$R^g$; —SC(S)$R^g$; —C(O)N$R^d R^e$; —N$R^h$C(O)$R^i$; —OC(O)N$R^d R^e$;

$R^i$ is $R^g$; O$R^g$; N$R^d R^e$; or heterocyclyl including 3-16 atoms; or heterocycloalkenyl including 3-16 atoms; each of which is optionally substituted with from 1-10 $R^b$;

$R^j$ is N$R^d R^e$; nitro; azido; hydroxy; oxo, thioxo, =N$R^k$, $C_1$-$C_{12}$ alkoxy or $C_1$-$C_{12}$ thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^{a'}$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; $C_1$-$C_3$ alkylenedioxy; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^d R^e$; —N$R^h$C(O)$R^i$; —OC(O)N$R^d R^e$; and $R^m$ is (i) $C_1$-$C_{12}$ alkyl or $C_1$-$C_{12}$ haloalkyl; each of which is optionally substituted with from 1-5 $R^j$; or (ii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) $C_6$-$C_{16}$ aryl or heteroaryl including 5-16 atoms, each of which is optionally substituted with from 1-10 $R^a$.

In some embodiments, one, two, three, or four of the following conditions apply:

(a) when V and Y are both N, and $R^2$ is substituted pyridyl or pyrimidinyl, then $R^c$ cannot be $C_1$-$C_{12}$ alkoxy optionally substituted with 1-5 $R^f$; $C_1$-$C_{12}$ haloalkoxy; or SO$_2 R^m$;

(b) when V and Y are both N, X is SO$_2$, and $R^2$ is $C_3$-$C_{16}$ cycloalkyl, then $R^1$ cannot be a monosubstituted phenyl ring that is substituted at the para-position with either substituted $C_1$-$C_{12}$ alkyl or substituted $C_1$-$C_{12}$ haloalkyl;

(c) when V and Y are both N, X is CO, then $R^1$ cannot be unsubstituted or mono, di, or trisubstituted pyrazolo[1,5-a]pyrimidin-2-yl;

(d) when V is N and Y is CH, and X is CO, then $R^2$ cannot be C(O)$R^5$.

In certain embodiments, conditions (a), (b), (c), and (d) apply. In certain embodiments, conditions (b), (c), and (d) apply. In certain embodiments, (a), (b), and (d) apply. In certain embodiments, (b) and (d) apply.

In another aspect, this invention relates to a compound of formula (I), in which:

$R^2$ is:

(i) $C_6$-$C_{18}$ aryl, optionally substituted with from 1-10 $R^c$; or heteroaryl including 5-20 atoms, optionally substituted with from 1-10 $R^n$;

(ii) $C_3$-$C_{16}$ cycloalkyl; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) O$R^1$; S$R^1$; or N$R^3 R^4$, wherein $R^3$ and $R^4$ are each, independently, hydrogen or $R^1$; or (iv) C(O)R$^5$, wherein R$^5$ is C$_1$-C$_{20}$ alkyl or C$_7$-C$_{20}$ aralkoxy;

R$^n$ at each occurrence is, independently:

(i) halo; nitro; hydroxy; cyano; or C$_1$-C$_3$ alkylenedioxy (e.g., halo; nitro; hydroxy; cyano); or (ii) C$_1$-C$_{12}$ alkyl or C$_1$-C$_{12}$ haloalkyl; each of which is optionally substituted with from 1-5 R$^j$; or (iii) C$_7$-C$_{20}$ aralkyl; C$_3$-C$_{16}$ cycloalkyl; heteroaralkyl including 6-20 atoms; C$_3$-C$_{16}$ cycloalkenyl; heterocyclyl including 3-16 atoms; or heterocycloalkenyl including 3-16 atoms; each of which is optionally substituted with from 1-10 R$^b$; or (iv) C$_2$-C$_{20}$ alkenyl or C$_2$-C$_{20}$ alkynyl; or (v) C$_6$-C$_{16}$ aryl or heteroaryl including 5-16 atoms, each of which is optionally substituted with from 1-10 R$^a$;

provided:

(b) when V and Y are both N, X is SO$_2$, and R$^2$ is C$_3$-C$_{16}$ cycloalkyl, then R$^1$ cannot be a monosubstituted phenyl ring that is substituted at the para-position with either substituted C$_1$-C$_{12}$ alkyl or substituted C$_1$-C$_{12}$ haloalkyl; and (c) when V and Y are both N, X is CO, then R$^1$ cannot be unsubstituted or mono, di, or trisubstituted pyrazolo[1,5-a]pyrimidin-2-yl; and (d) when V is N and Y is CH, and X is CO, then R$^2$ cannot be C(O)R$^5$; and R$^1$, R$^3$, R$^4$, R$^5$, R$^6$, R$^7$, X, V, Y, W$^1$, Z$^1$, W$^2$, Z$^2$, R$^a$, R$^{a'}$, R$^b$, R$^c$, R$^d$, R$^e$, R$^f$, R$^g$, R$^h$, R$^i$, R$^j$, R$^k$, and R$^m$ can be as defined anywhere herein.

In a further aspect, this invention relates to a compound of formula (I), in which:

R$^2$ is:

(i) C$_6$-C$_{18}$ aryl or heteroaryl including 5-20 atoms, each of which is optionally substituted with from 1-10 R$^c$; or (ii) C$_6$-C$_{16}$ cycloalkyl; C$_3$-C$_{16}$ cycloalkenyl; heterocyclyl including 3-16 atoms; or heterocycloalkenyl including 3-16 atoms; each of which is optionally substituted with from 1-10 R$^b$; or (iii) OR$^1$; SR$^1$; or NR$^3$R$^4$, wherein R$^3$ and R$^4$ are each, independently, hydrogen or R$^1$; or (iv) C(O)R$^5$, wherein R$^5$ is C$_1$-C$_{20}$ alkyl or C$_7$-C$_{20}$ aralkoxy;

provided:

(a) when V and Y are both N, and R$^2$ is substituted pyridyl or pyrimidinyl, then R$^c$ cannot be C$_1$-C$_{12}$ alkoxy optionally substituted with 1-5 R$^f$; C$_1$-C$_{12}$ haloalkoxy; or SO$_2$R$^m$; and (c) when V and Y are both N, X is CO, then R$^1$ cannot be unsubstituted or mono, di, or trisubstituted pyrazolo[1,5-a]pyrimidin-2-yl; and (d) when V is N and Y is CH, and X is CO, then R$^2$ cannot be C(O)R$^5$; and R$^1$, R$^3$, R$^4$, R$^5$, R$^6$, R$^7$, X, V, Y, W$^1$, Z$^1$, W$^2$, Z$^2$, R$^a$, R$^{a'}$, R$^b$, R$^c$, R$^d$, R$^e$, R$^f$, R$^g$, R$^h$, R$^i$, R$^j$, R$^k$, R$^m$, and R$^n$ can be as defined anywhere herein.

In another aspect, this invention relates to a compound of formula (I), in which:

R$^2$ is:

(i) C$_6$-C$_{18}$ aryl or heteroaryl including 5-20 atoms, each of which is optionally substituted with from 1-10 R$^c$; or (ii) C$_3$-C$_{16}$ cycloalkyl; C$_3$-C$_{16}$ cycloalkenyl; heterocyclyl including 3-16 atoms; or heterocycloalkenyl including 3-16 atoms; each of which is optionally substituted with from 1-10 R$^b$; or (iii) OR$^1$; SR$^1$; or NR$^3$R$^4$, wherein R$^3$ and R$^4$ are each, independently, hydrogen or R$^1$;

provided:

(a) when V and Y are both N, and R$^2$ is substituted pyridyl or pyrimidinyl, then R$^c$ cannot be C$_1$-C$_{12}$ alkoxy optionally substituted with 1-5 R$^f$; C$_1$-C$_{12}$ haloalkoxy; or SO$_2$R$^m$; and (b) when V and Y are both N, X is SO$_2$, and R$^2$ is C$_3$-C$_{16}$ cycloalkyl, then R$^1$ cannot be a monosubstituted phenyl ring that is substituted at the para-position with either substituted C$_1$-C$_{12}$ alkyl or substituted C$_1$-C$_{12}$ haloalkyl; and (c) when V and Y are both N, X is CO, then R$^1$ cannot be unsubstituted or mono, di, or trisubstituted pyrazolo[1,5-a]pyrimidin-2-yl; and R$^1$, R$^3$, R$^4$, R$^5$, R$^6$, R$^7$, X, V, Y, W$^1$, Z$^1$, W$^2$, Z$^2$, R$^a$, R$^{a'}$, R$^b$, R$^c$, R$^d$, R$^e$, R$^f$, R$^g$, R$^h$, R$^i$, R$^j$, R$^k$, and R$^m$ can be as defined anywhere herein.

In a further aspect, this invention relates to a compound of formula (I), in which:

R$^2$ is:

(i) C$_6$-C$_{18}$ aryl, optionally substituted with from 1-10 R$^c$; or heteroaryl including 5-20 atoms, optionally substituted with from 1-10 R$^n$;

(ii) C$_6$-C$_{16}$ cycloalkyl; C$_3$-C$_{16}$ cycloalkenyl; heterocyclyl including 3-16 atoms; or heterocycloalkenyl including 3-16 atoms; each of which is optionally substituted with from 1-10 R$^b$; or (iii) OR$^1$; SR$^1$; or NR$^3$R$^4$, wherein R$^3$ and R$^4$ are each, independently, hydrogen or R$^1$; or (iv) C(O)R$^5$, wherein R$^5$ is C$_1$-C$_{20}$ alkyl or C$_7$-C$_{20}$ aralkoxy;

provided:

(c) when V and Y are both N, X is CO, then R$^1$ cannot be unsubstituted or mono, di, or trisubstituted pyrazolo[1,5-a]pyrimidin-2-yl; and (d) when V is N and Y is CH, and X is CO, then R$^2$ cannot be C(O)R$^5$; and R$^1$, R$^3$, R$^4$, R$^5$, R$^6$, R$^7$, X, V, Y, W$^1$, Z$^1$, W$^2$, Z$^2$, R$^a$, R$^{a'}$, R$^b$, R$^c$, R$^d$, R$^e$, R$^f$, R$^g$, R$^h$, R$^i$, R$^j$, R$^k$, R$^m$, and R$^n$ can be as defined anywhere herein.

In a further aspect, this invention relates to a compound of formula (I), in which:

R$^2$ is:

(i) C$_6$-C$_{18}$ aryl, optionally substituted with from 1-10 R$^c$; or heteroaryl including 5-20 atoms, optionally substituted with from 1-10 R$^n$;

(ii) C$_3$-C$_{16}$ cycloalkyl; C$_3$-C$_{16}$ cycloalkenyl; heterocyclyl including 3-16 atoms; or heterocycloalkenyl including 3-16 atoms; each of which is optionally substituted with from 1-10 R$^b$; or (iii) OR$^1$; SR$^1$; or NR$^3$R$^4$, wherein R$^3$ and R$^4$ are each, independently, hydrogen or R$^1$;

provided:

(b) when V and Y are both N, X is SO$_2$, and R$^2$ is C$_3$-C$_{16}$ cycloalkyl, then R$^1$ cannot be a monosubstituted phenyl ring that is substituted at the para-position with either substituted C$_1$-C$_{12}$ alkyl or substituted C$_1$-C$_{12}$ haloalkyl; and (c) when V and Y are both N, X is CO, then R$^1$ cannot be unsubstituted or mono, di, or trisubstituted pyrazolo[1,5-a]pyrimidin-2-yl; and R$^1$, R$^3$, R$^4$, R$^5$, R$^6$, R$^7$, X, V, Y, W$^1$, Z$^1$, W$^2$, Z$^2$, R$^a$, R$^{a'}$, R$^b$, R$^c$, R$^d$, R$^e$, R$^f$, R$^g$, R$^h$, R$^i$, R$^j$, R$^k$, and R$^m$ can be as defined anywhere herein.

In a further aspect, this invention relates to a compound of formula (I), in which:

R$^2$ is:

(i) C$_6$-C$_{18}$ aryl or heteroaryl including 5-20 atoms, each of which is optionally substituted with from 1-10 R$^c$; or (ii) $C_6$-$C_{16}$ cycloalkyl; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) $OR^1$; $SR^1$; or $NR^3R^4$, wherein $R^3$ and $R^4$ are each, independently, hydrogen or $R^1$;

provided (a) when V and Y are both N, and $R^2$ is substituted pyridyl or pyrimidinyl, then $R^c$ cannot be $C_1$-$C_{12}$ alkoxy optionally substituted with 1-5 $R^f$, $C_1$-$C_{12}$ haloalkoxy; or $SO_2R^m$; and (c) when V and Y are both N, X is CO, then $R^1$ cannot be unsubstituted or mono, di, or trisubstituted pyrazolo[1,5-a]pyrimidin-2-yl; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In a further aspect, this invention relates to a compound of formula (I), in which:

$R^2$ is:

(i) $C_6$-$C_{18}$ aryl, optionally substituted with from 1-10 $R^c$; or heteroaryl including 5-20 atoms, optionally substituted with from 1-10 $R^n$;

(ii) $C_6$-$C_{16}$ cycloalkyl; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) $OR^1$; $SR^1$; or $NR^3R^4$, wherein $R^3$ and $R^4$ are each, independently, hydrogen or $R^1$;

provided:

(c) when V and Y are both N, X is CO, then $R^1$ cannot be unsubstituted or mono, di, or trisubstituted pyrazolo[1,5-a]pyrimidin-2-yl; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In a further aspect, this invention relates to a compound of formula (I), in which:

$R^2$ is:

(i) $C_6$-$C_{18}$ aryl or heteroaryl including 5-20 atoms, each of which is optionally substituted with from 1-10 $R^c$; or (iii) $OR^1$; $SR^1$; or $NR^3R^4$, wherein $R^3$ and $R^4$ are each, independently, hydrogen or $R^1$; or (iv) $C(O)R^5$, wherein $R^5$ is $C_1$-$C_{20}$ alkyl or $C_7$-$C_{20}$ aralkoxy;

provided:

(a) when V and Y are both N, and $R^2$ is substituted pyridyl or pyrimidinyl, then $R^c$ cannot be $C_1$-$C_{12}$ alkoxy optionally substituted with 1-5 $R^f$, $C_1$-$C_{12}$ haloalkoxy; or $SO_2R^m$; and (c) when V and Y are both N, X is CO, then $R^1$ cannot be unsubstituted or mono, di, or trisubstituted pyrazolo[1,5-a]pyrimidin-2-yl; and (d) when V is N and Y is CH, and X is CO, then $R^2$ cannot be $C(O)R^5$; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In a further aspect, this invention relates to a compound of formula (I), in which:

$R^2$ is:

(i) $C_6$-$C_{18}$ aryl, optionally substituted with from 1-10 $R^c$; or heteroaryl including 5-20 atoms, optionally substituted with from 1-10 $R^n$;

(iii) $OR^1$; $SR^1$; or $NR^3R^4$, wherein $R^3$ and $R^4$ are each, independently, hydrogen or $R^1$; or (iv) $C(O)R^5$, wherein $R^5$ is $C_1$-$C_{20}$ alkyl or $C_7$-$C_{20}$ aralkoxy;

provided:

(c) when V and Y are both N, X is CO, then $R^1$ cannot be unsubstituted or mono, di, or trisubstituted pyrazolo[1,5-a]pyrimidin-2-yl; and (d) when V is N and Y is CH, and X is CO, then $R^2$ cannot be $C(O)R^5$; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, $R^m$, and $R^n$ can be as defined anywhere herein.

In a further aspect, this invention relates to a compound of formula (I), in which:

$R^2$ is:

(i) $C_6$-$C_{18}$ aryl or heteroaryl including 5-20 atoms, each of which is optionally substituted with from 1-10 $R^c$; or (iii) $OR^1$; $SR^1$; or $NR^3R^4$, wherein $R^3$ and $R^4$ are each, independently, hydrogen or provided (a) when V and Y are both N, and $R^2$ is substituted pyridinyl or pyrimidinyl, then $R^c$ cannot be $C_1$-$C_{12}$ alkoxy optionally substituted with 1-5 $R^f$; $C_1$-$C_{12}$ haloalkoxy; or $SO_2R^m$; and (c) when V and Y are both N, X is CO, then $R^1$ cannot be unsubstituted or mono, di, or trisubstituted pyrazolo[1,5-a]pyrimidin-2-yl; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In a further aspect, this invention relates to a compound of formula (I), in which:

$R^2$ is:

(i) $C_6$-$C_{18}$ aryl, optionally substituted with from 1-10 $R^c$; or heteroaryl including 5-20 atoms, optionally substituted with from 1-10 $R^n$;

(iii) $OR^1$; $SR^1$; or $NR^3R^4$, wherein $R^3$ and $R^4$ are each, independently, hydrogen or $R^1$;

provided:

(c) when V and Y are both N, X is CO, then $R^1$ cannot be unsubstituted or mono, di, or trisubstituted pyrazolo[1,5-a]pyrimidin-2-yl; and $R^1$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In one aspect, this invention relates to a compound of formula (I), in which:

$R^1$ is:

(i) $C_6$-$C_{18}$ aryl or heteroaryl including 5-20 atoms, each of which is optionally substituted with from 1-10 $R^a$; or (ii) $C_7$-$C_{20}$ aralkyl; heteroaralkyl including 6-20 atoms; arylheterocyclyl including 8-20 atoms; arylcycloalkenyl including 8-20 atoms; or arylheterocycloalkenyl including 8-20 atoms; each of which is optionally substituted with from 1-10 $R^b$;

$R^2$ is $C_6$-$C_{18}$ aryl or heteroaryl including 5-20 atoms, each of which is optionally substituted with from 1-10 $R^c$;

X is $S(O)_n$ or $S(O)_nNR^6$, wherein n is 1 or 2, and $R^6$ is hydrogen, $C_1$-$C_{12}$ alkyl, or $C_3$-$C_{16}$ cycloalkyl;

one, two, three, or four of $W^1$, $Z^1$, $W^2$, and $Z^2$ are each, independently:

(i) $C_1$-$C_{12}$ alkyl; or (ii) oxo; or (iii) $C_6$-$C_{18}$ aryl or heteroaryl including 5-20 atoms, each of which is optionally substituted with from 1-10 $R^a$; or (iv) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; and the others are hydrogen; and $R^6$, $R^7$, V, Y, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In some embodiments, one or more of the following conditions apply:

(a) when V and Y are both N, and $R^2$ is substituted pyridyl or pyrimidinyl, then $R^c$ cannot be $C_1$-$C_{12}$ alkoxy optionally substituted with 1-5 $R^f$; $C_1$-$C_{12}$ haloalkoxy; or $SO_2R^m$;

(e) when V and Y are both N, X is $SO_2$, one of $Z^1$ and $W^2$ is $C_1$-$C_4$ alkyl (e.g., $CH_3$), and $R^2$ is phenyl substituted with from 1-5 $R^c$, then 1 $R^c$ must be halo; $C_1$-$C_{12}$ haloalkoxy; cyano; or $C_1$-$C_{12}$ haloalkyl, optionally substituted with from 1-5 $R^j$ (i.e., if 1 $R^c$ is present, then that $R^c$ substitutent must be halo; $C_1$-$C_{12}$ haloalkoxy; cyano; or $C_1$-$C_{12}$ haloalkyl, optionally substituted with from 1-5 $R^j$; if more than 1 $R^c$ is present, then one of the $R^c$ substitutents must be one of the four aforementioned substitutents);

(f) when V and Y are both N, X is $SO_2$, and $R^2$ is phenyl substituted with from 1-5 $R^c$, then 1 $R^c$ must be halo; $C_1$-$C_{12}$ haloalkoxy; cyano; or $C_1$-$C_{12}$ haloalkyl, optionally substituted with from 1-5 $R^j$;

(g) when V and Y are both N, X is $SO_2$, and one of $Z^1$ and $W^2$ is $C_1$-$C_4$ alkyl (e.g., $CH_3$), then $R^1$ cannot be 4-chlorophenyl;

(h) when V and Y are both N and X is $SO_2$, then $R^1$ cannot be 4-chlorophenyl;

(i) when V and Y are both N, X is $SO_2$, and one of $Z^1$ and $W^2$ is $C_1$-$C_4$ alkyl (e.g., $CH_3$), then $R^2$ cannot be phenyl monosubstituted with $C_1$-$C_4$ alkyl ($CH_3$) or $C_1$-$C_4$ alkoxy ($OCH_3$);

(j) when V and Y are both N and X is $SO_2$, then $R^2$ cannot be phenyl monosubstituted with $C_1$-$C_4$ alkyl ($CH_3$) or $C_1$-$C_4$ alkoxy ($OCH_3$).

In certain embodiments, (a) applies. In certain embodiments, (a) and any one of (e)-(j) apply. In certain embodiments, any one of (e)-(j) applies. In certain embodiments, any two or three of (e)-(j) applies, optionally in combination with (a). For example, (e) or (f) and (g) or (h) and/or (i) and (j), optionally in combination with (a).

In one aspect, this invention relates to a compound of formula (I), in which:
$R^1$ is:
(i) $C_6$-$C_{18}$ aryl or heteroaryl including 5-20 atoms, each of which is optionally substituted with from 1-10 $R^a$; or
(ii) $C_7$-$C_{20}$ aralkyl or heteroaralkyl including 6-20 atoms; each of which is optionally substituted with from 1-10 $R^b$;
$R^2$ is:
(i) $C_6$-$C_{18}$ aryl substituted with from 1-10 $R^c$; or heteroaryl including 5-20 atoms, optionally substituted with from 1-10 $R^c$; or
(iii) $OR^1$; $SR^1$; or $NR^3R^4$, wherein $R^3$ and $R^4$ are each, independently, hydrogen or
X is $S(O)_n$ or $S(O)_nNR^6$, wherein n is 1 or 2, and $R^6$ is hydrogen, $C_1$-$C_{12}$ alkyl, or $C_3$-$C_{16}$ cycloalkyl;
each of $W^1$, $Z^1$, $W^2$, and $Z^2$ is hydrogen; and
$R^3$, $R^4$, $R^6$, $R^7$, V, Y, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In some embodiments, one or more of the following conditions apply:
(a) when V and Y are both N, and $R^2$ is substituted pyridyl or pyrimidinyl, then $R^c$ cannot be $C_1$-$C_{12}$ alkoxy optionally substituted with 1-5 $R^f$; $C_1$-$C_{12}$ haloalkoxy; or $SO_2R^m$;

(k) when V and Y are both N and X is $SO_2$, then $R^1$ cannot be 4-chlorophenyl;

(l) when V and Y are both N and X is $SO_2$, then $R^1$ cannot be 1-chlorophenyl when $R^2$ is: phenyl monosubstituted with hydroxyl, $C_1$-$C_6$ alkoxy, chloro, or nitro; unsubstituted pyridyl; pyridyl monosubstituted with hydroxyl, chloro, or nitro; unsubstituted thiazolyl; thiazolyl monosubstituted with nitro or hydroxymethyl; unsubstituted indolyl; or unsubstituted indazolyl;

(m) when V and Y are both N and X is $SO_2$, then $R^1$ cannot be naphthyl when $R^2$ is: unsubstituted pyridyl; unsubstituted pyrimidinyl; phenyl monosubstituted with hydroxyl or $C_1$-$C_6$ alkoxy; unsubstituted thiazolyl; or 5-chloro-2-methylphenyl;

(n) when Y is N and V is CH and X is $SO_2$, then $R^1$ cannot be 1-chlorophenyl when $R^2$ is: phenyl monosubstituted with $C_1$-$C_6$ alkoxy or $C_1$-$C_6$ alkyl; or substituted benzo[d]isoxazole;

(o) when Y is N and V is CH and X is $SO_2$, then $R^1$ cannot be naphthyl when $R^2$ is phenyl monosubstituted with hydroxymethyl.

In certain embodiments, (a) applies. In certain embodiments, (a) and/or (k) applies. In certain embodiments, (a), (k) and any one, two, three, or four of (l)-(o) apply.

In one aspect, this invention relates to a compound of formula (I), in which:
$R^1$ is $C_7$-$C_{20}$ aralkyl, $C_3$-$C_{16}$ cycloalkyl, or ($C_1$-$C_{12}$ alkyl)-($C_3$-$C_{16}$ cycloalkyl), each of which is optionally substituted with from 1-10 $R^b$;
$R^2$ is:
(i) $C_6$-$C_{18}$ aryl or heteroaryl including 5-20 atoms, each of which is optionally substituted with from 1-10 $R^c$; or
(ii) $OR^1$; $SR^1$; or $NR^3R^4$, wherein $R^3$ and $R^4$ are each, independently, hydrogen or $R^1$;
X is CO; and
$R^3$, $R^4$, $R^6$, $R^7$, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, and $R^m$ can be as defined anywhere herein.

In one aspect, this invention relates to a compound of formula (I), in which:
$R^2$ is $C_6$-$C_{18}$ aryl or heteroaryl including 5-20 atoms, each of which is optionally substituted with from 1-10 $R^a$;
$R^2$ is $C_6$-$C_{16}$ cycloalkyl; $C_6$-$C_{16}$ cycloalkenyl; heterocyclyl including 3-16 atoms; or heterocycloalkenyl including 3-16 atoms; each of which is optionally substituted with from 1-10 $R^b$;
X is $S(O)_n$ or $S(O)_nNR^6$, wherein n is 1 or 2, and $R^6$ is hydrogen, $C_1$-$C_{12}$ alkyl, or $C_3$-$C_{16}$ cycloalkyl; and
$R^6$, $R^7$, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$ and $R^m$ can be as defined anywhere herein.

In some embodiments, (p) and/or (q) apply:
(p) when V and Y are both N and X is $SO_2$, then $R^1$ cannot be 1-chlorophenyl when $R^2$ is unsubstituted adamantyl or substituted or unsubstituted cyclohexyl; and
(q) when Y is N, V is CH, and X is $SO_2$, then $R^1$ cannot be 1-chlorophenyl when $R^2$ is unsubstituted piperidyl, piperidyl substituted with oxo, unsubstituted morpholinyl, or unsubstituted pyrrolidinyl; or a pharmaceutically acceptable salt thereof.

In one aspect, this invention relates to a compound of formula (VI-A):

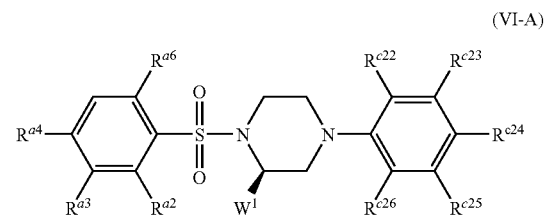

in which:
one or two of $R^{a2}$, $R^{a3}$, $R^{a4}$, and $R^{a6}$ are each, independently, halo; $NR^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)O$R^g$; —C(O)N$R^dR^e$; or —N$R^h$C(O)$R^i$; and the others are hydrogen;

$W^1$ is $C_1$-$C_4$ alkyl; and one or two of $R^{c22}$, $R^{c23}$, $R^{c24}$, $R^{c25}$, and $R^{c26}$ are each, independently, halo; $C_1$-$C_{12}$ alkyl or $C_1$-$C_{12}$ haloalkyl, each of which is optionally substituted with from 1-3 $R^j$; $C_1$-$C_{12}$ alkoxy; $C_1$-$C_{12}$ haloalkoxy; cyano; nitro; or $C_6$-$C_{10}$ aryl or heteroaryl including 5-12 atoms, each of which is optionally substituted with from 1-2 $R^a$; and the others are hydrogen.

In certain embodiments, one or more of the conditions delineated in the Summary can apply. For example, (a) can apply. In certain embodiments, (a) and any one of (e)-(j) apply. In certain embodiments, any one of (e)-(j) applies. In certain embodiments, any two or three of (e)-(j) applies, optionally in combination with (a). For example, (e) or (f) and (g) or (h) and/or (i) and (j), optionally in combination with (a).

In certain embodiments, (a) applies. In certain embodiments, (a) and/or (k) applies. In certain embodiments, (a), (k) and any one, two, three, or four of (l)-(o) apply.

Embodiments can include one or more of the following features.

The compounds can be in the form of a pharmaceutically acceptable salt. The compounds can be an N-oxide thereof and can also be in the form of a pharmaceutically acceptable salt.

Each of V and Y can both be N. V can be $CR^7$ (e.g., CH), and Y can be N. Y can be $CR^7$ (e.g., CH), and V can be N.

X can be $SO_2$, $SO_2$NH, or C(O).

One or two of $W^1$, $Z^1$, $W^2$, and $Z^2$ (e.g., $W^1$ and $Z^2$, e.g., $W^1$) can each be, independently, other than hydrogen (e.g., $C_1$-$C_4$ alkyl or oxo), and the others can be hydrogen. One or two of $W^1$, $Z^1$, $W^2$, and $Z^2$ (e.g., $W^1$ and $Z^2$, e.g., $W^1$) can each be, independently, $C_1$-$C_4$ alkyl, and the others can be hydrogen. Each of $Z^1$ and $W^2$ can be hydrogen. One or both of $W^1$ and $Z^2$ (e.g., $W^1$) can each be, independently, $C_1$-$C_4$ alkyl; and each of $Z^1$ and $W^2$ can be hydrogen. $W^1$ can be $C_1$-$C_4$ alkyl (e.g., $CH_3$). Each of $W^1$, $Z^1$, $W^2$, and $Z^2$ can be hydrogen.

$R^1$ can be $C_6$-$C_{10}$ aryl, optionally substituted with 1-4 $R^a$. In some embodiments, $R^1$ is other than substituted or unsubstituted naphthyl.

$R^a$ at each occurrence can be, independently, halo; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; $C_3$-$C_{10}$ heterocyclyl, $C_3$-$C_{10}$ cycloalkyl, $C_7$-$C_{12}$ aralkoxy or heteroaralkoxy including 6-12 atoms, each of which is optionally substituted with 1-2 $R^b$; or —N$R^h$C(O)$R^i$. In some embodiments, $R^a$ is other than halo (e.g., chloro).

$R^a$ at each occurrence is, independently, halo; N$R^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-2 $R^b$; —C(O)O$R^g$; —C(O)N$R^dR^e$; or —N$R^h$C(O)$R^i$. In some embodiments, $R^a$ is other than halo (e.g., chloro).

$R^1$ can be 1-naphthyl, 2-naphthyl, or phenyl (i.e., unsubstituted).

$R^1$ can have formula (II):

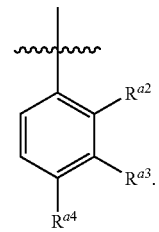

(II)

In certain embodiments, one of $R^{a2}$, $R^{a3}$, and $R^{a4}$ is halo; $C_1$-$C_{12}$ alkyl or $C_1$-$C_{12}$ haloalkyl, each of which is optionally substituted with 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy, optionally substituted with from 1-2 $R^{a'}$; $C_3$-$C_{10}$ heterocyclyl, $C_3$-$C_{10}$ cycloalkyl, or $C_7$-$C_{12}$ aralkoxy, each of which is optionally substituted with 1-2 $R^b$; or —N$R^h$C(O)$R^i$; and the others are hydrogen.

In other embodiments, one of $R^{a2}$, $R^{a3}$, and $R^{a4}$ is halo; N$R^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)O$R^g$; —C(O)N$R^dR^e$; or —N$R^h$C(O)$R^i$; and the others are hydrogen.

$R^{a2}$, $R^{a3}$, or $R^{a4}$ (e.g., $R^{a3}$ or $R^{a4}$, e.g., $R^{a3}$) can be $C_1$-$C_{12}$ haloalkyl (e.g., $C_1$-$C_4$ haloalkyl), optionally substituted with 1-2 (e.g., 1) $R^j$. For example, $R^{a3}$ or $R^{a4}$ can be 1,1,1-trifluoro-2-hydroxy-2-propyl, in which the stereogenic carbon (i.e., the carbon attached to the hydroxyl group) can have the R or S configuration or some combination thereof (e.g., about 50% R and about 50% S or any other non-racemic combination of configurations). In some embodiments, $R^{a3}$ or $R^{a4}$ (e.g., $R^{a3}$) can be:

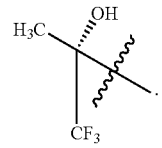

In these embodiments, each of the remaining substituents can be hydrogen.

$R^{a2}$, $R^{a3}$, or $R^{a4}$ can be $C_1$-$C_{12}$ alkyl, optionally substituted with 1 $R^j$. For example, $R^{a4}$ can be $CH_3$ or a $C_3$-$C_{12}$ branched alkyl, such as tert-butyl. As another example, $R^{a3}$ or $R^{a4}$ can be $C_1$-$C_{12}$ alkyl, optionally substituted with 1 $R^j$ (e.g., 2-hydroxy-2-propyl).

$R^{a3}$ or $R^{a4}$ (e.g., $R^{a3}$) can be heterocyclyl including 3-8 atoms, optionally substituted with from 1-3 (e.g., 1) $R^b$. In embodiments, $R^{a3}$ or $R^{a4}$ (e.g., $R^{a3}$) can be piperazinyl, piperidyl, morpholinyl, or pyrrolidinyl, each of which is optionally substituted with 1-3 (e.g., 1) $R^b$. For example, $R^{a3}$ or $R^{a4}$ (e.g., $R^{a3}$) can be 3-hydroxypyrrolidin-1-yl or 3-carboxypyrrolidin-1-yl.

In embodiments, $R^b$ at each occurrence can be, independently, halo; $NR^dR^e$; hydroxyl; oxo; $C_1$-$C_{12}$ alkyl or $C_1$-$C_{12}$ haloalkyl, each of which is optionally substituted with from 1-3 $R^j$; $C_1$-$C_{12}$ alkoxy, optionally substituted with 1-2 $R^f$, $C_1$-$C_{12}$ haloalkoxy; heterocyclyl including 3-10 atoms or $C_3$-$C_{10}$ cycloalkyl, each of which is optionally substituted with 1-3 $R^b$; —C(O)$R^g$; —C(O)O$R^g$; —C(O)N$R^dR^e$; —OC(O)$R^g$; or —N$R^h$C(O)$R^i$.

$R^{a3}$ or $R^{a4}$ (e.g., $R^{a3}$) can be heteroaryl including 5 or 6 atoms, optionally substituted with from 1-2 $R^{a'}$ (e.g., 1H-1,2,4-triazolyl).

$R^{a2}$, $R^{a3}$, or $R^{a4}$ can be halo (e.g., chloro). $R^{a3}$ or $R^{a4}$ can be phenyl or phenoxy, each of which is optionally substituted with from 1-2 halo. $R^{a4}$ can be $C_1$-$C_4$ alkoxy, optionally substituted with 1 $R^f$. $R^{a4}$ can be —NHC(O)$R^i$. In embodiments, $R^i$ can be $C_1$-$C_4$ alkyl; or $R^i$ can be $NR^dR^e$, in which $R^d$ and $R^e$ can each be, independently, hydrogen or $C_1$-$C_4$ alkyl; or $R^i$ can be heterocyclyl including 3-8 atoms. $R^{a2}$, $R^{a3}$, or $R^{a4}$ can be $C_3$-$C_{10}$ cycloalkyl, optionally substituted with 1 $R^b$ (e.g., 1-hydroxycyclopropyl).

$R^1$ can have formula (II-A):

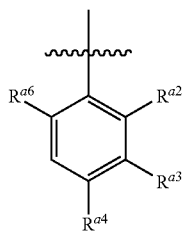

(II-A)

In certain embodiments, two of $R^{a2}$, $R^{a3}$, $R^{a4}$, and $R^{a6}$ can each be, independently, halo; $NR^dR^e$; hydroxyl; $C_1$-$C_{12}$ alkyl or $C_1$-$C_{12}$ haloalkyl, each of which is optionally substituted with 1-2 $R^j$; $C_1$-$C_{12}$ alkoxy, optionally substituted with 1-2 $R^f$; $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; —C(O)O$R^g$; —C(O)N$R^dR^e$; or —N$R^h$C(O)$R^i$; and the others can be hydrogen.

In other embodiments, one or two of $R^{a2}$, $R^{a3}$, $R^{a4}$, and $R^{a6}$ can each be, independently, halo; $NR^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)O$R^g$; —C(O)N$R^dR^e$; or —N$R^h$C(O)$R^i$; and the others can be hydrogen.

$R^{a2}$ can be halo (e.g., chloro), and $R^{a4}$ can be a substitutent other than hydrogen, such as halo; $NR^dR^e$; hydroxyl; $C_1$-$C_{12}$ alkoxy, optionally substituted with from 1-2 $R^f$; $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; —C(O)O$R^g$; —C(O)N$R^dR^e$; or —N$R^h$C(O)$R^i$. For example, $R^{a2}$ can be halo (e.g., chloro), and $R^{a4}$ can be heterocyclyl including 5-8 atoms, optionally substituted with from 1-3 $R^b$.

$R^1$ can be 3,4-dichlorophenyl, 3-fluoro-4-bromophenyl, 2,6-dichlorophenyl, 2,4-difluorophenyl, 3,4-dimethoxyphenyl, 2-bromo-4-(trifluoromethyl)phenyl, or

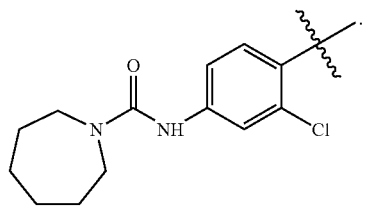

$R^1$ can be heteroaryl including 5-14 atoms, optionally substituted with from 1-5 (e.g., 1-2) $R^a$.

$R^1$ can be a monocyclic heteroaryl including 5-6 atoms, optionally substituted with from 1-2 $R^a$. In embodiments, $R^1$ can be thienyl, isoxazolyl, or pyridinyl, each of which is optionally substituted with from 1-2 $R^a$, wherein $R^a$ at each occurrence is, independently, halo, $C_1$-$C_4$ alkyl, or heterocyclyl including 3-8 atoms.

In certain embodiments, $R^1$ can have formula (II-B):

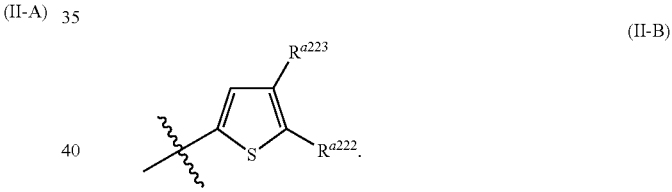

(II-B)

In some embodiments, $R^{a222}$ and $R^{a223}$ can each be, independently, hydrogen; halo; $NR^dR^e$; $C_1$-$C_{12}$ alkyl or $C_1$-$C_{12}$ haloalkyl, each of which is optionally substituted with from 1-2 $R^j$; $C_6$-$C_{10}$ aryl or heteroaryl including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)$R^g$; —C(O)O$R^g$; —C(O)N$R^dR^e$; or —N$R^h$C(O)$R^i$.

$R^{a222}$ can be halo; $NR^dR^e$; $C_1$-$C_{12}$ alkyl or $C_1$-$C_{12}$ haloalkyl, each of which is optionally substituted with from 1-2 $R^j$; $C_6$-$C_{10}$ aryl or heteroaryl including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)$R^g$; —C(O)O$R^g$; —C(O)N$R^dR^e$; or —N$R^h$C(O)$R^i$; and $R^{a223}$ can be hydrogen. For example, $R^{a222}$ can be heterocyclyl including 3-8 atoms, optionally substituted with from 1-3 $R^b$ (e.g., piperazinyl, piperidyl, morpholinyl, or pyrrolidinyl, each of which is optionally substituted with 1-3 $R^b$).

$R^1$ can be a bicyclic or tricyclic heteroaryl including 8-12 atoms, each of which is optionally substituted with from 1-2 $R^a$. For example, $R^1$ can be quinolyl, benzothienyl, dibenzothienyl, benzofuryl, dibenzofuryl, or benzothiazolyl, each of which is optionally substituted with from 1-2 $R^a$, wherein $R^a$ at each occurrence is, independently, halo, $C_1$-$C_4$ alkyl, or heterocyclyl including 3-8 atoms.

$R^1$ can be $C_3$-$C_{12}$ cycloalkyl, optionally substituted with from 1-5 $R^b$. For example, $R^1$ can be cyclopropyl, cyclopentyl, cyclohexyl, or adamantyl, each of which is optionally substituted with from 1-5 $R^b$, wherein $R^b$ at each occurrence is, independently, halo or $C_1$-$C_4$ alkyl.

$R^1$ can be ($C_1$-$C_6$ alkyl)-($C_3$-$C_{12}$ cycloalkyl), wherein the cycloalkyl ring is optionally substituted with from 1-3 $R^b$. For example, $R^1$ can be —$CH_2$-(cyclopentyl), —$CH_2$-(cyclohexyl), or —$CH_2$-(bicycloheptyl), wherein the cycloalkyl ring is optionally substituted with from 1-3 $C_1$-$C_4$ alkyl.

$R^1$ can be $C_7$-$C_{12}$ aralkyl, optionally substituted with from 1-2 $R^b$ (e.g., benzyl, optionally substituted with from 1-2 halo). $R^1$ can be arylheterocyclyl including 9-12 atoms.

$R^2$ can be $C_6$-$C_{10}$ aryl, optionally substituted with from 1-3 $R^c$.

$R^2$ can have formula (IV):

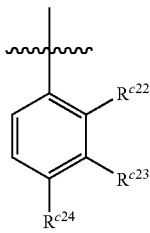

(IV)

In some embodiments, one of $R^{c22}$, $R^{c23}$, and $R^{c24}$ is halo; hydroxyl; $C_1$-$C_{12}$ alkyl; $C_1$-$C_{12}$ haloalkyl; $C_1$-$C_{12}$ alkoxy; $C_1$-$C_{12}$ haloalkoxy; cyano; nitro; or $C_6$-$C_{10}$ aryl, optionally substituted with from 1-2 $R^a$; and the others are hydrogen.

$R^{c22}$ or $R^{c23}$ (e.g., $R^{c22}$) can be $C_1$-$C_4$ haloalkyl (e.g., $CF_3$). $R^{c22}$ can be $C_1$-$C_4$ alkyl or $C_1$-$C_4$ alkoxy. $R^{c22}$, $R^{c23}$, or $R^{c24}$ (e.g., $R^{c23}$ or $R^{c24}$, e.g., $R^{c24}$) can be halo (e.g., fluoro). $R^{c24}$ can be phenyl substituted with 1 $R^a$.

$R^2$ can have formula (IV-A):

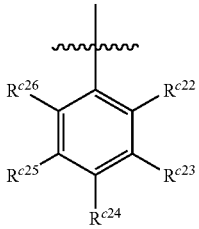

(IV-A)

In certain embodiments, two of $R^{c22}$, $R^{c23}$, $R^{c24}$, $R^{c25}$ and $R^{c26}$ can each be, independently, halo; $C_1$-$C_{12}$ alkyl; $C_1$-$C_{12}$ haloalkyl; cyano, $C_1$-$C_{12}$ alkoxy; heterocyclyl including 3-10 atoms, optionally substituted with from 1-2 $R^b$; heteroaryl including from 5-10 atoms, optionally substituted with from 1-2 $R^a$; or $SO_2R^m$; and the others are hydrogen.

In other embodiments, one or two of $R^{c22}$, $R^{c23}$, $R^{c24}$, $R^{c25}$, and $R^{c26}$ can each be, independently, halo; $C_1$-$C_{12}$ alkyl or $C_1$-$C_{12}$ haloalkyl, each of which is optionally substituted with from 1-3 $R^j$; $C_1$-$C_{12}$ alkoxy; $C_1$-$C_{12}$ haloalkoxy; cyano; nitro; or $C_6$-$C_{10}$ aryl or heteroaryl including 5-12 atoms, each of which is optionally substituted with from 1-2 $R^a$; and the others are hydrogen.

Two of $R^{c22}$, $R^{c23}$, $R^{c24}$, $R^{c25}$, and $R^{c26}$ can each be, independently; $C_1$-$C_4$ haloalkyl, optionally substituted with from 1-3 $R^j$; cyano; or heteroaryl including 5-6 atoms, optionally substituted with from 1-2 $R^a$.

$R^{c22}$ can be $C_1$-$C_4$ haloalkyl (e.g., $CF_3$), halo (e.g., chloro), $C_1$-$C_6$ alkoxy (e.g., OCH3), cyano, or $C_1$-$C_6$ alkyl (e.g., $CH_3$); and one of $R^{c23}$, $R^{c24}$, and $R^{c25}$ can be: heterocyclyl including 3-8 atoms, optionally substituted with 1 $R^b$; heteroaryl including 5 or 6 atoms, optionally substituted with 1 $R^a$; or halo. In embodiments, $R^{c22}$ can be $CF_3$, chloro, $OCH_3$, cyano, or $CH_3$; and one of $R^{c23}$, $R^{c24}$, and $R^{c25}$ can be: heterocyclyl including 3-8 atoms, optionally substituted with 1 $R^b$; heteroaryl including 5 or 6 atoms, optionally substituted with 1 $R^a$; or halo. In these embodiments, one of $R^{c23}$, $R^{c24}$, and $R^{c25}$ can be piperazinyl, optionally substituted with 1 $R^b$; morpholinyl, optionally substituted with 1 $R^b$; 1H-1,2,4-triazolyl; or fluoro.

Two of $R^{c22}$, $R^{c23}$, $R^{c24}$, $R^{c25}$, and $R^{c26}$ can each be, independently, halo (e.g., fluoro) or $C_1$-$C_4$ haloalkyl (e.g., $CF_3$).

$R^{c22}$ can be $C_1$-$C_4$ haloalkyl (e.g., $CF_3$), optionally substituted with from 1-3 $R^j$; and $R^{c24}$ can be halo; $C_1$-$C_4$ haloalkyl, optionally substituted with from 1-3 $R^j$; cyano; or heteroaryl including 5-6 atoms, optionally substituted with from 1-2 $R^a$. For example, $R^{c22}$ can be $CF_3$. $R^{c22}$ can be $CF_3$, and $R^{c24}$ can be halo (and the others can be hydrogen).

$R^{c22}$ and $R^{c24}$ can each be, independently, fluoro or chloro. For example, $R^c$ can be chloro, and $R^{c24}$ can be fluoro.

$R^2$ can be 4-fluoro-2-(sulfonylmethyl)phenyl; 4-fluoro-2-(trifluoromethyl)phenyl; 2,3-dichlorophenyl; 2,4-difluorophenyl; 2,4-dimethylphenyl; 2,6-dichlorophenyl; 2,6-dimethylphenyl; 3,4-dichlorophenyl; or 3-fluoro-2-(trifluoromethyl)phenyl.

$R^2$ can be heteroaryl including 5-12 atoms, optionally substituted with from 1-3 (e.g., 1-2) $R^c$.

$R^2$ can have formula (III):

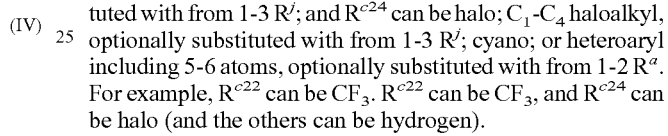

(III)

In some embodiments, one or two of $R^{c3}$, $R^{c4}$, $R^{c5}$, and $R^{c6}$ can each be, independently, halo; $C_1$-$C_{12}$ alkyl; $C_1$-$C_{12}$ haloalkyl, optionally substituted with 1-2 $R^j$; cyano; or nitro; and the others are hydrogen.

One of $R^{c3}$, $R^{c4}$, or $R^{c5}$ (e.g., $R^{c3}$) can be $C_1$-$C_4$ haloalkyl (e.g., $CF_3$). $R^{c3}$ or $R^{c5}$ can be chloro or fluoro. $R^{c3}$ can be $C_1$-$C_4$ alkyl. $R^{c3}$ can be $CF_3$, chloro, fluoro, cyano, $CH_3$, or nitro.

Two of $R^{c3}$, $R^{c4}$, $R^{c5}$, and $R^{c6}$ are each, independently, halo or $C_1$-$C_4$ haloalkyl. For example, two of $R^{c3}$, $R^{c4}$, $R^{c5}$, and $R^6$ are each, independently, fluoro or $CF_3$.

$R^2$ can be 1-quinolyl, 2-quinolyl, 1-isoquinolyl, or 3,5-dichloro-4-pyridyl.

$R^2$ can be $OR^1$, wherein $R^1$ is $C_6$-$C_{10}$ aryl, or heteroaryl including 5-10 atoms, each of which is optionally substituted with from 1-3 $R^a$; or $C_7$-$C_{12}$ aralkyl, optionally substituted with from 1-3 $R^b$.

$R^2$ can have formula (V):

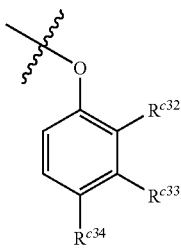

In some embodiments, one of $R^{c32}$, $R^{c33}$, and $R^{c34}$ can be halo; $C_1$-$C_{12}$ alkyl; $C_1$-$C_{12}$ haloalkyl; $C_1$-$C_{12}$ alkoxy; $C_1$-$C_{12}$ haloalkoxy; cyano; or nitro; and the others can be hydrogen. $R^{c32}$ can be $C_1$-$C_4$ haloalkyl (e.g., $CF_3$) or $C_1$-$C_4$ alkyl. $R^{c32}$ or $R^{c34}$ can be $C_1$-$C_4$ alkoxy. $R^{c32}$ can be halo. For example, $R^2$ can be 2,6-dichlorophenoxy.

$R^2$ can be $NR^3R^4$, in which one of $R^3$ and $R^4$ is hydrogen, and the other can be $C_6$-$C_{10}$ aryl, optionally substituted with from 1-3 $R^a$. For example, $R^2$ can be 2-chlorophenylamino.

$R^2$ is $C_3$-$C_{12}$ cycloalkyl, optionally substituted with from 1-5 $R^b$ (e.g., $C_6$-$C_{12}$ cycloalkyl, optionally substituted with from 1-5 $R^b$). For example, $R^2$ can be cyclohexyl, bicycloheptyl, cycloheptyl, or adamantyl, each of which is optionally substituted with from 1-2 $R^b$, in which $R^b$ at each occurrence can be, independently, halo or $C_1$-$C_4$ alkyl.

Each of V and Y is N, and X is $SO_2$, and embodiments can include one or more of the features described anywhere herein.

The compound of formula (I) can be (2R)-1,1,1-trifluoro-2-[3-({(2R)-4-[4-fluoro-2-(trifluoromethyl)phenyl]-2-methylpiperazin-1-yl}sulfonyl)phenyl]propan-2-ol.

In one aspect, this invention features a pharmaceutical composition, which includes a compound of formula (I) or a salt (e.g., a pharmaceutically acceptable salt) or a prodrug thereof (e.g., an effective amount thereof) and a pharmaceutically acceptable adjuvant, carrier or diluent. In some embodiments, the composition can further include an additional therapeutic agent.

In one aspect, this invention relates to a method for treating a disease or condition mediated by excess or uncontrolled amounts of cortisol and/or other corticosteroids, which includes administering to a subject in need thereof an effective amount of a compound of formula (I) or a salt (e.g., a pharmaceutically acceptable salt) or prodrug thereof.

In one aspect of the invention, this invention relates to methods for treating diabetes (e.g., type I diabetes, type 2 diabetes), which includes administering to a subject in need thereof an effective amount of a compound of formula I or a pharmaceutically acceptable salt thereof.

In another aspect of the invention, this invention relates to methods for treating Syndrome X, which includes administering to a subject in need thereof an effective amount of a compound of formula I or a pharmaceutically acceptable salt thereof.

In a further aspect of the invention, this invention relates to methods for treating hyperglycemia, diabetes or insulin resistance, which includes administering to a subject in need thereof an effective amount of a compound of formula I or a pharmaceutically acceptable salt thereof.

In one aspect of the invention, this invention relates to methods for treating obesity, which includes administering to a subject in need thereof an effective amount of a compound of formula I or a pharmaceutically acceptable salt thereof.

In another aspect of the invention, this invention relates to methods for treating a lipid disorder selected from the group consisting of dyslipidemia, hyperlipidemia, hypertriglyceridemia, hypercholesterolemia, low HDL and high LDL, which includes administering to a subject in need thereof an effective amount of a compound of formula I or a pharmaceutically acceptable salt thereof.

In a further aspect of the invention, this invention relates to methods for treating atherosclerosis, which include administering to a subject in need thereof an effective amount of a compound of formula I or a pharmaceutically acceptable salt thereof.

In one aspect of the invention, this invention relates to methods for treating a cognitive disorder (e.g., Alzheimer's disease), which includes administering to a subject in need thereof an effective amount of a compound of formula I or a pharmaceutically acceptable salt thereof.

In another aspect of the invention, this invention relates to methods for promoting wound healing, which includes administering to a subject in need thereof an effective amount of a compound of formula I or a pharmaceutically acceptable salt thereof.

In a further aspect of the invention, this invention relates to methods for treating, controlling, ameliorating, preventing, delaying the onset of, or reducing the risk of developing one or more of diabetes (e.g., type 1 or type 2 diabetes), Syndrome X, hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, hypertension, coronary heart disease, stroke, peripheral vascular disease, Cushing's syndrome, glaucoma, osteoporosis, hyperinsulinemia, tuberculosis, psoriasis, cognitive disorders and dementia (e.g., impairment associated with aging and of neuronal dysfunction, e.g., Alzheimer's disease), depression, viral diseases, inflammatory disorders, immune disorders); or promoting wound healing, which includes administering to a subject in need thereof an effective amount of a compound of formula I or a pharmaceutically acceptable salt thereof.

The invention also relates generally to inhibiting 11-beta HSD1 with a compound having formula (I). In some embodiments, the methods can include, e.g., contacting an 11βHSD1 in a sample (e.g., a tissue) with a compound having formula (I). In other embodiments, the methods can include administering a compound having formula (I) to a subject (e.g., a mammal, e.g., a mammal subject to or at risk for diseases mediated by abnormally high levels of cortisol and other 11β-hydroxysteroids, e.g., NIDDM, obesity, dyslipidemia, syndrome X, and hypertension). Accordingly, in yet another aspect, this invention includes methods of screening for compounds that inhibit 11βHSD1.

In some embodiments, the subject can be a subject in need thereof (e.g., a subject identified as being in need of such treatment). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

In a further aspect, this invention also relates to methods of making compounds described herein. Alternatively, the method includes taking any one of the intermediate compounds described herein and reacting it with one or more chemical reagents in one or more steps to produce a compound described herein.

In one aspect, this invention relates to any of the compounds described herein.

In one aspect, this invention relates to a packaged product. The packaged product includes a container, one of the aforementioned compounds in the container, and a legend (e.g., a label or an insert) associated with the container and indicating administration of the compound for treatment and control of diseases mediated by abnormally high levels of cortisol and other 11β-hydroxysteroids, e.g., NIDDM and Syndrome X.

The term "mammal" includes organisms, which include mice, rats, cows, sheep, pigs, rabbits, goats, and horses, monkeys, dogs, cats, and preferably humans.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/Kg to about 1000 mg/Kg, (e.g., from about 0.1 to about 100 mg/Kg, from about 1 to about 100 mg/Kg). Effective doses will also vary depending on route of administration, as well as the possibility of co-usage with other agents.

The term "halo" or "halogen" refers to any radical of fluorine, chlorine, bromine or iodine. The term "carboxy" refers to the —COOH radical.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

The term "alkyl" refers to a saturated hydrocarbon chain that may be a straight chain or branched chain, containing the indicated number of carbon atoms. For example, $C_1$-$C_{20}$ alkyl indicates that the group may have from 1 to 20 (inclusive) carbon atoms in it. Any atom can be substituted. Examples of alkyl groups include without limitation methyl, ethyl, and tert-butyl.

The term "cycloalkyl" refers to saturated monocyclic, bicyclic, tricyclic, or other polycyclic hydrocarbon groups. Any atom can be substituted, e.g., by one or more substitutents. A ring carbon serves as the point of attachment of a cycloalkyl group to another moiety. Cycloalkyl groups can contain fused rings. Fused rings are rings that share a common carbon atom. Cycloalkyl moieties can include, e.g., cyclopropyl, cyclohexyl, methylcyclohexyl (provided that the methylcyclohexyl group is attached to another moiety via a cyclohexyl ring carbon and not the methyl group), adamantyl, and norbornyl (bicycle[2.2.1]heptyl).

The term "haloalkyl" refers to an alkyl group, in which at least one hydrogen atom is replaced by halo. In some embodiments, more than one hydrogen atom (2, 3, 4, 5, 6, 7, 8, 9, 10, 11, 12, 13, 14, 15, 16, 17, 18, 19, 20, 21, 22, 23, 24, 25, 26, etc. hydrogen atoms) on a alkyl group can be replaced by more than one halogen (e.g., 2, 3, 4, 5, 6, 7, 8, 9, 10, 11, 12, 13, 14, 15, 16, 17, 18, 19, 20, 21, 22, 23, 24, 25, 26, etc. halogen atoms). In these embodiments, the hydrogen atoms can each be replaced by the same halogen (e.g., fluoro) or the hydrogen atoms can be replaced by a combination of different halogens (e.g., fluoro and chloro). The term "haloalkyl" also includes alkyl moieties in which all hydrogens have been replaced by halo (e.g., sometimes referred to as perhaloalkyl moieties, such as trifluoromethyl).

The term "aralkyl" refers to an alkyl moiety in which an alkyl hydrogen atom is replaced by an aryl group. One of the carbons of the alkyl moiety serves as the point of attachment of the aralkyl group to another moiety. Aralkyl includes groups in which more than one hydrogen atom on an alkyl moiety has been replaced by an aryl group. Any ring or chain atom can be substituted e.g., by one or more substitutents. Examples of "aralkyl" include without limitation benzyl, 2-phenylethyl, 3-phenylpropyl, benzhydryl (diphenylmethyl), and trityl (triphenylmethyl) groups.

The term "heteroaralkyl" refers to an alkyl moiety in which an alkyl hydrogen atom is replaced by a heteroaryl group. One of the carbons of the alkyl moiety serves as the point of attachment of the aralkyl group to another moiety. Heteroaralkyl includes groups in which more than one hydrogen atom on an alkyl moiety has been replaced by a heteroaryl group. Any ring or chain atom can be substituted e.g., by one or more substitutents. Heteroaralkyl can include, for example, 2-pyridylethyl.

The term "(alkyl)-(cycloalkyl)" refers to an alkyl moiety in which an alkyl hydrogen atom is replaced by a cycloalkyl group. One of the carbons of the alkyl moiety serves as the point of attachment of the (alkyl)-(cycloalkyl) to another moiety. Any ring or chain atom can be substituted e.g., by one or more substitutents. (alkyl)-(cycloalkyl) can include, for example:

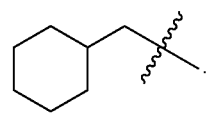

The term "alkenyl" refers to a straight or branched hydrocarbon chain containing 2-20 carbon atoms and having one or more double bonds. Any atom can be substituted, e.g., by one or more substitutents. Alkenyl groups can include, e.g., allyl, 1-butenyl, 2-hexenyl and 3-octenyl groups. One of the double bond carbons can optionally be the point of attachment of the alkenyl substitutent. The term "alkynyl" refers to a straight or branched hydrocarbon chain containing 2-20 carbon atoms and having one or more triple bonds. Any atom can be substituted, e.g., by one or more substitutents. Alkynyl groups can include, e.g., ethynyl, propargyl, and 3-hexynyl. One of the triple bond carbons can optionally be the point of attachment of the alkynyl substitutent.

The term "alkoxy" refers to an —O-alkyl radical. The term "mercapto" refers to an SH radical. The term "thioalkoxy" refers to an —S-alkyl radical. The terms "aryloxy" and "heteroaryloxy" refer to an —O-aryl radical and —O-heteroaryl radical, respectively. The term "thioaryloxy" refers to an —S-aryl radical. The terms "aralkoxy" and "heteroaralkoxy" refer to an —O-aralkyl radical and —O-heteroaralkyl radical, respectively. The term "cycloalkoxy" refers to an —O-cycloalkyl radical. The terms "cycloalkenyloxy" and "heterocycloalkenyloxy" refer to an —O-cycloalkenyl radical and —O-heterocycloalkenyl radical, respectively. The term "heterocyclyloxy" refers to an —O-heterocyclyl radical. The terms "alkenyloxy" and "alkynyloxy" refer to —O-alkenyl and —O-alkynyl radicals, respectively.

The term "heterocyclyl" refers to a saturated monocyclic, bicyclic, tricyclic or other polycyclic ring system having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). The heteroatom or ring carbon is the point of attachment of the heterocyclyl substituent to another moiety. Any atom can be substituted, e.g., by one or more substitutents. The heterocyclyl groups can contain fused rings. Fused rings are rings that share a common carbon atom. Heterocyclyl groups can include, e.g., tetrahydrofuryl, tetrahydropyranyl, piperidyl (piperidino), piperazinyl, morpholinyl (morpholino), pyrrolinyl, and pyrrolidinyl.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be substituted e.g., by one or more substitutents. The cycloalkenyl groups can contain fused rings. Fused rings are rings that share a common carbon atom. Cycloalkenyl moieties can include, e.g., cyclohexenyl, cyclohexadienyl, or norbornenyl.

The term "heterocycloalkenyl" refers to partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). A ring carbon (e.g., saturated or unsaturated) or heteroatom is the point of attachment of the heterocycloalkenyl substituent. Any atom can be substituted, e.g., by one or more substitutents. The heterocycloalkenyl groups can contain fused rings. Fused rings are rings that share a common carbon atom. Heterocycloalkenyl groups can include, e.g., tetrahydropyridyl, and dihydropyranyl.

The term "aryl" refers to an aromatic monocyclic, bicyclic, or tricyclic hydrocarbon ring system, wherein any ring atom can be substituted, e.g., by one or more substitutents. Aryl groups can contain fused rings. Fused rings are rings that share a common carbon atom. Aryl moieties can include, e.g., phenyl, naphthyl, anthracenyl, and pyrenyl.

The term "heteroaryl" refers to an aromatic monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). Any atom can be substituted, e.g., by one or more substitutents. Heteroaryl groups can contain fused rings. Fused rings are rings that share a common carbon atom. Heteroaryl groups include pyridyl, thienyl, furyl (furanyl), imidazolyl, isoquinolyl, quinolyl and pyrrolyl.

The terms "arylcycloalkenyl," "arylheterocyclyl," and "arylheterocycloalkenyl" refer to bicyclic, tricyclic, or other polycyclic ring systems that include an aryl ring fused to a cycloalkenyl, heterocyclyl, and heterocycloalkenyl, respectively. Any atom can be substituted, e.g., by one or more substitutents. For example, arylcycloalkenyl can include indenyl; arylheterocyclyl can include 2,3-dihydrobenzofuryl, 1,2,3,4-tetrahydroisoquinolyl, and 2,2-dimethylchromanyl; and arylheterocycloalkenyl can include 1,4-dihydro-1,4-epoxynaphthyl.

The term "oxo" refers to an oxygen atom, which forms a carbonyl (C=O) when attached to carbon or which forms part of a sulfinyl or sulfonyl group when attached to a sulfur atom. The term "thioxo" refers to an oxygen atom, which forms a thiocarbonyl (C=S) when attached to carbon.

The term "substitutent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, heteroaryl, arylcycloalkenyl, arylheterocyclyl, or arylheterocycloalkenyl group at any atom of that group. In one aspect, the substitutent(s) (e.g., $R^a$) on a group are independently any one single, or any combination of two or more of the permissible atoms or groups of atoms delineated for that substitutent. In another aspect, a substitutent may itself be substituted with any one of the above substitutents (e.g., substitutent $R^a$ can be substituted with $R^{a'}$).

In general, when a definition for a particular variable includes both hydrogen and non-hydrogen (halo, alkyl, aryl, etc.) possibilities, the term "substitutent(s) other than hydrogen" and the like refers collectively to the non-hydrogen possibilities for that particular variable.

The details of one or more embodiments of the invention are set forth in the description below. Other features and advantages of the invention are in the claims.

DETAILED DESCRIPTION

This invention relates to 11-beta HSD1 inhibitor compounds, pharmaceutical compositions and related methods.

The 11-beta HSD1 inhibitor compounds have the general formula (I) below:

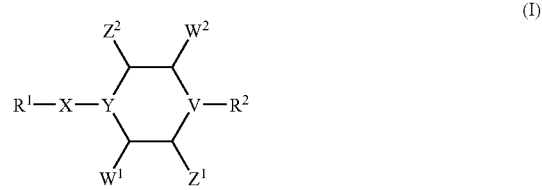

in which $R^1$, $R^2$, $R^3$, $R^4$, $R^5$, $R^6$, $R^7$, X, V, Y, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, $R^m$, and $R^n$ can be as defined anywhere herein.

For ease of exposition, it is understood that where in this specification (including the claims), a group is defined by "as defined anywhere herein" (or the like), the definitions for that particular group include the first occurring and broadest generic definition as well as any subgeneric and specific definitions delineated anywhere in this specification.

For ease of exposition, it is understood that any recitation of ranges (e.g., $C_1$-$C_{20}$, 1-3) or subranges of a particular range (e.g., $C_1$-$C_4$, $C_2$-$C_6$, 1-2) for any of $R^1$, $R^2$, $R^3$, $R^4$, $R^5$, $R^6$, $R^7$, X, V, Y, $W^1$, $Z^1$, $W^2$, $Z^2$, $R^a$, $R^{a'}$, $R^c$, $R^d$, $R^e$, $R^f$, $R^g$, $R^h$, $R^i$, $R^j$, $R^k$, $R^m$, and $R^n$ expressly includes each of the individual values that fall within the recited range, including the upper and lower limits of the recited range. For example, the range $C_1$-$C_4$ alkyl is understood to mean $C_1$, $C_2$, $C_3$, or $C_4$ alkyl or the range 1-3 $R^a$ is understood to mean 1, 2, or 3 $R^a$.

In some embodiments, $R^1$ can be:

(A) $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms, each of which is optionally substituted with from 1-10 (e.g., 1-5, 1-4, 1-3, 1-2, or 1) $R^a$; or (B) $C_3$-$C_{16}$ (e.g., $C_3$-$C_{14}$ or $C_3$-$C_{10}$) cycloalkyl, optionally substituted with from 1-10 (e.g., 1-5, 1-4, 1-3, 1-2, or 1) $R^b$; or (C) ($C_1$-$C_{12}$ alkyl)-($C_3$-$C_{16}$ cycloalkyl) (e.g., ($C_1$-$C_6$ alkyl)-($C_3$-$C_{12}$ cycloalkyl) or ($CH_2$)—($C_3$-$C_{12}$ cycloalkyl), optionally substituted with from 1-10 (e.g., 1-5, 1-4, 1-3, 1-2, or 1) $R^b$; or (D) $C_7$-$C_{20}$ (e.g., $C_7$-$C_{16}$, $C_7$-$C_{12}$, $C_7$-$C_{10}$) aralkyl, optionally substituted with from 1-10 (e.g., 1-5, 1-4, 1-3, 1-2, or 1) $R^b$; or (E) arylheterocyclyl including 8-20 (e.g., 8-16 or 9-12) atoms, optionally substituted with from 1-10 (e.g., 1-5, 1-4, 1-3, 1-2, or 1) $R^b$.

In some embodiments, $R^1$ can be $C_6$-$C_{10}$ aryl, optionally substituted with from 1-3 (e.g., 1-2 or 1) $R^a$.

In certain embodiments, $R^1$ can be unsubstituted phenyl or unsubstituted napthyl (e.g., 1-naphthyl or 2-naphthyl).

In certain embodiments, $R^1$ can be a monosubstituted (1 $R^a$), disubstituted (2 $R^a$), trisubstituted (3 $R^a$), tetrasubstituted (4 $R^a$), or pentasubstituted (5 $R^a$) phenyl group of the general formula P-1:

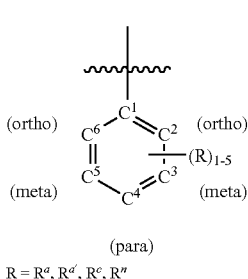

(P-1)

$R = R^a, R^{a'}, R^e, R^n$

For purposes of clarification, each of the terms "ortho (o) (or 2- or 6-); meta (m) (or 3- or 5-); or para (p) (or 4-)," when used in conjunction with any substituted phenyl group, indicates the location of the substitutent(s) relative to the ring carbon that is attached to the remainder of the molecule (i.e., $C^1$ in formula P-1 above). For example, a monosubstituted phenyl group that is para substituted (or 4-substituted) is one having a substitutent attached to $C^4$ in formula P-1 above. As another example, a 2,6-(or ortho, ortho-) disubstituted phenyl group is one having a substitutent attached to $C^2$ and to $C^6$, respectively, in formula P-1. As a further example, a 3,5-(or meta, meta) disubstituted phenyl group is one having a substitutent attached to $C^3$ and to $C^5$, respectively, in formula P-1.

In certain embodiments, $R^a$ at each occurrence can be, independently, halo; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; $C_3$-$C_{10}$ heterocyclyl, $C_3$-$C_{10}$ cycloalkyl, $C_7$-$C_{12}$ aralkoxy or heteroaralkoxy including 6-12 atoms, each of which is optionally substituted with 1-2 $R^b$; or —$NR^hC(O)R^i$. In some embodiments, $R^a$ is other than halo (e.g., chloro).

$R^a$ at each occurrence is, independently, halo; $NR^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with from 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-2 $R^b$; —$C(O)OR^g$; —$C(O)NR^dR^e$; or —$NR^hC(O)R^i$. In some embodiments, $R^a$ is other than halo (e.g., chloro).

For example, $R^a$ at each occurrence can be, independently, chloro, fluoro, bromo, methyl, tert-butyl, trifluoromethyl, trifluoromethoxy, methoxy, cyano, nitro, phenyl, 4-bromophenyl, 4-fluorophenyl, phenoxy, acetamido, (e.g., R or S) 1,1,1-trifluoro-2-hydroxypropan-2-yl, 2-hydroxypropan-2-yl, 1-hydroxycyclopropan-1-yl, 4-fluorophenoxy, pyrrolidin-1-yl, 3-hydroxypyrrolidin-1-yl, 3-carboxypyrrolidin-1-yl, morpholin-4-yl, 1-piperidyl, 4-piperidyl, 2-cyanopropoxy, piperazin-1-yl, 4-methylpiperazin-1-yl, 1H-1,2,4-triazolyl, or —$NHC(O)R^i$ in which $R^i$ is morpholin-4-yl, N,N-dimethylamino, methylamino, 1-piperidyl, pyrrolidin-1-yl, or azapan-1-yl.

In certain embodiments, $R^1$ can be a monosubstituted phenyl group having formula (II):

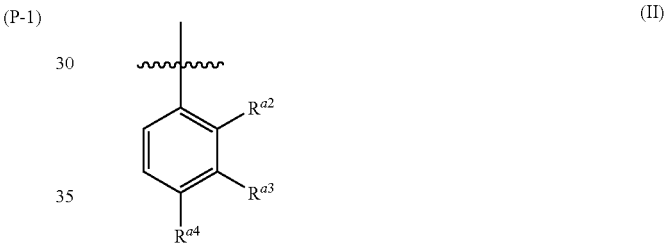

(II)

in which one of $R^{a2}$, $R^{a3}$, and $R^{a4}$ can be halo; $C_1$-$C_{12}$ alkyl or $C_1$-$C_{12}$ haloalkyl, each of which is optionally substituted with 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy, optionally substituted with from 1-2 $R^{a'}$; $C_3$-$C_{10}$ heterocyclyl, $C_3$-$C_{10}$ cycloalkyl, or $C_7$-$C_{12}$ aralkoxy, each of which is optionally substituted with 1-2 $R^b$; or —$NR^hC(O)R^i$; and the others are hydrogen.

In other embodiments, one of $R^{a2}$, $R^{a3}$, and $R^{a4}$ is halo; $NR^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —$C(O)OR^g$; —$C(O)NR^dR^e$; or —$NR^hC(O)R^i$; and the others are hydrogen. For example, $R^1$ can be a meta or para monosubstituted phenyl ring.

$R^{a2}$, $R^{a3}$, or $R^{a4}$ can be halo (e.g., chloro, bromo, or fluoro, preferably chloro).

$R^{a2}$, $R^{a3}$, or $R^{a4}$ (e.g., $R^{a3}$ or $R^{a4}$) can be $C_1$-$C_{12}$ alkyl, optionally substituted with 1 $R^j$(e.g., hydroxyl). For example, $R^{a2}$, $R^{a3}$, or $R^{a4}$ (e.g., $R^{a3}$ or $R^{a4}$, e.g., $R^{a4}$) can be $CH_3$ or $C_3$-$C_{12}$ branched alkyl (e.g., tert-butyl). As another example, $R^{a2}$, $R^{a3}$, or $R^{a4}$ (e.g., $R^{a3}$ or $R^{a4}$) can be 2-hydroxypropan-2-yl, i.e., ($CH_3C(OH)(CH_3)$).

$R^{a2}$, $R^{a3}$, or $R^{a4}$ can be $C_1$-$C_4$ haloalkyl, optionally substituted with 1 $R^j$ (e.g., hydroxyl). For example, $R^{a2}$, $R^{a3}$, or $R^{a4}$ (e.g., $R^{a3}$ or $R^{a4}$, e.g., $R^{a4}$) can be $CF_3$. As another example, $R^{a2}$, $R^{a3}$, or $R^{a4}$ (e.g., $R^{a3}$ or $R^{a4}$) can be (e.g., R or S) 1,1,1-trifluoro-2-hydroxypropan-2-yl, i.e., $CF_3C(OH)(CH_3)$).

$R^{a2}$, $R^{a3}$, or $R^{a4}$ can be $C_3$-$C_{10}$ cycloalkyl, optionally substituted with 1 $R^b$ (e.g., hydroxyl). For example, $R^2$, $R^{a3}$, or $R^{a4}$ (e.g., $R^{a3}$ or $R^{a4}$, e.g., $R^{a4}$) can be 1-hydroxycyclopropan-1-yl.

$R^{a3}$ or $R^{a4}$ can be heterocyclyl including 3-8 atoms, optionally substituted with 1-3 (e.g., 1) $R^b$ (e.g., $C_1$-$C_4$ alkyl (e.g., $CH_3$), OH, $C_3$-$C_{10}$ cycloalkyl, or $COOR^g$ (e.g., COOH)). For example, $R^{a3}$ or $R^{a4}$ can be optionally substituted pyrrolidinyl (e.g., pyrrolidin-1-yl, 3-hydroxypyrrolidin-1-yl, or 3-carboxypyrrolidin-1-yl), morpholinyl (e.g., morpholin-4-yl), piperidyl (e.g., 1-piperidyl or 4-piperidyl) or piperazinyl (e.g., piperazin-1-yl, 4-methylpiperazin-1-yl). For example, $R^{a3}$ is optionally substituted pyrrolidin-1-yl (e.g., 3-hydroxypyrrolidin-1-yl).

In these embodiments, $R^b$ at each occurrence can be, independently, halo; $NR^dR^e$; hydroxyl; oxo; $C_1$-$C_{12}$ alkyl or $C_1$-$C_{12}$ haloalkyl, each of which is optionally substituted with from 1-3 $R^j$; $C_1$-$C_{12}$ alkoxy, optionally substituted with 1-2 $R^f$; $C_1$-$C_{12}$ haloalkoxy; heterocyclyl including 3-10 atoms or $C_3$-$C_{10}$ cycloalkyl, each of which is optionally substituted with 1-3 $R^b$; $-C(O)R^g$; $-C(O)OR^g$; $-C(O)NR^dR^e$; $-OC(O)R^g$; or $-NR^hC(O)R^i$.

$R^{a3}$ or $R^{a4}$ can be heteroaryl including 5 or 6 atoms (e.g., 1H-1,2,4-triazolyl).

$R^{a3}$ or $R^{a4}$ can be phenyl or phenoxy, each of which can be optionally substituted with from 1-2 halo (e.g., bromo or fluoro). For example, $R^{a3}$ or $R^{a4}$ can be phenyl, phenoxy, 4-bromophenyl, 4-fluorophenyl, or 4-fluorophenoxy.

$R^{a4}$ can be $C_1$-$C_4$ alkoxy, optionally substituted with 1 $R^f$ (e.g., cyano). For example, $R^{a4}$ can be $OCH_3$ or 2-cyanopropoxy.

$R^{a4}$ can be $-NHC(O)R^i$. $R^i$ can be $C_1$-$C_4$ alkyl (e.g., $CH_3$). $R^i$ can be $NR^dR^e$, in which $R^d$ and $R^e$ can each be, independently, hydrogen or $C_1$-$C_4$ alkyl (e.g., $CH_3$). For example, $R^i$ can be $-N(CH_3)_2$ or $-NHCH_3$. $R^i$ can be heterocyclyl including 3-8 atoms (e.g., morpholin-4-yl, 1-piperidyl, pyrrolidin-1-yl, or azapan-1-yl).

$R^{a4}$ can be $C_1$-$C_4$ haloalkoxy (e.g., $OCF_3$).

$R^{a2}$ can be nitro or cyano.

$R^{a4}$ can be $C_7$-$C_{12}$ aralkoxy, optionally substituted with 1-2 $R^b$ (e.g., chloro). For example, $R^{a4}$ can be benzyloxy or 4-chlorobenzyloxy.

In certain embodiments, $R^1$ can be a disubstituted phenyl group having formula (II-A):

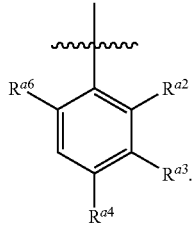

(II-A)

In certain embodiments, two of $R^{a2}$, $R^{a3}$, $R^{a4}$, and $R^{a6}$ can be, independently, halo; $C_1$-$C_{12}$ haloalkyl, optionally substituted with 1-2 $R^j$; $C_1$-$C_{12}$ alkoxy, optionally substituted with 1-2 $R^f$; or $-NR^hC(O)R^i$; and the others are hydrogen.

In certain embodiments, two of $R^{a2}$, $R^{a3}$, $R^{a4}$, and $R^{a6}$ can each be, independently, halo; $NR^dR^e$; hydroxyl; $C_1$-$C_{12}$ alkyl or $C_1$-$C_{12}$ haloalkyl, each of which is optionally substituted with 1-2 $R^j$; $C_1$-$C_{12}$ alkoxy, optionally substituted with from 1-2 $R^f$; $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; $-C(O)OR^g$; $-C(O)NR^dR^e$; or $-NR^hC(O)R^i$; and the others can be hydrogen.

In other embodiments, two of $R^{a2}$, $R^{a3}$, $R^{a4}$, and $R^{a6}$ can each be, independently, halo; $NR^dR^e$; hydroxyl; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; $-C(O)OR^g$; $-C(O)NR^dR^e$; or $-NR^hC(O)R^i$; and the others can be hydrogen.

$R^{a3}$ and $R^{a4}$ can each be, independently, halo (e.g., chloro, bromo or phenyl) or $C_1$-$C_4$ alkoxy (e.g., $OCH_3$).

$R^{a2}$ and $R^{a4}$ can each be, independently, halo (e.g., fluoro or bromo), $C_1$-$C_4$ haloalkyl (e.g., $CF_3$), or $-NR^hC(O)R^i$, in which $R^i$ can be heterocyclyl including 3-8 atoms.

$R^{a2}$ and $R^{a6}$ can each be, independently, halo (e.g., chloro).

For example, $R^1$ can be 3,4-dichlorophenyl, 3-fluoro-4-bromophenyl, 2,6-dichlorophenyl, 2,4-difluorophenyl, 3,4-dimethoxyphenyl, 2-bromo-4-(trifluoromethyl)phenyl, or

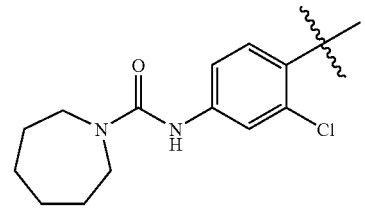

In other embodiments, $R^{a2}$ can be halo (e.g., chloro), and $R^{a4}$ can be a substitutent other than hydrogen, such as halo; $NR^dR^e$; hydroxyl; $C_1$-$C_{12}$ alkoxy, optionally substituted with from 1-2 $R^f$, $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; $-C(O)OR^g$; $-C(O)NR^dR^e$; or $-NR^hC(O)R^i$. For example, $R^{a2}$ can be halo (e.g., chloro), and $R^{a4}$ can be heterocyclyl including 5-8 atoms, optionally substituted with from 1-3 $R^b$.

In certain embodiments, $R^1$ can be napthyl substituted with from 1-2 $R^a$ (e.g., chloro). For example, $R^1$ can be 5-chloronaphth-2-yl or 8-chloro-2-naphth-2-yl.

In some embodiments, $R^1$ can be heteroaryl including 5-14 atoms, optionally substituted with from 1-3 (e.g., 1-2 or 1) $R^a$.

$R^1$ can be a monocyclic heteroaryl including 5-6 atoms, optionally substituted with from 1-2 $R^a$ (e.g., thienyl, isoxazolyl, or pyridyl, each of which is optionally substituted with from 1-2 $R^a$, in which $R^a$ at each occurrence is, independently, halo, $C_1$-$C_4$ alkyl, or heterocyclyl including 3-8 atoms). For example, $R^1$ can be 2-thienyl, 5-chlorothien-2-yl, 3,5-dimethylisoxazol-4-yl, or 2-morpholinopyridin-5-yl. As another example, $R^1$ can have formula (II-B) as described in the Summary.

$R^1$ can be a bicyclic or tricyclic heteroaryl including 8-12 atoms, each of which is optionally substituted with from 1-2 $R^a$ (e.g., quinolyl, benzothienyl, dibenzothienyl, benzofuryl, dibenzofuryl, or benzothiazolyl, each of which is optionally substituted with from 1-2 $R^a$, in which $R^a$ at each occurrence is, independently, halo, $C_1$-$C_4$ alkyl, or heterocyclyl including 3-8 atoms). For example, $R^1$ can be 2-quinolyl, 2-benzo[b]thienyl, 3-benzo[b]thienyl, 5-chloro-3-methylbenzo[b]thien-2-yl, dibenzo[b,d]fur-2-yl, dibenzo[b,d]thien-2-yl, dibenzo[b,d]thien-3-yl, dibenzo[b,d]fur-3-yl, 4-chloro-3-methylbenzo[b]thien-2-yl, 1,3-benzothiazol-2-yl, 5-morpholino-3-methylbenzo[b]thien-2-yl, or 5-(piperazin-1-yl)-3-methylbenzo[b]thien-2-yl.

In certain embodiments (e.g., when V and Y are both N, and X is CO), when $R^1$ is a bicyclic heteroaryl, then 1 heteroatom can be present in the bicyclic heteroaryl (e.g., 1 oxygen, 1 nitrogen, or 1 sulfur, e.g., 1 oxygen or 1 sulfur); or 2 heteroatoms can be present (e.g., 2 oxygens, or 2 sulfurs, or 2 nitrogens, or 1 oxygen and 1 sulfur, or 1 oxygen and 1 nitrogen, or 1 sulfur and 1 nitrogen); or 3 heteroatoms can be present (e.g., 1 oxygen and 2 nitrogens; or 1 sulfur and 2 nitogens; or 3 nitrogens, provided that the bicyclic heterocycle is other than pyrazolo[1,5-a]pyrimidinyl:

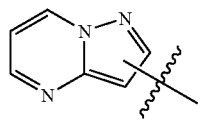

(e.g., other than unsubstituted or mono-, di-, or tri-substituted pyrazolo[1,5-a]pyrimidinyl, e.g., other than unsubstituted or mono-, di-, or tri-substituted pyrazolo[1,5-a]pyrimidin-2-yl); or 4 heteroatoms can be present (e.g., 1 oxygen and 3 nitrogens, or 1 sulfur and 3 nitrogens, or 4 nitrogens). In other embodiments, when $R^1$ is a nitrogenous, bicyclic heteroaryl (including those nitrogenous bicyclic heteroaryls in which one or more oxygens and/or sulfur(s) are also present), then $R^1$ has other than 3 nitrogen atoms (e.g., 1 or 2 nitrogen atoms, e.g., more than three nitrogen atoms, e.g., 4-8 nitrogen atoms).

In some embodiments, $R^1$ can be $C_3$-$C_{12}$ (e.g., $C_3$-$C_{10}$) cycloalkyl, optionally substituted with from 1-5 (e.g., 1-4, 1-3, 1-2, or 1) $R^b$ (e.g., halo or $C_1$-$C_4$ alkyl). $R^1$ can be monocyclic (e.g., optionally substituted cyclopropyl, cyclopentyl, or cyclohexyl), bicyclic (e.g., optionally substituted bicycloheptyl), or polycyclic (e.g., optionally substituted adamantyl). For example, $R^1$ can be adamant-1-yl, cyclohexyl, 2-methylcyclohexan-1-yl, 3-methylcyclohexan-1-yl, 2,2,3,3-tetramethylcyclopropan-1-yl, 2,2-dichloro-1-methylcyclopropan-1-yl, or 1-methyl-3-isopropyl-cyclopentan-1-yl.

In some embodiments, $R^1$ can be ($C_1$-$C_6$ alkyl)-($C_3$-$C_{12}$ cycloalkyl), in which the cycloalkyl ring is optionally substituted with from 1-3 $R^b$. $R^1$ can be —$(CH_2)_{1-6}$—($C_3$-$C_{10}$ cycloalkyl), in which the cycloalkyl ring is optionally substituted with from 1-3 $C_1$-$C_4$ alkyl (e.g., $CH_3$). For example, $R^1$ can be —$CH_2$-(cyclopentyl), —$CH_2$-(cyclohexyl), —$CH_2$-(4-methylcyclohexyl), or —$CH_2$-(bicycloheptyl).

In some embodiments, $R^1$ can be $C_7$-$C_{12}$ aralkyl, optionally substituted with from 1-2 $R^b$ (e.g., halo). $R^1$ can be —$(CH_2)_{1-6}$—($C_6$-$C_{10}$ aryl), in which the aryl ring is optionally substituted with from 1-2 halo (e.g., chloro). For example, $R^1$ can be benzyl, 4-chlorobenzyl; or —$(CH_2)$-(naphthyl), in which the $CH_2$ group is attached to the 1 or 2 position of the naphthalene ring.

In some embodiments, $R^1$ can be arylheterocyclyl including 9-12 atoms, optionally substituted with from 1-5 (e.g., 1-4, 1-3, 1-2, or 1) $R^b$ (e.g., oxo, halo or $C_1$-$C_4$ alkyl), in which the heterocyclyl portion can include 1 or 2 heteroatoms (e.g., nitrogen or oxygen). For example, $R^1$ can be 2,2-dimethylchromanyl.

In some embodiments, $R^2$ can be:

(A) heteroaryl including 5-20 (e.g., 5-16, 5-12, or 5-6) atoms, optionally substituted with from 1-10 (e.g., 1-5, 1-4, 1-3, 1-2, or 1) $R^c$ or $R^n$; or $C_6$-$C_{18}$ (e.g., $C_6$-$C_{14}$, $C_6$-$C_{10}$, or phenyl) aryl optionally substituted with from 1-10 (e.g., 1-5, 1-4, 1-3, 1-2, or 1) $R^c$; or (B) $C_3$-$C_{16}$ (e.g., $C_3$-$C_{14}$, $C_3$-$C_{10}$, $C_6$-$C_{16}$, $C_6$-$C_{14}$, $C_6$-$C_{10}$, $C_7$-$C_{16}$, $C_8$-$C_{16}$, $C_9$-$C_{16}$, $C_{10}$-$C_{16}$, $C_7$-$C_{14}$, $C_8$-$C_{14}$, $C_9$-$C_{14}$, $C_{10}$-$C_{14}$, $C_7$-$C_{10}$, $C_8$-$C_{10}$, or $C_9$-$C_{10}$) cycloalkyl, optionally substituted with from 1-10 (e.g., 1-5, 1-4, 1-3, 1-2, or 1) $R^b$; or (C) $OR^1$; or $NR^3R^4$, in which $R^3$ and $R^4$ can each be, independently, hydrogen or $R^1$ (e.g., $R^1$ can be $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms; each of which is optionally substituted with from 1-10 (e.g., 1-5, 1-4, 1-3, 1-2, or 1) $R^a$); or (D) heterocyclyl including 3-16 (e.g., 3-12, 3-10, 5-12, or 5-6) atoms, optionally substituted with from 1-10 (e.g., 1-5, 1-4, 1-3, 1-2, or 1) $R^b$; or (E) $C(O)R^5$, in which $R^5$ is $C_1$-$C_{20}$ (e.g., $C_1$-$C_{12}$, $C_1$-$C_6$, or $C_1$-$C_4$) alkyl or $C_7$-$C_{20}$ (e.g., $C_7$-$C_{12}$ aralkoxy).

In certain embodiments, $R^2$ can be (A), (B), (C), and/or (D); or (A), (C), (D), and/or (E); or (A), (C), and/or (D); or (A) and/or (C).

In certain embodiments, when $R^2$ is (A), $R^2$ is optionally substituted heteroaryl including 5-20 (e.g., 5-16, 5-12, or 5-6) atoms. In other embodiments, when $R^2$ is (A), $R^2$ is optionally substituted $C_6$-$C_{18}$ (e.g., $C_6$-$C_{14}$, $C_6$-$C_{10}$, or phenyl) aryl.

In some embodiments, $R^2$ can be heteroaryl including 5-12 atoms, optionally substituted with from 1-3 (e.g., 1-2 or 1) $R^c$ or $R^n$.

In certain embodiments, $R^2$ can be a monosubstituted pyridyl ring having formula (III):

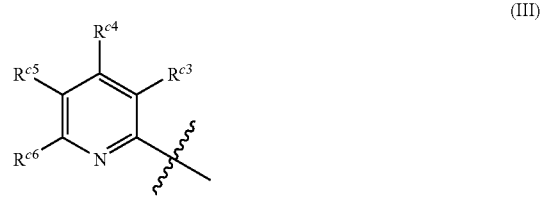

in which one or two of $R^{c3}$, $R^{c4}$, $R^{c5}$, and $R^{c6}$ can each be, independently, halo; $C_1$-$C_{12}$ alkyl; $C_1$-$C_{12}$ haloalkyl, optionally substituted with 1-2 $R^j$; cyano; or nitro; and the others are hydrogen.

One of $R^{c3}$, $R^{c4}$, or $R^{c5}$ can be $C_1$-$C_4$ haloalkyl (e.g., $CF_3$). For example, $R^2$ can be:

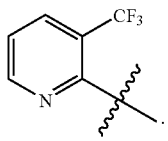

One of $R^{c3}$, $R^{c4}$, $R^{c5}$, and $R^{c6}$ can be halo (e.g., $R^{c3}$ or $R^{c5}$ can be chloro or fluoro).

One of $R^{c3}$, $R^{c4}$, $R^{c5}$, and $R^{c6}$ can be $C_1$-$C_4$ alkyl (e.g., $R^{c3}$ can be $C_1$-$C_4$ alkyl, e.g., $CH_3$).

One of $R^{c3}$, $R^{c4}$, $R^{c5}$, and $R^{c6}$ can be cyano or nitro (e.g., $R^{c3}$ or $R^{c5}$ can be nitro or $R^{c3}$ can be cyano).

Two of $R^{c3}$, $R^{c4}$, $R^{c5}$, and $R^{c6}$ can each be, independently, halo or $C_1$-$C_4$ haloalkyl. For example, two of $R^{c3}$, $R^{c4}$, $R^{c5}$, and $R^{c6}$ can each be, independently, fluoro or $CF_3$.

In certain embodiments, $R^2$ can be a disubstituted (2 $R^c$ or 2 $R''$), trisubstituted (3 $R^c$ or 3 $R''$), tetrasubstituted (4 $R^c$ or 4 $R''$) pyridyl ring. For example, $R^2$ can be 3,5-dichloro-4-pyridyl.

In certain embodiments, $R^2$ can be 1-quinolyl, 2-quinolyl, 1-isoquinolyl, or pyrazinyl (e.g., 2-cyanopyrazin-2-yl).

In some embodiments, $R^2$ can be $C_6$-$C_{10}$ aryl, optionally substituted with from 1-3 (e.g., 1-2 or 1) $R^c$.

In certain embodiments, $R^2$ can be a monosubstituted (1 $R^c$), disubstituted (2 $R^c$), trisubstituted (3 $R^c$), tetrasubstituted (4 $R^c$), or pentasubstituted (5 $R^c$) phenyl group of the general formula P-1 described elsewhere.

In certain embodiments, $R^2$ can be a monosubstituted phenyl group having formula (IV):

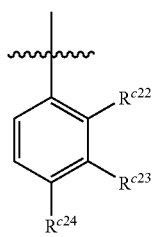

(IV)

in which one of $R^{c22}$, $R^{c23}$, and $R^{c24}$ can be halo; hydroxyl; $C_1$-$C_{12}$ alkyl; $C_1$-$C_{12}$ haloalkyl; $C_1$-$C_{12}$ alkoxy; $C_1$-$C_{12}$ haloalkoxy; cyano; nitro; or $C_6$-$C_{10}$ aryl, optionally substituted with from 1-2 $R^a$; and the others are hydrogen.

$R^{c22}$ or $R^{c23}$ can be $C_1$-$C_4$ haloalkyl (e.g., $CF_3$).

$R^{c22}$ can be $C_1$-$C_4$ alkyl (e.g., $CH_3$ or $CH_2CH_3$); or nitro; or cyano; or hydroxyl; or $C_1$-$C_4$ alkoxy (e.g., $OCH_3$).

$R^{c22}$, $R^{c23}$, or $R^{c24}$ can be halo (e.g., $R^{c22}$, $R^{c23}$, or $R^{c24}$ can be fluoro; or $R^{c22}$ can be bromo; or $R^{c24}$ can be chloro).

$R^{c22}$ or $R^{c24}$ can be phenyl optionally substituted with 1 $R^a$ (e.g., $C_1$-$C_4$ alkoxy, e.g., $OCH_3$). For example, $R^{c22}$ can be 2-methoxyphenyl.

In certain embodiments, $R^2$ can be a disubstituted phenyl group having formula (IV-A):

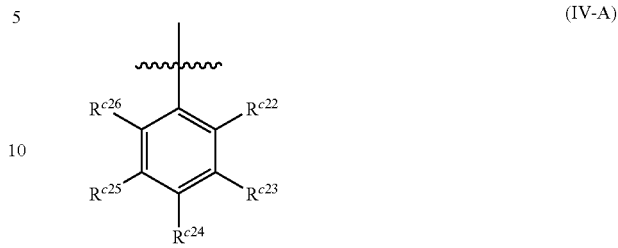

(IV-A)

In certain embodiments, two of $R^{c22}$, $R^{c23}$, $R^{c24}$, $R^{c25}$, and $R^{c26}$ can each be, independently, halo; $C_1$-$C_{12}$ alkyl; $C_1$-$C_{12}$ haloalkyl; cyano; $C_1$-$C_{12}$ alkoxy; heterocyclyl including 3-10 atoms, optionally substituted with from 1-2 $R^b$ (e.g., $C_1$-$C_{12}$ alkyl (e.g., $CH_3$)); heteroaryl including from 5-10 atoms, optionally substituted with from 1-2 $R^a$; or $SO_2R^m$; and the others are hydrogen.

In other embodiments, two of $R^{c22}$, $R^{c23}$, $R^{c24}$, $R^{c25}$, and $R^{c26}$ can each be, independently, halo; $C_1$-$C_{12}$ alkyl or $C_1$-$C_{12}$ haloalkyl, each of which is optionally substituted with from 1-3 $R^j$; $C_1$-$C_{12}$ alkoxy; $C_1$-$C_{12}$ haloalkoxy; cyano; nitro; or $C_6$-$C_{10}$ aryl or heteroaryl including 5-12 atoms, each of which is optionally substituted with from 1-2 $R^a$; and the others are hydrogen.

Two of $R^{c22}$, 3, $R^{c24}$, $R^{c25}$, and $R^{c26}$ can each be, independently, halo or $C_1$-$C_4$ haloalkyl (e.g., two of $R^{c22}$, $R^{c23}$, $R^{c24}$, $R^{c25}$, and $R^{c26}$ can each be, independently, fluoro or $CF_3$). For example, $R^{c22}$ can be $C_1$-$C_4$ haloalkyl (e.g., $CF_3$) and $R^{c23}$ or $R^{c24}$ (e.g., $R^{c24}$) can be halo (e.g., fluoro).

$R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and one of $R^{c23}$, $R^{c24}$, and $R^{c25}$ can be heterocyclyl including 3-8 atoms, optionally substituted with 1 $R^b$ (e.g., $C_1$-$C_{12}$, e.g., $C_1$-$C_6$ alkyl, e.g., $CH_3$); heteroaryl including 5 or 6 atoms, optionally substituted with 1 $R^a$; or halo (e.g., fluoro).

$R^{c22}$ can be $CF_3$, chloro, $OCH_3$, cyano, or $CH_3$; and one of $R^{c23}$, $R^{c24}$, and $R^{c25}$ can be heterocyclyl including 3-8 atoms, optionally substituted with 1 $R^b$; heteroaryl including 5 or 6 atoms, optionally substituted with 1 $R^a$; or halo.

In these embodiments, one of $R^{c23}$, $R^{c24}$, and $R^{c25}$ can be optionally substituted piperazinyl (e.g., piperazin-1-yl or 4-($C_1$-$C_6$ alkyl)piperazin-1-yl); optionally substituted morpholinyl (e.g., morpholin-4-yl); 1H-1,2,4-triazolyl; or fluoro.

$R^{c22}$ and $R^{c24}$ can each be, independently, halo (e.g., chloro or fluoro); $C_1$-$C_4$ alkyl (e.g., $CH_3$); or $SO_2R^m$ (e.g., $SO_2CH_3$).

$R^{c22}$ and $R^{c23}$; or $R^{c22}$ and $R^{c26}$; or $R^{c23}$ and $R^{c24}$ can each be, independently, halo (e.g., chloro or fluoro) or $C_1$-$C_4$ alkyl (e.g., $CH_3$).

$R^{c22}$ can be $C_1$-$C_4$ haloalkyl (e.g., $CF_3$), optionally substituted with from 1-3 $R^j$; and $R^{c24}$ can be halo; $C_1$-$C_4$ haloalkyl, optionally substituted with from 1-3 $R^j$; cyano; or heteroaryl including 5-6 atoms, optionally substituted with from 1-2 $R^a$. For example, $R^{c22}$ can be $CF_3$. $R^{c22}$ can be $CF_3$, and $R^{c24}$ can be halo (and the others can be hydrogen).

$R^{c22}$ and $R^{c24}$ can each be, independently, fluoro or chloro. For example, $R^{c22}$ can be chloro, and $R^{c24}$ can be fluoro.

For example, $R^2$ can be 4-fluoro-2-(sulfonylmethyl)phenyl; 4-fluoro-2-(trifluoromethyl)phenyl; 2,3-dichlorophenyl; 2,4-difluorophenyl; 2,4-dimethylphenyl; 2,6-dichlorophenyl; 2,6-dimethylphenyl; 3,4-dichlorophenyl; or 3-fluoro-2-(trifluoromethyl)phenyl.

In some embodiments, $R^2$ can be $OR^1$, in which $R^1$ can be $C_6$-$C_{10}$ aryl, or heteroaryl including 5-10 atoms, each of which can be optionally substituted with from (e.g., 1-2 or 1) $R^a$; or $R^1$ can be $C_7$-$C_{12}$ aralkyl, optionally substituted with from 1-3 $R^b$.

In certain embodiments, $R^2$ can be unsubstituted phenoxy.

In certain embodiments, $R^2$ can be a monosubstituted phenoxy group having formula (V):

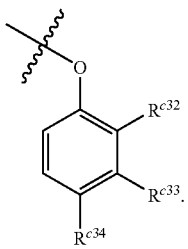

(V)

in which one of $R^{c32}$, $R^{c33}$, and $R^{c34}$ can be halo; $C_1$-$C_{12}$ alkyl; $C_1$-$C_{12}$ haloalkyl; $C_1$-$C_{12}$ alkoxy; $C_1$-$C_{12}$ haloalkoxy; cyano; or nitro; and the others are hydrogen.

$R^{c32}$ can be $C_1$-$C_4$ haloalkyl (e.g., $CF_3$).

$R^{c32}$ can be $C_1$-$C_4$ alkyl (e.g., $CH_3$, $CH_2CH_3$, n-propyl, or iso-propyl).

$R^{c32}$ or $R^{c34}$ is $C_1$-$C_4$ alkoxy (e.g., $OCH_3$).

$R^{c32}$ can be halo (e.g., chloro or bromo); nitro or cyano. In certain embodiments, $R^2$ can be a disubstituted phenoxy group in which the phenyl ring is substituted, e.g., at the 2- and 6-positions with, e.g., $C_1$-$C_4$ alkyl (e.g., $CH_3$) or halo (e.g., chloro). A preferred disubstituted phenoxy group is 2,6-dichlorophenoxy:

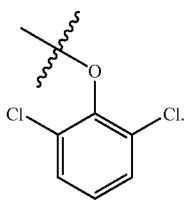

In certain embodiments, $R^2$ can be an unsubstituted, monosubstituted, or disubstituted pyridyloxy group. For example, $R^2$ can be:

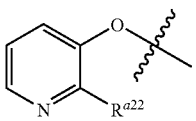

in which $R^{a22}$ can be, e.g., hydrogen or halo (e.g., chloro).

In certain embodiments, $R^2$ can be an unsubstituted, monosubstituted, or disubstituted aralkoxy group. In certain embodiments, $R^2$ can be benzyloxy or monosubstituted benzyloxy (e.g., 2-methoxybenzyloxy).

In some embodiments, $R^2$ can be $NR^3R^4$, in which one of $R^3$ and $R^4$ can be hydrogen, and the other is $C_6$-$C_{10}$ aryl, optionally substituted with from 1-3 (e.g., 1-2 or 1) $R^a$. In certain embodiments, one of $R^3$ and $R^4$ can be hydrogen, and the other is phenyl or monosubstituted phenyl (e.g., substituted with halo, e.g., chloro). For example, $R^2$ can be 2-chlorophenylamino:

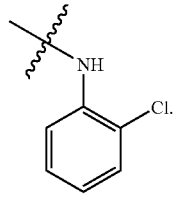

In some embodiments, $R^2$ can be $C_3$-$C_{12}$ (e.g., $C_3$-$C_{10}$) cycloalkyl, optionally substituted with from 1-5 (e.g., 1-4, 1-3, 1-2, or 1) $R^b$ (e.g., halo or $C_1$-$C_4$ alkyl).

In some embodiments, $R^2$ can be $C_6$-$C_{12}$ (e.g., $C_6$-$C_{10}$, $C_7$-$C_{12}$, $C_8$-$C_{12}$, $C_9$-$C_{12}$, $C_{10}$-$C_{12}$) cycloalkyl, optionally substituted with from 1-5 (e.g., 1-4, 1-3, 1-2, or 1) $R^b$ (e.g., halo or $C_1$-$C_4$ alkyl).

In certain embodiments, $R^2$ can be monocyclic (e.g., optionally substituted cyclohexyl or cycloheptyl), bicyclic (e.g., optionally substituted bicycloheptyl), or polycyclic (e.g., optionally substituted adamantyl). For example, $R^1$ can be 1-adamantyl, 3-methylcyclohexyl, cycloheptyl, or bicycloheptyl.

In some embodiments, $R^2$ can be heterocyclyl including 3-8 atoms, optionally substituted with 1 $R^b$ (e.g., $C_1$-$C_4$ alkyl (e.g., $CH_3$)). For example, $R^2$ can be morpholino or tetrahydropyranyl.

In some embodiments, $R^2$ can be $C(O)R^5$, in which $R^5$ is $C_1$-$C_{20}$ alkyl or $C_7$-$C_{20}$ aralkoxy. In certain embodiments, $R^5$ can be $C_1$-$C_{12}$ alkyl (e.g., $C_3$-$C_{12}$ branched alkyl, e.g., tert-butyl). In certain embodiments, $R^5$ can be an unsubstituted or monosubstituted aralkoxy group (e.g., benzyloxy).

In some embodiments, X can be $S(O)_n$, (e.g., $SO_2$).

In some embodiments, X can be CO.

In some embodiments, X can be $S(O)_nNR^6$, in which n can be 2, and $R^6$ can be hydrogen, $C_1$-$C_4$ alkyl, or $C_3$-$C_8$ cycloalkyl. In certain embodiments, X can be $S(O)_2NH$.

In some embodiments, each of $W^1$, $Z^1$, $W^2$, and $Z^2$ can be hydrogen.

In some embodiments, one or two of $W^1$, $Z^1$, $W^2$, and $Z^2$ can each be, independently, $C_1$-$C_4$ alkyl (e.g., $CH_3$) or oxo, and the others are hydrogen. For example, $W^1$ can be $C_1$-$C_4$ alkyl (e.g., $CH_3$) or oxo; or $W^2$ can be oxo; or $W^1$ and $W^2$ or $W^1$ and $Z^2$ can both be $C_1$-$C_4$ alkyl (e.g., $CH_3$). Each of the carbons bearing $W^1$, $Z^1$, $W^2$, and $Z^2$ can have, independently, the R or the S stereochemical configuration when $W^1$, $Z^1$, $W^2$, or $Z^2$ is other than hydrogen. In certain embodiments, $W^1$ can be $C_1$-$C_4$ alkyl (e.g., $CH_3$), and the carbon bearing $W^1$ can have the R configuration.

One or two of $W^1$, $Z^1$, $W^2$, and $Z^2$ (e.g., $W^1$ and $Z^2$, e.g., $W^1$) can each be, independently, other than hydrogen (e.g., $C_1$-$C_4$ alkyl or oxo), and the others can be hydrogen. One or two of $W^1$, $Z^1$, $W^2$, and $Z^2$ (e.g., $W^1$ and $Z^2$, e.g., $W^1$) can each be, independently, $C_1$-$C_4$ alkyl, and the others can be hydrogen. Each of $Z^1$ and $W^2$ can be hydrogen. One or both of $W^1$ and $Z^2$ (e.g., $W^1$) can each be, independently, $C_1$-$C_4$ alkyl; and each of $Z^1$ and $W^2$ can be hydrogen. $W^1$ can be $C_1$-$C_4$ alkyl (e.g., $CH_3$).

In some embodiments, Y and V can both be nitrogen, and the 11-beta HSD1 inhibitor compounds can have formula (VI):

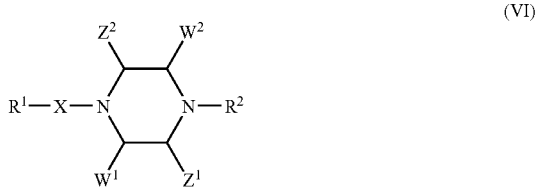

(VI)

in which $R^1$, $R^2$, $R^3$, $R^4$, $R^5$, $R^6$, $R^7$, X, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, $R^m$, and $R^n$ can be as defined anywhere herein.

In some embodiments, X can be $SO_2$, and the 11-beta HSD1 inhibitor compounds can include one or more of the following features.

$R^1$ can be:

(A) $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms, each of which is optionally substituted with from 1-10 (e.g., 1-5, 1-4, 1-3, 1-2, or 1) $R^a$; for example, $R^1$ can be $C_6$-$C_{10}$ aryl, optionally substituted with from 1-3 (e.g., 1-2 or 1) $R^a$ or heteroaryl including 5-14 atoms, optionally substituted with from 1-3 (e.g., 1-2 or 1) $R^a$ as described herein; and/or (D) $C_7$-$C_{20}$ (e.g., $C_7$-$C_{16}$, $C_7$-$C_{12}$, $C_7$-$C_{10}$) aralkyl, optionally substituted with from 1-10 (e.g., 1-5, 1-4, 1-3, 1-2, or 1) $R^b$; for example, $R^1$ can be $C_7$-$C_{12}$ aralkyl, optionally substituted with from 1-2 $R^b$ (e.g., halo) as described herein; and/or (E) arylheterocyclyl including 8-20 (e.g., 8-16 or 9-12) atoms, optionally substituted with from 1-10 (e.g., 1-5, 1-4, 1-3, 1-2, or 1) $R^b$; for example, $R^1$ can be arylheterocyclyl including 9-12 atoms, optionally substituted with from 1-5 (e.g., 1-4, 1-3, 1-2, or 1) $R^b$ (e.g., oxo, halo or $C_1$-$C_4$ alkyl), in which the heterocyclyl portion can include 1 or 2 heteroatoms (e.g., nitrogen or oxygen) as described herein.

$R^2$ can be:

(A) heteroaryl including 5-20 (e.g., 5-16, 5-12, or 5-6) atoms, optionally substituted with from 1-10 (e.g., 1-5, 1-4, 1-3, 1-2, or 1) $R^c$ or $R^n$; or $C_6$-$C_{18}$ (e.g., $C_6$-$C_{14}$, $C_6$-$C_{10}$, or phenyl) aryl, optionally substituted with from 1-10 (e.g., 1-5, 1-4, 1-3, 1-2, or 1) $R^c$; for example, $R^2$ can be heteroaryl including 5-12 atoms, optionally substituted with from 1-3 (e.g., 1-2 or 1) $R^c$ or $R^n$; or $R^2$ can be $C_6$-$C_{10}$ aryl, optionally substituted with from 1-3 (e.g., 1-2 or 1) $R^c$ as described herein; and/or (B) $C_3$-$C_{16}$ (e.g., $C_3$-$C_{14}$, $C_3$-$C_{10}$, $C_6$-$C_{16}$, $C_6$-$C_{14}$, or $C_6$-$C_{10}$) cycloalkyl, optionally substituted with from 1-10 (e.g., 1-5, 1-4, 1-3, 1-2, or 1) $R^b$; for example, $R^2$ can be $C_3$-$C_{12}$ (e.g., $C_3$-$C_{10}$) cycloalkyl, optionally substituted with from 1-5 (e.g., 1-4, 1-3, 1-2, or 1) $R^b$ (e.g., halo or $C_1$-$C_4$ alkyl) or $C_6$-$C_{12}$ (e.g., $C_6$-$C_{10}$) cycloalkyl, optionally substituted with from 1-5 (e.g., 1-4, 1-3, 1-2, or 1) $R^b$ (e.g., halo or $C_1$-$C_4$ alkyl); as described herein; and/or (D) heterocyclyl including 3-16 (e.g., 3-12, 3-10, 5-12, or 5-6) atoms, optionally substituted with from 1-10 (e.g., 1-5, 1-4, 1-3, 1-2, or 1) $R^b$; for example, $R^2$ can be heterocyclyl including 3-8 atoms, optionally substituted with 1 $R^b$ (e.g., $C_1$-$C_4$ alkyl (e.g., $CH_3$)) as described herein; and/or (E) $C(O)R^5$, in which $R^5$ is $C_1$-$C_{20}$ (e.g., $C_1$-$C_{12}$, $C_1$-$C_6$, or $C_1$-$C_4$) alkyl or $C_7$-$C_{20}$ (e.g., $C_7$-$C_{12}$ aralkoxy) as described herein.

In certain embodiments, $R^2$ can be (A), (B), (C), and/or (D); or (A), (C), (D), and/or (E); or (A), (C), and/or (D); or (A) and/or (C).

In certain embodiments, when $R^2$ is substituted pyridyl or pyrimidinyl (e.g., 2-, 3-, or 4-pyridyl; or 2- or 3-pyrimidinyl), then $R^c$ cannot be $C_1$-$C_{12}$ alkoxy optionally substituted with 1-5 $R^f$, $C_1$-$C_{12}$ haloalkoxy; or $SO_2R^m$.

In certain embodiments, when $R^2$ is a substituted heteroaryl including 5-14 atoms (e.g., 5-12 atoms, 5-8 atoms, 5-6 atoms, or 6 atoms), then $R^2$ is substituted with $R^n$.

In certain embodiments, when $R^2$ is $C_3$-$C_{16}$ cycloalkyl (e.g., $C_3$-$C_5$ cycloalkyl, e.g., $C_5$ cycloalkyl, e.g., substituted $C_5$ cycloalkyl, e.g., $C_5$ cycloalkyl substituted with hydroxyl or imidazolyl) then $R^1$ cannot be a monosubstituted phenyl ring that is substituted at the para-position with either substituted $C_1$-$C_{12}$ alkyl or substituted $C_1$-$C_{12}$ haloalkyl (e.g., a phenyl ring substituted at the para-position with —$CR^{21}R^{22}R^{23}$, in which $R^{21}$, $R^{22}$ and $R^{23}$ are each independently hydrogen, halo, hydroxyl, cyano, nitro, $C_1$-$C_6$ alkyl, $C_2$-$C_8$ alkenyl, $C_2$-$C_8$ alkynyl, alkoxy, haloalkyl, hydroxyalkyl, cycloalkyl, heterocycloalkyl, heteroaryl or aryl and at least one of $R^{21}$, $R^{22}$ and $R^{23}$ is other than hydrogen, e.g., a phenyl ring substituted at the para-position with 2-hydroxy-1,1,1-trifluoro-2-propyl, i.e., $CF_3C(OH)(CH_3)$).

In certain embodiments, one or more of the other conditions delineated in the Summary can apply. For example, (a) can apply. In certain embodiments, (a) and any one of (e)-(j) apply. In certain embodiments, any one of (e)-(j) applies. In certain embodiments, any two or three of (e)-(j) applies, optionally in combination with (a). For example, (e) or (f) and (g) or (h) and/or (i) and (j), optionally in combination with (a).

In certain embodiments, (a) applies. In certain embodiments, (a) and/or (k) applies. In certain embodiments, (a), (k) and any one, two, three, or four of (l)-(o) apply.

In certain embodiments, $R^2$ can be $C_6$-$C_{16}$ (e.g., $C_6$-$C_{14}$, $C_6$-$C_{10}$, $C_7$-$C_{16}$, $C_8$-$C_{16}$, $C_9$-$C_{16}$, $C_{10}$-$C_{16}$, $C_7$-$C_{14}$, $C_8$-$C_{14}$, $C_9$-$C_{14}$, $C_{10}$-$C_{14}$, $C_7$-$C_{10}$, $C_8$-$C_{10}$, or $C_9$-$C_{10}$) cycloalkyl, optionally substituted with from 1-5 (e.g., 1-4, 1-3, 1-2, or 1) $R^b$ (e.g., halo or $C_1$-$C_4$ alkyl).

A subset of compounds includes those having formula (VI-A):

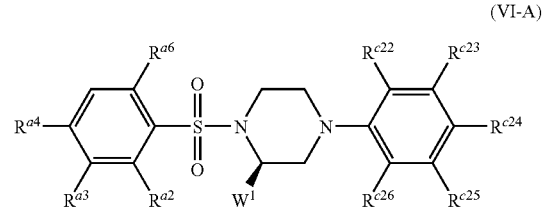

(VI-A)

in which:

one or two of $R^{a2}$, $R^{a3}$, $R^{a4}$, and $R^{a6}$ can each be, independently, halo; $C_1$-$C_{12}$ alkyl or $C_1$-$C_{12}$ haloalkyl, each of which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^a$; $C_6$-$C_{10}$ aryloxy, optionally substituted with from 1-2 $R^a$; $C_3$-$C_{10}$ heterocyclyl, $C_3$-$C_{10}$ cycloalkyl, or $C_7$-$C_{12}$ aralkoxy, each of which is optionally substituted with 1-2 $R^b$; or —$NR^hC(O)R^i$; and the others are hydrogen;

$W^1$ can be hydrogen or $C_1$-$C_4$ alkyl (e.g., $CH_3$); and one or two $R^{c22}$, $R^{c23}$, $R^{c24}$, $R^{c25}$, and $R^{c26}$ can each be, independently, halo; hydroxyl; $C_1$-$C_{12}$ alkyl; $C_1$-$C_{12}$ haloalkyl; $C_1$-$C_{12}$ alkoxy; $C_1$-$C_{12}$ haloalkoxy; cyano; nitro; $C_6$-$C_{10}$ aryl, optionally substituted with from 1-2 $R^{a'}$; heterocyclyl including 3-10 atoms, optionally substituted with from 1-2 $R^b$ (e.g., $C_1$-$C_{12}$ alkyl (e.g., $CH_3$)); heteroaryl including from 5-10 atoms, optionally substituted with from 1-2 $R^{a'}$; or $SO_2R^m$; and the others are hydrogen. The variables delineated in formula (VI) above can also be as defined in the Summary and the conditions delineated therein can apply.

In some embodiments, $R^{a2}$, $R^{a3}$, or $R^{a4}$ can be $C_1$-$C_4$ haloalkyl, optionally substituted with 1 $R^j$(e.g., hydroxyl). For example, $R^{a2}$, $R^{a3}$, or $R^{a4}$ (e.g., $R^{a3}$ or $R^{a4}$) can be (e.g., R or S) 1,1,1-trifluoro-2-hydroxypropan-2-yl, i.e., $CF_3C(OH)$ $(CH_3)$, in which the stereogenic carbon (i.e., the carbon attached to the hydroxyl group) can have the R or S configuration or some combination thereof (e.g., about 50% R and about 50% S or any other non-racemic combination of configurations). In some embodiments, $R^{a3}$ or $R^{a4}$ (e.g., $R^{a3}$) can be:

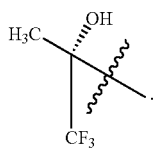

In these embodiments, each of the remaining substitutents can be hydrogen.

In some embodiments, $R^{a2}$, $R^{a3}$, or $R^{a4}$ (e.g., $R^{a3}$ or $R^{a4}$) can be $C_1$-$C_{12}$ alkyl, optionally substituted with 1 $R^j$(e.g., hydroxyl). For example, $R^{a2}$, $R^{a3}$, or $R^{a4}$ (e.g., $R^{a3}$or $R^{a4}$) can be 2-hydroxy-2-propan-2-yl, i.e., $CH_3C(OH)(CH_3)$.

In some embodiments, $R^{a2}$, $R^{a3}$, or $R^{a4}$ can be $C_3$-$C_{10}$ cycloalkyl, optionally substituted with 1 $R^b$ (e.g., hydroxyl). For example, $R^{a2}$, $R^{a3}$, or $R^{a4}$ (e.g., $R^{a3}$ or $R^{a3}$, e.g., $R^{a4}$) can be 1-hydroxycyclopropan-1-yl.

In some embodiments, $R^{a3}$ or $R^{a4}$ can be heterocyclyl including 3-8 atoms, optionally substituted with 1 $R^b$ (e.g., $C_1$-$C_4$ alkyl (e.g., $CH_3$), OH, $C_3$-$C_{10}$ cycloalkyl, or $COOR^g$ (e.g., COOH)). For example, $R^{a3}$ or $R^{a4}$ can be optionally substituted pyrrolidinyl (e.g., pyrrolidin-1-yl, 3-hydroxypyrrolidin-1-yl, or 3-carboxypyrrolidin-1-yl), morpholinyl (e.g., morpholin-4-yl), piperidyl (e.g., 1-piperidyl or 4-piperidyl) or piperazinyl (e.g., piperazin-1-yl, 4-methylpiperazin-1-yl). In a preferred embodiment, $R^{a3}$ is optionally substituted pyrrolidin-1-yl (e.g., 3-hydroxypyrrolidin-1-yl).

In some embodiments, $R^{a3}$ or $R^{a4}$ can be heteroaryl including 5 or 6 atoms (e.g., 1H-1,2,4-triazolyl).

In some embodiments, $W^1$ can be $C_1$-$C_4$ alkyl (e.g., $CH_3$).

In some embodiments, two of $R^{c22}$, $R^{c23}$, $R^{c24}$, $R^{c25}$ and $R^{c26}$ can each be, independently, halo or $C_1$-$C_4$ haloalkyl (e.g., two of $R^{c22}$, $R^{c23}$, $R^{c24}$, $R^{c25}$, and $R^{c26}$ can each be, independently, fluoro or $CF_3$). For example, $R^{c22}$ can be $C_1$-$C_4$ haloalkyl (e.g., $CF_3$) and $R^{c23}$ or $R^{c24}$ (e.g., $R^{c24}$) can be halo (e.g., fluoro).

In some embodiments, $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and one of $R^{c23}$, $R^{c24}$, and $R^{c25}$ can be heterocyclyl including 3-8 atoms, optionally substituted with 1 $R^b$ (e.g., $C_1$-$C_{12}$, e.g., $C_1$-$C_6$ alkyl, e.g., $CH_3$); heteroaryl including 5 or 6 atoms, optionally substituted with 1 $R^{a'}$; or halo (e.g., fluoro). For example, one of $R^{c23}$, $R^{c24}$, and $R^{c25}$ can be optionally substituted piperazinyl (e.g., piperazin-1-yl or 4-($C_1$-$C_6$ alkyl)piperazin-1-yl); optionally substituted morpholinyl (e.g., morpholin-4-yl); 1H-1,2,4-triazolyl; or fluoro.

In certain embodiments, $R^{a4}$ can be 1,1,1-trifluoro-2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and $R^{c23}$, $R^{c24}$, or $R^{c25}$ can be optionally substituted piperazinyl (e.g., piperazin-1-yl or piperazin-1-yl substituted with $C_1$-$C_6$ alkyl, e.g., 4-($C_1$-$C_6$ alkyl)piperazin-1-yl).

In certain embodiments, $R^{a4}$ can be 1,1,1-trifluoro-2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and $R^{c23}$, $R^{c24}$, or $R^{c25}$ can be optionally substituted morpholinyl (e.g., morpholin-4-yl or morpholin-4-yl substituted with $C_1$-$C_6$ alkyl).

In certain embodiments, $R^{a4}$ can be 1,1,1-trifluoro-2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and $R^{c23}$, $R^{c24}$, or $R^{c25}$ can be optionally substituted 1H-1,2,4-triazolyl.

In certain embodiments, $R^{a3}$ can be 1,1,1-trifluoro-2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$); and $R^{c23}$, $R^{c24}$, or $R^{c25}$ can be fluoro.

In certain embodiments, $R^{a3}$ can be 2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$ or $R^{c25}$ can be fluoro.

In certain embodiments, $R^{a4}$ can be 2-hydroxypropan-2-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$, or $R^{c25}$ can be fluoro.

In certain embodiments, $R^{a4}$ can be 1-hydroxycyclopropan-1-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$, or $R^{c25}$ can be fluoro.

In certain embodiments, $R^{a3}$ can be piperazin-1-yl, 4-($C_1$-$C_4$ alkyl)piperazin-1-yl, or 4-($C_3$-$C_{10}$ cycloalkyl)piperazin-1-yl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$, or $R^{c25}$ can be fluoro.

In certain embodiments, $R^{a3}$ can be 4-piperidyl, 1-($C_1$-$C_4$ alkyl)-4-piperidyl, or 1-($C_3$-$C_{10}$ cycloalkyl)piperidyl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$, or $R^{c25}$ can be fluoro.

In certain embodiments, $R^{a3}$ can be 1H-1,2,4-triazolyl; $W^1$ can be $CH_3$; $R^{c22}$ can be $C_1$-$C_4$ haloalkyl (e.g., $CF_3$), halo (e.g., chloro), $C_1$-$C_6$ alkoxy (e.g., $OCH_3$), cyano, or $C_1$-$C_6$ alkyl (e.g., $CH_3$), and $R^{c23}$, $R^{c24}$, or $R^{c25}$ can be fluoro.

In certain embodiments, $R^{a3}$ can be 3-hydroxypyrrolidin-1-yl; $W^1$ can be $CH_3$; $R^{c22}$ can be $CF_3$; and $R^{c23}$, $R^{c24}$, or $R^{c25}$ can be fluoro.

In certain embodiments, $R^{a3}$ can be 3-carboxypyrrolidin-1-yl; $W^1$ can be $CH_3$; $R^{c22}$ can be $CF_3$; and $R^{c23}$, $R^{c24}$, or $R^{c25}$ can be fluoro.

In some embodiments, X can be CO, and the 11-beta HSD1 inhibitor compounds can include one or more of the following features.

$R^1$ can be:

(B) $C_3$-$C_{16}$ (e.g., $C_3$-$C_{14}$ or $C_3$-$C_{10}$) cycloalkyl, optionally substituted with from 1-10 (e.g., 1-5, 1-4, 1-3, 1-2, or 1); $R^b$ as described herein; and/or (C) ($C_1$-$C_{12}$ alkyl)-($C_3$-$C_{16}$ cycloalkyl) (e.g., ($C_1$-$C_6$ alkyl)-($C_3$-$C_{12}$ cycloalkyl) or $(CH_2)$—($C_3$-$C_{12}$ cycloalkyl), optionally substituted with from 1-10 (e.g., 1-5, 1-4, 1-3, 1-2, or 1) $R^b$ as described herein.

$R^2$ can be heteroaryl including 5-20 (e.g., 5-16, 5-12, or 5-6) atoms, optionally substituted with from 1-10 (e.g., 1-5, 1-4, 1-3, 1-2, or 1) $R^c$ or $R^n$; or $C_6$-$C_{18}$ (e.g., $C_6$-$C_{14}$, $C_6$-$C_{10}$, or phenyl) aryl, optionally substituted with from 1-10 (e.g., 1-5, 1-4, 1-3, 1-2, or 1) $R^c$; for example, $R^2$ can be heteroaryl including 5-12 atoms, optionally substituted with from 1-3 (e.g., 1-2 or 1) $R^c$ or $R^n$ or $C_6$-$C_{10}$ aryl, optionally substituted with from 1-3 (e.g., 1-2 or 1) $R^c$ as described herein. In certain embodiments, $R^2$ can be heteroaryl including 5-12 atoms, optionally substituted with from 1-3 (e.g., 1-2 or 1) $R^c$ or $R^n$.

In some embodiments, Y can be $CR^7$ (e.g., CH) and V can be nitrogen, and the 11-beta HSD1 inhibitor compounds can have formula (VII):

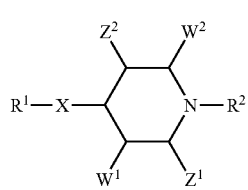

(VII)

in which $R^1$, $R^2$, $R^3$, $R^4$, $R^5$, $R^6$, $R^7$, X, $W^1$, $Z^1$, $W^2$, $Z^2$, $R^a$, $R^{a'}$, $R^b$, $R^c$, $R^d$, $R^e$, $R^f$, $R^g$, $R^h$, $R^i$, $R^j$, $R^k$, $R^m$, and $R^n$ can be as defined.

In certain embodiments, X can be $SO_2$ or $SO_2NH$, and the 11-beta HSD1 inhibitor compounds can include one or more of the following features.

$R^1$ can be $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms, each of which is optionally substituted with from 1-10 (e.g., 1-5, 1-4, 1-3, 1-2, or 1) $R^a$; for example, $R^1$ can be $C_6$-$C_{10}$ aryl, optionally substituted with from 1-3 (e.g., 1-2 or 1) $R^a$ or heteroaryl including 5-14 atoms, optionally substituted with from 1-3 (e.g., 1-2 or 1) $R^a$ as described herein.

$R^2$ can be heteroaryl including 5-20 (e.g., 5-16, 5-12, or 5-6) atoms, optionally substituted with from 1-10 (e.g., 1-5, 1-4, 1-3, 1-2, or 1) $R^c$ or $R^n$; or $C_6$-$C_{18}$ (e.g., $C_6$-$C_{14}$, $C_6$-$C_{10}$, or phenyl) aryl, optionally substituted with from 1-10 (e.g., 1-5, 1-4, 1-3, 1-2, or 1) $R^c$; for example, $R^2$ can be heteroaryl including 5-12 atoms, optionally substituted with from 1-3 (e.g., 1-2 or 1) $R^c$ or $R^n$ or $C_6$-$C_{10}$ aryl, optionally substituted with from 1-3 (e.g., 1-2 or 1) $R^c$ as described herein. In certain embodiments, $R^2$ can be heteroaryl including 5-12 atoms, optionally substituted with from 1-3 (e.g., 1-2 or 1) $R^c$ or $R^n$ as described herein.

In some embodiments, Y can be nitrogen and V can be $CR^7$ (e.g., CH), and the 11-beta HSD1 inhibitor compounds can have formula (VIII):

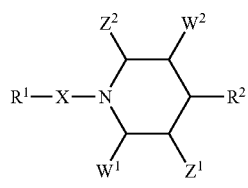

(VIII)

in which $R^1$, $R^2$, $R^3$, $R^4$, $R^5$, $R^6$, $R^7$, X, $W^1$, $Z^1$, $W^2$, $Z^2$, $R^a$, $R^{a'}$, $R^b$, $R^c$, $R^d$, $R^e$, $R^f$, $R^g$. $R^h$, $R^i$, $R^j$, $R^k$, $R^m$, and $R^n$ can be as defined.

In certain embodiments, X can be $SO_2$, and the 11-beta HSD1 inhibitor compounds can include one or more of the following features.

$R^1$ can be $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms, each of which is optionally substituted with from 1-10 (e.g., 1-5, 1-4, 1-3, 1-2, or 1) $R^a$; for example, $R^1$ can be $C_6$-$C_{10}$ aryl, optionally substituted with from 1-3 (e.g., 1-2 or 1) $R^a$ or heteroaryl including 5-14 atoms, optionally substituted with from 1-3 (e.g., 1-2 or 1) $R^a$ as described herein.

$R^2$ can be:

(A) heteroaryl including 5-20 (e.g., 5-16, 5-12, or 5-6) atoms, optionally substituted with from 1-10 (e.g., 1-5, 1-4, 1-3, 1-2, or 1) $R^c$ or $R^n$; or $C_6$-$C_{18}$ (e.g., $C_6$-$C_{14}$, $C_6$-$C_{10}$, or phenyl) aryl, optionally substituted with from 1-10 (e.g., 1-5, 1-4, 1-3, 1-2, or 1) $R^c$; for example, $R^2$ can be heteroaryl including 5-12 atoms, optionally substituted with from 1-3 (e.g., 1-2 or 1) $R^c$ or $R^n$; or $R^2$ can be $C_6$-$C_{10}$ aryl, optionally substituted with from 1-3 (e.g., 1-2 or 1) $R^c$ as described herein; and/or (C) $OR^1$; or $NR^3R^4$, in which $R^3$ and $R^4$ are each, independently, hydrogen or $R^1$ (e.g., $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms; each of which is optionally substituted with from 1-10 (e.g., 1-5, 1-4, 1-3, 1-2, or 1) $R^a$); for example, $R^2$ can be $OR^1$, in which $R^1$ can be $C_6$-$C_{10}$ aryl, or heteroaryl including 5-10 atoms, each of which can be optionally substituted with from (e.g., 1-2 or 1) $R^a$ or $R^1$ can be $C_7$-$C_{12}$ aralkyl, optionally substituted with from 1-3 $R^b$; or $R^2$ can be $NR^3R^4$, in which one of $R^3$ and $R^4$ can be hydrogen, and the other is $C_6$-$C_{10}$ aryl, optionally substituted with from 1-3 (e.g., 1-2 or 1) $R^a$ as described herein; and/or (D) heterocyclyl including 3-16 (e.g., 3-12, 3-10, 5-12, or 5-6) atoms, optionally substituted with from 1-10 (e.g., 1-5, 1-4, 1-3, 1-2, or 1) $R^b$; for example, $R^2$ can be heterocyclyl including 3-8 atoms, optionally substituted with 1 $R^b$ (e.g., $C_1$-$C_4$ alkyl (e.g., $CH_3$)) as described herein.

In certain embodiments, when $R^2$ is (A), $R^2$ is optionally substituted heteroaryl including 5-20 (e.g., 5-16, 5-12, or 5-6) atoms. In other embodiments, when $R^2$ is (A), $R^2$ is optionally substituted $C_6$-$C_{18}$ (e.g., $C_6$-$C_{14}$, $C_6$-$C_{10}$, or phenyl) aryl.

In certain embodiments, X can be CO, and the 11-beta HSD1 inhibitor compounds can include one or more of the following features.

$R^1$ can be:

(B) $C_3$-$C_{16}$ (e.g., $C_3$-$C_{14}$ or $C_3$-$C_{10}$) cycloalkyl, optionally substituted with from 1-10 (e.g., 1-5, 1-4, 1-3, 1-2, or 1); $R^b$ as described herein; and/or (D) $C_7$-$C_{20}$ (e.g., $C_7$-$C_{16}$, $C_7$-$C_{12}$, $C_7$-$C_{10}$) aralkyl, optionally substituted with from 1-10 (e.g., 1-5, 1-4, 1-3, 1-2, or 1) $R^b$; for example, $R^1$ can be $C_7$-$C_{12}$ aralkyl, optionally substituted with from 1-2 $R^b$ (e.g., halo) as described herein.

$R^2$ can be $OR^1$; or $NR^3R^4$, in which $R^3$ and $R^4$ are each, independently, hydrogen or $R^1$ (e.g., $C_6$-$C_{18}$ (e.g., $C_6$-$C_{14}$, $C_6$-$C_{10}$, or phenyl) aryl or heteroaryl including 5-20 (e.g., 5-16, 5-12, or 5-6) atoms; each of which is optionally substituted with from 1-10 (e.g., 1-5, 1-4, 1-3, 1-2, or 1) $R^a$); for example, $R^2$ can be $OR^1$, in which $R^1$ can be $C_6$-$C_{10}$ aryl, or heteroaryl including 5-10 atoms, each of which can be optionally substituted with from (e.g., 1-2 or 1) $R^a$; or $R^1$ can be $C_7$-$C_{12}$ aralkyl, optionally substituted with from 1-3 $R^b$; or $R^2$ can be $NR^3R^4$, in which one of $R^3$ and $R^4$ can be hydrogen, and the other is $C_6$-$C_{10}$ aryl, optionally substituted with from 1-3 (e.g., 1-2 or 1) $R^a$ as described herein. In certain embodiments, $R^2$ can be $OR^1$, in which $R^1$ can be $C_6$-$C_{10}$ aryl, or heteroaryl including 5-10 atoms, each of which can be optionally substituted with from (e.g., 1-2 or 1) $R^a$; or $R^1$ can be $C_7$-$C_{12}$ aralkyl, optionally substituted with from 1-3 $R^b$.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species.

The compounds described herein can be synthesized according to methods described herein and/or conventional, organic chemical synthesis methods from commercially available starting materials and reagents. The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2 d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

In some embodiments, the compounds described herein can be prepared according to the general schemes below:

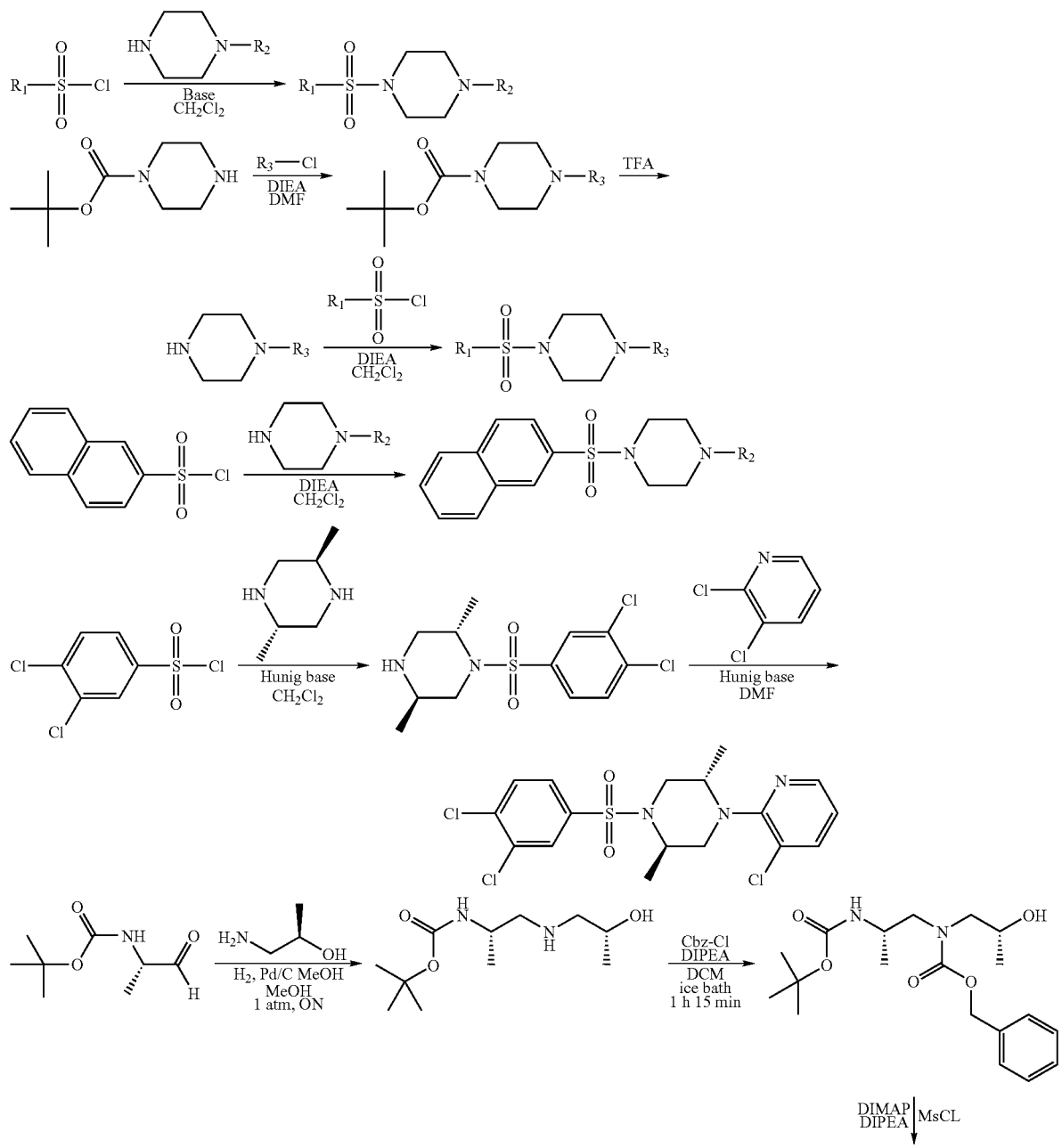

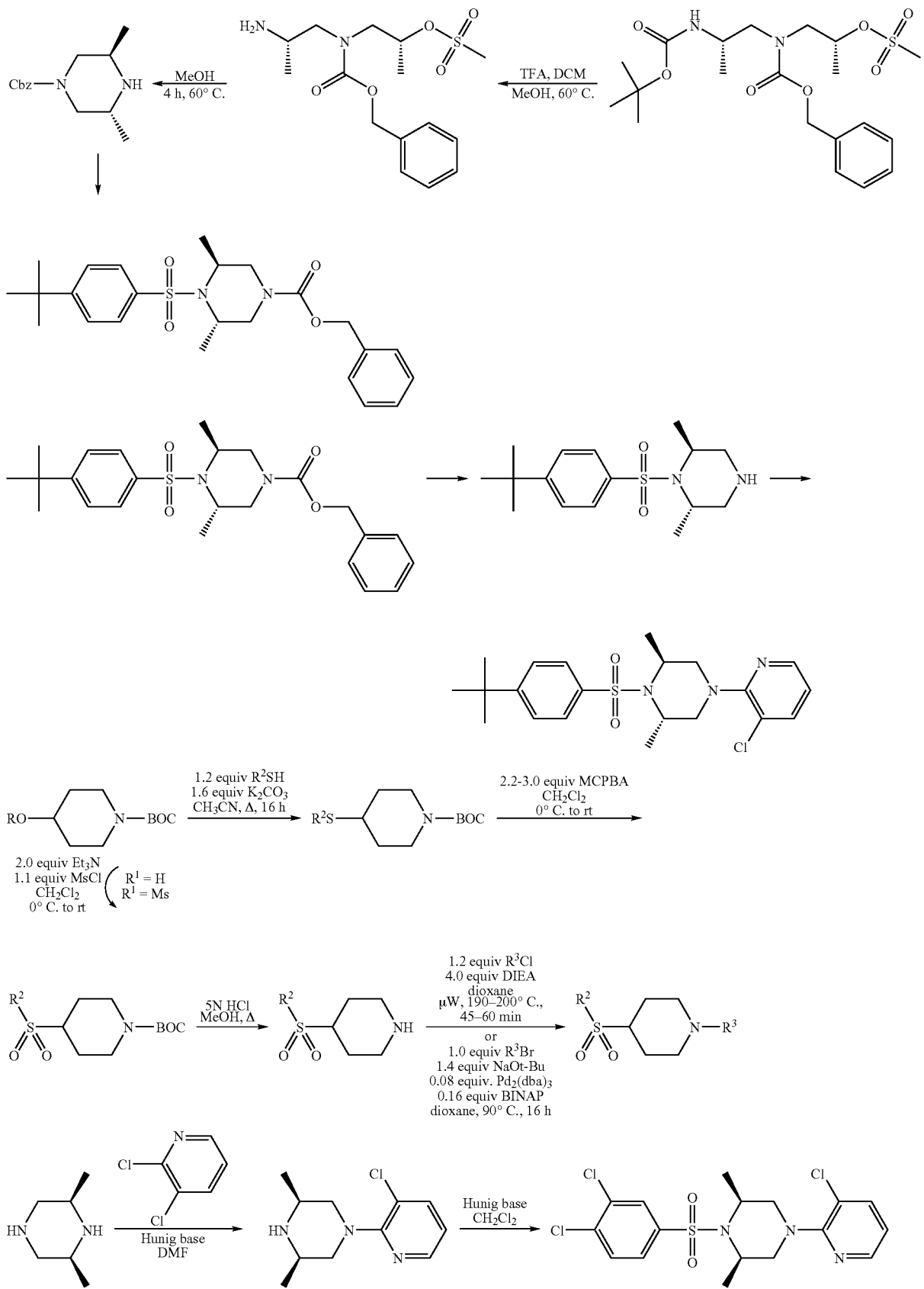

-continued
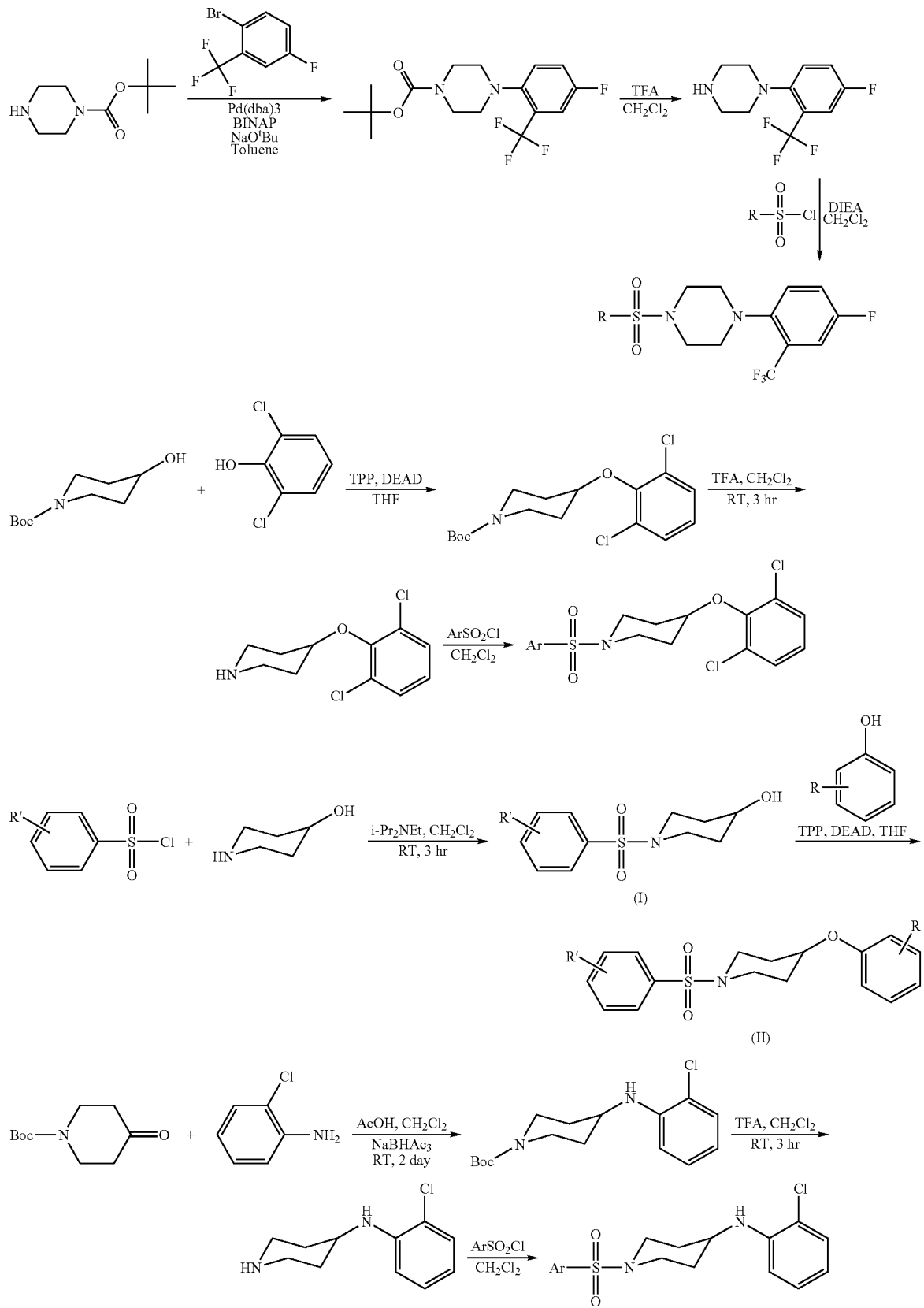

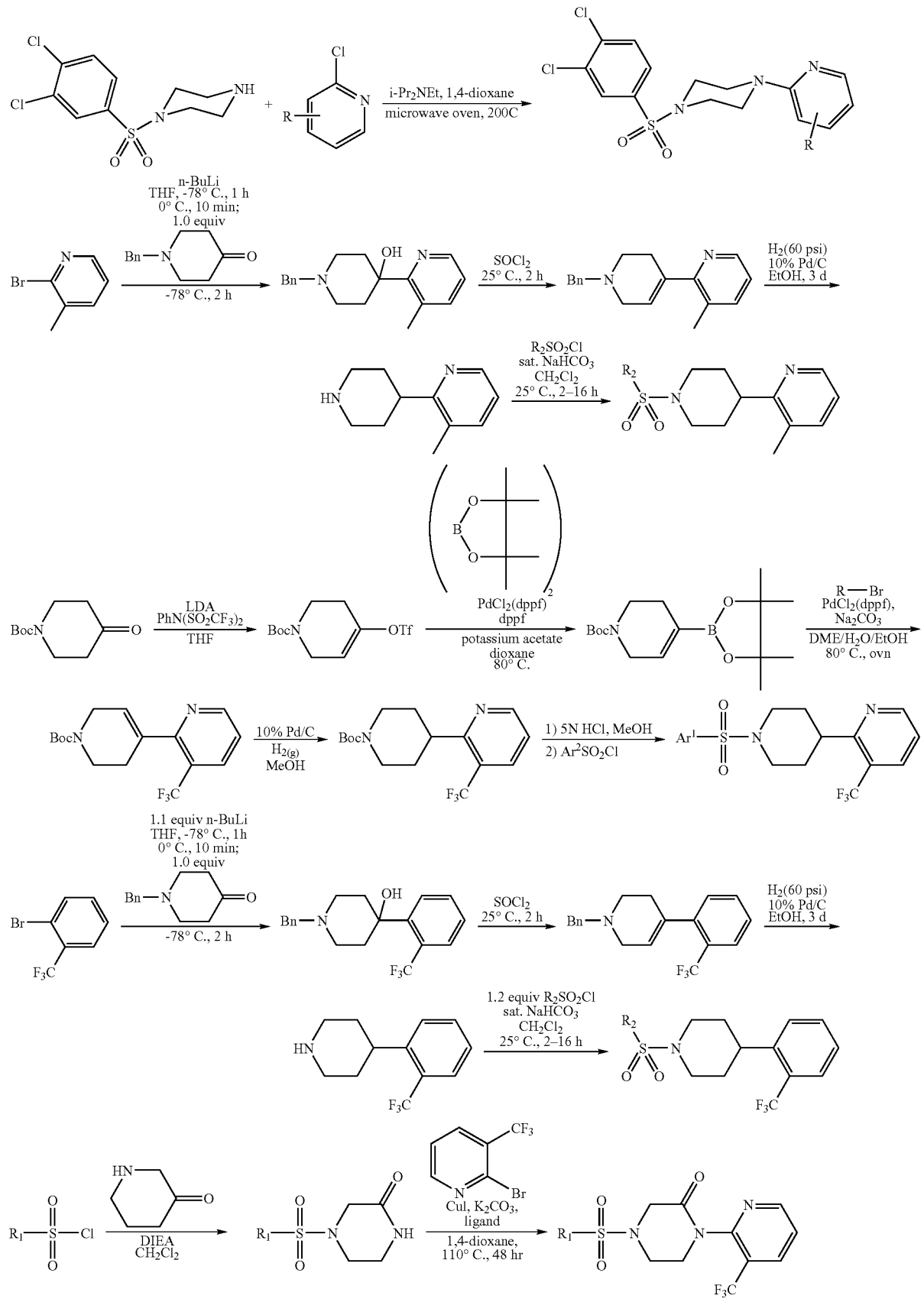

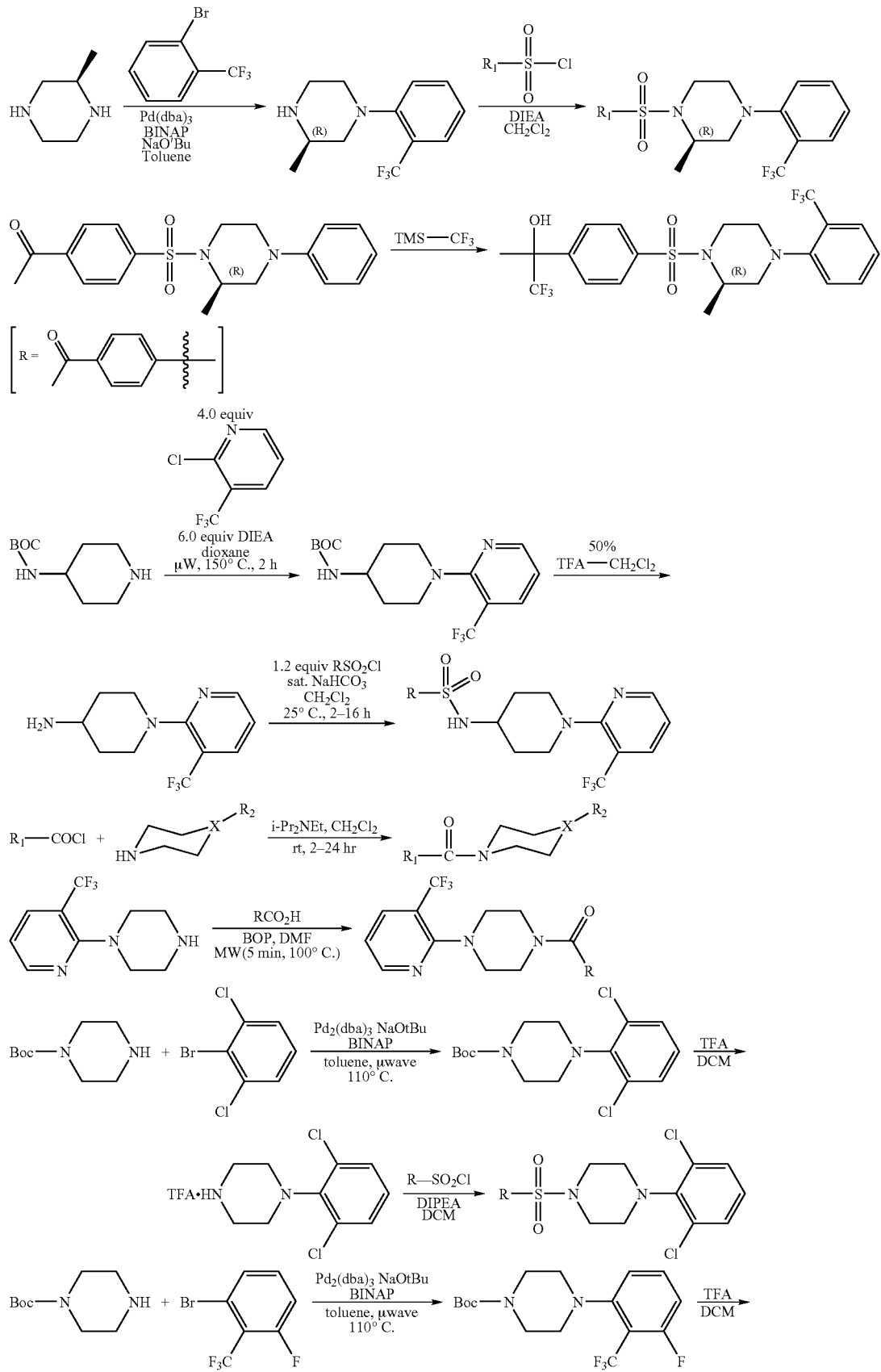

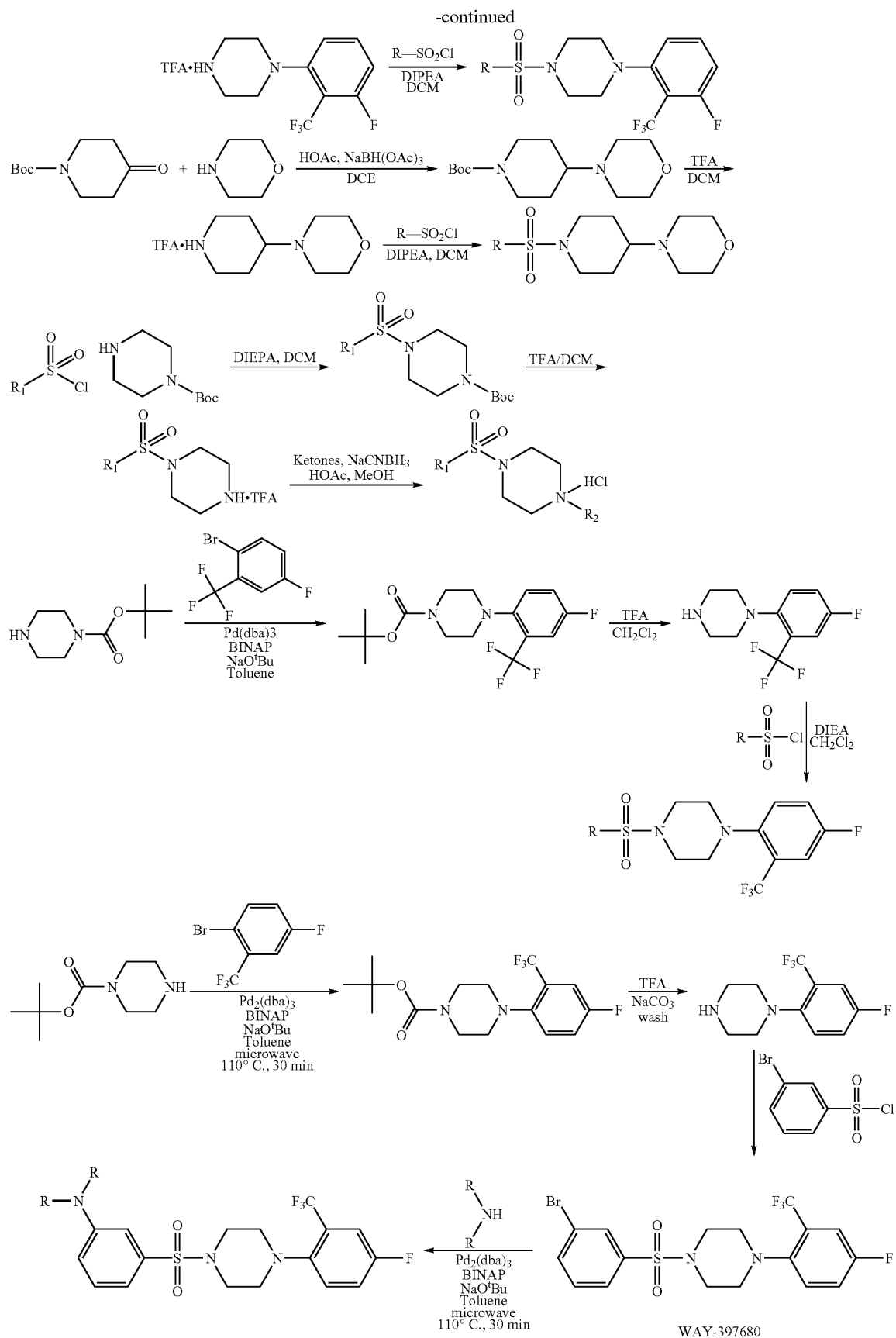

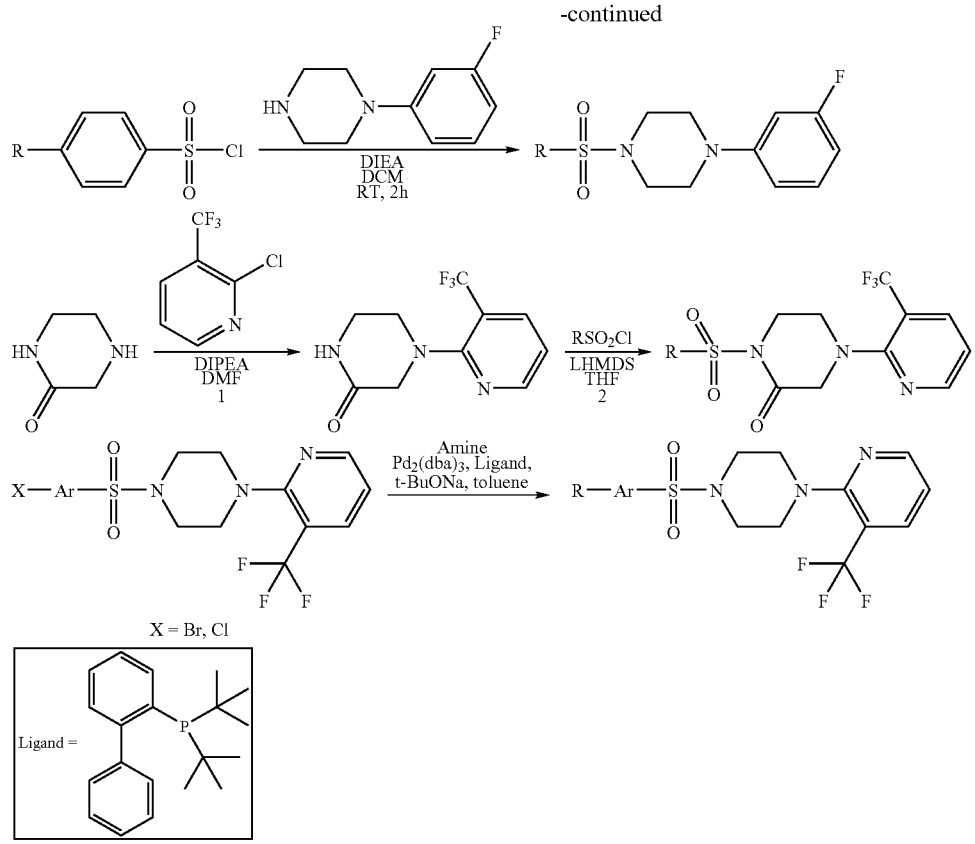

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substitutent (e.g., amino) on a compound described herein. Suitable anions include chloride, bromide, iodide, sulfate, nitrate, phosphate, citrate, methane-sulfonate, trifluoroacetate, and acetate. Likewise, a salt can also be formed between a cation and a negatively charged substitutent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalene-sulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The term "pharmaceutically acceptable carrier or adjuvant" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In general, the compounds described herein can be used for treating, controlling, ameliorating, preventing, delaying the onset of, or reducing the risk of developing one or more diseases, disorders, conditions or symptoms mediated by excess or uncontrolled amounts of cortisol and/or other corticosteroids. While not wishing to be bound by any theory, it is believed that the compounds described herein can reduce the levels of cortisol and other corticosteroids (e.g., 11β-hydroxysteroids) by inhibiting the reductase activity of 11β-HSD1. The diseases, disorders, conditions or symptoms mediated by excess or uncontrolled amounts of cortisol and/or other corticosteroids can include diabetes (e.g., type 1 or type 2 diabetes), Syndrome X, hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, hypertension, coronary heart disease, stroke, peripheral vascular disease, Cushing's syndrome, glaucoma, osteoporosis, hyperinsulinemia, tuberculosis, psoriasis, cognitive disorders and dementia (e.g., impairment associated with aging and of neuronal dysfunction, e.g., Alzheimer's disease), depression, viral diseases, inflammatory disorders, immune disorders. In some embodiments, the diseases, disorders conditions or symptoms can further include those where insulin resistance is a component. In other embodiments, the compounds described herein can be used for promoting wound healing.

The compounds described herein generally have an inhibition constant $IC_{50}$ of less than about 10 μM. Examples of such compounds include those described herein in Examples 1A through 1Z; 1AA through 1AZ; 2A, 2B, 2D, 2E, 2F, 2G, 2H, 2I, 2J; 3A through 3D; 5, 6; 7A through 7Z; 7AA through 7AZ; 7BB through 7BD; 9F; 10A through 10X; 11A through 11U; 12A through 12F; 13A; 13A-1 through 13A-7; 13B; 13B-1 through 13B-6; 13C; 14A through 14G; 18A through 18F; 29A through 29AD; 29AF through 29BI; 29BK though 29HN; and 29HP through 29IT. Generally, the $IC_{50}$ ratio for 11-beta-HSD2 to 11-beta-HSD1 of a compound is at least about 100 or greater.

In some embodiments, the compounds described herein can be coadministered with one or more other therapeutic agents. In certain embodiments, the additional agents may be administered separately, as part of a multiple dose regimen, from the compounds of this invention (e.g., sequentially, e.g., on different overlapping schedules with the administration of one or more compounds of formula (I)). Alternatively, these agents may be part of a single dosage form, mixed together with the compounds of this invention in a single composition. In still another embodiment, these agents can be given as a separate dose that is administered at about the same time that one or more compounds of formula (I) are administered (e.g., simultaneously with the administration of one or more compounds of formula (I)). When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen.

Other therapeutic agents can include DP-IV inhibitors; insulin sensitizers (e.g., (i) PPAR agonists and (ii) biguanides); insulin and insulin analogues and mimetics; sulfonylureas and other insulin secretagogues; prandial glucose regulators, alpha.-glucosidase inhibitors; glucagon receptor antagonists; GLP-1, GLP-1 mimetics, and GLP-1 receptor agonists; GIP, GIP mimetics, and GIP receptor agonists; PACAP, PACAP mimetics, and PACAP receptor 3 agonists; cholesterol lowering agents (e.g., (i) HMG-CoA reductase inhibitors, (ii) sequestrants, (iii) nicotinyl alcohol, nicotinic acid and salts thereof, (iv) PPAR.alpha. agonists, (v) PPAR.alpha./.gamma. dual agonists, (vi) inhibitors of cholesterol absorption, (vii) acyl CoA:cholesterol acyltransferase inhibitors, and (viii) anti-oxidants; PPAR.delta. agonists); antiobesity compounds (e.g., sibutramine and orlisat); an ileal bile acid transporter inhibitor; anti-inflammatory agents excluding glucocorticoids (e.g., aspirin); protein tyrosine phosphatase-1B (PTP-1B) inhibitors; agents that suppress hepatic glucose output (e.g., metformin); agents designed to reduce the absorption of glucose from the intestine (e.g., acarbose); agents designed to treat the complications of prolonged hyperglycemia (e.g., aldose reductase inhibitors); antidiabetic agents (e.g., glucose phosphatase inhibitors, glucose-6-phosphatase inhibitors, glucagon receptor antagonists, glucose kinase activators, glycogen phosphorylase inhibitors, fructose 1,6 bisphosphatase inhibitors, glutamine:fructose-6-phosphate amidotransferase inhibitors); antihypertensive agents (e.g., β blockers (e.g., atenolol, inderal), ACE inhibitors (e.g., lisinopril), calcium agonists (e.g., nifedipine), angiotensin receptor antagonists (e.g., candesartan), a agonists and diuretic agents (e.g., furosemide, benzthiazide)); and haemostasis modulators (e.g., antithrombotics, activators of fibrinolysis and antiplatelet agents (e.g., clopidogrel, aspirin), thrombin antagonists, factor Xa inhibitors, factor VIIa inhibitors, anticoagulants (e.g., heparin and low molecular weight analogues, hirudin), warfarin).

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/Kg to about 1000 mg/Kg, (e.g., from about 0.01 to about 100 mg/kg, from about 0.1 to about 100 mg/Kg, from about 1 to about 100 mg/Kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous, suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

The invention will be further described in the following examples. It should be understood that these examples are for illustrative purposes only and are not to be construed as limiting this invention in any manner.

EXAMPLES

Example 1

Scheme 1

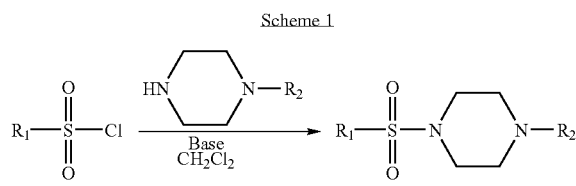

Representative sulfonation (Step 1A): To a stirred solution of 1-(3-(trifluoromethyl)phenyl)piperazine (300 mg, 1.3 mmol) and 4-methylbenzene-1-sulfonyl chloride (248 mg, 1.3 mmol) in anhydrous dichloromethane (3 mL) was added diisopropylethylamine (0.27 mL, 1.6 mmol). The mixture was stirred overnight. Reaction was complete as determined by TLC. The reaction mixture was purified with flash column chromatography to yield 1-(4-methylphenylsulfonyl)-4-[3-(trifluoromethyl)phenyl]piperazine in 81% yield (405 mg) as white solid.

$^1$H NMR (400 MHz, DMSO-D$_6$) δ ppm 2.41 (s, 3H) 2.85-3.06 (m, 4H) 3.27-3.33 (m, 4H) 7.09 (d, J=7.58 Hz, 1H) 7.13-7.22 (m, 2H) 7.41 (t, J=7.96 Hz, 1H) 7.48 (d, J=8.08 Hz, 2H) 7.62-7.70 (m, 2H); HRMS: calcd for $C_{18}H_{19}F_3N_2O_2S+H+$, 385.11921. found (ESI-FTMS, [M+H]$^{1+}$), 385.1198. HPLC Method 1: room temperature, 6.642 min, 97.94%. HPLC Method 2: room temperature, 7.178 min, 97.99%.

Example 1A

1-[(3,4-dichlorophenyl)sulfonyl]-4-(2-fluorophenyl)piperazine

Step 1A: Sulfonylation of 1-(2-fluorophenyl)piperazine-.HCl (325 mg, 1.5 mmol) with 3,4-dichlorobenzene-1-sulfonyl chloride (368.3 mg, 1.5 mmol) was carried out according to a similar procedure described for step 1A using anhydrous dichloromethane (3 mL) as solvent and diisopropylethylamine (0.575 mL, 3.3 mmol) as base. 1-[(3,4-dichlorophenyl)sulfonyl]-4-(2-fluorophenyl)piperazine was obtained in 85.8% yield (501 mg) as white solid.

1H NMR (400 MHz, DMSO-D6) δ ppm 3.02-3.16 (m, 8H) 6.94-7.19 (m, 4H) 7.76 (dd, J=8.46, 2.15 Hz, 1H) 7.96 (d, J=8.34 Hz, 1H) 7.99 (d, J=2.02 Hz, 1H); HRMS: calcd for $C_{16}H_{15}C_{12}FN_2O_2S+H+$, 389.02881. found (ESI-FTMS, [M+H]1+), 389.029. HPLC Method 1: room temperature, 6.830 min, 98.81%. HPLC Method 2: room temperature, 7.491 min, 98.91%.

Example 1B

1-[(2-chlorophenyl)sulfonyl]-4-(2-fluorophenyl)piperazine

Step 1A: Sulfonylation of 1-(2-fluorophenyl)piperazine.HCl (325 mg, 1.5 mmol) with 2-chlorobenzene-1-sulfonyl chloride (316.6 mg, 1.5 mmol) was carried out according to a similar procedure described for step 1A using anhydrous dichloromethane (3 mL) as solvent and diisopropylethylamine (0.575 mL, 3.3 mmol) as base. 1-[(2-chlorophenyl)sulfonyl]-4-(2-fluorophenyl)piperazine was obtained in 75.5% yield (402 mg) as white solid.

1H NMR (400 MHz, DMSO-D6) δ ppm 2.99-3.09 (m, 4H) 3.29-3.37 (m, 4H) 6.95-7.19 (m, 4H) 7.56-7.64 (m, 1H) 7.66-7.78 (m, 2H) 8.02 (dd, J=7.96, 1.64 Hz, 1H); HRMS: calcd for $C_{16}H_{16}ClFN_2O_2S+H+$, 355.06778. found (ESI-FTMS, [M+H]1+), 355.0686. HPLC Method 1: room temperature, 6.281 min, 99.76%. HPLC Method 2: room temperature, 6.916 min, 99.80%.

Example 1C 1-(2,6-dimethylphenyl)-4-(2-naphthylsulfonyl)piperazine

Sulfonylation was carried out according to a similar procedure described for step 1A. 1-(2,6-dimethylphenyl)-4-(2-naphthylsulfonyl)piperazine was obtained in 85% yield as white solid.

1H NMR (400 MHz, CHLOROFORM-D) δ ppm 2.19 (s, 6H) 2.80-3.68 (m, 8H) 6.74-7.06 (m, 3H) 7.52-7.72 (m, 2H) 7.80 (d, J=7.07 Hz, 1H) 7.87-8.24 (m, 3H) 8.39 (s, 1H). HRMS: calcd for $C_{22}H_{24}N_2O_2S+H+$, 381.16312. found (ESI-FTMS, [M+H]$^{1+}$), 381.1619.

Example 1D

1-[(2-chlorophenyl)sulfonyl]-4-(2,3-dichlorophenyl) piperazine

Sulfonylation was carried out according to a similar procedure described for step 1A. 1-[(2-chlorophenyl)sulfonyl]-4-(2,3-dichlorophenyl)piperazine was obtained in 95% yield as white solid.

1H NMR (400 MHz, CHLOROFORM-D) δ ppm 2.96-3.18 (m, 4H) 3.33-3.64 (m, 4H) 6.93 (d, J=7.83 Hz, 1H) 7.07-7.22 (m, 3H) 7.43 (t, J=7.45 Hz, 1H) 7.48-7.68 (m, 2H) 8.08 (d, J=8.08 Hz, 1H). HRMS: calcd for $C_{16}H_{15}Cl_3N_2O_2S$+H+, 404.99925. found (ESI-FTMS, [M+H]$^{1+}$), 404.9995. HPLC Method 1, room temperature, 6.90 min, 98.56%; HPLC Method 2, room temperature, 7.45 min, 98.84%.

Example 1E 1-(2,3-dichlorophenyl)-4-(2-naphthylsulfonyl)piperazine

Sulfonylation was carried out according to a similar procedure described for step 1A. 1-(2,3-dichlorophenyl)-4-(2-naphthylsulfonyl)piperazine was obtained in 90% yield as white solid.

1H NMR (400 MHz, CHLOROFORM-D) δ ppm 3.12 (t, J=4.67 Hz, 4H) 3.28 (s, 4H) 6.93 (d, J=6.32 Hz, 1H) 7.07-7.23 (m, 2H) 7.53-7.74 (m, 2H) 7.74-7.89 (m, 1H) 7.91-8.00 (m, 1H) 8.02 (dd, J=8.21, 4.17 Hz, 2H) 8.38 (s, 1H). HRMS: calcd for $C_{20}H_{18}Cl_2N_2O_2S$+H+, 421.05388. found (ESI-FTMS, [M+H]$^{1+}$), 421.054. HPLC Method 1, room temperature, 6.98 min, 98.97%; HPLC Method 2, room temperature, 7.58 min, 95.34%.

Example 1F 1-(phenylsulfonyl)-4-[3-(trifluoromethyl)pyridin-2-yl]piperazine

Step 1Q: A solution of 1-[3-(trifluoromethyl)-2-pyridyl]piperazine (60 mg, 0.26 mmol), and Benzene sulfonyl chloride (0.043 mL, 0.31 mmol) in DCM (4 mL) and saturated sodium bicarbonate (2 mL) was stirred at room temperature for 12 hours. The mixture was diluted with DCM (5 mL) and water (5 mL). The organic layer was collected and washed two times with water, dried with magnesium sulfate, and concentrated. The product was purified using column chromatography (20% Ethyl Acetate in Hexanes) to produce 1-(phenylsulfonyl)-4-[3-(trifluoromethyl)pyridin-2-yl]piperazine (81.1 mg, 84%).

1H NMR (400 MHz, CHLOROFORM-D) δ ppm 3.18 (t, 4H) 3.35 (t, 4H) 7.03 (t, 1H) 7.57 (t, J=7.33 Hz, 2H) 7.64 (t, J=7.33 Hz, 1H) 7.80 (d, J=8.59 Hz, 2H) 7.85 (d, J=6.06 Hz, 1H) 8.42 (d, J=4.55 Hz, 1H); HRMS: calcd for $C_{16}H_{16}F_3N_3O_2S$+H+, 372.09881. found (ESI-FTMS, [M+H]$^{1+}$), 372.0996.

Example 1G

1-[(2-chlorophenyl)sulfonyl]-4-[3-(trifluoromethyl)pyridin-2-yl]piperazine

In an analogous manner to Example 1F, step 1Q 1-[(2-chlorophenyl)sulfonyl]-4-[3-(trifluoromethyl)pyridin-2-yl] piperazine was prepared from 2-chlorosulfonyl chloride (44% yield).

1H NMR (400 MHz, CHLOROFORM-D) δ ppm 3.27-3.35 (m, 4H) 3.42-3.52 (m, 4H) 7.02-7.10 (m, 1H) 7.42 (t, J=7.58 Hz, 1H) 7.48-7.59 (m, 2H) 7.88 (d, J=9.09 Hz, 1H) 8.09 (d, J=9.09 Hz, 1H) 8.44 (d, J=3.79 Hz, 1H); HRMS: calcd for $C_{16}H_{15}ClF_3N_3O_2S$+H+, 406.05983. found (ESI-FTMS, [M+H]$^{1+}$), 406.0611.

Example 1H

1-[(3-chlorophenyl)sulfonyl]-4-[3-(trifluoromethyl)pyridin-2-yl]piperazine

In an analogous manner to Example 1F, step 1Q 1-[(3-chlorophenyl)sulfonyl]-4-[3-(trifluoromethyl)pyridin-2-yl] piperazine was prepared from 3-chlorosulfonyl chloride (37% yield).

1H NMR (400 MHz, CHLOROFORM-D) δ ppm 3.16-3.27 (m, 4H) 3.33-3.42 (m, 4H) 7.01-7.10 (m, 1H) 7.52 (t, J=7.83 Hz, 1H) 7.61 (d, J=8.08 Hz, 1H) 7.68 (d, J=7.58 Hz, 1H) 7.79 (s, 1H) 7.87 (d, J=7.83 Hz, 1H) 8.44 (d, J=4.80 Hz, 1H); HRMS: calcd for $C_{16}H_{15}ClF_3N_3O_2S$+H+, 406.05983. found (ESI-FTMS, [M+H]$^{1+}$), 406.0609.

Example 1I 1-(benzylsulfonyl)-4-[3-(trifluoromethyl)pyridin-2-yl]piperazine

In an analogous manner to Example 1F, step 1Q 1-(benzylsulfonyl)-4-[3-(trifluoromethyl)pyridin-2-yl]piperazine was prepared from α-toluenesulfonyl chloride (45% yield).

1H NMR (400 MHz, CHLOROFORM-D) δ ppm 3.19-3.24 (m, 4H) 3.24-3.30 (m, 4H) 4.24-4.31 (m, 2H) 7.05 (dd, J=7.71, 4.93 Hz, 1H) 7.35-7.47 (m, 5H) 7.88 (d, 1H) 8.44 (d, J=4.55 Hz, 1H); HRMS: calcd for $C_{17}H_{18}F_3N_3O_2S$+H+, 386.11446. found (ESI-FTMS, [M+H]$^{1+}$), 386.1153.

Example 1J

1-[(3-chlorobenzyl)sulfonyl]-4-[3-(trifluoromethyl)pyridin-2-yl]piperazine

In an analogous manner to Example 1F, step 1Q 1-[(3-chlorobenzyl)sulfonyl]-4-[3-(trifluoromethyl)pyridin-2-yl] piperazine was prepared from 3-chlorophenylmethane sulfonyl chloride (26% yield).

1H NMR (400 MHz, CHLOROFORM-D) δ ppm 3.25 (t, 4H) 3.32 (t, 4H) 4.20 (s, 2H) 7.00-7.15 (m, 1H) 7.30-7.42 (m, 3H) 7.45 (s, 1H) 7.89 (d, J=9.60 Hz, 1H) 8.45 (d, J=3.28 Hz, 1H); HRMS: calcd for $C_{17}H_{17}ClF_3N_3O_2S$+H+, 420.07548. found (ESI-FTMS, [M+H]$^{1+}$), 420.0769.

Example 1K

1-[(3,4-dichlorobenzyl)sulfonyl]-4-[3-(trifluoromethyl)pyridin-2-yl]piperazine

In an analogous manner to Example 1F, step 1Q 1-[(3,4-dichlorobenzyl)sulfonyl]-4-[3-(trifluoromethyl)pyridin-2-yl]piperazine was prepared from 3,4-dichlorophenylmethane sulfonyl chloride (29% yield).

1H NMR (400 MHz, CHLOROFORM-D) δ ppm 3.27 (t, 4H) 3.35 (t, 4H) 4.16 (s, 2H) 7.07 (none, 1H) 7.08 (dd, J=5.43 Hz, 1H) 7.29 (d, J=2.27 Hz, 1H) 7.48 (d, J=8.08 Hz, 1H) 7.54 (d, J=2.02 Hz, 1H) 7.90 (d, J=7.83 Hz, 1H) 8.46 (d, J=3.54

Hz, 1H); HRMS: calcd for $C_{17}H_{16}Cl_2F_3N_3O_2S+H+$, 454.03651. found (ESI-FTMS, $[M+H]^{1+}$), 454.0381.

Example 1L

1-[(2-chlorophenyl)sulfonyl]-4-(3,5-dichloropyridin-4-yl)piperazine

In an analogous manner to Example 1F, step 1Q 1-[(2-chlorophenyl)sulfonyl]-4-(3,5-dichloropyridin-4-yl)piperazine was prepared from 1-(3,5-dichloro-4-pyridyl)piperazine (0.1 g, 0.43 mmol) and 2-chlorobenzene sulfonyl chloride (59% yield).

1H NMR (400 MHz, CHLOROFORM-D) δ ppm 3.35-3.43 (m, 4H) 3.45-3.50 (m, 4H) 7.39-7.46 (m, 1H) 7.49-7.60 (m, 2H) 8.09 (d, J=7.83 Hz, 1H) 8.36 (s, 2H); HRMS: calcd for $C_{15}H_{14}Cl_3N_3O_2S+H+$, 405.99450. found (ESI-FTMS, $[M+H]^{1+}$), 405.9951.

Example 1M

1-[(3-chlorophenyl)sulfonyl]-4-(3,5-dichloropyridin-4-yl)piperazine

In an analogous manner to Example 1F, step 1Q 1-[(3-chlorophenyl)sulfonyl]-4-(3,5-dichloropyridin-4-yl)piperazine was prepared from 1-(3,5-dichloro-4-pyridyl)piperazine (0.1 g, 0.43 mmol) and 3-chlorobenzene sulfonyl chloride (66% yield).

1H NMR (400 MHz, CHLOROFORM-D) δ ppm 3.19-3.27 (m, 4H) 3.41-3.51 (m, 4H) 7.26 (s, 1H) 7.53 (t, J=7.83 Hz, 1H) 7.59-7.72 (m, 2H) 7.79 (s, 1H) 8.37 (s, 2H); HRMS: calcd for $C_{15}H_{14}Cl_3N_3O_2S+H+$, 405.99450. found (ESI-FTMS, $[M+H]^{1+}$), 405.9956.

Example 1N

1-[(3,4-dichlorobenzyl)sulfonyl]-4-(3,5-dichloropyridin-4-yl)piperazine

In an analogous manner to Example 1F, step 1Q 1-[(3,4-dichlorobenzyl)sulfonyl]-4-(3,5-dichloropyridin-4-yl)piperazine was prepared from 1-(3,5-dichloro-4-pyridyl)piperazine (0.1 g, 0.43 mmol) and 3,4-dichlorophenylmethyl sulfonyl chloride (61% yield).

1H NMR (400 MHz, CHLOROFORM-D) δ ppm 3.18-3.29 (m, 4H) 3.40-3.48 (m, 4H) 7.26 (s, 1H) 7.59-7.70 (m, 2H) 7.89 (d, J=1.77 Hz, 1H) 8.36 (s, 2H); HRMS: calcd for $C_{16}H_{15}Cl_4N_3O_2S+H+$, 453.97118. found (ESI-FTMS, $[M+H]^{1+}$), 453.9733.

Example 1O

1-[(3-chlorophenyl)sulfonyl]-4-[2-(trifluoromethyl)phenyl]piperazine

In an analogous manner to Example 1E, step 1P 1-[(3-chlorophenyl)sulfonyl]-4-[2-(trifluoromethyl)phenyl]piperazine was prepared from 1-(2-trifluoromethylphenyl)piperazine (0.1 g, 0.43 mmol) and 3-chlorobenzyl sulfonyl chloride (71% yield).

1H NMR (400 MHz, CHLOROFORM-D) δ ppm 3.01 (t, J=4.80 Hz, 4H) 3.20 (s, 4H) 7.54 (d, J=8.08 Hz, 1H) 7.55-7.60 (m, 1H) 7.59-7.64 (m, 1H) 7.68 (d, J=6.57 Hz, 1H) 7.73 (d, J=6.82 Hz, 1H) 7.79 (t, J=1.89 Hz, 1H) 7.95 (d, J=8.08 Hz, 1H) 8.04 (t, J=1.89 Hz, 1H); HRMS: calcd for $C_{17}H_{16}ClF_3N_2O_2S+H+$, 405.06458. found (ESI-FTMS, $[M+H]^{1+}$), 405.0649.

Example 1P

1-[(4-chlorophenyl)sulfonyl]-4-[2-(trifluoromethyl)phenyl]piperazine

In an analogous manner to Example 1E, step 1P 1-[(4-chlorophenyl)sulfonyl]-4-[2-(trifluoromethyl)phenyl]piperazine was prepared from 1-(2-trifluoromethylphenyl)piperazine (0.1 g, 0.43 mmol) and 4-chlorobenzyl sulfonyl chloride (69% yield).

1H NMR (400 MHz, CHLOROFORM-D) δ ppm 3.01 (t, J=4.80 Hz, 4H) 3.18 (s, 4H) 7.35 (d, J=8.08 Hz, 2H) 7.50-7.65 (m, 3H) 7.73 (d, J=8.59 Hz, 2H) 7.99 (d, J=8.59 Hz, 1H); HRMS: calcd for $C_{17}H_{16}ClF_3N_2O_2S+H+$, 405.06458. found (ESI-FTMS, $[M+H]^{1+}$), 405.0649.

Example 1Q

1-[(3,4-dichlorophenyl)sulfonyl]-4-[2-(trifluoromethyl)phenyl]piperazine

In an analogous manner to Example 1E, step 1P 1-[(3,4-dichlorophenyl)sulfonyl]-4-[2-(trifluoromethyl)phenyl]piperazine was prepared from 1-(2-trifluoromethylphenyl)piperazine (0.1 g, 0.43 mmol) and 3,4-dichlorobenzene sulfonyl chloride (82% yield).

1H NMR (400 MHz, CHLOROFORM-D) δ ppm 3.02 (t, J=4.80 Hz, 4H) 3.20 (s, 4H) 7.35 (d, J=8.08 Hz, 1H) 7.59-7.64 (m, 3H) 7.65-7.69 (m, 1H) 7.72 (d, J=8.59 Hz, 1H) 8.14 (d, J=2.27 Hz, 1H); HRMS: calcd for $C_{17}H_{15}Cl_2F_3N_2O_2S+H+$, 439.02561. found (ESI-FTMS, $[M+H]^{1+}$), 439.0251.

Example 1R

1-[(3,4-dichlorobenzyl)sulfonyl]-4-[2-(trifluoromethyl)phenyl]piperazine

In an analogous manner to Example 1E, step 1P 1-[(3,4-dichlorobenzyl)sulfonyl]-4-[2-(trifluoromethyl)phenyl]piperazine was prepared from 1-(2-trifluoromethylphenyl)piperazine (0.1 g, 0.43 mmol) and 3,4-dichlorophenylmethyl sulfonyl chloride (93% yield).

1H NMR (400 MHz, CHLOROFORM-D) δ ppm 1.60 (s, 2H) 2.92-2.96 (m, 4H) 3.31-3.38 (m, 4H) 7.25-7.35 (m, 4H) 7.48-7.58 (m, 2H) 7.64 (d, J=6.32 Hz, 1H); HRMS: calcd for $C_{18}H_{17}Cl_2F_3N_2O_2S+H+$, 453.04126. found (ESI-FTMS, $[M+H]^{1+}$), 453.0396.

Example 1S

3-{4-[(4-chlorophenyl)sulfonyl]piperazin-1-yl}pyrazine-2-carbonitrile

In an analogous manner to Example 1E, step 1P 3-{4-[(4-chlorophenyl)sulfonyl]piperazin-1-yl}pyrazine-2-carbonitrile was prepared from (3-piperazine-1-ly)pyperazine-2-carbonitrile (0.1 g, 0.53 mmol) and 4-chlorobenzene sulfonyl chloride (40% yield).

1H NMR (400 MHz, CHLOROFORM-D) δ ppm 3.17-3.23 (m, 4H) 3.82-3.90 (m, 4H) 7.54 (d, J=8.84 Hz, 2H) 7.72 (d, J=8.59 Hz, 2H) 8.08 (d, J=2.27 Hz, 1H) 8.26 (d, J=2.27 Hz, 1H); HRMS: calcd for $C_{15}H_{14}ClN_5O_2S+H+$, 364.06295. found (ESI-FTMS, $[M+H]^{1+}$), 364.0636.

Example 1T

3-{4-[(3,4-dichlorophenyl)sulfonyl]piperazin-1-yl}pyrazine-2-carbonitrile

In an analogous manner to Example 1E, step 1P 3-{4-[(3,4-dichlorophenyl)sulfonyl]piperazin-1-yl}pyrazine-2-carbonitrile was prepared from (3-piperazine-1-ly)pyperazine-2-carbonitrile (0.1 g, 0.53 mmol) and 3,4-dichlorobenzene sulfonyl chloride (75% yield).

1H NMR (400 MHz, CHLOROFORM-D) δ ppm 3.21-3.26 (m, 4H) 3.87 (t, 4H) 7.73 (s, 1H) 7.87 (t, J=2.15 Hz, 1H) 8.10 (d, J=2.27 Hz, 1H) 8.14 (d, J=2.27 Hz, 1H) 8.27 (d, J=2.27 Hz, 1H); HRMS: calcd for $C_{15}H_{13}Cl_2N_5O_2S+H+$, 398.02397. found (ESI-FTMS, $[M+H]^{1+}$), 398.0223.

Example 1U

1-[(3,4-dichlorophenyl)sulfonyl]-4-(3'-methoxybiphenyl-2-yl)piperazine

In an analogous manner to Example 1E, step 1P, 1-[(3,4-dichlorophenyl)sulfonyl]-4-(3'-methoxybiphenyl-2-yl)piperazine was prepared from (3-piperazine-1-ly)pyperazine-2-carbonitrile (0.1 g, 0.53 mmol) and 3,4-dichlorphenyl methyl sulfonyl chloride (18% yield).

1H NMR (400 MHz, CHLOROFORM-D) δ ppm 2.92 (s, 8H) 4.60 (d, J=5.56 Hz, 3H) 7.00 (d, J=8.08 Hz, 1H) 7.11 (t, J=6.95 Hz, 1H) 7.22-7.34 (m, 4H) 7.42 (d, J=7.33 Hz, 1H) 7.55 (d, J=8.34 Hz, 2H) 7.65 (d, J=8.59 Hz, 1H) 7.81 (s, 1H); HRMS: calcd for $C_{23}H_{22}Cl_2N_2O_3S+H+$, 477.08009. found (ESI-FTMS, $[M+H]^{1+}$), 477.0784.

Example 1V

N-[4-({4-[3-(trifluoromethyl)pyridin-2-yl]piperazin-1-yl}sulfonyl)phenyl]acetamide The desired product was obtained in 98% yield as white solid. 1H NMR (400 MHz, CHLOROFORM-D) δ ppm 2.13-2.33 (m, 3H) 3.07-3.23 (m, 4H) 3.26-3.45 (m, 4H) 6.99-7.08 (m, 1H) 7.46 (s, 1H) 7.66-7.80 (m, 4H) 7.85 (dd, J=7.71, 1.89 Hz, 1H) 8.42 (dd, J=4.80, 1.26 Hz, 1H). HRMS: calcd for $C_{18}H_{19}F_3N_4O_3S+H+$, 429.12027. found (ESI-FTMS, $[M+H]^{1+}$), 429.1207.

Example 1W

1-[(3,4-dimethoxyphenyl)sulfonyl]-4-[3-(trifluoromethyl 3 pyridin-2-yl]piperazine The desired product was obtained in 83% yield as white solid. 1H NMR (400 MHz, CHLOROFORM-D) δ ppm 3.09-3.24 (m, 4H) 3.26-3.42 (m, 4H) 3.85-4.09 (m, 6H) 6.99 (d, J=8.59 Hz, 1H) 7.03 (dd, J=7.83, 4.80 Hz, 1H) 7.24 (d, J=2.02 Hz, 1H) 7.41 (dd, J=8.46, 2.15 Hz, 1H). HRMS: calcd for $C_{18}H_{20}F_3N_3O_4S+H+$, 432.11994. found (ESI-FTMS, $[M+H]^{1+}$), 432.1212.

Example 1X

1-[(2,4-difluorophenyl)sulfonyl]-4-[3-(trifluoromethyl)pyridin-2-yl]piperazine

The desired product was obtained in 100% yield as white solid. 1H NMR (400 MHz, CHLOROFORM-D) δ ppm 3.31-3.39 (m, 4H) 3.39-3.47 (m, 4H) 7.01-7.12 (m, 3H) 7.50-7.60 (m, 1H) 7.88 (dd, J=7.83, 2.02 Hz, 1H) 8.45 (dd, J=4.80, 1.26 Hz, 1H). HRMS: calcd for $C_{16}H_{14}F_5N_3O_2S+H+$, 408.07996. found (ESI-FTMS, $[M+H]^{1+}$), 408.0811.

Example 1Y 1-(2-naphthylsulfonyl)-4-[3-(trifluoromethyl)pyridin-2-yl]piperazine The desired product was obtained in 92% yield as white solid. 1H NMR (400 MHz, CHLOROFORM-D) δ ppm 3.16-3.31 (m, 4H) 3.32-3.50 (m, 4H) 6.97-7.10 (m, 1H) 7.58-7.73 (m, 2H) 7.76-7.87 (m, 2H) 7.95 (d, 1H) 8.01 (d, 2H) 8.35-8.46 (m, 2H). HRMS: calcd for $C_{20}H_{18}F_3N_3O_2S+H+$, 422.11446. found (ESI-FTMS, $[M+H]^{1+}$), 422.1145.

Example 1Z 1-(1-benzothien-2-ylsulfonyl)-4-[3-(trifluoromethyl)pyridin-2-yl]piperazine The desired product was obtained in 100% yield as white solid. 1H NMR (400 MHz, CHLOROFORM-D) δ ppm 3.23-3.49 (m, 8H) 6.97-7.10 (m, 1H) 7.40-7.59 (m, 2H) 7.75-7.99 (m, 4H) 8.43 (dd, J=4.80, 1.77 Hz, 1H). HRMS: calcd for $C_{18}H_{16}F_3N_3O_2S_2+H+$, 428.07088. found (ESI-FTMS, $[M+H]^{1+}$), 428.0716.

Example 1AA 1-(1-benzothien-3-ylsulfonyl)-4-[3-(trifluoromethyl)pyridin-2-yl]piperazine The desired product was obtained in 80% yield as white solid. 1H NMR (400 MHz, CHLOROFORM-D) δ ppm 3.21-3.41 (m, 8H) 7.02 (dd, J=7.45, 5.18 Hz, 1H) 7.43-7.59 (m, 2H) 7.84 (dd, J=7.58, 1.77 Hz, 1H) 7.92 (d, J=7.07, 1.01 Hz, 1H) 8.21 (s, 1H) 8.29 (dd, 1H) 8.41 (dd, J=4.80, 1.26 Hz, 1H). HRMS: calcd for $C_{18}H_{16}F_3N_3O_2S_2+H+$, 428.07088. found (ESI-FTMS, $[M+H]^{1+}$), 428.072.

Example 1AB 1-(dibenzo[b,d]furan-3-ylsulfonyl)-4-[3-(trifluoromethyl)pyridin-2-yl]piperazine The desired product was obtained in 61% yield as white solid. 1H NMR (400 MHz, CHLOROFORM-D) δ ppm 3.16-3.30 (m, 4H) 3.29-3.46 (m, 4H) 7.01 (dd, J=7.33, 4.29 Hz, 1H) 7.43 (t, 1H) 7.58 (t, 1H) 7.65 (d, 1H) 7.75-7.88 (m, 2H) 8.01-8.07 (m, 2H) 8.12 (d, J=8.08 Hz, 1H) 8.41 (dd, J=4.80, 1.26 Hz, 1H). HRMS: calcd for $C_{22}H_{18}F_3N_3O_3S+H+$, 462.10937. found (ESI-FTMS, $[M+H]^{1+}$), 462.1102.

Example 1AC

1-[(2,4-difluorophenyl)sulfonyl]-4-(3-methylpyridin-2-yl)piperazine

The desired product was obtained in 100% yield as white solid. 1H NMR (400 MHz, CHLOROFORM-D) δ ppm 2.23 (s, 3H) 3.11-3.30 (m, 4H) 3.37-3.57 (m, 4H) 6.88 (dd, J=7.45, 4.93 Hz, 1H) 7.06 (t, J=8.46 Hz, 2H) 7.41 (d, J=7.45, 1.14 Hz, 1H) 7.48-7.61 (m, 1H) 8.14 (dd, J=4.80, 1.26 Hz, 1H). HRMS: calcd for $C_{16}H_{17}F_2N_3O_2S+H+$, 354.10823. found (ESI-FTMS, $[M+H]^{1+}$), 354.1084.

Example 1AD

1-[(3,4-dichlorobenzyl)sulfonyl]-4-(3-methylpyridin-2-yl)piperazine

The desired product was obtained in 70% yield as white solid. 1H NMR (400 MHz, CHLOROFORM-D) δ ppm 2.25 (s, 3H) 3.07-3.29 (m, 4H) 3.24-3.45 (m, 4H) 6.86-6.94 (m, J=7.33, 4.80 Hz, 1H) 7.27-7.30 (m, J=8.21, 2.15 Hz, 1H) 7.42 (dd, J=7.33, 1.01 Hz, 1H) 7.47 (d, J=8.34 Hz, 1H) 7.54 (d, J=2.27 Hz, 1H) 8.16 (dd, J=4.93, 1.39 Hz, 1H). HRMS: calcd for $C_{17}H_{19}Cl_2N_3O_2S$+H+, 400.06478. found (ESI-FTMS, [M+H]$^{1+}$), 400.0653.

Example 1AE 1-(3-methylpyridin-2-yl)-4-(2-naphthylsulfonyl)piperazine

The desired product was obtained in 100% yield as white solid. 1H NMR (400 MHz, CHLOROFORM-D) δ ppm 2.10-2.19 (m, 3H) 3.16-3.41 (m, 8H) 6.85 (dd, J=7.33, 4.80 Hz, 1H) 7.36 (dd, J=7.33, 1.01 Hz, 1H) 7.59-7.73 (m, 2H) 7.81 (dd, J=8.72, 1.89 Hz, 1H) 7.95 (d, J=7.83 Hz, 1H) 8.01 (d, J=9.09 Hz, 2H) 8.11 (dd, J=4.80, 1.26 Hz, 1H) 8.39 (d, J=1.01 Hz, 1 H). HRMS: calcd for $C_{20}H_{21}N_3O_2S$+H+, 368.14272. found (ESI-FTMS, [M+H]$^{1+}$), 368.1436.

Example 1AF 1-(1-benzothien-2-ylsulfonyl)-4-(3-methylpyridin-2-yl)piperazine The desired product was obtained in 100% yield as white solid. 1H NMR (400 MHz, CHLOROFORM-D) δ ppm 2.13-2.26 (m, 3H) 3.29 (d, 8H) 6.87 (dd, J=7.33, 4.80 Hz, 1H) 7.38 (dd, J=7.33, 1.01 Hz, 1H) 7.45-7.57 (m, 2H) 7.85 (s, 1H) 7.87-7.96 (m, 2H) 8.13 (dd, J=5.18, 1.64 Hz, 1H). HRMS: calcd for $C_{18}H_{19}N_3O_2S_2$+H+, 374.09914. found (ESI-FTMS, [M+H]$^{1+}$), 374.0998.

Example 1AG 1-(1-benzothien-3-ylsulfonyl)-4-(3-methylpyridin-2-yl)piperazine The desired product was obtained in 100% yield as white solid. 1H NMR (400 MHz, CHLOROFORM-D) δ ppm 2.11-2.23 (m, 3H) 3.11-3.29 (m, 4H) 3.26-3.44 (m, 4H) 6.86 (t, J=7.33, 4.80 Hz, 1H) 7.37 (dd, J=7.33, 1.26 Hz, 1H) 7.44-7.59 (m, 2H) 7.92 (dd, J=7.07, 1.01 Hz, 1H) 8.22 (s, 1H) 8.31 (dd, 1H). HRMS: calcd for $C_{18}H_{19}N_3O_2S_2$+H+, 374.09914. found (ESI-FTMS, [M+H]$^{1+}$), 374.1004.

Example 1AH

1-[(2-chlorophenyl)sulfonyl]-4-(3-methylpyridin-2-yl)piperazine

The desired product was obtained in 73% yield as white solid. 1H NMR (400 MHz, CHLOROFORM-D) δ ppm 2.24 (s, 1H) 3.07-3.26 (m, 4H) 3.38-3.56 (m, 4H) 6.88 (dd, J=7.45, 4.93 Hz, 1H) 7.38-7.45 (m, 2H) 7.46-7.61 (m, 2H) 8.09 (dd, J=7.83, 1.77 Hz, 1H) 8.14 (dd, J=4.80, 1.26 Hz, 1H). HRMS: calcd for $C_{16}H_{18}ClN_3O_2S$+H+, 352.08810. found (ESI-FTMS, [M+H]$^{1+}$), 352.0883.

Example 1AI 1-(dibenzo[b,d]furan-3-ylsulfonyl)-4-(3-methylpyridin-2-yl)piperazine The desired product was obtained in 78% yield as white solid. 1H NMR (400 MHz, CHLOROFORM-D) δ ppm 2.07-2.19 (m, 3H) 3.17-3.34 (m, 8H) 6.85 (dd, J=7.33, 5.05 Hz, 1 H) 7.35 (dd, J=7.33, 1.26 Hz, 1H) 7.44 (t, 1H) 7.58 (t, 1H) 7.65 (dd, 1H) 7.81 (dd, J=8.08, 1.52 Hz, 1H) 8.01-8.06 (m, 2H) 8.08-8.16 (m, 2H). HRMS: calcd for $C_{22}H_{21}N_3O_3S$+H+, 408.13764. found (ESI-FTMS, [M+H]$^{1+}$), 408.1388.

Example 1AJ

1-[(3,4-dichlorophenyl)sulfonyl]-4-(3-methylpyridin-2-yl)piperazine

The desired product was obtained in 94% yield as white solid. 1H NMR (400 MHz, CHLOROFORM-D) δ ppm 2.11-2.26 (m, 3H) 3.08-3.35 (m, 8H) 6.75-6.95 (m, J=7.33, 4.80 Hz, 1H) 7.40 (dd, J=7.45, 1.14 Hz, 1H) 7.59-7.68 (m, 2H) 7.89 (d, J=1.77 Hz, 1H) 8.14 (dd, J=4.67, 1.64 Hz, 1H), HRMS: calcd for $C_{16}H_{17}Cl_2N_3O_2S$+H+, 386.04913. found (ESI-FTMS, [M+H]$^{1+}$), 386.0484.

Example 1AK 1-(3-methylpyridin-2-yl)-4-{[2-(trifluoromethyl)phenyl]sulfonyl}piperazine The desired product was obtained in 68% yield as white solid. 1H NMR (400 MHz, CHLOROFORM-D) δ ppm 2.23 (s, 3H) 3.13-3.26 (m, 4H) 3.35-3.49 (m, 4H) 6.85-6.93 (m, J=7.20, 4.67 Hz, 1H) 7.40 (dd, J=7.33, 1.01 Hz, 1H) 7.66-7.76 (m, 2H) 7.92 (dd, 1H) 8.11-8.20 (m, 2H). HRMS: calcd for $C_{17}H_{18}F_3N_3O_2S$+H+, 386.11446. found (ESI-FTMS, [M+H]$^{1+}$), 386.115.

Example 1AL

1-[(4-chlorophenyl)sulfonyl]-4-(3-methylpyridin-2-yl)piperazine

The desired product was obtained in 63% yield as white solid. 1H NMR (400 MHz, CHLOROFORM-D) δ ppm 2.18 (s, 3H) 3.11-3.30 (m, 8H) 6.83-6.92 (m, J=7.20, 4.93 Hz, 1H) 7.40 (d, J=1.01 Hz, 1H) 7.51-7.59 (m, 2H) 7.71-7.78 (m, 2H) 8.13 (dd, J=4.80, 1.26 Hz, 1H). HRMS: calcd for $C_{16}H_{18}ClN_3O_2S$+H+, 352.08810. found (ESI-FTMS, [M+H]$^{1+}$), 352.0879.

Example 1AM 1-(dibenzo[b,d]thien-3-ylsulfonyl)-4-[3-(trifluoromethyl)pyridin-2-yl]piperazine The desired product was obtained in 90% yield as white solid. 1H NMR (400 MHz, CHLOROFORM-D) δ ppm 3.16-3.29 (m, 4H) 3.30-3.42 (m, 4H) 6.97-7.05 (m, J=7.83, 4.80 Hz, 1H) 7.49-7.62 (m, 2H) 7.79-7.88 (m, 2H) 7.92 (dd, J=6.57, 1.26 Hz, 1H) 8.25 (dd, 1H) 8.28-8.35 (m, 2H) 8.41

(dd, J=4.80, 1.26 Hz, 1H). HRMS: calcd for $C_{22}H_{18}F_3N_3O_2S_2$+H+, 478.08653. found (ESI-FTMS, [M+H]$^{1+}$), 478.0881.

Example 1AN

1-[(3,5-dimethylisoxazol-4-yl)sulfonyl]-4-[3-(trifluoromethyl)pyridin-2-yl]piperazine The desired product was obtained in 65% yield as white solid. 1H NMR (400 MHz, CHLOROFORM-D) δ ppm 2.43-2.46 (m, 3H) 2.65-2.70 (m, 3H) 3.24-3.31 (m, 4H) 3.31-3.38 (m, 4H) 7.05-7.13 (m, J=7.83, 4.80 Hz, 1H) 7.90 (dd, J=7.83, 2.02 Hz, 1H) 8.46 (dd, J=4.55, 1.52 Hz, 1H). HRMS: calcd for $C_{15}H_{17}F_3N_4O_3S$+H+, 391.10462. found (ESI-FTMS, [M+H]$^{1+}$), 391.1061.

Example 1AO 1-(dibenzo[b,d]furan-2-ylsulfonyl)-4-[3-(trifluoromethyl)pyridin-2-yl]piperazine The desired product was obtained in 90% yield as white solid. 1H NMR (400 MHz, CHLOROFORM-D) δ ppm 3.17-3.30 (m, 4H) 3.31-3.43 (m, 4H) 6.98-7.08 (m, 1H) 7.44 (t, 1H) 7.56 (t, 1H) 7.64 (d, 1H) 7.74 (d, J=9.35 Hz, 1H) 7.84 (dd, J=7.83, 1.77 Hz, 1H) 7.91 (dd, J=8.72, 1.89 Hz, 1H) 8.04 (d, J=7.83 Hz, 1H) 8.41 (d, J=4.80, 1.26 Hz, 1H) 8.43 (d, J=1.26 Hz, 1H). HRMS: calcd for $C_{22}H_{18}F_3N_3O_3S$+H+, 462.10937. found (ESI-FTMS, [M+H]$^{1+}$), 462.1081.

Example AP 1-(biphenyl-4-ylsulfonyl)-4-[3-(trifluoromethyl)pyridin-2-yl]piperazine The desired product was obtained in 92% yield as white solid. 1H NMR (400 MHz, CHLOROFORM-D) δ ppm 3.16-3.34 (m, 4H) 3.32-3.47 (m, 4H) 7.01-7.09 (m, J=7.71, 4.93 Hz, 1H) 7.41-7.48 (m, 1H) 7.48-7.56 (m, 1H) 7.66 (d, 2H) 7.79 (d, 2H) 7.88 (d, 3H) 8.45 (dd, J=4.55, 1.52 Hz, 1H). HRMS: calcd for $C_{22}H_{20}F_3N_3O_2S$+H+, 448.13011. found (ESI-FTMS, [M+H]$^{1+}$), 448.1279.

Example 1AQ

1-[(2-chlorobenzyl)sulfonyl]-4-[3-(trifluoromethyl)pyridin-2-yl]piperazine

The desired product was obtained in 58% yield as white solid. 1H NMR (400 MHz, CHLOROFORM-D) δ ppm 3.20-3.28 (m, 4H) 3.28-3.36 (m, 4H) 4.44-4.49 (m, 2H) 6.98-7.09 (m, 1H) 7.28-7.34 (m, 2H) 7.39-7.45 (m, 1H) 7.57-7.63 (m, 1H) 7.87 (dd, J=7.71, 1.89 Hz, 1H) 8.42 (dd, J=4.80, 1.26 Hz, 1H). HRMS: calcd for $C_{17}H_{17}ClF_3N_3O_2S$+H+, 420.07548. found (ESI-FTMS, [M+H]$^{1+}$), 420.0742.

Example 1AR

1-[(4'-fluorobiphenyl-4-yl)sulfonyl]-4-[3-(trifluoromethyl)pyridin-2-yl]piperazine The desired product was obtained in 94% yield as white solid. 1H NMR (400 MHz, CHLOROFORM-D) δ ppm 3.15-3.29 (m, 4H) 3.32-3.45 (m, 4H) 7.04 (dd, J=7.71, 4.93 Hz, 1H) 7.13-7.22 (m, 2H) 7.55-7.64 (m, 2H) 7.67-7.76 (m, 2H) 7.82-7.91 (m, 3H) 8.43 (dd, J=4.93, 1.39 Hz, 1H). HRMS: calcd for $C_{22}H_{19}F_4N_3O_2S$+H+, 466.12068. found (ESI-FTMS, [M+H]$^{1+}$), 466.119.

Example 1AS 1-(dibenzo[b,d]thien-2-ylsulfonyl)-4-[3-(trifluoromethyl)pyridin-2-yl]piperazine The desired product was obtained in 95% yield as white solid. 1H NMR (400 MHz, CHLOROFORM-D) δ ppm 3.19-3.29 (m, 4H) 3.37-3.45 (m, 4H) 6.98-7.06 (m, J=6.95, 4.93 Hz, 1H) 7.50-7.61 (m, 2H) 7.80-7.88 (m, 2H) 7.88-7.94 (m, 1H) 8.03 (d, J=9.09 Hz, 1H) 8.41 (dd, J=5.05, 1.26 Hz, 1H) 8.57 (d, J=1.26 Hz, 1H). HRMS: calcd for $C_{22}H_{18}F_3N_3O_2S_2$+H+, 478.08653. found (ESI-FTMS, [M+H]$^{1+}$), 478.0862.

Example 1AT

1-[(5-chloro-3-methyl-1-benzothien-2-yl)sulfonyl]-4-[3-(trifluoromethyl)pyridin-2-yl]piperazine The desired product was obtained in 98% yield as white solid. 1H NMR (400 MHz, CHLOROFORM-D) δ ppm 2.71 (s, 3H) 3.37 (s, 8H) 7.05 (t, 1H) 7.47 (dd, J=8.59, 2.02 Hz, 1H) 7.77 (d, J=8.34 Hz, 1H) 7.81-7.90 (m, 2H) 8.43 (dd, J=4.80, 1.26 Hz, 1H). HRMS: calcd for $C_{19}H_{17}ClF_3N_3O_2S_2$+H+, 476.04755. found (ESI-FTMS, [M+H]$^{1+}$), 476.0475.

Example 1AU

1-[(2-chlorophenyl)sulfonyl]-4-[2-(trifluoromethyl)phenyl]piperazine

In an analogous manner to Example 1E, step 1P 1-[(2-chlorophenyl)sulfonyl]-4-[2-(trifluoromethyl)phenyl]piperazine was prepared from 1-(2-trifluoromethylphenyl)piperazine (0.1 g, 0.43 mmol) and 2-chlorobenzyl sulfonyl chloride (73% yield).

1H NMR (400 MHz, CHLOROFORM-D) δ ppm 2.94-3.01 (m, 4H) 3.45 (d, J=4.29 Hz, 4H) 7.22-7.30 (m, 1H) 7.35 (d, J=7.83 Hz, 1H) 7.42 (t, J=8.08 Hz, 1H) 7.47-7.59 (m, 3H) 7.63 (d, J=8.08 Hz, 1H) 8.08 (d, J=7.83 Hz, 1H); HRMS: calcd for $C_{17}H_{16}ClF_3N_2O_2S$+H+, 405.06458. found (ESI-FTMS, [M+H]$^{1+}$), 405.0648.

Example 1AV 2-({4-[3-(trifluoromethyl)pyridin-2-yl]piperazin-1-yl}sulfonyl)-1,3-benzothiazole The desired product was obtained in 30% yield as white solid. 1H NMR (400 MHz, CHLOROFORM-D) δ ppm 3.23-3.39 (m, 4H) 3.44-3.62 (m, 4H) 6.94-7.01 (m, J=7.83, 4.80 Hz, 1H) 7.44-7.60 (m, 2H) 8.15 (d, J=7.33 Hz, 1H) 8.36 (dd, J=4.80, 1.26 Hz, 1H). HRMS: calcd for $C_{17}H_{15}F_3N_4O_2S_2$+H+, 429.06613. found (ESI-FTMS, [M+H]$^{1+}$), 429.0661.

Example 1AW 1-(dibenzo[b,d]furan-2-ylsulfonyl)-4-(3-methylpyridin-2-yl)piperazine The desired product was obtained in 91% yield as white solid. HRMS: calcd for $C_{22}H_{21}N_3O_3S$+H+, 408.13764. found (ESI-FTMS, [M+H]$^{1+}$), 408.137. 1H NMR (400 MHz, CHLOROFORM-D) δ ppm 2.07-2.20 (m, 3H) 3.14-3.34 (m, 8H) 6.80-6.89 (m, J=7.33, 4.80 Hz, 3H) 7.35 (dd, J=7.33, 1.26 Hz, 1H) 7.44 (t, 1H) 7.56 (t, 1H) 7.64 (d, 1H) 7.73 (d, J=8.34 Hz, 1H) 7.92 (dd, J=8.72, 1.89 Hz, 1H) 8.03 (d, J=7.07 Hz, 1H) 8.11 (dd, J=4.93, 1.39 Hz, 1H) 8.44 (d, J=1.52 Hz, 1H).

Example 1AX 1-(dibenzo[b,d]thien-2-ylsulfonyl)-4-(3-methylpyridin-2-yl)piperazine The desired product was obtained in 94% yield as white solid. 1H NMR (400 MHz, CHLOROFORM-D) δ ppm 2.07-2.19 (m, 3H) 3.15-3.31 (m, 8H) 6.84 (dd, J=7.33, 4.80 Hz, 1H) 7.35 (dd, J=7.33, 1.01 Hz, 1H) 7.50-7.61 (m, 2H) 7.86 (dd, J=8.59, 1.77 Hz, 1H) 7.89-7.95 (m, 1H) 8.03 (d, J=8.34 Hz, 1H) 8.11 (dd, J=4.93, 1.39 Hz, 1H) 8.24-8.32 (m, 1H) 8.59 (d, J=1.26 Hz, 1H). HRMS: calcd for $C_{22}H_{21}N_3O_2S_2$+H+, 424.11479. found (ESI-FTMS, [M+H]$^{1+}$), 424.1152.

Example 1AY 1-(dibenzo[b,d]thien-3-ylsulfonyl)-4-(3-methylpyridin-2-yl)piperazine The desired product was obtained in 91% yield as white solid. 1H NMR (400 MHz, CHLOROFORM-D) δ ppm 2.10-2.17 (m, 8H) 6.82-6.89 (m, J=7.33, 5.05 Hz, 1H) 7.35 (dd, J=7.33, 1.26 Hz, 1H) 7.50-7.63 (m, 2H) 7.87 (dd, J=8.34, 1.52 Hz, 1H) 7.92 (dd, J=7.20, 1.89 Hz, 1H) 8.12 (dd, J=4.55, 1.52 Hz, 1H) 8.22-8.28 (m, 1H) 8.29-8.38 (m, 2H). HRMS: calcd for $C_{22}H_{21}N_3O_2S_2$+H+, 424.11479. found (ESI-FTMS, [M+H]$^{1+}$), 424.1137.

Example 1AZ 1-(biphenyl-4-ylsulfonyl)-4-(3-methylpyridin-2-yl)piperazine

The desired product was obtained in 95% yield as white solid. 1H NMR (400 MHz, CHLOROFORM-D) δ ppm 2.09-2.23 (m, 3H) 3.16-3.34 (m, 8H) 6.86 (dd, J=7.33, 5.05 Hz, 1 H) 7.38 (dd, J=6.95, 1.64 Hz, 1H) 7.39-7.45 (m, 1H) 7.45-7.54 (m, 2H) 7.58-7.67 (m, 2H) 7.72-7.80 (m, 2H) 7.81-7.91 (m, 2H) 8.13 (dd, J=4.93, 1.89 Hz, 1H). HRMS: calcd for $C_{22}H_{23}N_3O_2S$+H+, 394.15837. found (ESI-FTMS, [M+H]$^{1+}$), 394.1594.

Example 2

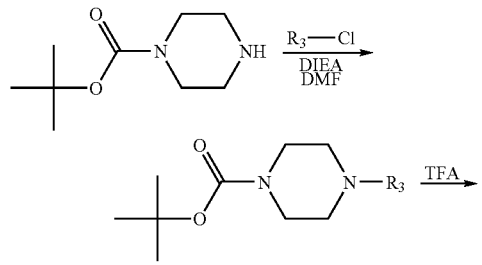

Scheme 2

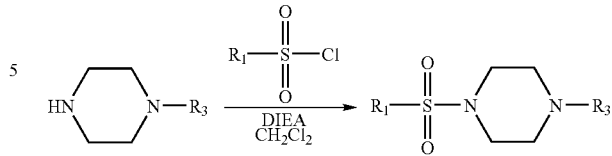

Example 2A

1-[(4-tert-butylphenyl)sulfonyl]-4-(3-chloropyridin-2-yl)piperazine

Step 2A: tert-butyl piperazine-1-carboxylate (1.0 g, 5.37 mmol) and 2,3-dichloropyridine (795 mg, 5.37 mmol) charged to a microwave vial was added with diisopropylethylamine (2.34 mL, 13.42 mmol) and DMF (1.0 mL). The reaction mixture was subject to microwave irradiation at 165° C. for 30 minutes. The reaction was repeated six times in order to scale up. Combined reaction mixture was partitioned between EtOAc and water, organic layer washed with brine and dried over MgSO$_4$. The crude product obtained by solvent evaporation was purified via flash column chromatography. tert-butyl 4-(3-chloropyridin-2-yl)piperazine-1-carboxylate was obtained in 20% yield (1.9 g) as yellow oil.

1H NMR (400 MHz, CHLOROFORM-D) δ ppm 1.49 (s, 9H) 3.26-3.34 (m, 4H) 3.53-3.64 (m, 4H) 6.86 (dd, J=7.71, 4.67 Hz, 1H) 7.60 (dd, J=7.83, 1.77 Hz, 1H) 8.18 (dd, J=4.80, 1.77 Hz, 1H). HRMS: calcd for $C_{14}H_{20}ClN_3O_2$+H+, 298.13168. found (ESI-FTMS, [M+H]$^{1+}$), 298.1319. HPLC Method 1: room temperature, 6.051 min, 97.69%, HPLC Method 2: room temperature, 7.085 min, 98.91%.

Step 2B: To a clear solution of tert-butyl 4-(3-chloropyridin-2-yl)piperazine-1-carboxylate in anhydrous dichloromethane (25 mL) was added TFA (25 mL) dropwise. The yellow solution was stirred at room temperature for 2.5 hour. Reaction was complete as determined by TLC. TFA was azeotropped with dichloroethane to give 1-(3-chloropyridin-2-yl)piperazine in quantitative yield (1.265 g).

1H NMR (400 MHz, DMSO-D6) δ ppm 3.19-3.32 (m, 4H) 3.39-3.51 (m, 4H) 7.10 (dd, J=7.83, 4.55 Hz, 2H) 7.87 (dd, J=7.83, 1.52 Hz, 2H) 8.27 (dd, J=4.80, 1.52 Hz, 2H) 8.87 (s, 1H).

Step 2C: To a stirred solution of 1-(3-chloropyridin-2-yl)piperazine (316 mg, 1.6 mmol) in anhydrous dichloromethane (5 mL) was added diisopropylethylamine (0.975 mL, 5.6 mmol) then 4-tert-butylbenzene-1-sulfonyl chloride (372.4 mg, 1.6 mmol). The mixture was stirred at room temperature for 1.5 hour. Reaction was complete as determined by TLC. The reaction mixture was purified with flash column chromatography to yield 1-[(4-tert-butylphenyl)sulfonyl]-4-(3-chloropyridin-2-yl)piperazine in 59.3% yield (374 mg) as white solid.

1H NMR (400 MHz, CHLOROFORM-D) δ ppm 1.36 (s, 9H) 3.17-3.25 (m, 4H) 3.39-3.47 (m, 4H) 6.86 (dd, J=7.71, 4.67 Hz, 1H) 7.52-7.60 (m, 3H) 7.68-7.75 (m, 2H) 8.16 (dd, J=4.80, 1.52 Hz, 1H). HRMS: calcd for $C_{19}H_{24}ClN_3O_2S$+H+, 394.13505. found (ESI-FTMS, [M+H]$^{1+}$), 394.1358. HPLC Method 1: room temperature, 6.924 min, 99.05%, HPLC Method 2: room temperature, 7.499 min, 99.48%.

Example 2B 1-(3-chloropyridin-2-yl)-4-(2-naphthylsulfonyl)piperazine

Step 2C: Sulfonylation of 1-(3-chloropyridin-2-yl)piperazine (632 mg, 3.2 mmol) with naphthalene-2-sulfonyl chloride (725 mg, 3.2 mmol) was carried out according to a similar procedure described for example 2A (except that the sulfonyl chloride was added before the diisopropylethylamine) using anhydrous dichloromethane (10 mL) as solvent and diisopropylethylamine (1.4 mL, 8.0 mmol) as base. 1-(3-chloropyridin-2-yl)-4-(2-naphthylsulfonyl)piperazine was obtained in 17.0% yield (210.2 mg) as white solid.

1H NMR (400 MHz, CHLOROFORM-D) δ ppm 3.21-3.32 (m, 4H) 3.41-3.50 (m, 4H) 6.87 (dd, J=7.83, 4.80 Hz, 1H) 7.51-7.72 (m, 3H) 7.79 (dd, J=8.72, 1.89 Hz, 1H) 7.91-7.98 (m, 1H) 8.01 (d, J=8.34 Hz, 2H) 8.17 (dd, J=4.80, 1.77 Hz, 1H) 8.38 (d, J=1.77 Hz, 1H). HRMS: calcd for $C_{19}H_{18}ClN_3O_2S+H+$, 388.08810. found (ESI-FTMS, $[M+H]^{1+}$), 388.0885. HPLC Method 1: room temperature, 6.432 min, 99.82%, HPLC Method 2: room temperature, 7.178 min, 99.6%.

Example 2C 1-(3-chloropyridin-2-yl)-4-(1-naphthylsulfonyl)piperazine

Step 2C: Sulfonylation of 1-(3-chloropyridin-2-yl)piperazine (316 mg, 1.6 mmol) with naphthalene-1-sulfonyl chloride (362.7 mg, 1.6 mmol) was carried out according to a similar procedure described for example 2A (Except sulfonyl chloride was added before diisopropylethylamine) using anhydrous dichloromethane (3 mL) as solvent and diisopropylethylamine (1.4 mL, 8.0 mmol) as base. 1-(3-chloropyridin-2-yl)-4-(1-naphthylsulfonyl)piperazine was obtained in 70.0% yield (434.0 mg) as white solid.

1H NMR (400 MHz, DMSO-D6) δ ppm 3.25 (s, 8H) 7.00 (dd, J=7.71, 4.67 Hz, 1H) 7.63-7.82 (m, 4H) 8.08-8.22 (m, 3H) 8.33 (d, J=8.34 Hz, 1H) 8.73 (d, J=7.83 Hz, 1H). HRMS: calcd for $C_{19}H_{18}ClN_3O_2S+H+$, 388.08810. found (ESI-FTMS, $[M+H]^{1+}$), 388.0886. HPLC Method 1: room temperature, 6.476 min, 100%, HPLC Method 2: room temperature, 7.149 min, 100.0%.

Example 2D

1-[(2-chlorophenyl)sulfonyl]-4-(3-chloropyridin-2-yl)piperazine

Preparation of 1-[(2-chlorophenyl)sulfonyl]-4-(3-chloropyridin-2-yl)piperazine was carried out according to a similar procedure described for example 2A. Yield 75%.

1H NMR (400 MHz, CHLOROFORM-D) δ ppm 3.36-3.44 (m, 4H) 3.44-3.55 (m, 4H) 6.78-6.93 (m, J=7.83, 4.80 Hz, 1H) 7.38-7.46 (m, 1H) 7.47-7.52 (m, 1H) 7.52-7.56 (m, 1H) 7.59 (dd, J=7.71, 1.64 Hz, 1H) 8.09 (d, J=7.83 Hz, 1H) 8.17 (d, J=4.80 Hz, 1H). HRMS: calcd for $C_{15}H_{15}Cl_2N_3O_2S+H+$, 372.03348. found (ESI-FTMS, $[M+H]^{1+}$), 372.0355.

Example 2E

1-[(4-chlorophenyl)sulfonyl]-4-(3-chloropyridin-2-yl)piperazine

Preparation of 1-[(4-chlorophenyl)sulfonyl]-4-(3-chloropyridin-2-yl)piperazine was carried out according to a similar procedure described for example 2A. Yield 78%.

1H NMR (400 MHz, CHLOROFORM-D) δ ppm 3.20 (br s, 4H) 3.43 (br s, 4H) 6.58-7.04 (m, 1H) 7.10-7.40 (m, 1H) 7.41-7.96 (m, 4H) 8.17 (s, 1H). HRMS: calcd for $C_{15}H_{15}Cl_2N_3O_2S+H+$, 372.03348. found (ESI-FTMS, $[M+H]^{1+}$), 372.0345. HPLC Method 1, room temperature, 6.00 min, 97.89%; HPLC Method 2, room temperature, 6.99 min, 97.48%.

Example 2F 1-(3-chloropyridin-2-yl)-4-[(4-methylphenyl)sulfonyl]piperazine

Preparation of 1-(3-chloropyridin-2-yl)-4-[(4-methylphenyl)sulfonyl]piperazine was carried out according to a similar procedure described for example 2A. Yield 78%.

1H NMR (400 MHz, DMSO-D6) δ ppm 2.42 (s, 3H) 2.88-3.18 (m, 4H) 3.20-3.45 (m, 4H) 6.74-7.21 (m, J=7.58 Hz, 1H) 7.49 (d, J=8.08 Hz, 2H) 7.67 (d, J=8.08 Hz, 2H) 7.79 (d, J=7.58 Hz, 1H) 8.20 (d, J=4.55 Hz, 1H). HRMS: calcd for $C_{16}H_{18}ClN_3O_2S+H+$, 352.08810. found (ESI-FTMS, $[M+H]^{1+}$), 352.0897.

Example 2G 1-(3-chloropyridin-2-yl)-4-[(4-methoxyphenyl)sulfonyl]piperazine

Preparation of 1-(3-chloropyridin-2-yl)-4-[(4-methoxyphenyl)sulfonyl]piperazine was carried out according to a similar procedure described for example 2A. Yield 75%.

1H NMR (400 MHz, CHLOROFORM-D) δ ppm 2.99-3.28 (m, 4H) 3.36-3.51 (m, 4H) 3.89 (s, 3H) 6.87 (d, J=4.80 Hz, 1H) 6.98-7.07 (m, 2H) 7.56 (d, J=1.77 Hz, 1H) 7.67-7.84 (m, 2H) 8.16 (dd, J=4.67, 1.64 Hz, 1H). HRMS: calcd for $C_{16}H_{18}ClN_3O_3S+H+$, 368.08301. found (ESI-FTMS, $[M+H]^{1+}$), 368.0839.

Example 2H 1-(biphenyl-4-ylsulfonyl)-4-(3-chloropyridin-2-yl)piperazine

Preparation of 1-(biphenyl-4-ylsulfonyl)-4-(3-chloropyridin-2-yl)piperazine was carried out according to a similar procedure described for example 2A. Yield 75%.

1H NMR (400 MHz, CHLOROFORM-D) δ ppm 3.25 (d, J=8.84 Hz, 4H) 3.38-3.59 (m, J=8.84 Hz, 4H) 6.74-6.97 (m, 1H) 7.33-7.54 (m, 3H) 7.57 (d, J=7.83 Hz, 1H) 7.59-7.68 (m, J=8.08 Hz, 2H) 7.71-7.81 (m, 2H) 7.82-7.99 (m, 2H) 8.16 (d, J=4.80 Hz, 1H). HRMS: calcd for $C_{21}H_{20}ClN_3O_2S+H+$, 414.10375. found (ESI-FTMS, $[M+H]^{1+}$), 414.1042.

Example 2I 1-(benzylsulfonyl)-4-(3-chloropyridin-2-yl)piperazine

Preparation of 1-(benzylsulfonyl)-4-(3-chloropyridin-2-yl)piperazine was carried out according to a similar procedure described for example 2A. Yield 75%.

1H NMR (400 MHz, CHLOROFORM-D) δ ppm 3.11-3.56 (m, 8H) 4.26 (s, 2H) 6.91 (dd, J=7.83, 4.80 Hz, 1H) 7.32-7.55 (m, 5H) 7.64 (d, J=7.83 Hz, 1H) 8.20 (d, J=4.80 Hz, 1H). HRMS: calcd for $C_{16}H_{18}ClN_3O_2S+H+$, 352.08810. found (ESI-FTMS, $[M+H]^{1+}$), 352.0881.

Example 2J

1-{[2-bromo-4-(trifluoromethyl)phenyl]sulfonyl}-4-(3-chloropyridin-2-yl)piperazine Preparation of 1-{[2-bromo-4-(trifluoromethyl)phenyl]sulfonyl}-4-(3-chloropyridin-2-yl)piperazine was carried out according to a similar procedure described for example 2A. Yield 75%.

1H NMR (400 MHz, CHLOROFORM-D) δ ppm 3.38-3.46 (m, J=4.80 Hz, 4H) 3.48-3.58 (m, J=4.80 Hz, 4H) 6.73-7.04 (m, 1H) 7.60 (d, J=7.58 Hz, 1H) 7.73 (d, J=8.08 Hz, 1H) 8.02 (s, 1H) 8.18 (d, J=4.80 Hz, 1H) 8.25 (d, J=8.08 Hz, 1H). HRMS: calcd for $C_{16}H_{14}BrClF_3N_3O_2S+H+$, 483.97035. found (ESI-FTMS, $[M+H]^{1+}$), 483.9716.

Example 2K

1-{[4-(benzyloxy)phenyl]sulfonyl}-4-[3-(trifluoromethyl)pyridin-2-yl]piperazine

Step 2A: tert-butyl piperazine-1-carboxylate (3.0 g, 16.11 mmol) and 2-chloro-3-trifluoromethyl pyridine (2.93 g, 16.11 mmol) charged to a microwave vial was added with diisopropylethylamine (7.05 mL, 40.28 mmol) and DMF (1.0 mL). The reaction mixture was subject to microwave irradiation at 160° C. for 30 minutes. The reaction mixture was partitioned between EtOAc and water, organic layer washed with brine and dried over $Na_2SO_4$. The crude product obtained by solvent evaporation was purified via flash column chromatography. 4-(3-trifluoromethyl-pyridin-2-yl)-piperazine-1-carboxylic acid tert-butyl ester was obtained in 33.9% yield (1.81 g) as light yellow oil.

1H NMR (400 MHz, CHLOROFORM-D) δ ppm 1.48 (s, 9H) 3.18-3.27 (m, 4H) 3.53-3.61 (m, 4H) 7.00-7.06 (m, 1H) 7.88 (dd, J=7.83, 1.77 Hz, 1H) 8.44 (dd, J=4.80, 1.26 Hz, 1H).

Step 2B: To a clear solution of 4-(3-trifluoromethyl-pyridin-2-yl)-piperazine-1-carboxylic acid tert-butyl ester in anhydrous dichloromethane (15 mL) was added TFA (8 mL) dropwise. The yellow solution was stirred at room temperature for 2.5 hour. Reaction was complete as determined by TLC. TFA was removed under reduced pressure. The residue was redissolved in dichloromethane (50 mL), and washed with sat. $K_2CO_3$ solution first, then washed with brine and dried over $Na_2SO_4$, filtered and concentrated down to give 1-(3-trifluoromethyl-pyridin-2-yl)-piperazine as a light yellow oil (1.19 g, 96.0% yield).

1H NMR (400 MHz, CHLOROFORM-D) δ ppm 1.60 (s, 1H) 2.93-3.08 (m, 4H) 3.17-3.36 (m, 4H) 6.97 (dd, J=7.20, 4.67 Hz, 1H) 7.85 (dd, J=7.83, 1.77 Hz, 1H) 8.37-8.52 (m, 1H).

Step 2C: To a stirred solution of 1-(3-trifluoromethyl-pyridin-2-yl)-piperazine (100 mg, 0.39 mmol) in anhydrous dichloromethane (2 mL) was added 4-benzyloxy-benzenesulfonyl chloride (110.27 mg, 0.39 mmol) then diisopropylethylamine (0.17 mL, 0.98 mmol). The mixture was stirred at room temperature for 4 hour. Reaction was complete as determined by TLC. The reaction mixture was purified with flash column chromatography to yield 1-{[4-(benzyloxy)phenyl]sulfonyl}-4-[3-(trifluoromethyl)pyridin-2-yl]piperazine in 78.9% yield (147 mg) as white solid.

1H NMR (400 MHz, CHLOROFORM-D) δ ppm 3.12-3.20 (m, 4H) 3.32-3.39 (m, 4H) 5.14 (s, 2H) 7.00-7.06 (m, 1H) 7.07-7.13 (m, 2H) 7.34-7.47 (m, 5H) 7.70-7.77 (m, 2H) 7.85 (dd, J=7.83, 1.77 Hz, 1H) 8.43 (dd, J=4.80, 1.26 Hz, 1H). HRMS: calcd for $C_{23}H_{22}F_3N_3O_3S+H+$, 478.14067. found (ESI-FTMS, $[M+H]^{1+}$), 478.1398. HPLC Method 1: room temperature, 6.793 min, 99.02%; HPLC Method 2: room temperature, 7.419 min, 99.60%.

Example 2L

N-[4-({4-[3-(trifluoromethyl)pyridin-2-yl]piperazin-1-yl}sulfonyl)phenyl]morpholine-4-carboxamide The title compound was prepared according to a similar procedure for Example 2A, step 2C. Yield 78.9%.

1H NMR (400 MHz, CHLOROFORM-D) δ ppm 3.12-3.19 (m, 4H) 3.31-3.37 (m, 4H) 3.48-3.56 (m, 4H) 3.72-3.81 (m, 4H) 6.55-6.60 (m, 1H) 7.03 (dd, J=7.71, 4.93 Hz, 1H) 7.52-7.59 (m, 2H) 7.68-7.75 (m, 2H) 7.85 (dd, J=7.83, 2.02 Hz, 1H) 8.42 (dd, J=4.80, 1.77 Hz, 1H). HRMS: calcd for $C_{21}H_{24}F_3N_5O_4S+H+$, 500.15738. found (ESI-FTMS, $[M+H]^{1+}$), 500.1567. HPLC Method 1: room temperature, 5.217 min, 99.80%, HPLC Method 2: room temperature, 6.178 min, 99.84%.

Example 2M

1-{[4-(4-fluorophenoxy)phenyl]sulfonyl}-4-[3-(trifluoromethyl)pyridin-2-yl]piperazine The title compound was prepared according to a similar procedure for Example 2A, step 2C. Yield 89%.

1H NMR (400 MHz, CHLOROFORM-D) δ ppm 3.14-3.20 (m, 4H) 3.32-3.38 (m, 4H) 7.00-7.16 (m, 7H) 7.70-7.77 (m, 2H) 7.86 (dd, J=7.83, 1.77 Hz, 1H) 8.44 (dd, J=4.80, 1.77 Hz, 1H). HRMS: calcd for $C_{22}H_{19}F_4N_3O_3S+H+$, 482.11560. found (ESI-FTMS, $[M+H]^{1+}$), 482.1148. HPLC Method 1: room temperature, 6.823 min, 99.77%, HPLC Method 2: room temperature, 7.414 min, 97.29%.

Example 2N

3-[4-({4-[3-(trifluoromethyl)pyridin-2-yl]piperazin-1-yl}sulfonyl)phenoxy]propanenitrile The title compound was prepared according to a similar procedure for Example 2A, step 2C. Yield 55.7%.

1H NMR (400 MHz, CHLOROFORM-D) δ ppm 2.90 (t, J=6.32 Hz, 2H) 3.12-3.20 (m, 4H) 3.30-3.38 (m, 4H) 4.28 (t, J=6.32 Hz, 2H) 7.00-7.08 (m, 3H) 7.72-7.80 (m, 2H) 7.85 (dd, J=7.71, 1.89 Hz, 1H) 8.43 (dd, J=4.80, 1.26 Hz, 1H). HRMS: calcd for $C_{19}H_{19}F_3N_4O_3S+H+$, 441.12027. found (ESI-FTMS, $[M+H]^{1+}$), 441.1197. HPLC Method 1: room temperature, 5.657 min, 99.00%, HPLC Method 2: room temperature, 6.226 min, 99.30%.

Example 2O

1-[(2,2-dimethyl-3,4-dihydro-2H-chromen-6-yl)sulfonyl]-4-[3-(trifluoromethyl)pyridin-2-yl]piperazine The title compound was prepared according to a similar procedure for Example 2A, step 2C. Yield 81.7%.

1H NMR (400 MHz, CHLOROFORM-D) δ ppm 1.37 (s, 6H) 1.86 (t, J=6.69 Hz, 2H) 2.84 (t, J=6.69 Hz, 2H) 3.13-3.19 (m, 4H) 3.32-3.39 (m, 4H) 6.88 (d, J=8.59 Hz, 1H) 7.02 (dd, J=7.83, 4.80 Hz, 1H) 7.47-7.54 (m, 2H) 7.85 (dd, J=7.71, 1.89 Hz, 1H) 8.43 (dd, J=4.42, 1.64 Hz, 1H). HRMS: calcd for $C_{21}H_{24}F_3N_3O_3S+H+$, 456.15632. found (ESI-FTMS, $[M+H]^{1+}$), 456.156. HPLC Method 1: room temperature, 6.762 min, 95.21%, HPLC Method 2: room temperature, 7.372 min, 95.92%.

Example 2P

N,N-dimethyl-N'-[4-({4-[3-(trifluoromethyl)pyridin-2-yl]piperazin-1-yl}sulfonyl)phenyl]urea The title compound was prepared according to a similar procedure for Example 2A, step 2C. Yield 63.1%.

1H NMR (400 MHz, CHLOROFORM-D) δ ppm 3.06 (s, 6H) 3.11-3.19 (m, 4H) 3.30-3.38 (m, 4H) 6.55 (s, 1H) 6.98-7.05 (m, 1H) 7.54-7.62 (m, 2H) 7.67-7.73 (m, 2H) 7.84 (dd, J=7.83, 1.77 Hz, 1H) 8.39-8.44 (m, 1H). HRMS: calcd for $C_{19}H_{22}F_3N_5O_3S+H+$, 458.14682. found (ESI-FTMS, [M+H]$^{1+}$), 458.1464. HPLC Method 1: room temperature, 5.264 min, 99.31%, HPLC Method 2: room temperature, 6.137 min, 99.80%.

Example 2Q

N-methyl-N'-[4-({4-[3-(trifluoromethyl)pyridin-2-yl]piperazin-1-yl}sulfonyl)phenyl]urea The title compound was prepared according to a similar procedure for Example 2A, step 2C. Yield 85%.

1H NMR (400 MHz, CHLOROFORM-D) δ ppm 2.90 (d, J=4.80 Hz, 3H) 3.12-3.19 (m, 4H) 3.30-3.38 (m, 4H) 4.64 (s, 1H), 6.51 (s, 1H) 6.98-7.06 (m, 1H) 7.51-7.57 (m, 2H) 7.70 (d, J=8.59 Hz, 2H) 7.81-7.87 (m, 1H) 8.40-8.45 (m, 1H). HRMS: calcd for $C_{18}H_{20}F_3N_5O_3S+H+$, 444.13117. found (ESI-FTMS, [M+H]$^{1+}$), 444.1306. HPLC Method 1: room temperature, 5.042 min, 99.00%, HPLC Method 2: room temperature, 6.003 min, 99.53%.

Example 2R

N-[4-({4-[3-(trifluoromethyl)pyridin-2-yl]piperazin-1-yl}sulfonyl)phenyl]piperidine-1-carboxamide The title compound was prepared according to a similar procedure for Example 2A, step 2C. Yield 88.8%.

1H NMR (400 MHz, CHLOROFORM-D) δ ppm 1.63-1.71 (m, 6H) 3.11-3.18 (m, 4H) 3.30-3.37 (m, 4H) 3.43-3.53 (m, 4H) 6.58 (s, 1H) 7.02 (dd, J=7.83, 4.80 Hz, 1H) 7.52-7.59 (m, 2H) 7.67-7.73 (m, 2H) 7.84 (dd, J=7.96, 1.64 Hz, 1H) 8.42 (dd, J=4.93, 1.64 Hz, 1H). HRMS: calcd for $C_{22}H_{26}F_3N_5O_3S+H+$, 498.17812. found (ESI-FTMS, [M+H]$^{1+}$), 498.1786. HPLC Method 1: room temperature, 5.883 min, 100%, HPLC Method 2: room temperature, 6.748 min, 100%.

Example 3

Scheme 3

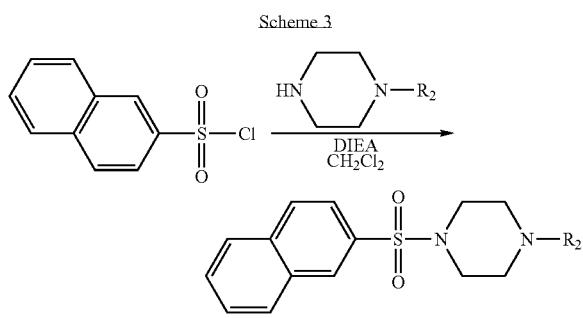

Example 3A 1-(2,4-difluorophenyl)-4-(2-naphthylsulfonyl)piperazine

Step 3A: To a stirred solution of naphthalene-2-sulfonyl chloride (350 mg, 1.54 mmol) and 1-(2,4-difluorophenyl)piperazine (305.0 mg, 1.54 mmol) in anhydrous dichloromethane (5 mL) was added diisopropylethylamine (0.670 mL, 3.85 mmol). The mixture was stirred for 30 minutes. Reaction was complete as determined by TLC. The reaction mixture was purified via flash column chromatography to afford 1-(2,4-difluorophenyl)-4-(2-naphthylsulfonyl)piperazine in 55% yield (327 mg) as white solid.

1H NMR (400 MHz, DMSO-D6) δ ppm 3.00-3.07 (m, 4H) 3.07-3.15 (m, 4H) 6.94-7.02 (m, 1H) 7.03-7.12 (m, 1H) 7.12-7.21 (m, 1H) 7.67-7.84 (m, 3H) 8.11 (d, J=8.08 Hz, 1H) 8.21 (d, J=8.59 Hz, 1H) 8.25 (d, J=8.08 Hz, 1H) 8.49 (d, J=1.77 Hz, 1H). HRMS: calcd for $C_{20}H_{18}F_2N_2O_2S+H+$, 389.11298. found (ESI-FTMS, [M+H]$^{1+}$), 389.113. HPLC Method 1: room temperature, 6.658 min, 96.32%, HPLC Method 2: room temperature, 7.312 min, 99.29%.

Example 3B 1-(2,4-dimethylphenyl)-4-(2-naphthylsulfonyl)piperazine

Step 3A: Sulfonylation of 1-(2,4-dimethylphenyl)piperazine (293 mg, 1.54 mmol) with naphthalene-2-sulfonyl chloride (350 mg, 1.54 mmol) was carried out according to a similar procedure described for example 3A using anhydrous dichloromethane (5 mL) as solvent and diisopropylethylamine (0.670 mL, 3.85 mmol) as base. 1-(2,4-dimethylphenyl)-4-(2-naphthylsulfonyl)piperazine was obtained in 92% yield (539 mg) as white solid.

1H NMR (400 MHz, DMSO-D6) δ ppm 2.03 (s, 3H) 2.18 (s, 3H) 2.86 (t, J=4.80 Hz, 4H) 3.11 (s, 4H) 6.92 (s, 3H) 7.67-7.85 (m, 3H) 8.11 (d, J=8.08 Hz, 1H) 8.22 (d, J=8.84 Hz, 1H) 8.25 (d, J=8.08 Hz, 1H) 8.49 (d, J=1.52 Hz, 1H); HRMS: calcd for $C_{22}H_{24}N_2O_2S+H+$, 381.16312. found (ESI-FTMS, [M+H]1+), 381.163. HPLC Method 1: room temperature, 7.258 min, 99.49%, HPLC Method 2: room temperature, 7.817 min, 99.52%.

Example 3C 1-(2-ethylphenyl)-4-(2-naphthylsulfonyl)piperazine

Step 3A: Sulfonylation of 1-(2-ethylphenyl)piperazine (293 mg, 1.54 mmol) with naphthalene-2-sulfonyl chloride (350 mg, 1.54 mmol) was carried out according to a similar procedure described for example 3A using anhydrous dichloromethane (5 mL) as solvent and diisopropylethylamine (0.670 mL, 3.85 mmol) as base. 1-(2-ethylphenyl)-4-(2-naphthylsulfonyl)piperazine was obtained in 99% yield (579 mg) as white solid.

1H NMR (400 MHz, DMSO-D6) δ ppm 1.02 (t, J=7.45 Hz, 3H) 2.46 (d, J=7.33 Hz, 2H) 2.89 (t, J=4.67 Hz, 4H) 3.12 (s, 4H) 6.90-7.20 (m, 4H) 7.61-7.80 (m, 2H) 7.82 (d, J=8.59 Hz, 1H) 8.12 (d, J=7.83 Hz, 1H) 8.17-8.31 (m, 2H) 8.50 (d, J=1.77 Hz, 1H); HRMS: calcd for $C_{22}H_{24}N_2O_2S+H+$, 381.16312. found (ESI-FTMS, [M+H]$^{1+}$), 381.1631. HPLC Method 1:

room temperature, 7.204 min, 99.62%, HPLC Method 2: room temperature, 7.759 min, 99.62%.

Example 3D

1-[4-fluoro-2-(methylsulfonyl)phenyl]-4-(2-naphthylsulfonyl)piperazine

Step 3A: Sulfonylation of 1-(4-fluoro-2-(methylsulfonyl)phenyl)piperazine (316.6 mg, 1.23 mmol) with naphthalene-2-sulfonyl chloride (278 mg, 1.54 mmol) was carried out according to a similar procedure described for example 3A using anhydrous dichloromethane (5 mL) as solvent and diisopropylethylamine (0.256 mL, 1.47 mmol) as base. 1-[4-fluoro-2-(methylsulfonyl)phenyl]-4-(2-naphthylsulfonyl)piperazine was obtained in 61.8% yield (340 mg) as white solid.

1H NMR (400 MHz, DMSO-D6) δ ppm 3.05 (s, 4H) 3.14 (s, 4H) 3.33 (s, 3H) 7.51-7.67 (m, 2H) 7.67-7.88 (m, 4H) 8.12 (d, J=8.08 Hz, 1H) 8.17-8.31 (m, 2H) 8.51 (d, J=1.52 Hz, 1H). HRMS: calcd for $C_{21}H_{21}FN_2O_4S_2$+H+, 449.09995. found (ESI-FTMS, [M+H]1+), 449.1003. HPLC Method 1: room temperature, 5.864 min, 97.14%, HPLC Method 2: room temperature, 6.426 min, 97.56%.

Example 3E 1-(2-naphthylsulfonyl)-4-[2-(trifluoromethyl)phenyl]piperazine

Preparation of 1-(2-naphthylsulfonyl)-4-[2-(trifluoromethyl)phenyl]piperazine was carried out according to a similar procedure described for example 3A. Yield 85%.

1H NMR (400 MHz, CHLOROFORM-D) δ ppm 2.84-3.09 (m, J=9.60 Hz, 4H) 3.12-3.46 (m, 4H) 7.15-7.30 (m, 1H) 7.35 (d, J=8.08 Hz, 1H) 7.44-7.58 (m, 1H) 7.58 (d, J=7.83 Hz, 1H) 7.62-7.74 (m, 2H) 7.79 (d, J=10.36 Hz, 1H) 7.96 (d, J=7.83 Hz, 1H) 7.99-8.17 (m, 2H) 8.38 (s, 1H). HRMS: calcd for $C_{21}H_{19}F_3N_2O_2S$+H+, 421.11921. found (ESI-FTMS, [M+H]$^{1+}$), 421.1192. HPLC Method 1, room temperature, 6.78 min, 99.04%; HPLC Method 2, room temperature, 7.43 min, 99.17%.

Example 3F 1-(2-bromophenyl)-4-(2-naphthylsulfonyl)piperazine

Preparation of 1-(2-bromophenyl)-4-(2-naphthylsulfonyl)piperazine was carried out according to a similar procedure described for example 3A. Yield 85%.

1H NMR (400 MHz, CHLOROFORM-D) δ ppm 2.95-3.19 (m, 4H) 3.19-3.44 (m, 4H) 6.83-6.99 (m, 1H) 6.98-7.12 (m, 1H) 7.19-7.35 (m, 1H) 7.51 (d, J=9.60 Hz, 1H) 7.58-7.74 (m, 2H) 7.80 (d, J=10.61 Hz, 1H) 7.95 (d, J=8.08 Hz, 1H) 8.02 (d, J=8.59 Hz, 2H) 8.38 (s, 1H). HRMS: calcd for $C_{20}H_{19}BrN_2O_2S$+H+, 431.04233. found (ESI-FTMS, [M+H]$^{1+}$), 431.0424. HPLC Method 1, room temperature, 6.85 min, 100%; HPLC Method 2, room temperature, 7.49 min, 99.60%.

Example 4

1-(3-chloropyridin-2-yl)-4-[(3,4-dichlorophenyl)sulfonyl]-trans-2,5-dimethylpiperazine Step 4A: To a stirred solution of 3,4-dichlorobenzene-1-sulfonyl chloride (840 mg, 3.42 mmol) and 2,5-dimethylpiperazine (1.171 g, 10.26 mmol) in anhydrous dichloromethane (5 mL) was added diisopropylethylamine (1.2 mL, 6.84 mmol). The mixture was stirred overnight at room temperature. Reaction was complete as determined by TLC. The reaction mixture was diluted with dichloromethane, washed with water and dried over MgSO$_4$. After solvent evaporation crude product was treated with ethyl acetate/hexanes. Solid impurity was filtered of and the filtrate was concentrated to afford 1-(3,4-dichlorophenylsulfonyl)-2,5-dimethylpiperazine in quantitative yield. It was carried to the next step without further purification.

Step 4B: 1-(3,4-dichlorophenylsulfonyl)-2,5-dimethylpiperazine (1.04 g, 3.22 mmol), 2,3-dichloropyridine (476.5 mg. 3.22 mmol), diisopropylethylamine (1.4 mL, 8.05 mmol) and DMF (1.2 mL) were charged to a microwave vial and the mixture was irradiated at 200° C. for 1 hour. Reaction was complete as determined by TLC. The reaction mixture was diluted with ethyl acetate and washed with water. After solvent evaporation crude product was purified with flash column chromatography to yield 1-(3-chloropyridin-2-yl)-4-[(3,4-dichlorophenyl)sulfonyl]-2,5-dimethylpiperazine in 2% yield (27.1 mg) as yellow solid.

1H NMR (400 MHz, CHLOROFORM-D) δ ppm 1.08 (d, J=6.57 Hz, 3H) 1.12 (d, J=6.57 Hz, 3H) 3.26 (d, J=13.39 Hz, 1H) 3.44-3.52 (m, 1H) 3.54-3.66 (m, 2H) 4.14-4.37 (m, 2H) 6.84 (dd, J=7.58, 4.80 Hz, 1H) 7.50-7.70 (m, 3H) 7.93 (d, J=2.02 Hz, 1H) 8.15 (dd, J=4.80, 1.77 Hz, 1H). HRMS: calcd for $C_{17}H_{18}Cl_3N_3O_2S$+H+, 434.02580. found (ESI-FTMS, [M+H]$^{1+}$), 434.028. HPLC Method 1: room temperature, 7.140 min, 99.62%, HPLC Method 2: room temperature, 7.684 min, 99.56%.

Example 5

Benzyl (3S,5S)-4-[(4-tert-butylphenyl)sulfonyl]-3,5-dimethylpiperazine-1-carboxylate Step 5A: (S)-tert-butyl 1-oxopropan-2-ylcarbamate (Boc-L-Alaninal) (3.0 g, 17.32 mmol) and (R)-1-aminopropan-2-ol (1.95 g, 25.98 mmol) in anhydrous methanol (120 mL) was hydrogenated at 1 atmosphere overnight using palladium, 10% wt. on activated carbon (900 mg) as catalyst. Reaction was complete as determined by TLC using CAN spray to visualize. The reaction mixture was then filtered through a celite bed. After solvent evaporation crude product was diluted with ethyl acetate, washed with saturated NAHCO$_3$ (aq.) and dried over MgSO$_4$. Solvent evaporation afforded tert-butyl (S)-1-[(R)-2-hydroxypropylamino]propan-2-ylcarbamate] in 98.5% yield (3.95 g). It was carried to the next step without further purification.

1H NMR (400 MHz, CHLOROFORM-D) δ ppm 1.14 (d, J=6.57 Hz, 3H) 1.15 (d, J=6.32 Hz, 3H) 1.45 (s, 9H) 2.39 (dd, J=12.13, 9.35 Hz, 1H) 2.53-2.78 (m, 3H) 3.14 (s, 1H) 3.70-3.81 (m, 2H) 4.52 (s, 1H)

Step 5B: To a stirred solution of tert-butyl (S)-1-[(R)-2-hydroxypropylamino]propan-2-ylcarbamate (3.0 g, 12.93 mmol) and diisopropylethylamine (3.38 mL, 19.4 mmol) in anhydrous dichloromethane (100 mL) at 0° C. was added benzyl chloroformate (2.65 g, 15.5 mmol). After stirring at 0° C. for 1 hour, the cooling bath was removed and the reaction mixture was allowed to stir at room temperature for an additional 45 minutes. Reaction was complete as determined by TLC. The reaction mixture was added with 1N HCl and extracted with dichloromethane. Organic layer washed with water then brine and it was dried over MgSO$_4$. Solvent evaporation afforded benzyl {(2S)-2-[(tert-butoxycarbonyl)amino]

propyl}[(2R)-2-hydroxypropyl]carbamate in 84.5% yield (3.95 g) as colorless gummy oil.

1H NMR (400 MHz, DMSO-D6) δ ppm 0.90-1.04 (m, 6H) 1.35 (s, 9H) 1.99 (s, 1H) 3.10-3.22 (m, 2H) 3.28 (d, J=5.56 Hz, 1H) 3.80 (d, J=5.56 Hz, 2H) 4.69 (dd, J=17.18, 4.80 Hz, 1H) 5.00-5.10 (m, 2H) 6.59-6.71 (m, 1H) 7.29-7.42 (m, 5H). HRMS: calcd for $C_{19}H_{30}N_2O_5$+H+, 367.22275. found (ESI-FTMS, [M+H]$^{1+}$), 367.2235.

Step 5C: To a stirred solution of benzyl {(2S)-2-[(tert-butoxycarbonyl)amino]propyl}[(2R)-2-hydroxypropyl]carbamate (1.95 g, 5.32 mmol) and diisopropylethylamine (1.85 mL, 10.64 mmol) in anhydrous dichloromethane (110 mL) was added dimethylaminopyridine (135 mg) and methane sulfonyl chloride (0.535 mL, 6.92 mmol). The mixture was stirred at room temperature for 1 hour. Reaction was complete as determined by TLC. The reaction mixture was concentrated and purified using flash column chromatography. (1R)-2-([(benzyloxy)carbonyl]{(2S)-2-[(tert-butoxycarbonyl)amino]propyl}amino)-1-methylethyl methanesulfonate was obtained in 97.0% yield (2.29 g) as light yellow oil.

1H NMR (400 MHz, DMSO-D6) δ ppm 0.91-1.02 (m, 3H) 1.21-1.32 (m, 3H) 1.35 (s, 9H) 3.05 (d, 3H) 3.22 (d, J=8.59 Hz, 2H) 3.34-3.54 (m, 2H) 3.66-3.88 (m, 1H) 4.76-4.94 (m, 1H) 4.98-5.16 (m, 2H) 6.60-6.76 (m, 1H) 7.23-7.44 (m, 5H).

Step 5D: To a stirred solution of (1R)-2-([(benzyloxy)carbonyl]{(2S)-2-[(tert-butoxycarbonyl)amino]propyl}amino)-1-methylethyl methanesulfonate (2.29 g, 5.15 mmol) in anhydrous dichloromethane (38 mL) was added TFA (38 mL) dropwise at 0° C. The reaction mixture was stirred at room temperature for 1 hour. Reaction was complete as determined by TLC. Most of TFA was azeotropped with dichloroethane. The residue was then diluted with dichloromethane and washed with 2N $Na_2CO_3$ (aq.), organic layer was dried over $MgSO_4$. Solvent evaporation afforded (R)-1-(((S)-2-aminopropyl)(benzyloxycarbonyl)amino)propan-2-yl methanesulfonate in quantitative yield (1.8 g) as oil. It was carried to the next step immediately.

Step 5E: (R)-1-(((S)-2-aminopropyl)(benzyloxycarbonyl)amino)propan-2-yl methanesulfonate (1.8 g, 5.15 mmol) dissolved in anhydrous MeOH (120 mL) was heated up to 60° C. for 4 hours. Reaction was complete as determined by TLC. After overnight stirring at room temperature solvent was evaporated to afford (3R,5R)-benzyl 3,5-dimethylpiperazine-1-carboxylate [L31285-103-1] in quantitative yield (1.28 g) as gummy off white solid.

1H NMR (400 MHz, CHLOROFORM-D) δ ppm 1.31-1.44 (m, 6H) 3.38-3.64 (m, 4H) 3.73-3.96 (m, 2H) 7.29-7.43 (m, 5H) 8.96 (s, 1H).

Step 5F: To a stirred solution of (3R,5R)-benzyl 3,5-dimethylpiperazine-1-carboxylate (500 mg, 2.02 mmol) in anhydrous dichloromethane (8 mL) was added diisopropylethylamine (1.4 mL, (8.08 mmol) followed by 4-tert-butylbenzene-1-sulfonyl chloride (940 mg, 4.04 mmol). The reaction mixture was stirred for 68 hours. Reaction was complete as determined by TLC. After solvent evaporation the crude product was purified by flash column chromatography to afford benzyl (3S,5S)-4-[(4-tert-butylphenyl)sulfonyl]-3,5-dimethylpiperazine-1-carboxylate in 42% yield (377 mg) as light yellow oil.

1H NMR (400 MHz, DMSO-D6) δ ppm 1.12 (d, J=6.57 Hz, 6H) 1.30 (s, 9H) 3.25 (s, 1H) 3.35 (s, 1H) 3.45-3.59 (m, 2H) 4.00 (s, 2H) 5.00-5.15 (m, 2H) 7.21-7.42 (m, 5H) 7.59 (d, J=8.84 Hz, 2H) 7.75 (d, J=8.59 Hz, 2H). HRMS: calcd for $C_{24}H_{32}N_2O_4S$+H+, 445.21555. found (ESI-FTMS, [M+H]$^{1+}$), 445.2169. HPLC Method 1: room temperature, 6.990 min, 98.43%, HPLC Method 2: room temperature, 7.534 min, 99.66%.

Example 6

(2S,6S)-1-[(4-tert-butylphenyl)sulfonyl]-4-(3-chloropyridin-2-yl)-2,6-dimethylpiperazine Step 6A: A solution of benzyl (3S,5S)-4-[(4-tert-butylphenyl)sulfonyl]-3,5-dimethylpiperazine-1-carboxylate (340 mg, 0.77 mmol) in anhydrous MeOH was hydrogenated at 1 atmosphere for 2 days using palladium, 10% wt. on activated carbon (144 mg) as catalyst. Reaction was complete as determined by TLC. The reaction mixture was then filtered through a celite bed. After solvent evaporation crude product was purified via flash column chromatography to afford (2S,6S)-1-[(4-tert-butylphenyl)sulfonyl]-2,6-dimethylpiperazine in 53.9% yield (128 mg) as pale yellow oil.

1H NMR (400 MHz, CHLOROFORM-D) δ ppm 1.23 (s, 3H) 1.24 (s, 3H) 1.33 (s, 9H) 2.63-2.67 (m, 1H) 2.68 (d, J=6.32 Hz, 1H) 2.94 (d, J=3.28 Hz, 1H) 2.97 (d, J=3.54 Hz, 1H) 3.92-4.00 (m, 2H) 7.47 (d, J=8.84 Hz, 2H) 7.75 (d, J=8.84 Hz, 2H). HRMS: calcd for $C_{16}H_{26}N_2O_2S$+H+, 311.17877. found (ESI-FTMS, [M+H]$^{1+}$), 311.179. HPLC Method 1: room temperature, 5.557 min, 99.41%, HPLC Method 2: room temperature, 4.760 min, 100.0%.

Step 6B: To a solution of (2S,6S)-1-[(4-tert-butylphenyl)sulfonyl]-2,6-dimethylpiperazine (120 mg, 0.39 mmol) and 2,3-Dichloropyridine (115 mg, 0.78 mmol) in anhydrous 1,4-Dioxane (0.2 mL) was added diisopropylethylamine (0.201 mL, 1.16 mmol). The mixture was subject to microwave irradiation at 200° C. for 1 hour. Reaction was half complete as determined by TLC. The reaction mixture was diluted with ethyl acetate and washed with saturated $NH_4Cl$ (aq.), 10% HCl (aq.), water and brine. Organic layer was dried over $MgSO_4$. Solvent evaporation followed by flash column chromatography afforded (2S,6S)-1-[(4-tert-butylphenyl)sulfonyl]-4-(3-chloropyridin-2-yl)-2,6-dimethylpiperazine in 27.7% yield (45 mg) as off white solid.

1H NMR (400 MHz, CHLOROFORM-D) δ ppm 1.33 (s, 9H) 1.36 (s, 3H) 1.38 (s, 3H) 3.22 (d, J=6.32 Hz, 1H) 3.25 (d, J=6.32 Hz, 1H) 3.41 (d, J=3.03 Hz, 1H) 3.44 (d, J=3.28 Hz, 1 H) 4.19-4.29 (m, 2H) 6.86 (dd, J=7.71, 4.67 Hz, 1H) 7.47 (d, J=8.84 Hz, 2H) 7.59 (dd, J=7.83, 1.52 Hz, 1H) 7.78 (d, J=8.84 Hz, 2H) 8.07-8.22 (m, 1H). HRMS: calcd for $C_{21}H_{28}ClN_3O_2S$+5H+, 422.16635. found (ESI-FTMS, [M+H]$^{1+}$), 422.1665. HPLC Method 1: room temperature, 7.378 min, 96.04%, HPLC Method 2: room temperature, 7.756 min, 95.34%.

Example 7

Scheme 7

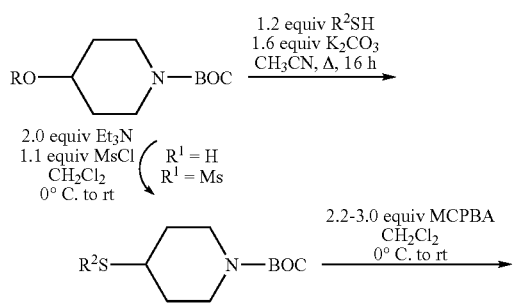

-continued

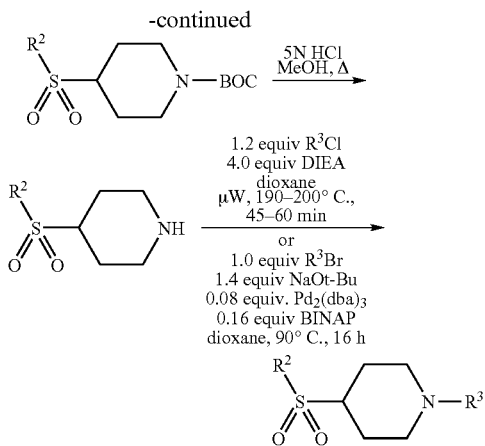

Example 7A

2-{4-[(3,4-dichlorophenyl)sulfonyl]piperidin-1-yl}-3-(trifluoromethyl)pyridine

Step 7A: tert-butyl 4-[(methylsulfonyl)oxy]piperidine-1-carboxylate. The mesylate was prepared from tert-butyl-4-hydroxy-1-piperidinecarboxylate using the procedure from WO 0053362 Cheng S., et al. To a 0° C. solution of tert-butyl-4-hydroxy-1-piperidinecarboxylate (9.80 g, 49 mmol), Et$_3$N (9.92 g, 13.7 mL, 98 mmol), and CH$_2$Cl$_2$ (90 mL) was added MsCl (6.17 g, 4.20 mL, 53 mmol). After 15 min, the ice bath was removed and the mixture was stirred overnight at room temperature, poured into 1M HCl (90 mL) and extracted with CH$_2$Cl$_2$ (2×60 mL). The organic phase washed with H2O and brine, dried (MgSO$_4$), and concentrated to afford the mesylate (12.9 g), an off-white solid, in 95% yield.

$^1$H NMR (400 MHz, CDCl$_3$) δ 1.71-1.91 (m, 2H), 1.90-2.15 (m, 2H), 3.04 (s, 3H), 3.18-3.50 (m, 2H), 3.49-3.96 (m, 2H), 4.68-5.04 (m, 1H).

Step 7B: tert-butyl 4-[(3,4-dichlorophenyl)thio]piperidine-1-carboxylate. A suspension of the mesylate from Step 2 (3.8 g, 7.1 mmol), 3,4-dichlorothiophenol (2.9 g, 2.1 mL), and K$_2$CO$_3$ (3.0 g, 11.4 mmol) in CH$_3$CN (30 mL) was heated in a 90° C. bath for 16 h. The resulting mixture was diluted with H$_2$O (100 mL) and EtOAc (100 mL). The aqueous phase was extracted with EtOAc (50 mL). The combined organic phases were washed with H$_2$O and brine, dried (MgSO$_4$) and concentrated to afford a yellow oil which was purified by SiO$_2$ chromatography (elution with 5 to 10% EtOAc-hex) to afford the thioether (3.97 g), a pale yellow oil, in 80% yield.

$^1$H NMR (400 MHz, CDCl$_3$) δ 1.35-1.59 (m, 11H), 1.92 (d, J=13.1 Hz, 2H), 2.93 (t, J=11.7 Hz, 2H), 3.13-3.32 (m, 1H), 3.96 (s, 2H), 7.23 (d, J=8.3 Hz, 1H), 7.37 (d, J=8.3 Hz, 1H), 7.49 (s, 1H).

Step 7C: tert-butyl 4-[(3,4-dichlorophenyl)sulfonyl]piperidine-1-carboxylate. To a 0° C. solution to the thioether from Step 2 (2.65 g, 7.3 mmol) in CH$_2$Cl$_2$ (150 mL) was added MCPBA (77%, 3.60 g, 16 mmol). After 2 h, sat. NaHCO$_3$ solution (150 mL) was added and the resulting suspension was stirred at room temperature for 15 min. The organic phase was separated and washed with 1N NaOH (50 mL), H$_2$O (50 mL), and brine (50 mL), dried (MgSO$_4$), and concentrated partially. The crude product was adhered to SiO$_2$ and purified by SiO$_2$ chromatography (elution with 20 to 30% EtOAc-hex) to afford the sulfone (2.79 g), a white solid, in 97% yield.

$^1$H NMR (400 MHz, CDCl$_3$) δ 1.44 (s, 9H), 1.54-1.71 (m, 2H), 1.98 (d, J=11.9 Hz, 2H), 2.67 (br s, 2H), 2.95-3.13 (m, 1H), 4.26 (br s, 2H), 7.67-7.70 (m; 2H), 7.96 (d, J=1.3 Hz, 1H).

Step 7D: 4-[(3,4-dichlorophenyl)sulfonyl]piperidine. A mixture of the sulfone from Step 7C (3.09 g, 7.8 mmol), MeOH (21 mL), and 5N HCl (4.5 mL) was heated to reflux for 1.5 h. The mixture was cooled to room temperature and sat. Na$_2$CO$_3$ solution (80 mL) was added. The mixture was extracted with CH$_2$Cl$_2$ (2×100 mL). The organic phase washed with H$_2$O and brine, dried (MgSO$_4$) and concentrated to afford the amine (1.82 g), a white foam, in 79% yield.

$^1$H NMR (400 MHz, CDCl$_3$) δ 1.39-1.70 (m, 3H), 2.00 (d, J=12.4 Hz, 2H), 2.57 (t, J=12.4 Hz, 2H), 3.04 (t, J=12.3 Hz, 1H), 3.20 (d, J=12.6 Hz, 2H), 7.68 (q, J=8.3 Hz, 2H), 7.96 (s, 1H).

Step 7E: 2-{4-[(3,4-dichlorophenyl)sulfonyl]piperidin-1-yl}-3-(trifluoromethyl)pyridine. A mixture of the amine from Step 7D (200 mg, 0.68 mmol), 2-chloro-3-(trifluoromethyl)pyridine (200 mg, 1.36 mmol), DIEA (0.36 mL, 2.04 mmol), and 1,4-dioxane (0.10 mL) was heated in the Emrys Creator microwave to 200° C. for 1 h. The mixture was diluted with sat. NH$_4$Cl (20 mL) and EtOAc (50 mL). The organic phase washed with 10% HCl (25 mL), H$_2$O (3×25 mL), and brine (25 mL), dried (MgSO$_4$), and concentrated. The resulting yellow oil was purified by SiO$_2$ chromatography (elution with 10 to 30% EtOAc-hexanes), and lyophilized to afford the title compound (0.19 g), a white solid, 64%.

$^1$H NMR (400 MHz, CDCl$_3$) δ 1.80-2.01 (m, 2H), 2.02-2.16 (m, 2H), 2.75-2.95 (m, 2H), 3.02-3.24 (m, 1H), 3.69 (dd, J=10.5, 2.7 Hz, 2H), 6.91-7.13 (m, 1H), 7.69 (d, J=8.3 Hz, 1H), 7.74 (dd, J=8.3, 2.2 Hz, 1H), 7.87 (dd, J=7.8, 1.5 Hz, 1H), 8.00 (d, J=2.0 Hz, 1H), 8.42 (dd, J=4.8, 1.3 Hz, 1H). HRMS: calcd for C$_{17}$H$_{15}$Cl$_2$F$_3$N$_2$O$_2$S+H+, 439.02561. found (ESI-FTMS, [M+H]$^{1+}$), 439.0261. HPLC Method 1: room temperature, 6.56 min, 97.0%. HPLC Method 2: room temperature, 7.24 min, 96.9%.

Example 7B 3-chloro-2-{4-[(3,4-dichlorophenyl)sulfonyl]piperidin-1-yl}pyridine Step 7E: Using the procedure from Example 7A, Step 7E, 4-[(3,4-dichlorophenyl)sulfonyl]piperidine (200 mg, 0.68 mmol) was reacted with 2,3-dichloropyridine (201 mg, 1.36 mmol) to afford the title compound (90 mg), a white solid, in 33% yield.

$^1$H NMR (400 MHz, CDCl$_3$) δ 1.83-2.02 (m, 2H), 2.04-2.21 (m, 2H), 2.70-2.89 (m, 2H), 3.02-3.28 (m, 1H), 3.81-4.05 (m, 2H), 6.86 (dd, J=7.8, 4.8 Hz, 1H), 7.59 (dd, J=7.7, 1.6 Hz, 1H), 7.68 (d, J=8.3 Hz, 1H), 7.74 (dd, J=8.4, 2.1 Hz, 1H), 8.00 (d, J=2.0 Hz, 1H), 8.16 (dd, J=4.8, 1.8 Hz, 1H). HRMS: calcd for C$_{16}$H$_{15}$Cl$_3$N$_2$O$_2$S+H+, 404.99925. found (ESI-FTMS, [M+H]$^{1+}$), 405.0012. HPLC Method 1: room temperature, 6.44 min, 97.4%. HPLC Method 2: room temperature, 7.24 min, 97.9%.

Example 7C

2-{4-[(3,4-dichlorophenyl)sulfonyl]piperidin-1-yl}-5-(trifluoromethyl)pyridine

Step 7E: Using the procedure from Example 7A, Step 7E, 4-[(3,4-dichlorophenyl)sulfonyl]piperidine (200 mg, 0.68 mmol) was reacted with 2-chloro-5-(trifluoromethyl)pyridine (172 mg, 0.96 mmol) to afford the title compound (110 mg), a white solid, in 37% yield.

$^1$H NMR (400 MHz, CDCl$_3$) δ 1.66-1.88 (m, 2H), 2.10 (d, J=12.4 Hz, 2H), 2.89 (t, J=12.8 Hz, 2H), 3.07-3.35 (m, 1H), 4.57 (d, J=13.4 Hz, 2H), 6.65 (d, J=8.8 Hz, 1H), 7.57-7.82 (m, 3H), 7.97 (s, 1H), 8.38 (s, 1H). HRMS: calcd for C$_{17}$H$_{15}$Cl$_2$F$_3$N$_2$O$_2$S+H+, 439.02561. found (ESI-FTMS, [M+H]$^{1+}$), 439.0273. HPLC Method 1: room temperature, 6.70 min, 98.8%. HPLC Method 2: room temperature, 7.32 min, 99.8%.

Example 7D

2-{4-[(3,4-dichlorophenyl)sulfonyl]piperidin-1-yl}-3-nitropyridine

Step 7E: Using the procedure from Example 7A, Step 7E, 4-[(3,4-dichlorophenyl)sulfonyl]piperidine (150 mg, 0.51 mmol) was reacted with 2-chloro-3-nitropyridine (97 mg, 0.61 mmol) to afford the title compound (212 mg), a yellow solid, in 74% yield.

$^1$H NMR (400 MHz, CDCl$_3$) δ 1.80-1.95 (m, 2H), 2.03-2.13 (m, 2H), 2.95-3.08 (m, 2H), 3.12-3.26 (m, 1H), 3.90-4.01 (m, 2H), 6.81 (dd, J=8.1, 4.5 Hz, 1H), 7.68 (d, J=8.3 Hz, 1H), 7.72 (dd, J=8.4, 1.9 Hz, 1H), 7.98 (d, J=2.9 Hz, 1H), 8.15 (dd, J=8.0, 1.6 Hz, 1H), 8.34 (dd, J=4.5, 1.8 Hz, 1H). HRMS: calcd for C$_{16}$H$_{15}$Cl$_2$N$_3$O$_4$S+H+, 416.02331. found (ESI-FTMS, [M+H]$^{1+}$), 416.0227.

Example 7E

1-{4-[(3,4-dichlorophenyl)sulfonyl]piperidin-1-yl}isoquinoline

Step 7E: Using the procedure from Example 7A, Step 7E, 4-[(3,4-dichlorophenyl)sulfonyl]piperidine (Example 1, Step 4, 150 mg, 0.51 mmol) was reacted with 1-chloroisoquinoline (100 mg, 0.61 mmol) to afford the title compound (215 mg), a white solid, in 51% yield.

$^1$H NMR (400 MHz, CDCl$_3$) δ 1.97-2.29 (m, 4H), 2.80-3.05 (m, 2H), 3.08-3.28 (m, 1H), 3.93 (d, J=13.1 Hz, 2H), 7.19-7.36 (m, 2H), 7.53 (t, J=7.7 Hz, 1H), 7.63 (t, J=7.6 Hz, 1H), 7.70 (d, J=8.3 Hz, 1H), 7.77 (t, J=8.1 Hz, 2H), 7.95-8.07 (m, 2H), 8.12 (d, J=5.6 Hz, 1H). HRMS: calcd for C$_{20}$H$_{18}$Cl$_2$N$_2$O$_2$S+H+, 421.05388. found (ESI-FTMS, [M+H]$^{1+}$), 421.0558. HPLC Method 1: room temperature, 4.83 min, 98.8%. HPLC Method 2: room temperature, 6.63 min, 99.8%.

Example 7F

2-{4-[(3,4-dichlorophenyl)sulfonyl]piperidin-1-yl}nicotinonitrile

Step 7E: Using the procedure from Example 7A, Step 7E, 4-[(3,4-dichlorophenyl)sulfonyl]piperidine (150 mg, 0.51 mmol) was reacted with 2-chloro-3-cyanopyridine (85 mg, 0.61 mmol) to afford the title compound (202 mg), a white solid, in 77% yield.

$^1$H NMR (400 MHz, CDCl$_3$) δ 1.78-1.96 (m, 2H), 2.11 (d, J=11.9 Hz, 2H), 2.99 (t, J=12.6 Hz, 2H), 3.10-3.27 (m, 1H), 4.50 (d, J=13.6 Hz, 2H), 6.80 (dd, J=7.6, 4.8 Hz, 1H), 7.61-7.75 (m, 2H), 7.78 (d, J=7.6 Hz, 1H), 7.99 (s, 1H), 8.34 (d, J=4.8 Hz, 1H). HRMS: calcd for C$_{17}$H$_{15}$Cl$_2$N$_3$O$_2$S+H+, 396.03348. found (ESI-FTMS, [M+H]$^{1+}$), 396.0337. HPLC Method 1: room temperature, 6.01 min, 99.1%. HPLC Method 2: room temperature, 6.74 min, 99.4%.

Example 7G 3,5-dichloro-4-{4-[(3,4-dichlorophenyl)sulfonyl]piperidin-1-yl}pyridine Step 7E: Using the procedure from Example 7A, Step 7E, 4-[(3,4-dichlorophenyl)sulfonyl]piperidine (150 mg, 0.51 mmol) was reacted with 3,4,5-trichloropyridine (224 mg, 1.22 mmol) to afford the title compound (66 mg), a white solid, in 55% yield.

$^1$H NMR (400 MHz, CDCl$_3$) δ 1.85-2.12 (m, 4H), 2.98-3.17 (m, 1H), 3.19-3.33 (m, 2H), 3.35-3.53 (m, 2H), 7.69 d, J=8.3 Hz, 1H), 7.74 (dd, J=8.3, 2.0 Hz, 1H), 8.00 (d, J=2.0 Hz, 1H), 8.35 (s, 2H). HRMS: calcd for C$_{16}$H$_{14}$Cl$_4$N$_2$O$_2$S+H+, 438.96028. found (ESI-FTMS, [M+H]$^{1+}$), 438.9612.

Example 7H

2-{4-[(3,4-dichlorophenyl)sulfonyl]piperidin-1-yl}quinoline

Step 7E: Using the procedure from Example 7A, Step 7E, 4-[(3,4-dichlorophenyl)sulfonyl]piperidine (150 mg, 0.51 mmol) was reacted with 2-chloroquinoline (328 mg, 2.0 mmol) to afford the title compound (39 mg), a white solid, in 18% yield.

$^1$H NMR (400 MHz, CDCl$_3$) δ 1.65-1.92 (m, 2H), 1.95-2.32 (m, 2H), 2.80-3.01 (m, 2H), 2.99-3.35 (m, 1H), 4.63-4.77 (m, 2H), 6.96 (d, J=9.1 Hz, 1H), 7.19-7.28 (m, 1H), 7.50-7.58 (m, 1H), 7.60 (dd, J=8.0, 1.4 Hz, 1H), 7.63-7.74 (m, 3H), 7.90 (d, J=8.8 Hz, 1H), 7.98 (d, J=2.0 Hz, 1H). HRMS: calcd for C$_{20}$H$_{18}$Cl$_2$N$_2$O$_2$S+H+, 421.05388. found (ESI-FTMS, [M+H]$^{1+}$), 421.0543. HPLC Method 1: room temperature, 4.52 min, 99.1%. HPLC Method 2: room temperature, 5.38 min, 99.4%.

Example 7I

2-[4-(2-naphthylsulfonyl)piperidin-1-yl]-3-(trifluoromethyl)pyridine

Step 7E: The corresponding naphthyl amine from Step 7D (175 mg, 0.63 mmol) was reacted with 2-chloro-3-(trifluoromethyl)pyridine (231 mg, 1.3 mmol) as in Example 7A, Step 7E to afford the title compound (196 mg), a white powder, in 73% yield.

$^1$H NMR (400 MHz, CDCl$_3$) δ 1.87-2.19 (m, 4H), 2.87 (t, J=12.3 Hz, 2H), 3.16 (t, J=11.9 Hz, 1H), 3.68 (d, J=12.4 Hz, 2H), 6.92-7.07 (m, 1H), 7.57-7.74 (m, 2H), 7.87 (dd, J=16.3, 8.2 Hz, 2H), 7.96 (d, J=7.8 Hz, 1H), 8.03 (d, J=8.6 Hz, 2H), 8.40 (d, J=4.5 Hz, 1H), 8.50 (s, 1H). HRMS: calcd for C$_{21}$H$_{19}$F$_3$N$_2$O$_2$S+H+, 421.11921. found (ESI-FTMS, [M+H]$^{1+}$), 421.1208. HPLC Method 1: room temperature, 6.37 min, 98.4%. HPLC Method 2: room temperature, 7.07 min, 98.7%.

Example 7J 3-chloro-2-[4-(2-naphthylsulfonyl)piperidin-1-yl]pyridine

Step 7E: Using the procedure from Example 7A, Step 7E, 4-(2-naphthylsulfonyl)piperidine (Example 11, Step 3, 175 mg, 0.63 mmol) was reacted with 2,3-dichloropyridine (188 mg, 1.3 mmol) to afford the title compound (119 mg), a white solid, in 48% yield.

¹H NMR (400 MHz, CDCl₃) δ 1.86-2.08 (m, 2H), 2.07-2.17 (m, 2H), 2.67-2.93 (m, 2H), 2.98-3.30 (m, 1H), 3.94 (dd, J=10.9, 2.3 Hz, 2H), 6.83 (dd, J=7.6, 4.8 Hz, 1H), 7.56 (dd, J=7.8, 1.8 Hz, 1H), 7.60-7.74 (m, 2H), 7.89 (dd, J=8.6, 1.8 Hz, 1H), 7.96 (d, J=8.3 Hz, 1H), 8.00-8.09 (m, 2H), 8.14 (dd, J=4.7, 1.6 Hz, 1H), 8.50 (d, J=1.8 Hz, 1H). HRMS: calcd for $C_{20}H_{19}ClN_2O_2S+H+$, 387.09285. found (ESI-FTMS, [M+H]$^{1+}$), 387.0942. HPLC Method 1: room temperature, 6.25 min, 100%. HPLC Method 2: room temperature, 7.01 min, 100%.

Example 7K

2-[4-(2-naphthylsulfonyl)piperidin-1-yl]-5-(trifluoromethyl)pyridine

Step 7E: Using the procedure from Example 7A, Step 7E, 4-(2-naphthylsulfonyl)piperidine (130 mg, 0.51 mmol) was reacted with 2-chloro-5-(trifluoromethyl)pyridine (181 mg, 1.0 mmol) to afford the title compound (180 mg), a white solid, in 84% yield.

¹H NMR (400 MHz, CDCl₃) δ 1.70-1.88 (m, 2H), 2.02-2.37 (m, 2H), 2.80-2.98 (m, 2H), 3.15-3.40 (m, 1H), 4.54 (d, J=13.6 Hz, 2H), 6.62 (d, J=8.8 Hz, 1H), 7.53-7.77 (m, 3H), 7.85 (dd, J=8.6, 1.8 Hz, 1H), 7.95 (d, J=8.1 Hz, 1H), 7.98-8.08 (m, 2H), 8.29-8.39 (m, 1H), 8.46 (s, 1H). HRMS: calcd for $C_{21}H_{19}F_3N_2O_2S+H+$, 421.11921. found (ESI-FTMS, [M+H]$^{1+}$), 421.1207. HPLC Method 1: room temperature, 6.49 min, 99.6%. HPLC Method 2: room temperature, 7.11 min, 99.6%.

Example 7L 3,5-dichloro-4-[4-(2-naphthylsulfonyl)piperidin-1-yl]pyridine

Step 7L: Using the procedure from Example 7A, Step 7E, 4-(2-naphthylsulfonyl)piperidine (130 mg, 0.51 mmol) was reacted with 3,4,5-trichloropyridine (182 mg, 1.0 mmol) to afford the title compound (26 mg), a white solid, in 12% yield.

¹H NMR (400 MHz, CDCl₃) δ 1.91-2.18 (m, 4H), 3.09-3.32 (m, 3H), 3.42 (d, J=12.9 Hz, 2H), 7.59-7.76 (m, 2H), 7.89 (dd, J=8.6, 1.8 Hz, 1H), 7.97 (d, J=8.1 Hz, 1H), 7.99-8.10 (m, 2H), 8.32 (s, 2H), 8.50 (s, 1H). HRMS: calcd for $C_{20}H_{18}Cl_2N_2O_2S+H+$, 421.05388. found (ESI-FTMS, [M+H]$^{1+}$), 421.0544. HPLC Method 1: room temperature, 6.43 min, 99.6%. HPLC Method 2: room temperature, 7.21 min, 100%.

Example 7M

2-[4-(2-naphthylsulfonyl)piperidin-1-yl]-3-nitropyridine

Step 7E: Using the procedure from Example 7A, Step 7E, 4-(2-naphthylsulfonyl)piperidine (130 mg, 0.51 mmol) was reacted with 2-chloro-3-nitropyridine (158 mg, 1.0 mmol) to afford the title compound (148 mg), a yellow solid, in 73% yield.

¹H NMR (400 MHz, CDCl₃) δ 1.80-1.99 (m, 2H), 2.11 (dd, J=12.5, 2.1 Hz, 2H), 2.86-3.12 (m, 2H), 3.16-3.34 (m, 1H), 3.94 (d, J=13.4 Hz, 2H), 6.77 (dd, J=8.1, 4.5 Hz, 1H), 7.59-7.77 (m, 1H), 7.86 (dd, J=8.6, 1.8 Hz, 1H), 7.95 (d, J=8.1 Hz, 1H), 7.98-8.08 (m, 2H), 8.12 (dd, J=8.1, 1.8 Hz, 1H), 8.31 (dd, J=4.5, 1.8 Hz, 1H), 8.47 (s, 1H). HRMS: calcd for $C_{20}H_{19}N_3O_4S+H+$, 398.11690. found (ESI-FTMS, [M+H]$^{1+}$), 398.1162. HPLC Method 1: room temperature, 5.94 min, 99.1%. HPLC Method 2: room temperature, 6.64 min, 99.4%.

Example 7N

2-[4-(2-naphthylsulfonyl)piperidin-1-yl]-5-nitropyridine

Step 7E: Using the procedure from Example 7A, Step 7E, 4-(2-naphthylsulfonyl)piperidine (Example 11, Step 3, 130 mg, 0.51 mmol) was reacted with 2-chloro-5-nitropyridine (158 mg, 1.0 mmol) to afford the title compound (63 mg), a yellow solid, in 31% yield.

¹H NMR (400 MHz, CDCl₃) δ 1.71-1.93 (m, 2H), 2.18 (d, J=10.1 Hz, 2H), 2.88-3.10 (m, 2H), 3.16-3.42 (m, 1H), 4.65 (d, J=13.9 Hz, 2H), 6.56 (d, J=9.3 Hz, 1H), 7.62-7.79 (m, 2H), 7.85 (dd, J=8.6, 1.8 Hz, 1H), 7.96 (d, J=7.8 Hz, 1H), 7.99-8.09 (m, 2H), 8.19 (dd, J=9.6, 2.8 Hz, 1H), 8.46 (d, J=1.8 Hz, 1H), 8.99 (d, J=2.3 Hz, 1H). HRMS: calcd for $C_{20}H_{19}N_3O_4S+H+$, 398.11690. found (ESI-FTMS, [M+H]$^{1+}$), 398.1161. HPLC Method 1: room temperature, 5.94 min, 97.6%. HPLC Method 2: room temperature, 6.63 min, 98.1%.

Example 7O

1-[4-(2-naphthylsulfonyl)piperidin-1-yl]isoquinoline

Step 7E: Using the procedure from Example 7A, Step 7E, 4-(2-naphthylsulfonyl)piperidine (130 mg, 0.51 mmol) was reacted with 1-chloroisoquinoline (164 mg, 1.0 mmol) to afford the title compound (151 mg), a white solid, in 31% yield.

¹H NMR (400 MHz, CDCl₃) δ 2.07-2.28 (m, 4H), 2.77-2.98 (m, 2H), 3.15-3.33 (m, 1H), 3.91 (d, J=13.1 Hz, 2H), 7.23-7.31 (m, 1H), 7.46-7.55 (m, 1H), 7.57-7.63 (m, 1H), 7.64-7.77 (m, 3H), 7.93 (dd, J=8.7, 1.9 Hz, 1H), 7.99 (t, J=9.0 Hz, 2H), 8.02-8.09 (m, 2H), 8.10 (d, J=5.8 Hz, 1H), 8.54 (d, J=1.5 Hz, 1H). HRMS: calcd for $C_{24}H_{22}N_2O_2S+H+$, 403.14747. found (ESI-FTMS, [M+H]$^{1+}$), 403.1477. HPLC Method 1: room temperature, 4.80 min, 99.2%. HPLC Method 2: room temperature, 6.61 min, 99.3%.

Example 7P

2-[4-(2-naphthylsulfonyl)piperidin-1-yl]nicotinonitrile

Step 7E: Using the procedure from Example 7A, Step 7E, 4-(2-naphthylsulfonyl)piperidine (Example 11, Step 3, 130 mg, 0.51 mmol) was reacted with 2-chloro-3-cyanopyridine (139 mg, 1.0 mmol) to afford the title compound (151 mg), a white solid, in 78% yield.

¹H NMR (400 MHz, CDCl₃) δ 1.84-2.04 (m, 2H), 2.15 (dd, J=12.6, 1.8 Hz, 2H), 2.79-3.09 (m, 2H), 3.15-3.37 (m, 1H), 4.31-4.69 (m, 2H), 6.77 (dd, J=7.6, 4.8 Hz, 1H), 7.60-7.81 (m, 3H), 7.87 (dd, J=8.6, 1.8 Hz, 1H), 7.96 (d, J=8.1 Hz, 1H), 7.99-8.10 (m, 2H), 8.32 (dd, J=4.8, 2.0 Hz, 1H), 8.48 (d, J=1.5 Hz, 1H). HRMS: calcd for $C_{21}H_{19}N_3O_2S+H+$, 378.12707. found (ESI-FTMS, [M+H]$^{1+}$), 378.1275. HPLC Method 1: room temperature, 5.77 min, 99.5%. HPLC Method 2: room temperature, 6.46 min, 99.4%.

Example 7Q 4-(2-naphthylsulfonyl)-1-[2-(trifluoromethyl)phenyl]piperidine

Step 7E: A 5 mL microwave reaction vial was charged with 4-(2-naphthylsulfonyl)piperidine (82 mg, 0.30 mmol), 2-bromobenzotrifluoride (67 mg, 0.30 mmol), NaOt-Bu (40 mg, 0.42 mmol), Pd₂(dba)₃ (26 mg, 0.025 mmol), racemic BINAP (31 mg, 0.05 mmol), and dioxane (1.5 mL). The mixture was degassed with N₂, capped, and heated in a 90° C. oil bath for 16 h. The mixture was diluted with CH₂Cl₂ (10 mL) and filtered through a plug of SiO₂. The organic phase was concentrated and purified by SiO₂ chromatography (15 to 30% EtOAc-hex) to afford the title compound (63 mg), a yellow oil, in 50% yield.

¹H NMR (400 MHz, CDCl₃) δ 1.94-2.19 (m, 4H), 2.60-2.77 (m, 2H), 2.92-3.31 (m, 3H), 7.09-7.32 (m, 2H), 7.44-7.52 (m, 1H), 7.56-7.77 (m, 3H), 7.89 (dd, J=8.6, 1.8 Hz, 1H), 7.96 (d, J=8.3 Hz, 1H), 7.99-8.11 (m, 2H), 8.50 (d, J=1.5 Hz, 1H). HRMS: calcd for C₂₂H₂₀F₃NO₂S+H+, 420.12396. found (ESI-FTMS, [M+H]¹⁺), 420.1245. HPLC Method 1: room temperature, 6.82 min, 98.5%. HPLC Method 2: room temperature, 7.36 min, 98.4%.

Example 7R 3-methyl-2-[4-(2-naphthylsulfonyl)piperidin-1-yl]pyridine

Step 7E: Using the procedure from Example 7A, 4-(2-naphthylsulfonyl)piperidine (82 mg, 0.30 mmol) was reacted with 2-bromo-6-methylpyridine (51 mg, 0.30 mmol) to afford the title compound (40 mg), a yellow solid, in 54% yield.

¹H NMR (400 MHz, CDCl₃) δ 1.88-2.06 (m, 2H), 2.13 (dd, J=12.4, 1.5 Hz, 2H), 2.66-2.82 (m, 2H), 3.07-3.33 (m, 1H), 3.53 (dd, J=10.5, 2.1 Hz, 2H), 6.85 (dd, J=7.3, 5.1 Hz, 1H), 7.38 (dd, J=7.3, 1.3 Hz, 1H), 7.61-7.76 (m, 2H), 7.90 (dd, J=8.6, 1.8 Hz, 1H), 7.96 (d, J=8.1 Hz, 1H), 7.99-8.07 (m, 2H), 8.11 (dd, J=5.3, 1.5 Hz, 1H), 8.50 (d, J=1.8 Hz, 1H). HRMS: calcd for C₂₁H₂₂N₂O₂S+H+, 367.14747. found (ESI-FTMS, [M+H]¹⁺), 367.148. HPLC Method 1: room temperature, 4.60 min, 94.7%. HPLC Method 2: room temperature, 5.65 min, 91.7%.

Example 7S

2-{4-[(3,4-dichlorophenyl)sulfonyl]piperidin-1-yl}-3-methylpyridine

Step 7E: Using the procedure from Example 7A, Step 7E, 4-[(3,4-dichlorophenyl)sulfonyl]piperidine (88 mg, 0.30 mmol) was reacted with 2-bromo-6-methylpyridine (62 mg, 0.040 mL, 0.36 mmol) to afford the title compound (37 mg), a pale yellow solid, in 32% yield.

¹H NMR (400 MHz, CDCl₃) δ 1.84-2.01 (m, 2H), 2.08 (d, J=12.4 Hz, 2H), 2.24 (s, 3H), 2.68-2.85 (m, 2H), 2.96-3.18 (m, 1H), 3.55 (d, J=10.6 Hz, 2H), 6.87 (dd, J=7.3, 5.1 Hz, 1 H), 7.41 (dd, J=7.3, 1.3 Hz, 1H), 7.68 (d, J=8.3 Hz, 1H), 7.74 (dd, J=8.3, 2.1 Hz, 1H), 8.01 (d, J=2.0 Hz, 1H), 8.13 (dd, J=5.2, 1.6 Hz, 1H). HRMS: calcd for C₁₇H₁₈Cl₂N₂O₂S+H+, 385.05388. found (ESI-FTMS, [M+H]¹⁺), 385.0545.

Example 7T 2-({1-[3-(trifluoromethyl)pyridin-2-yl]piperidin-4-yl}sulfonyl)quinoline Step 7E: The corresponding quinoline amine from Step 7D (140 mg, 0.51 mmol) was reacted with 2-chloro-3-(trifluoromethyl)pyridine (182 mg, 1.0 mmol) as in Example 7A, Step 7E to afford the title compound (101 mg), a white powder, in 47% yield.

¹H NMR (400 MHz, CDCl₃) δ 2.03-2.25 (m, 4H), 2.88-3.01 (m, 2H), 3.70 (d, J=13.1 Hz, 2H), 3.83-4.02 (m, 1H), 7.02 (dd, J=7.8, 4.8 Hz, 1H), 7.66-7.78 (m, 1H), 7.81-7.92 (m, 2H), 7.92-8.03 (m, 1H), 8.17 (d, J=8.6 Hz, 1H), 8.28 (dd, J=8.6, 1.0 Hz, 1H), 8.42 (dd, J=4.8, 1.3 Hz, 1H), 8.45 (d, J=8.6 Hz, 1H). HRMS: calcd for C₂₀H₁₈F₃N₃O₂S+H+, 422.11446. found (ESI-FTMS, [M+H]¹⁺), 422.1148. HPLC Method 1: room temperature, 6.05 min, 91.1%. HPLC Method 2: room temperature, 6.74 min, 90.7%.

Example 7U

2-{[1-(3,5-dichloropyridin-4-yl)piperidin-4-yl]sulfonyl}quinoline

Step 7E: Using the procedure from Example 7A, Step 7E, 2-(piperidin-4-ylsulfonyl)quinoline (150 mg, 0.51 mmol) was reacted with 3,4,5-trichloropyridine (182 mg, 1.0 mmol) to afford the title compound (34 mg), an off-white solid, in 16% yield.

¹H NMR (400 MHz, CDCl₃) δ 2.06-2.24 (m, 4H), 3.25-3.40 (m, 2H), 3.40-3.52 (m, 2H), 3.84-4.01 (m, 1H), 7.69-7.79 (m, 1H), 7.83-7.92 (m, 1H), 7.97 (d, J=8.1 Hz, 1H), 8.18 (d, J=8.6 Hz, 1H), 8.28 (d, J=8.6 Hz, 1H), 8.34 (s, 2H), 8.47 (d, J=7.8 Hz, 1H). HRMS: calcd for C₁₉H₁₇Cl₂N₃O₂S+H+, 422.04913. found (ESI-FTMS, [M+H]¹⁺), 422.0496. HPLC Method 1: room temperature, 6.11 min, 97.5%. HPLC Method 2: room temperature, 6.91 min, 98.7%.

Example 7V

2-[4-(quinolin-2-ylsulfonyl)piperidin-1-yl]nicotinonitrile

Step 7E: Using the procedure from Example 7A, Step 7E, 2-(piperidin-4-ylsulfonyl)quinoline (Example 1T, Step 3, 150 mg, 0.51 mmol) was reacted with 2-chloro-3-cyanopyridine (139 mg, 1.0 mmol) to afford the title compound (166 mg), an off-white solid, in 86% yield.

¹H NMR (400 MHz, CDCl₃) δ 2.06-2.26 (m, 4H), 2.95-3.28 (m, 2H), 3.90-4.11 (m, 1H), 4.41-4.62 (m, 2H), 6.77 (dd, J=7.8, 4.8 Hz, 1H), 7.67-7.82 (m, 2H), 7.83-7.93 (m, 1H), 7.94-8.02 (m, 1H), 8.16 (d, J=8.3 Hz, 1H), 8.27 (dd, J=8.6, 1.0 Hz, 1H), 8.33 (dd, J=4.8, 2.0 Hz, 1H), 8.46 (d, J=7.8 Hz, 1H). HRMS: calcd for C₁₉H₁₇Cl₂N₃O₂S+H+, 422.04913. found (ESI-FTMS, [M+H]¹⁺), 422.0496. HPLC purity H₂O/CH₃CN 97.5%, H₂O/MeOH 98.7%. HRMS: calcd for C₂₀H₁₈N₄O₂S+H+, 379.12232. found (ESI-FTMS, [M+H]¹⁺), 379.1227. HPLC Method 1: room temperature, 5.38 min, 100%. HPLC Method 2: room temperature, 6.02 min, 100%.

Example 7W

2-[4-(phenylsulfonyl)piperidin-1-yl]-3-(trifluoromethyl)pyridine

Step 7E: To a microwave vial were charged 4-(phenylsulfonyl)piperidine (300 mg, 1.33 mmol), 2-chloro-3-(trifluoromethyl)pyridine, (484 mg, 2.66 mmol), diisopropylethylamine (0.695 mL, 3.99 mmol) and 1,4-Dioxane (0.2 mL). The reaction mixture thus prepared was irradiated at 200° C. for 1 hour. The reaction was complete as determined by TLC. The residue was added with saturated NH₄Cl (aq.) and extracted with ethylacetate, washed with 10% HCl (aq.), water then brine. Organic layer was dried over MgSO₄. Solvent evaporation afforded 2-[4-(phenylsulfonyl)piperidin-1-yl]-3-(trifluoromethyl)pyridine in 55% yield (270 mg) as white solid.

1H NMR (400 MHz, CHLOROFORM-D) δ ppm 1.93 (dd, J=12.63, 3.79 Hz, 2H) 2.01-2.13 (m, 2H) 2.78-2.94 (m, 2H)

3.08 (s, 1H) 3.68 (dd, J=10.61, 2.27 Hz, 2H) 7.02 (dd, J=7.83, 4.80 Hz, 1H) 7.60 (t, J=7.58 Hz, 2H) 7.65-7.74 (m, 1H) 7.86 (dd, J=7.83, 1.77 Hz, 1H) 7.88-7.97 (m, 2H) 8.41 (d, J=4.80, 1.77 Hz, 1H). HRMS: calcd for $C_{17}H_{17}F_3N_2O_2S+H+$, 371.10356. found (ESI-FTMS, [M+H]$^{1+}$), 371.1048. HPLC Method 1: room temperature, 5.733 min, 99.40%, HPLC Method 2: room temperature, 6.463 min, 99.24%.

Example 7X

2-{4-[(2-chlorophenyl)sulfonyl]piperidin-1-yl}-3-(trifluoromethyl)pyridine

The title compound was prepared according to a similar procedure described for Example 7A. Yield 74%.

1H NMR (400 MHz, CHLOROFORM-D) δ ppm 1.90-2.00 (m, 2H), 2.01-2.14 (m, 2H), 2.86-2.99 (m, 2H), 3.64-3.76 (m, 3H), 7.00-7.06 (m, 1H), 7.46-7.52 (m, 1H), 7.56-7.62 (m, 2H), 7.87 (dd, J=7.7, 1.9 Hz, 1H), 8.10-8.17 (m, 1H), 8.43 (dd, J=4.8, 2.0 Hz, 1H). HRMS: calcd for $C_{17}H_{16}ClF_3N_2O_2S+H+$, 405.06458. found (ESI-FTMS, [M+H]$^{1+}$), 405.0661.

Example 7Y

3-chloro-2-{4-[(2-chlorophenyl)sulfonyl]piperidin-1-yl}pyridine

Using the procedure from Example 7A, 4-[(2-chlorophenyl)sulfonyl]piperidine (150 mg, 0.58 mmol) was reacted with 2,3-dichloropyridine (173 mg, 1.16 mmol) to afford the title compound (110 mg), a white solid, in 51% yield.

1H NMR (400 MHz, CHLOROFORM-D) δ ppm 1.93-2.02 (m, 2H), 2.03-2.16 (m, 2H), 2.78-2.88 (m, 2H), 3.66-3.77 (m, 1H), 3.91-4.01 (m, J=10.5, 2.7 Hz, 2H), 6.85 (dd, J=7.8, 4.8 Hz, 1H), 7.46-7.52 (m, 1H), 7.56-7.61 (m, 3H), 8.11-8.15 (m, 1H), 8.16 (dd, J=4.8, 1.8 Hz, 1H). HRMS: calcd for $C_{16}H_{16}Cl_2N_2O_2S+H+$, 371.03823. found (ESI-FTMS, [M+H]$^{1+}$), 371.0384.

Example 7Z

3,5-dichloro-4-{4-[(2-chlorophenyl)sulfonyl]piperidin-1-yl}pyridine

Using the procedure from Example 7A, 4-[(2-chlorophenyl)sulfonyl]piperidine (100 mg, 0.38 mmol) was reacted with 2-chloro-5-(trifluoromethyl)pyridine (142 mg, 0.76 mmol) to afford the title compound (22 mg), a white solid, in 14% yield.

1H NMR (400 MHz, CHLOROFORM-D) δ ppm 1.89-2.00 (m, 2H), 2.03-2.17 (m, 2H), 3.24-3.36 (m, 2H), 3.40-3.49 (m, 2H), 3.65-3.77 (m, 1H), 7.44-7.54 (m, 1H), 7.57-7.63 (m, 2H), 8.06-8.19 (m, 1H), 8.35 (s, 2H). HRMS: calcd for $C_{16}H_{15}Cl_3N_2O_2S+H+$, 404.99925. found (ESI-FTMS, [M+H]$^{1+}$), 404.9996.

Example 7AA

2-{4-[(3-chlorophenyl)sulfonyl]piperidin-1-yl}-3-(trifluoromethyl)pyridine

The title compound (161 mg, 69% yield) was prepared according to a similar procedure described for example 7A.

1H NMR (400 MHz, CHLOROFORM-D) δ ppm 1.86-2.01 (m, 2H), 2.01-2.13 (m, 2H), 2.88 (t, J=12.3 Hz, 2H), 3.03-3.14 (m, 1H), 3.69 (d, J=12.1 Hz, 2H), 7.03 (dd, J=7.2, 5.2 Hz, 1H), 7.55 (t, J=7.8 Hz, 1H), 7.66 (d, J=7.6 Hz, 1H), 7.80 (d, J=7.6 Hz, 1H), 7.86 (d, J=7.8 Hz, 1H), 7.91 (s, 1H), 8.42 (d, J=4.3 Hz, 1H). HRMS: calcd for $C_{17}H_{16}ClF_3N_2O_2S+H+$, 405.06458. found (ESI-FTMS, [M+H]$^{1+}$), 405.0662.

Example 7AB

2-{4-[(3-chlorophenyl)sulfonyl]piperidin-1-yl}-5-(trifluoromethyl)pyridine

Step 7E: Using the procedure from Example 7A, Step 7E, 4-[(3-chlorophenyl)sulfonyl]piperidine (150 mg, 0.58 mmol) was reacted with 2-chloro-5-(trifluoromethyl)pyridine (211 mg, 1.16 mmol), DIEA (0.3 ml, 1.74) and 1,4-dioxane (0.2 ml) to afford the title compound (151 mg), a white solid, in 64% yield.

1H NMR (400 MHz, CHLOROFORM-D) δ ppm 1.66-1.83 (m, 2H), 2.03-2.13 (m, 2H), 2.81-2.95 (m, 2H), 3.11-3.30 (m, 1H), 4.43-4.63 (m, 2H), 6.64 (d, J=9.1 Hz, 1H), 7.54 (t, J=8.0 Hz, 1H), 7.59-7.70 (m, 2H), 7.78 (dd, J=7.8, 2.8 Hz, 1H), 7.88 (s, 1H), 8.38 (s, 1H). HRMS: calcd for $C_{17}H_{16}ClF_3N_2O_2S+H+$, 405.06458. found (ESI-FTMS, [M+H]$^{1+}$), 405.0655.

Example 7AC

3-chloro-2-{4-[(3-chlorophenyl)sulfonyl]piperidin-1-yl}pyridine

Step 1: Using the procedure from Example 7A, 4-[(3-chlorophenyl)sulfonyl]piperidine (150 mg, 0.58 mmol) was reacted with 2,3-dichloropyridine (173 mg, 1.16 mmol), DIEA (0.3 ml, 1.74) and 1,4-dioxane (0.2 ml) to afford the title compound (74 mg), a beige solid, in 34% yield.

1H NMR (400 MHz, CHLOROFORM-D) δ ppm 1.90-2.01 (m, 2H), 2.05-2.13 (m, J=12.3, 2.1 Hz, 2H), 2.74-2.84 (m, 2H), 3.06-3.17 (m, 1H), 3.92-3.99 (m, 2H), 6.85 (dd, J=7.8, 4.8 Hz, 1H), 7.55 (t, J=8.1 Hz, 1H), 7.58 (dd, J=7.8, 1.8 Hz, 1H), 7.64-7.69 (m, 1H), 7.81 (dd, J=8.1, 1.3 Hz, 1H), 7.91 (s, 1H), 8.15 (dd, J=4.7, 1.6 Hz, 1H). HRMS: calcd for $C_{16}H_{16}Cl_2N_2O_2S+H+$, 371.03823. found (ESI-FTMS, [M+H]$^{1+}$), 371.0399.

Example 7AD

3,5-dichloro-4-{4-[(3-chlorophenyl)sulfonyl]piperidin-1-yl}pyridine

Step 1: Using the procedure from Example 7A, 4-[(3-chlorophenyl)sulfonyl]piperidine (150 mg, 0.58 mmol) was reacted with 3,4,5-trichloropyridine (216 mg, 1.16 mmol), DIEA (0.3 ml, 1.74) and 1,4-dioxane (0.2 ml) to afford the title compound (35 mg), a white solid, in 15% yield.

1H NMR (400 MHz, CHLOROFORM-D) δ ppm 1.86-2.11 (m, 4H), 3.04-3.16 (m, 1H), 3.27 (t, J=12.3 Hz, 2H), 3.43 (d, J=13.4 Hz, 2H), 7.55 (t, J=7.8 Hz, 1H), 7.67 (d, J=7.8 Hz, 1H), 7.81 (d, J=7.8 Hz, 1H), 7.91 (s, 1H), 8.35 (s, 2H). HRMS: calcd for $C_{16}H_{15}Cl_3N_2O_2S+H+$, 404.99925. found (ESI-FTMS, [M+H]$^{1+}$), 405.001.

Example 7AE

2-{4-[(3-chlorophenyl)sulfonyl]piperidin-1-yl}-3-nitropyridine

Step 1: Using the procedure from Example 7A, 4-[(3-chlorophenyl)sulfonyl]piperidine (100 mg, 0.38 mmol) was reacted with 2-chloro-3-nitropyridine (122 mg, 0.76 mmol), DIEA (0.2 ml, 1.14) and 1,4-dioxane (0.3 ml) to afford the title compound (118 mg), a yellow solid, in 81% yield.

1H NMR (400 MHz, CHLOROFORM-D) δ ppm 1.79-1.96 (m, 2H), 2.02-2.12 (m, J=12.3, 2.7 Hz, 2H), 2.94-3.05 (m, 2H), 3.12-3.24 (m, 1H), 3.86-3.99 (m, 2H), 6.81 (dd, J=8.1, 4.5 Hz, 1H), 7.54 (t, J=7.7 Hz, 1H), 7.63-7.69 (m, 1H), 7.76-7.81 (m, 1H), 7.89 (s, 1H), 8.14 (dd, J=8.1, 1.8 Hz, 1H), 8.33 (dd, J=4.5, 1.8 Hz, 1H). HRMS: calcd for $C_{16}H_{16}ClN_3O_4S+H+$, 382.06228. found (ESI-FTMS, $[M+H]^{1+}$), 382.0624.

Example 7AF

2-{4-[(3-chlorophenyl)sulfonyl]piperidin-1-yl}-5-nitropyridine

Step 1: Using the procedure from Example 7A, 4-[(3-chlorophenyl)sulfonyl]piperidine (100 mg, 0.38 mmol) was reacted with 2-chloro-5-nitropyridine (122 mg, 0.76 mmol), DIEA (0.2 ml, 1.14) and 1,4-dioxane (0.3 ml) to afford the title compound (40 mg), a yellow solid, in 28% yield.

1H NMR (400 MHz, CHLOROFORM-D) δ ppm 1.64-1.89 (m, 2H), 2.13 (dd, J=14.3, 1.9 Hz, 2H), 2.91-3.04 (m, 2H), 3.16-3.33 (m, 1H), 4.67 (d, J=13.6 Hz, 2H), 6.59 (d, J=11.0 Hz, 1H), 7.55 (t, J=8.0 Hz, 1H), 7.61-7.72 (m, 1H), 7.74-7.81 (m, 1H), 7.88 (s, 1H), 8.22 (dd, J=9.5, 2.9 Hz, 1H), 9.02 (d, J=2.3 Hz, 1H). HRMS: calcd for $C_{16}H_{16}ClN_3O_4S+H+$, 382.06228. found (ESI-FTMS, $[M+H]^{1+}$), 382.0622.

Example 7AG

1-{4-[(3-chlorophenyl)sulfonyl]piperidin-1-yl}isoquinoline

Step 1: Using the procedure from Example 7A, 4-[(3-chlorophenyl)sulfonyl]piperidine (100 mg, 0.38 mmol) was reacted with 1-chloroisoquinoline (131 mg, 0.76 mmol), DIEA (0.2 ml, 1.14) and 1,4-dioxane (0.3 ml) to afford the title compound (4 mg), a beige solid, in 3% yield.

1H NMR (400 MHz, CHLOROFORM-D) δ ppm 2.05-2.25 (broad, m, 4H), 2.87-2.99 (m, 2H), 3.07-3.25 (m, 1H), 3.84-3.98 (m, J=12.6 Hz, 2H), 7.24-7.33 (m, 2H), 7.48-7.70 (m, 3H), 7.76 (d, J=8.3 Hz, 1H), 7.85 (d, J=7.8 Hz, 1H), 7.95 (s, 1H), 8.01 (d, J=8.6 Hz, 1H), 8.12 (d, J=5.6 Hz, 1H). HRMS: calcd for $C_{20}H_{19}ClN_2O_2S+H+$, 387.09285. found (ESI-FTMS, $[M+H]^{1+}$), 387.0933.

Example 7AH

2-{4-[(3-chlorophenyl)sulfonyl]piperidin-1-yl}nicotinonitrile

Step 1: Using the procedure from Example 7A, 4-[(3-chlorophenyl)sulfonyl]piperidine (100 mg, 0.38 mmol) was reacted with 2-chloro-3-cyanopyridine (108 mg, 0.76 mmol), DIEA (0.2 ml, 1.14) and 1,4-dioxane (0.3 ml) to afford the title compound (91 mg), a yellow solid, in 62% yield.

1H NMR (400 MHz, CHLOROFORM-D) δ ppm 1.84-1.96 (m, 2H), 2.06-2.14 (m, 2H), 2.93-3.04 (m, 2H), 3.11-3.23 (m, 1H), 4.45-4.54 (m, 2H), 6.80 (dd, J=7.6, 4.8 Hz, 1H), 7.55 (t, J=8.0 Hz, 1H), 7.59-7.67 (m, 1H), 7.72-7.83 (m, 2H), 7.89 (s, 1H), 8.34 (dd, J=4.8, 2.0 Hz, 1H). HRMS: calcd for $C_{17}H_{16}ClN_3O_2S+H+$, 362.07245. found (ESI-FTMS, $[M+H]^{1+}$), 362.0737.

Example 7AI

2-{4-[(3-chlorophenyl)sulfonyl]piperidin-yl}-3-fluoropyridine

Step 1: Using the procedure from Example 7A, 4-[(3-chlorophenyl)sulfonyl]piperidine (100 mg, 0.38 mmol) was reacted with 2-chloro-3-fluoropyridine (100 mg, 0.76 mmol), DIEA (0.2 ml, 1.14) and 1,4-dioxane (0.3 ml) to afford the title compound (9 mg), a yellow solid, in 7% yield.

1H NMR (400 MHz, CHLOROFORM-D) δ ppm 1.80-1.94 (m, 2H), 2.02-2.14 (m, 2H), 2.78-2.88 (m, 2H), 3.09-3.22 (m, 1H), 4.08-4.25 (m, 2H), 6.74-6.81 (m, 1H), 7.17-7.26 (m, 1H), 7.54 (t, J=8.1 Hz, 1H), 7.61-7.70 (m, 1H), 7.75-7.84 (m, 1H), 7.90 (s, 1H), 7.94-8.04 (m, 1H). HRMS: calcd for $C_{16}H_{16}ClFN_2O_2S+H+$, 355.06778. found (ESI-FTMS, $[M+H]^{1+}$), 355.0693.

Example 7AJ

2-{4-[(4-chlorophenyl)sulfonyl]piperidin-1-yl}-3-(trifluoromethyl)pyridine

Step 7E: The title compound (109 mg, 71% yield), a white solid, was prepared according to a similar procedure described for Example 7A.

1H NMR (400 MHz, CHLOROFORM-D) δ ppm 1.85-1.98 (m, 2H), 1.99-2.13 (m, 2H), 2.87 (t, J=12.3 Hz, 2H), 2.95-3.15 (m, 1H), 3.67 (d, J=12.6 Hz, 2H), 6.95-7.09 (broad, m, 1H), 7.57 (d, J=8.3 Hz, 2H), 7.85 (d, J=5.1 Hz, 3H), 8.41 (broad, s, 1H). HRMS: calcd for $C_{17}H_{16}ClF_3N_2O_2S+H+$, 405.06458. found (ESI-FTMS, $[M+H]^{1+}$), 405.0649.

Example 7AK

2-{4-[(4-chlorophenyl)sulfonyl]piperidin-1-yl}-5-(trifluoromethyl)pyridine

Step 1: Using the procedure from Example 7A, 4-[(4-chlorophenyl)sulfonyl]piperidine (100 mg, 0.38 mmol) was reacted with 2-chloro-5-(trifluoromethyl)pyridine (138 mg, 0.76 mmol), DIEA (0.27 ml, 1.52 mmol) and 1,4-dioxane (0.3 ml) at 190° C. to afford the title compound (112 mg), a white solid, in 73% yield.

1H NMR (400 MHz, CHLOROFORM-D) δ ppm 1.65-1.84 (m, 2H), 2.09 (d, J=13.4 Hz, 2H), 2.88 (t, J=12.9 Hz, 2H), 3.11-3.25 (m, 1H), 4.55 (d, J=14.9 Hz, 2H), 6.63 (d, J=8.3 Hz, 1H), 7.57 (d, J=6.8 Hz, 2H), 7.62 (d, J=8.8 Hz, 1H), 7.82 (d, J=8.8 Hz, 2H), 8.37 (s, 1H). HRMS: calcd for $C_{17}H_{16}ClF_3N_2O_2S+H+$, 405.06458. found (ESI-FTMS, $[M+H]^{1+}$), 405.0663.

Example 7AL 3-chloro-2-{4-[(4-chlorophenyl)sulfonyl]piperidin-1-yl}pyridine

Step 7E: Using the procedure from Example 7A, 4-[(4-chlorophenyl)sulfonyl]piperidine (100 mg, 0.38 mmol) was reacted with 2,3-dichloropyridine (114 mg, 0.76 mmol), DIEA (0.27 ml, 1.52) and 1,4-dioxane (0.3 ml) at 190° C. to afford the title compound (56 mg), a white solid, in 40% yield.

1H NMR (400 MHz, CHLOROFORM-D) δ ppm 1.79-1.97 (m, 2H), 2.02-2.22 (m, 2H), 2.77 (t, J=12.6 Hz, 2H), 2.97-3.19 (m, 1H), 3.94 (d, J=11.6 Hz, 2H), 6.71-6.95 (m, 1H), 7.58 (d, J=7.6 Hz, 3H), 7.85 (d, J=8.3 Hz, 2H), 8.15 (s, 1H). HRMS: calcd for $C_{16}H_{16}Cl_2N_2O_2S$+H+, 371.03823. found (ESI-FTMS, [M+H]$^{1+}$), 371.0385.

Example 7AM 3,5-dichloro-4-{4-[(4-chlorophenyl)sulfonyl]piperidin-1-yl}pyridine Step 1: Using the procedure from Example 7A, 4-[(4-chlorophenyl)sulfonyl]piperidine (100 mg, 0.38 mmol) was reacted with 3,4,5-trichloropyridine (141 mg, 0.76 mmol), DIEA (0.27 ml, 1.52) and 1,4-dioxane (0.3 ml) at 190° C. to afford the title compound (51 mg), a white solid, in 33% yield.

1H NMR (400 MHz, CHLOROFORM-D) δ ppm 1.86-2.00 (m, 2H), 2.01-2.13 (m, 2H), 2.97-3.13 (m, 1H), 3.25 (t, J=12.3 Hz, 2H), 3.42 (d, J=12.4 Hz, 2H), 7.58 (d, 2H), 7.76-7.91 (m, 2H), 8.34 (s, 2H). HRMS: calcd for $C_{16}H_{15}Cl_3N_2O_2S$+H+, 404.99925. found (ESI-FTMS, [M+H]$^{1+}$), 405.0012.

Example 7AN

1-{4-[(4-chlorophenyl)sulfonyl]piperidin-1-yl}isoquinoline

Step 1: Using the procedure from Example 7A, 4-[(4-chlorophenyl)sulfonyl]piperidine (100 mg, 0.38 mmol) was reacted with 1-chloroisoquinoline (131 mg, 0.76 mmol), DIEA (0.27 ml, 1.52) and 1,4-dioxane (0.3 ml) at 190° C. to afford the title compound (15 mg), an off-white solid, in 10% yield.

1H NMR (400 MHz, CHLOROFORM-D) δ ppm 2.00-2.19 (m, 4H), 2.81-2.99 (m, 2H), 3.05-3.28 (m, 1H), 3.92 (d, J=13.1 Hz, 2H), 7.27 (d, J=6.1 Hz, 1H), 7.43-7.54 (m, 1H), 7.56-7.64 (m, 3H), 7.75 (d, J=8.1 Hz, 1H), 7.81-7.94 (m, 2H), 8.00 (d, J=9.1 Hz, 1H), 8.12 (d, J=5.8 Hz, 1H). HRMS: calcd for $C_{20}H_{19}ClN_2O_2S$+H+, 387.09285. found (ESI-FTMS, [M+H]$^{1+}$), 387.0935.

Example 7AO

2-{4-[(4-chlorophenyl)sulfonyl]piperidin-1-yl}quinoline

Step 1: Using the procedure from Example 1A, 4-[(4-chlorophenyl)sulfonyl]piperidine (100 mg, 0.38 mmol) was reacted with 2-chloroquinoline (124 mg, 0.76 mmol), DIEA (0.27 ml, 1.52) and 1,4-dioxane (0.3 ml) at 190° C. to afford the title compound (11 mg), a white solid, in 8% yield.

1H NMR (400 MHz, CHLOROFORM-D) δ ppm 1.69-1.85 (m, 2H), 2.13 (d, J=13.1 Hz, 2H), 2.91 (t, J=13.3 Hz, 2H), 3.08-3.27 (m, 1H), 4.71 (d, J=13.9 Hz, 2H), 6.96 (d, J=7.8 Hz, 1H), 7.20-7.30 (m, 1H), 7.46-7.62 (m, 4H), 7.68 (d, J=8.6 Hz, 1H), 7.83 (d, J=8.3 Hz, 2H), 7.89 (d, J=9.3 Hz, 1H). HRMS: calcd for $C_{20}H_{19}ClN_2O_2S$+H+, 387.09285. found (ESI-FTMS, [M+H]$^{1+}$), 387.0947.

Example 7AP

2-{4-[(4-chlorophenyl)sulfonyl]piperidin-1-yl}-3-fluoropyridine

Step 1: Using the procedure from Example 7A, 4-[(4-chlorophenyl)sulfonyl]piperidine (100 mg, 0.38 mmol) was reacted with 2-chloro-3-fluoropyridine (78 μl, 0.76 mmol), DIEA (0.27 ml, 1.52) and 1,4-dioxane (0.3 ml) at 190° C. to afford the title compound (18 mg), a white solid, in 13% yield.

1H NMR (400 MHz, CHLOROFORM-D) δ ppm 1.75-1.92 (m, 2H), 2.01-2.13 (m, 2H), 2.67-2.88 (m, 2H), 3.04-3.18 (m, 1H), 4.14-4.23 (m, 2H), 6.71-6.81 (m, 1H), 7.17-7.26 (m, 1H), 7.51-7.61 (m, 2H), 7.79-7.87 (m, 2H), 7.93-8.02 (m, 1H). HRMS: calcd for $C_{16}H_{16}ClFN_2O_2S$+H+, 355.06778. found (ESI-FTMS, [M+H]$^{1+}$), 355.0691.

Example 7AQ

2-{4-[(4-chlorophenyl)sulfonyl]piperidin-1-yl}-4-(trifluoromethyl)pyridine

Step 1: Using the procedure from Example 1A, 4-[(4-chlorophenyl)sulfonyl]piperidine (100 mg, 0.38 mmol) was reacted with 2-chloro-4-(trifluoromethyl)pyridine (99 μl, 0.76 mmol), DIEA (0.27 ml, 1.52) and 1,4-dioxane (0.3 ml) at 190° C. to afford the title compound (49 mg), an off-white solid, in 32% yield.

1H NMR (400 MHz, CHLOROFORM-D) δ ppm 1.66-1.82 (m, 2H), 2.10 (dd, J=13.9, 3.3 Hz, 2H), 2.75-2.93 (m, 2H), 3.08-3.24 (m, 1H), 4.50 (d, J=13.6 Hz, 2H), 6.73-6.83 (m, 2H), 7.50-7.62 (m, 2H), 7.76-7.87 (m, 2H), 8.28 (d, J=5.1 Hz, 1H). HRMS: calcd for $C_{17}H_{16}ClF_3N_2O_2S$+H+, 405.06458. found (ESI-FTMS, [M+H]$^{1+}$), 405.0665.

Example 7AR

2-{4-[(4-tert-butylphenyl)sulfonyl]piperidin-1-yl}-3-(trifluoromethyl)pyridine

The title compound (75 mg, 49% yield), a white solid, was obtained according to a similar procedure described for Example 7A.

1H NMR (400 MHz, CHLOROFORM-D) δ ppm 1.37 (s, 9H), 1.85-2.01 (m, 2H), 2.01-2.17 (m, 2H), 2.69-2.89 (m, 2H), 2.94-3.16 (m, 1H), 3.69 (d, J=13.1 Hz, 2H), 7.01 (dd, J=7.8, 4.8 Hz, 1H), 7.48-7.65 (m, 2H), 7.75-7.94 (m, 3H), 8.41 (d, J=4.8 Hz, 1H). HRMS: calcd for $C_{21}H_{25}F_3N_2O_2S$+H+, 427.16616. found (ESI-FTMS, [M+H]$^{1+}$), 427.1666.

Example 7AS

2-{4-[(4-tert-butylphenyl)sulfonyl]piperidin-1-yl}-5-(trifluoromethyl)pyridine

The title compound (119 mg), an off-white solid, was obtained in 77% yield according to a similar procedure described for example 7A.

1H NMR (400 MHz, CHLOROFORM-D) δ ppm 1.36 (s, 9H), 1.67-1.81 (m, 2H), 2.05-2.17 (m, 2H), 2.83-2.93 (m, 2H), 3.11-3.24 (m, 1H), 4.54 (d, J=13.6 Hz, 2H), 6.63 (d, J=9.1 Hz, 1H), 7.54-7.59 (m, 2H), 7.60-7.66 (m, 1H), 7.71-7.85 (m, 2H), 8.36 (s, 1H). HRMS: calcd for $C_{21}H_{25}F_3N_2O_2S$+H+, 427.16616. found (ESI-FTMS, [M+H]$^{1+}$), 427.1675.

Example 7AT

2-{4-[(4-tert-butylphenyl)sulfonyl]piperidin-1-yl}-3-chloropyridine

Step 1: Using the procedure from Example 7A, 4-[(4-tert-butylphenyl)sulfonyl]piperidine (100 mg, 0.36 mmol) was reacted with 2,3-dichloropyridine (108 mg, 0.72 mmol), DIEA (0.25 ml, 1.44) and 1,4-dioxane (0.3 ml) at 185° C. to afford the title compound (40 mg), a white solid, in 28% yield.

1H NMR (400 MHz, CHLOROFORM-D) δ ppm 1.37 (s, 9H), 1.88-2.02 (m, 2H), 2.10 (dd, J=12.1, 2.0 Hz, 2H), 2.68-2.85 (m, 2H), 3.00-3.20 (m, 1H), 3.94 (d, J=13.1 Hz, 2H), 6.84 (dd, J=7.8, 4.8 Hz, 1H), 7.49-7.63 (m, 3H), 7.83 (d, J=8.6 Hz, 2H), 8.15 (dd, J=4.8, 1.5 Hz, 1H). HRMS: calcd for $C_{20}H_{25}ClN_2O_2S+H+$, 393.13980. found (ESI-FTMS, $[M+H]^{1+}$), 393.141.

Example 7AU

4-{4-[(4-tert-butylphenyl)sulfonyl]piperidin-1-yl}-3,5-dichloropyridine

Step 1: Using the procedure from Example 7A, 4-[(4-tert-butylphenyl)sulfonyl]piperidine (100 mg, 0.36 mmol) was reacted with 3,4,5-trichloropyridine (134 mg, 0.72 mmol), DIEA (0.25 ml, 1.44) and 1,4-dioxane (0.3 ml) at 185° C. to afford the title compound (16 mg), a white solid, in 10% yield.

1H NMR (400 MHz, CHLOROFORM-D) δ ppm 1.37 (s, 9H), 1.90-2.03 (m, 2H), 2.03-2.11 (m, 2H), 3.02-3.12 (m, 1H), 3.18-3.31 (m, 2H), 3.37-3.48 (m, 2H), 7.60 (d, J=8.8 Hz, 2H), 7.83 (d, J=8.6 Hz, 2H), 8.33 (s, 2H). HRMS: calcd for $C_{20}H_{24}Cl_2N_2O_2S+H+$, 427.10083. found (ESI-FTMS, $[M+H]^{1+}$), 427.1028.

Example 7AV

1-{4-[(4-tert-butylphenyl)sulfonyl]piperidin-1-yl}isoquinoline

Step 1: Using the procedure from Example 7A, 4-[(4-tert-butylphenyl)sulfonyl]piperidine (150 mg, 0.53 mmol) was reacted with 1-chloroisoquinoline (183 mg, 1.06 mmol), DIEA (0.37 ml, 2.12) and 1,4-dioxane (0.2 ml) at 185° C. to afford the title compound (40 mg), a white solid, in 18% yield.

1H NMR (400 MHz, CHLOROFORM-D) δ ppm 1.38 (s, 9H), 2.08-2.21 (m, 4H), 2.84-2.97 (m, 2H), 3.04-3.21 (m, 1H), 3.92 (d, J=12.9 Hz, 2H), 7.23-7.28 (m, 1H), 7.48-7.54 (m, 1H), 7.58-7.66 (m, 3H), 7.75 (d, J=8.1 Hz, 1H), 7.87 (d, J=8.3 Hz, 2H), 8.01 (d, J=8.3 Hz, 1H), 8.11 (d, J=5.8 Hz, 1H). HRMS: calcd for $C_{24}H_{28}N_2O_2S+H+$, 409.19442. found (ESI-FTMS, $[M+H]^{1+}$), 409.1959.

Example 7AX

2-{4-[(4-tert-butylphenyl)sulfonyl]piperidin-1-yl}quinoline

Step 1: Using the procedure from Example 7A, 4-[(4-tert-butylphenyl)sulfonyl]piperidine (150 mg, 0.53 mmol) was reacted with 2-chloroquinoline (175 mg, 1.06 mmol), DIEA (0.37 ml, 2.12) and 1,4-dioxane (0.2 ml) at 185° C. to afford the title compound (39 mg), a white solid, in 18% yield.

1H NMR (400 MHz, CHLOROFORM-D) δ ppm 1.35 (s, 9H), 1.70-1.86 (m, 2H), 2.15 (d, J=12.9 Hz, 2H), 2.83-2.96 (m, 2H), 3.13-3.23 (m, 1H), 4.69 (d, J=13.6 Hz, 2H), 6.95 (d, J=9.1 Hz, 1H), 7.20-7.28 (m, 1H), 7.50-7.61 (m, 4H), 7.67 (d, J=8.3 Hz, 1H), 7.80 (d, J=8.3 Hz, 2H), 7.88 (d, J=9.3 Hz, 1H). HRMS: calcd for $C_{24}H_{28}N_2O_2S+H+$, 409.19442. found (ESI-FTMS, $[M+H]^{1+}$), 409.1952.

Example 7AY

2-{4-[(4-tert-butylphenyl)sulfonyl]piperidin-1-yl}-3-fluoropyridine

Step 1: Using the procedure from Example 7A, 4-[(4-tert-butylphenyl)sulfonyl]piperidine (100 mg, 0.36 mmol) was reacted with 2-chloro-3-fluoropyridine (74 μl, 0.72 mmol), DIEA (0.25 ml, 1.44) and 1,4-dioxane (0.3 ml) at 185° C. to afford the title compound (13 mg), a white solid, in 10% yield.

1H NMR (400 MHz, CHLOROFORM-D) δ ppm 1.36 (s, 9H), 1.79-1.92 (m, 2H), 2.10 (d, J=12.9 Hz, 2H), 2.78-2.87 (m, 2H), 3.05-3.17 (m, 1H), 4.18 (d, J=13.1 Hz, 2H), 6.72-6.78 (m, 1H), 7.17-7.25 (m, 1H), 7.58 (d, J=8.6 Hz, 2H), 7.81 (d, J=8.3 Hz, 2H), 7.95-7.99 (m, 1H). HRMS: calcd for $C_{20}H_{25}FN_2O_2S+H+$, 377.16935. found (ESI-FTMS, $[M+H]^{1+}$), 377.1705.

Example 7AZ

2-{4-[(4-tert-butylphenyl)sulfonyl]piperidin-1-yl}-4-(trifluoromethyl)pyridine

Step 1: Using the procedure from Example 7A, 4-[(4-tert-butylphenyl)sulfonyl]piperidine (100 mg, 0.36 mmol) was reacted with 2-chloro-4-(trifluoromethyl)pyridine (94 μl, 0.72 mmol), DIEA (0.25 ml, 1.44) and 1,4-dioxane (0.3 ml) at 185° C. to afford the title compound (60 mg), an off-white solid, in 39% yield.

1H NMR (400 MHz, CHLOROFORM-D) δ ppm 1.36 (s, 9H), 1.68-1.82 (m, 2H), 2.12 (d, J=11.4 Hz, 2H), 2.82-2.92 (m, 2H), 3.11-3.22 (m, 1H), 4.49 (d, J=13.1 Hz, 2H), 6.75-6.79 (m, J=3.5 Hz, 2H), 7.58 (d, J=8.6 Hz, 2H), 7.80 (d, J=8.3 Hz, 2H), 8.27 (d, J=5.6 Hz, 1H). HRMS: calcd for $C_{21}H_{25}F_3N_2O_2S+H+$, 427.16616. found (ESI-FTMS, $[M+H]^{1+}$), 427.1681.

Example 7BB

2-{4-[(4-tert-butylphenyl)sulfonyl]piperidin-1-yl}-3-methylpyridine

The title compound (90 mg), a white solid, was obtained in 67% yield according to a similar procedure described for example 7A.

1H NMR (400 MHz, CHLOROFORM-D) δ ppm 1.37 (s, 9H), 1.87-2.02 (m, 2H), 2.05-2.14 (m, 2H), 2.24 (s, 3H), 2.69-2.80 (m, 2H), 3.01-3.12 (m, 1H), 3.53 (dd, J=10.6, 2.0 Hz, 2H), 6.86 (dd, J=7.3, 4.8 Hz, 1H), 7.35-7.42 (m, 1H), 7.59 (d, J=8.8 Hz, 2H), 7.83 (d, J=8.6 Hz, 2H), 8.12 (dd, J=5.2, 1.6 Hz, 1H). HRMS: calcd for $C_{21}H_{28}N_2O_2S+H+$, 373.19442. found (ESI-FTMS, $[M+H]^{1+}$), 373.1941.

Example 7BC

4-[(4-tert-butylphenyl)sulfonyl]-1-(2-methylphenyl)piperidine

Step 1: Using the procedure from Example 7A, 4-[(4-tert-butylphenyl)sulfonyl]piperidine (100 mg, 0.36 mmol) was reacted with 2-bromotoluene (53 μl, 0.43 mmol) to afford the title compound (59 mg), a yellow solid, in 44% yield.

1H NMR (400 MHz, CHLOROFORM-D) δ ppm 1.37 (s, 9H), 1.90-2.01 (m, 2H), 2.04-2.12 (m, 2H), 2.26 (s, 3H), 2.53-2.66 (m, 2H), 2.94-3.08 (m, 1H), 3.22 (d, J=11.9 Hz, 2H), 6.90-7.02 (m, 2H), 7.10-7.18 (m, 2H), 7.59 (d, J=8.6 Hz, 2H), 7.83 (d, J=8.8 Hz, 2H). HRMS: calcd for $C_{22}H_{29}NO_2S$+H+, 372.19917. found (ESI-FTMS, [M+H]$^{1+}$), 372.1988.

Example 7BD

4-[(4-tert-butylphenyl)sulfonyl]-1-[2-(trifluoromethyl)phenyl]piperidine

Step 7E: Using the procedure from Example 7A, 4-[(4-tert-butylphenyl)sulfonyl]piperidine (100 mg, 0.36 mmol) was reacted with 2-bromobenzotrifluoride (59 μl, 0.43 mmol) to afford the title compound (26 mg), a white solid, in 17% yield.

1H NMR (400 MHz, CHLOROFORM-D) δ ppm 1.37 (s, 9H), 1.90-2.02 (m, 2H), 2.02-2.10 (m, 2H), 2.63-2.74 (m, 2H), 2.95-3.05 (m, 1H), 3.17 (d, J=11.6 Hz, 2H), 7.22 (t, J=7.7 Hz, 1H), 7.24-7.29 (m, 1H), 7.49 (t, J=7.1 Hz, 1H), 7.56-7.63 (m, 3H), 7.83 (d, J=8.8 Hz, 2H). HRMS: calcd for $C_{22}H_{26}F_3NO_2S$+H+, 426.17091. found (ESI-FTMS, [M+H]$^{1+}$), 426.1706.

Example 8

4-(3-chloropyridin-2-yl)-1-[(3,4-dichlorophenyl)sulfonyl]-cis-2,6-dimethylpiperazine Step 8A: 2,6-dimethylpiperazine (291 mg, 2.55 mmol) and 2,3-dichloropyridine (377.4 mg, 2.55 mmol) were charged to a microwave vial, dissolved in DMF (0.25 mL) and added with diisopropylethylamine (1.11 mL, 6.38 mmol). The reaction mixture was irradiated at 165° C. for 30 minutes. The reaction was complete as determined by TLC. After solvent removal the crud product was purified via flush column chromatography to afford 1-(3-chloropyridin-2-yl)-3,5-dimethylpiperazine in 64.4% yield (370 mg).

1H NMR (400 MHz, CHLOROFORM-D) δ ppm 1.18 (d, J=6.32 Hz, 6H) 2.40-2.63 (m, 2H) 3.02-3.24 (m, 2H) 3.66-3.82 (m, 2H) 6.83 (dd, J=7.58, 4.80 Hz, 1H) 7.58 (dd, J=7.71, 1.64 Hz, 1H) 8.18 (dd, J=4.80, 1.77 Hz, 1H).

Step 8B: 1-(3-chloropyridin-2-yl)-3,5-dimethylpiperazine (370 mg, 1.644 mmol) was dissolved in anhydrous dichloromethane (6 mL) added with 3,4-dichlorobenzene sulfonyl chloride (509 mg, 1.97 mmol) and diisopropylethylamine (0.72 mL, 4.11 mmol). The reaction mixture thus prepared was stirred overnight at room temperature. The reaction was complete as determined by TLC. It was purified via flush column chromatography to afford 4-(3-chloropyridin-2-yl)-1-[(3,4-dichlorophenyl)sulfonyl]-2,6-dimethylpiperazin in 13% yield (110 mg) as a sticky solid.

1H NMR (400 MHz, CHLOROFORM-D) δ ppm 1.60 (d, J=6.82 Hz, 6H) 2.69 (dd, J=12.38, 4.29 Hz, 2H) 3.56 (d, J=12.38 Hz, 2H) 4.01-4.36 (m, 2H) 6.90 (dd, J=7.83, 4.80 Hz, 1H) 7.56 (d, J=8.34 Hz, 1H) 7.61 (d, J=6.06 Hz, 1H) 7.66 (d, J=8.34 Hz, 1H) 7.94 (s, 1H) 8.15 (d, J=6.57 Hz, 1H). HRMS: calcd for $C_{17}H_{18}Cl_3N_3O_2S$+H+, 434.02580. found (ESI-FTMS, [M+H]$^{1+}$), 434.0272.

Example 9

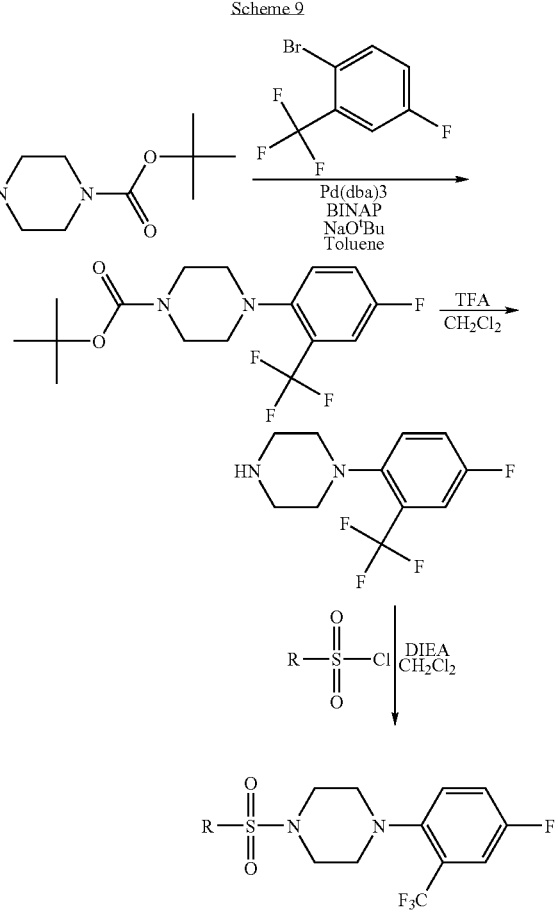

Scheme 9

Example 9A

1-[(3,4-dichlorophenyl)sulfonyl]-4-[4-fluoro-2-(trifluoromethyl)phenyl]piperazine Step 9A: A mixture of tert-butyl piperazine-1-carboxylate 1.04 g, (5.6 mmol), 2-bromo-5-fluoro benzotrifluoride (1.21 g, 5.0 mmol), tris(dibenzylidineacetone)dipalladium (0) (45.8 mg, 0.05 mmol), rac-2,2'-bis(diphenylphosphino)-1,1'-binaphthyl (93.4 mg, 0.15 mmol) and sodium tert-butoxide (600 mg, 6.25 mmol) were charged to a microwave vial. Toluene (10.0 mL) was introduced under nitrogen atmosphere and the reaction mixture was irradiated at 110° C. for 30 minutes. Reaction was complete as determined by TLC. The reaction was repeated four times. Reaction mixtures were combined, diluted with ethylacetate, washed with water, saturated brine then dried over $MgSO_4$ and concentrated. The crude product was purified via flash column chromatography to yield tert-butyl-4-(4-fluoro-2-(trifluoromethyl)phenyl)piperazine-1-carboxylate in quantitative yield (6.8 g) as yellow oil.

1H NMR (400 MHz, CHLOROFORM-D) δ ppm 1.49 (s, 9H) 2.82 (t, J=4.80 Hz, 4H) 3.55 (s, 4H) 7.15-7.26 (m, 1H)

7.27-7.39 (m, 2H). HPLC Method 1: room temperature, 7.000 min, 96.34%. HPLC Method 2: room temperature, 7.609 min, 97.90%.

Step 9B: To a stirred solution of tert-butyl-4-(4-fluoro-2-(trifluoromethyl)phenyl)piperazine-1-carboxylate (6.8 g, 19.5 mmol) in anhydrous dichloromethane (90 mL) was added TFA (45 mL) dropwise at 0° C. The reaction mixture was stirred at 0° C. for 15 minutes then the cooling bath was removed and it was allowed to stir at room temperature for 2 hours. Reaction was complete as determined by TLC. Most of TFA was azeotropped with dichloroethane. The residue was then diluted with dichloromethane and washed with saturated $Na_2CO_3$ (aq.). Organic layer was dried over $MgSO_4$. Solvent evaporation afforded 1-(4-fluoro-2-(trifluoromethyl)phenyl)piperazine in 79.9% yield (3.86 g) as light brown oil. 1H NMR (400 MHz, CHLOROFORM-D) δ ppm 2.78-2.90 (m, 4H) 2.96-3.04 (m, 4H) 7.18-7.25 (m, 1H) 7.29-7.42 (m, 2H).

Step 9C: To a stirred solution of 1-(4-fluoro-2-(trifluoromethyl)phenyl)piperazine (386 mg, 1.555 mmol) and 3,4-dichlorobenzene-1-sulfonyl chloride (381.8 mg, 1.555 mmol) in anhydrous dichloromethane (3 mL) was added diisopropylethylamine (1.35 mL, 7.775 mmol). The mixture was stirred at room temperature for 30 minutes. Reaction was complete as determined by TLC. The reaction mixture was diluted with dichloromethane, washed with saturated $Na_2CO_3$ (aq.), water then brine. Organic layer was dried over $MgSO_4$. The reaction mixture was purified via flash column chromatography to yield 1-[(3,4-dichlorophenyl)sulfonyl]-4-[4-fluoro-2-(trifluoromethyl)phenyl]piperazine in 75.7% yield (538 mg) as white solid.

1H NMR (400 MHz, DMSO-D6) δ ppm 2.93 (t, J=4.67 Hz, 4H) 3.08 (s, 4H) 7.47-7.61 (m, 2H) 7.68-7.82 (m, 2H) 7.94-8.04 (m, 2H). HRMS: calcd for $C_{17}H_{14}Cl_2F_4N_2O_2S+H+$, 457.01619. found (ESI-FTMS, $[M+H]^{1+}$), 457.0168. HPLC Method 1: room temperature, 7.212 min, 99.42%. HPLC Method 2: room temperature, 7.768 min, 99.76%.

Example 9B

1-[(2-chlorophenyl)sulfonyl]-4-[4-fluoro-2-(trifluoromethyl)phenyl]piperazine

Step 9C: Sulfonylation of 1-(4-fluoro-2-(trifluoromethyl)phenyl)piperazine (386 mg, 1.55 mmol) with 2-chlorobenzene-1-sulfonyl chloride (382.2 mg, 1.555 mmol) was carried out according to a similar to the representative sulfonation procedure described in Example 1 using anhydrous dichloromethane (3 mL) as solvent and diisopropylethylamine (1.35 mL, 7.775 mmol) as base. 1-[(2-chlorophenyl)sulfonyl]-4-[4-fluoro-2-(trifluoromethyl)phenyl]piperazine was obtained in 73.3% yield (481.8 mg) as white solid.

1H NMR (400 MHz, DMSO-D6) δ ppm 2.90 (t, J=4.67 Hz, 4H) 3.27 (s, 4H) 7.50-7.57 (m, 2H) 7.57-7.65 (m, 1H) 7.66-7.79 (m, 3H) 8.01 (dd, J=7.83, 1.52 Hz, 1H). HRMS: calcd for $C_{17}H_{15}ClF_4N_2O_2S+H+$, 423.05516. found (ESI-FTMS, $[M+H]^{1+}$), 423.0558. HPLC Method 1: room temperature, 6.787 min, 98.54%. HPLC Method 2: room temperature, 7.371 min, 99.64%.

Example 9C

1-[(4-chlorophenyl)sulfonyl]-4-[4-fluoro-2-(trifluoromethyl)phenyl]piperazine

Step 9C: Sulfonylation of 1-(4-fluoro-2-(trifluoromethyl)phenyl)piperazine (386 mg, 1.55 mmol) with 4-chlorobenzene-1-sulfonyl chloride (328.2 mg, 1.555 mmol) was carried out according to the representative sulfonation procedure described in Example 1 using anhydrous dichloromethane (3 mL) as solvent and diisopropylethylamine (1.35 mL, 7.775 mmol) as base. 1-[(4-chlorophenyl)sulfonyl]-4-[4-fluoro-2-(trifluoromethyl)phenyl]piperazine was obtained in 69.2% yield (455 mg) as white solid.

1H NMR (400 MHz, DMSO-D6) δ ppm 2.93 (t, J=4.29 Hz, 4H) 3.02 (s, 4H) 7.48-7.60 (m, 2H) 7.73 (dd, J=8.72, 5.18 Hz, 1H) 7.75-7.85 (m, 4H). HRMS: calcd for $C_{17}H_{15}ClF_4N_2O_2S+H+$, 423.05516. found (ESI-FTMS, $[M+H]^{1+}$), 423.0557. HPLC Method 1: room temperature, 6.908 min, 95.67%. HPLC Method 2: room temperature, 7.474 min, 99.78%.

Example 9D

1-[(5-chloro-2-naphthyl)sulfonyl]-4-[4-fluoro-2-(trifluoromethyl)phenyl]piperazine Step 1C: Sulfonylation of 1-(4-fluoro-2-(trifluoromethyl)phenyl)piperazine (193 mg, 3.888 mmol) with 5-chloronaphthalene-2-sulfonyl chloride (202.1 mg, 0.777 mmol) was carried out according to the representative sulfonation procedure described in Example 1 using anhydrous dichloromethane (3 mL) as solvent and diisopropylethylamine (0.7 mL, 3.887 mmol) as base. 1-[(5-chloro-2-naphthyl)sulfonyl]-4-[4-fluoro-2-(trifluoromethyl)phenyl]piperazine was obtained in 69% yield (256 mg) as white solid.

1H NMR (400 MHz, DMSO-D6) δ ppm 2.94 (t, J=4.55 Hz, 4H) 3.09 (s, 4H) 7.41-7.59 (m, 2H) 7.64-7.79 (m, 2H) 7.97 (dd, J=6.95, 5.94 Hz, 2H) 8.29 (d, J=8.34 Hz, 1H) 8.45 (d, J=8.84 Hz, 1H) 8.61 (d, J=1.77 Hz, 1H). HRMS: calcd for $C_{21}H_{17}ClF_4N_2O_2S+H+$, 473.07081. found (ESI-FTMS, $[M+H]^{1+}$), 473.0715. HPLC Method 1: room temperature, 7.443 min, 99.05%. HPLC Method 2: room temperature, 7.909 min, 99.73%.

Example 9E

1-[(5-chloro-3-methyl-1-benzothien-2-yl)sulfonyl]-4-[5-fluoro-2-(trifluoromethyl)phenyl]piperazine 1-[(5-chloro-3-methyl-1-benzothien-2-yl)sulfonyl]-4-[5-fluoro-2-(trifluoromethyl)phenyl]piperazine was prepared in a similar fashion as described in step 9C for example 9A.

1H NMR (400 MHz, CHLOROFORM-D) δ ppm 2.71 (s, 3H) 2.96-3.08 (m, 4H) 3.38 (d, 4H) 6.95 (dd, J=16.17, 2.27 Hz, 1H) 7.02 (dd, J=9.73, 2.40 Hz, 1H) 7.49 (dd, J=8.59, 2.02 Hz, 1H) 7.61 (dd, J=8.84, 6.06 Hz, 1H) 7.79 (d, J=8.59 Hz, 1H) 7.84 (d, J=2.02 Hz, 1H). HRMS: calcd for $C_{20}H_{17}ClF_4N_2O_2S_2+H+$, 493.04288. found (ESI-FTMS, $[M+H]^{1+}$), 493.0433.

Example 9F

1-[4-fluoro-2-(trifluoromethyl)phenyl]-4-(2-naphthylsulfonyl)piperazine

1-[4-fluoro-2-(trifluoromethyl)phenyl]-4-(2-naphthylsulfonyl)piperazine was prepared in a similar fashion as described in step 9C for example 9A. Yield 25%.

1H NMR (400 MHz, DMSO-D6) δ ppm 2.93 (t, J=4.67 Hz, 4H) 3.07 (s, 4H) 7.46-7.59 (m, 2H) 7.66-7.84 (m, 4H) 8.12 (d, J=8.08 Hz, 1H) 8.23 (t, J=9.22 Hz, 2H) 8.49 (s, 1H). HRMS: calcd for $C_{21}H_{18}F_4N_2O_2S+H+$, 439.10979. found (ESI-FTMS, $[M+H]^{1+}$), 439.1092. HPLC Method 1, room temperature, 6.97 min, 92.19%; HPLC method 2, room temperature, 7.54 min, 96.62%.

Example 10

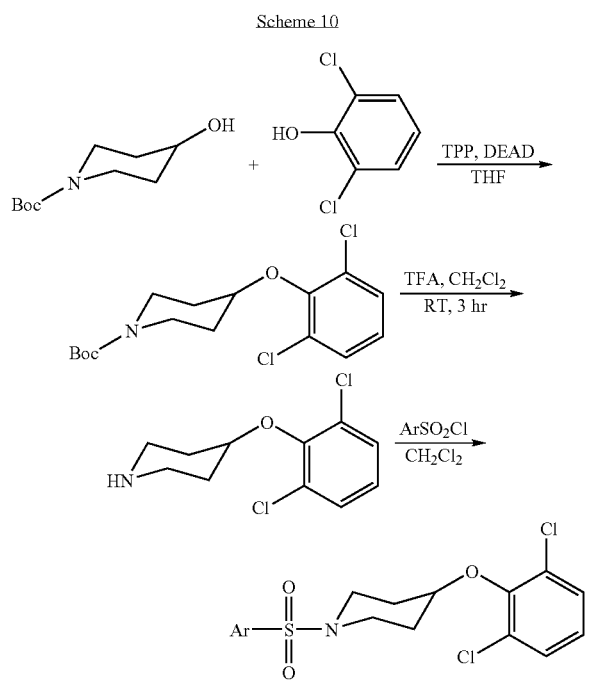

Scheme 10

Step 10A. A solution of tert-butyl 4-hydroxypiperidine-1-carboxylate (3.7 g, 23 mmol) and triphenyl phosphine (12.23 g, 46 mmol) in 50 ml THF was mixed in an ice-H$_2$O bath. A solution of diethyl azodicarboxylate (8.37 g, 46 mmol) in 50 ml THF was added drop-wise, followed by 2,6-dichlorophenol (3.87 g, 23 mmol). The mixture was warmed up to room temperature and stirred for 22 hr. Solvent was removed under vacuum and crude product was purified with column chromatography. tert-Butyl 4-(2,6-dichlorophenoxy)piperidine-1-carboxylate was obtained in 75% yield.

Step 10B. tert-Butyl 4-(2,6-dichlorophenoxy)piperidine-1-carboxylate (5.54 g) was mixed with 50 ml of mixture of TFA and CH$_2$Cl$_2$ (1:1). The mixture was stirred at room temperature for 4 hours. The solvents were removed under vacuum residue was Freeze-dried using CH$_3$CN/water system. The desired 4-(2,6-dichlorophenoxy)piperidine was obtained as TFA salt (white solid) in 100% yield.

Step 10C: piperazine or piperidine (0.5 mmol) was mixed with 2 ml of CH$_2$Cl$_2$ and diisopropylethyl amine (1 mmol), aryl sulfonyl chloride (0.5 mmol) was added in one portion. The reaction mixture was stirred at room temperature, and progress of the reaction was monitored by TLC. When the reaction was completed, the reaction mixture was loaded onto silica gel column the product was isolated and purified by column chromatography. The following compounds were prepared using this general procedure.

Example 10A

N-(4-{[4-(2,6-dichlorophenoxy)piperidin-1-yl]sulfonyl}phenyl)acetamide

The desired product was obtained in 34% yield as white solid. 1H NMR (400 MHz, CHLOROFORM-D) δ ppm 1.85-2.15 (m, 4H) 2.18-2.29 (m, 3H) 2.91-3.08 (m, 2H) 3.33-3.51 (m, 2H) 4.21-4.40 (m, 1H) 6.96 (t, 1H) 7.27 (d, 2H) 7.42 (s, 1H) 7.64-7.78 (m, 4H). HRMS: calcd for C$_{19}$H$_{20}$Cl$_2$N$_2$O$_4$S+H+, 443.05936. found (ESI-FTMS, [M+H]$^{1+}$), 443.0592.

Example 10B 4-(2,6-dichlorophenoxy)-1-[(3,4-dimethoxyphenyl)sulfonyl]piperidine The desired product was obtained in 42% yield as white solid. 1H NMR (400 MHz, CHLOROFORM-D) δ ppm 1.88-2.22 (m, 4H) 2.91-3.08 (m, 2H) 3.28-3.55 (m, 2H) 3.94 (d, J=7.58 Hz, 6H) 4.26-4.45 (m, 1H) 6.93-7.02 (m, 2H) 7.21-7.31 (m, 3H) 7.40 (dd, J=8.34, 2.02 Hz, 1H). HRMS: calcd for C$_{19}$H$_{21}$Cl$_2$NO$_5$S+H+, 446.05902. found (ESI-FTMS, [M+H]$^{1+}$), 446.0585.

Example 10C 4-(2,6-dichlorophenoxy)-1-[(3,4-dichlorophenyl)sulfonyl]piperidine The desired product was obtained in 48% yield as white solid. 1H NMR (400 MHz, CHLOROFORM-D) δ ppm 1.89-2.23 (m, 4H) 2.98-3.18 (m, 2H) 3.34-3.50 (m, 2H) 4.29-4.46 (m, 1H) 6.97 (t, 1H) 7.24-7.27 (m, 2H) 7.59-7.64 (m, 2H) 7.88 (d, J=1.77 Hz, 1H). HRMS: calcd for C$_{17}$H$_{15}$Cl$_4$NO$_3$S+H+, 453.95995. found (ESI-FTMS, [M+H]$^{1+}$), 453.959.

Example 10D 4-(2,6-dichlorophenoxy)-1-[(2,4-difluorophenyl)sulfonyl]piperidine The desired product was obtained in 36% yield as white solid. 1H NMR (400 MHz, CHLOROFORM-D) δ ppm 1.83-2.18 (m, 4H) 3.18-3.40 (m, 2H) 3.55-3.72 (m, 2H) 4.32-4.50 (m, 1H) 6.89-7.12 (m, 3H) 7.27 (d, J=3.28 Hz, 2H) 7.46-7.59 (m, 1H). HRMS: calcd for C$_{17}$H$_{15}$Cl$_2$F$_2$NO$_3$S+H+, 422.01905. found (ESI-FTMS, [M+H]$^{1+}$), 422.0187.

Example 10E

1-[(3,4-dichlorobenzyl)sulfonyl]-4-(2,6-dichlorophenoxy)piperidine

The desired product was obtained in 58% yield as white solid. 1H NMR (400 MHz, CHLOROFORM-D) δ ppm 1.82-2.10 (m, 4H) 3.11-3.32 (m, 2H) 3.37-3.66 (m, 2H) 4.34-4.52 (m, 1H) 6.99 (t, 1H) 7.25-7.27 (m, 1H) 7.27-7.30 (m, 2H) 7.47 (d, J=8.34 Hz, 1H) 7.53 (d, J=2.02 Hz, 1H). HRMS: calcd for C$_{18}$H$_{17}$Cl$_4$NO$_3$S+H+, 467.97560. found (ESI-FTMS, [M+H]$^{1+}$), 467.9742.

Example 10F 4-(2,6-dichlorophenoxy)-1-(2-naphthylsulfonyl)piperidine

The desired product was obtained in 36% yield as white solid. 1H NMR (400 MHz, CHLOROFORM-D) δ ppm 1.89-2.29 (m, 4H) 2.97-3.18 (m, 2H) 3.43-3.63 (m, 2H) 4.21-4.37 (m, 1H) 6.93 (t, 1H) 7.24 (t, 2H) 7.56-7.72 (m, 2H) 7.78 (dd, J=8.59, 1.77 Hz, 1H) 7.93 (d, J=7.58 Hz, 1H) 7.99 (d, J=8.84 Hz, 2H) 8.36 (d, J=1.26 Hz, 1H). HRMS: calcd for C$_{21}$H$_{19}$Cl$_2$NO$_3$S+H+, 436.05354. found (ESI-FTMS, [M+H]$^{1+}$), 436.0529.

Example 10G 1-(1-benzothien-2-ylsulfonyl)-4-(2,6-dichlorophenoxy)piperidine

The desired product was obtained in 56% yield as white solid. 1H NMR (400 MHz, CHLOROFORM-D) δ ppm 1.94-2.21 (m, 4H) 3.01-3.26 (m, 2H) 3.49-3.70 (m, 2H) 4.27-4.43 (m, 1H) 6.95 (t, 1H) 7.26 (s, 2H) 7.43-7.55 (m, 2H) 7.82 (s, 1H) 7.89 (t, 2H). HRMS: calcd for $C_{19}H_{17}Cl_2NO_3S_2$+H+, 442.00996. found (ESI-FTMS, [M+H]$^{1+}$), 442.0091.

Example 10H 1-(1-benzothien-3-ylsulfonyl)-4-(2,6-dichlorophenoxy)piperidine

The desired product was obtained in 49% yield as white solid. 1H NMR (400 MHz, CHLOROFORM-D) δ ppm 1.87-2.14 (m, 4H) 2.96-3.27 (m, 2H) 3.50-3.69 (m, 2H) 4.18-4.40 (m, 1H) 6.94 (t, 1H) 7.23 (d, J=8.08 Hz, 2H) 7.37-7.55 (m, 2H) 7.90 (dd, 1H) 8.19 (s, 1H) 8.28 (dd, J=6.95, 1.14 Hz, 1H). HRMS: calcd for $C_{19}H_{17}Cl_2NO_3S_2$+H+, 442.00996. found (ESI-FTMS, [M+H]$^{1+}$), 442.0093.

Example 10I

1-[(2-chlorophenyl)sulfonyl]-4-(2,6-dichlorophenoxy)piperidine

The desired product was obtained in 64% yield as colorless semi-solid. 1H NMR (400 MHz, CHLOROFORM-D) δ ppm 1.91-2.13 (m, 4H) 3.19-3.35 (m, 2H) 3.64-3.78 (m, 2H) 4.33-4.51 (m, 1H) 6.98 (t, 1H) 7.27 (d, 2H) 7.37-7.44 (m, 1H) 7.45-7.59 (m, 2H) 8.08 (dd, J=7.83, 1.77 Hz, 1H). HRMS: calcd for $C_{17}H_{16}Cl_3NO_3S$+H+, 419.99892. found (ESI-FTMS, [M+H]$^{1+}$), 419.9985.

Example 10J

1-[(2-bromophenyl)sulfonyl]-4-(2,6-dichlorophenoxy)piperidine

The desired product was obtained in 80% yield as white solid. 1H NMR (400 MHz, CHLOROFORM-D) δ ppm 1.90-2.16 (m, 4H) 3.24-3.35 (m, 2H) 3.67-3.81 (m, 2H) 4.30-4.49 (m, 1H) 6.98 (t, 1H) 7.29 (d, J=8.08 Hz, 2H) 7.36-7.50 (m, 2H) 7.76 (dd, J=7.96, 1.39 Hz, 1H) 8.12 (dd, J=7.71, 1.89 Hz, 1H); HRMS: calcd for $C_{17}H_{16}BrCl_2NO_3S$+H+, 463.94840. found (ESI-FTMS, [M+H]$^{1+}$), 463.9478.

Example 10K

1-[(2-chlorophenyl)sulfonyl]4-(2,6-dichlorophenoxy)piperidine

1H NMR (400 MHz, CHLOROFORM-D) δ ppm 1.90-2.18 (m, 4H) 3.24-3.35 (m, 2H) 3.66-3.77 (m, 2H) 4.34-4.51 (m, 1H) 6.98 (t, 1H) 7.28 (s, 1H) 7.29-7.31 (m, 1H) 7.40 (t, 1H) 7.45-7.58 (m, 2H) 8.08 (dd, J=7.83, 1.26 Hz, 1H). HRMS: calcd for $C_{17}H_{16}Cl_3NO_3S$+H+, 419.99892. found (ESI-FTMS, [M+H]$^{1+}$), 419.9985.

Example 10L

2-{[4-(2,6-dichlorophenoxy)piperidin-1-yl]sulfonyl}benzonitrile

The desired product was obtained in 70% yield as white solid. 1H NMR (400 MHz, CHLOROFORM-D) δ ppm 1.89-2.15 (m, 4H) 3.23-3.41 (m, 2H) 3.56-3.70 (m, 2H) 4.35-4.45 (m, 1H) 6.97 (t, 1H) 7.29 (s, 1H) 7.68-7.80 (m, 2H) 7.90 (dd, J=7.33, 1.77 Hz, 1H) 8.08 (dd, J=7.58, 1.26 Hz, 1H); HRMS: calcd for $C_{18}H_{16}Cl_2N_2O_3S$+H+, 411.03314. found (ESI-FTMS, [M+H]$^{1+}$), 411.0323.

Example 10M 4-(2,6-dichlorophenoxy)-1-[(2-nitrophenyl)sulfonyl]piperidine

The desired product was obtained in 82% yield as white solid. 1H NMR (400 MHz, CHLOROFORM-D) δ ppm 1.92-2.19 (m, 4H) 3.20-3.45 (m, 2H) 3.62-3.78 (m, 2H) 4.31-4.51 (m, 1H) 6.99 (t, 1H) 7.29 (d, J=8.08 Hz, 2H) 7.61-7.65 (m, 1H) 7.68-7.75 (m, 2H) 8.00-8.05 (m, 1H); HRMS: calcd for $C_{17}H_{16}Cl_2N_2O_5S$+H+, 431.02297. found (ESI-FTMS, [M+H]$^{1+}$), 431.0216.

Example 10N 4-(2,6-dichlorophenoxy)-1-[(4-phenoxyphenyl)sulfonyl]piperidine

The desired product was obtained in 50% yield as white solid. 1H NMR (400 MHz, CHLOROFORM-D) δ ppm 1.92-2.21 (m, 4H) 2.90-3.10 (m, 2H) 3.32-3.52 (m, 2H) 4.27-4.45 (m, 1H) 6.97 (t, 1H) 7.03-7.12 (m, 4H) 7.23 (t, 1H) 7.26 (s, 1H) 7.28 (s, 1H) 7.36-7.45 (m, 2H) 7.71-7.76 (m, 2H). HRMS: calcd for $C_{23}H_{21}Cl_2NO_4S$+H+, 478.06411. found (ESI-FTMS, [M+H]$^{1+}$), 478.063.

Example 10O 4-(2,6-dichlorophenoxy)-1-{[2-(trifluoromethyl)phenyl]sulfonyl}piperidine The desired product was obtained in 72% yield as white solid. 1H NMR (400 MHz, CHLOROFORM-D) δ ppm 1.91-2.13 (m, 4H) 3.19-3.37 (m, 2H) 3.59-3.73 (m, 2H) 4.35-4.49 (m, 1H) 6.98 (t, 1H) 7.29 (d, J=8.08 Hz, 2H) 7.68-7.77 (m, 2H) 7.89-7.93 (m, 1H) 8.13-8.18 (m, 1H). HRMS: calcd for $C_{18}H_{16}Cl_2F_3NO_3S$+H+, 454.02528. found (ESI-FTMS, [M+H]$^{1+}$), 454.0244.

Example 10P

1-[(4-chlorophenyl)sulfonyl]-4-(2,6-dichlorophenoxy)piperidine

The desired product was obtained in 74% yield as white solid. 1H NMR (400 MHz, CHLOROFORM-D) δ ppm 1.88-2.16 (m, 4H) 2.97-3.13 (m, 2H) 3.31-3.51 (m, 2H) 4.26-4.41 (m, 1H) 6.97 (t, 1H) 7.26 (d, 2H) 7.48-7.56 (m, 2H) 7.70-7.76 (m, 2H). HRMS: calcd for $C_{17}H_{16}Cl_3NO_3S$+H+, 419.99892. found (ESI-FTMS, [M+H]$^{1+}$), 419.9982.

Example 10Q 4-(2,6-dichlorophenoxy)-1-(2-thienylsulfonyl)piperidine

The desired product was obtained in 74% yield as white solid. 1H NMR (400 MHz, CHLOROFORM-D) δ ppm 1.92-2.21 (m, 4H) 3.03-3.15 (m, 2H) 3.38-3.55 (m, 2H) 4.31-4.48 (m, 1H) 6.97 (t, 1H) 7.15 (t, J=5.05, 3.79 Hz, 1H) 7.26 (s, 1H) 7.28 (s, 1H) 7.56 (dd, J=3.66, 1.39 Hz, 1H) 7.62 (dd, J=4.93, 1.39 Hz, 1H). HRMS: calcd for $C_{15}H_{15}Cl_2NO_3S_2$+H+, 391.99431. found (ESI-FTMS, [M+H]$^{1+}$), 391.9934.

Example 10R 1-(biphenyl-3-ylsulfonyl)-4-(2,6-dichlorophenoxy)piperidine

The desired product was obtained in 87% yield as white solid. 1H NMR (400 MHz, CHLOROFORM-D) δ ppm 1.93-2.17 (m, 4H) 2.95-3.10 (m, 2H) 3.42-3.55 (m, 2H) 4.23-4.43 (m, 1H) 6.94 (t, 1H) 7.26 (d, J=2.53 Hz, 2H) 7.37-7.45 (m, 1H) 7.45-7.52 (m, 2H) 7.57-7.66 (m, 3H) 7.73-7.79 (m, 1H) 7.79-7.85 (m, 1H) 7.99 (t, J=1.77 Hz, 1H). HRMS: calcd for $C_{23}H_{21}Cl_2NO_3S$+H+, 462.06919. found (ESI-FTMS, [M+H]$^{1+}$), 462.0675.

Example 10S

1-[(4'-bromobiphenyl-4-yl)sulfonyl]-4-(2,6-dichlorophenoxy)piperidine

The desired product was obtained in 90% yield as white solid. 1H NMR (400 MHz, CHLOROFORM-D) δ ppm 1.87-2.19 (m, 4H) 3.00-3.16 (m, 2H) 3.38-3.52 (m, 2H) 4.28-4.43 (m, 1H) 6.95 (t, J=8.08 Hz, 1H) 7.25 (d, J=7.83 Hz, 2H) 7.47 (d, J=8.34 Hz, 2H) 7.61 (d, J=8.34 Hz, 2H) 7.70 (d, J=8.34 Hz, 2H) 7.85 (d, J=8.34 Hz, 2H).

Example 10T 1-(dibenzo[b,d]furan-2-ylsulfonyl)-4-(2,6-dichlorophenoxy)piperidine The desired product was obtained in 95% yield as white solid. 1H NMR (400 MHz, CHLOROFORM-D) δ ppm 1.93-2.18 (m, 4H) 2.93-3.14 (m, 2H) 3.40-3.59 (m, 2H) 4.21-4.37 (m, 1H) 6.93 (t, 1H) 7.22 (d, J=7.83 Hz, 2H) 7.42 (t, 1H) 7.55 (t, 1H) 7.63 (d, 1H) 7.70 (d, J=9.35 Hz, 1H) 7.90 (dd, J=8.59, 2.02 Hz, 1H) 8.01 (d, J=7.83 Hz, 1H) 8.42 (d, J=1.26 Hz, 1H). HRMS: calcd for $C_{23}H_{19}Cl_2NO_4S$+H+, 476.04846. found (ESI-FTMS, [M+H]$^{1+}$), 476.0474.

Example 10U 1-(dibenzo[b,d]thien-2-ylsulfonyl)-4-(2,6-dichlorophenoxy)piperidine The desired product was obtained in 97% yield as white solid. 1H NMR (400 MHz, CHLOROFORM-D) δ ppm 1.93-2.20 (m, 4H) 2.97-3.13 (m, 2H) 3.47-3.61 (m, 2H) 4.22-4.34 (m, 1H) 6.92 (t, 1H) 7.22 (d, J=8.08 Hz, 2H) 7.51-7.58 (m, 2H) 7.83 (dd, J=8.34, 1.77 Hz, 1H) 7.86-7.94 (m, 1H) 8.00 (d, J=8.59 Hz, 1H) 8.21-8.28 (m, 1H) 8.56 (d, J=1.77 Hz, 1H). HRMS: calcd for $C_{23}H_{19}Cl_2NO_3S_2$+H+, 492.02561. found (ESI-FTMS, [M+H]$^{1+}$), 492.0271.

Example 10V 1-(dibenzo[b,d]thien-3-ylsulfonyl)-4-(2,6-dichlorophenoxy)piperidine The desired product was obtained in 93% yield as white solid. 1H NMR (400 MHz, CHLOROFORM-D) δ ppm 1.92-2.16 (m, 4H) 3.00-3.14 (m, 2H) 3.45-3.61 (m, 2H) 4.21-4.36 (m, 1H) 6.93 (t, 1H) 7.23 (d, J=8.08 Hz, 2H) 7.48-7.60 (m, 2H) 7.85 (dd, J=8.34, 1.77 Hz, 1H) 7.91 (dd, J=6.57, 1.26 Hz, 1H) 8.20-8.26 (m, 1H) 8.27-8.34 (m, 2H). HRMS: calcd for $C_{23}H_{19}Cl_2NO_3S_2$+H+, 492.02561. found (ESI-FTMS, [M+H]$^{1+}$), 492.0247.

Example 10W 4-(2,6-dichlorophenoxy)-1-[(4'-fluorobiphenyl-4-yl)sulfonyl]piperidine The desired product was obtained in 93% yield as white solid. 1H NMR (400 MHz, CHLOROFORM-D) δ ppm 1.89-2.17 (m, 4H) 2.98-3.13 (m, 2H) 3.36-3.55 (m, 2H) 4.28-4.40 (m, 1H) 6.95 (t, 1H) 7.17 (t, 2H) 7.26 (d, 2H) 7.54-7.62 (m, 2H) 7.70 (d, 2H) 7.84 (d, 2H). HRMS: calcd for $C_{23}H_{20}Cl_2FNO_3S$+H+, 480.05977. found (ESI-FTMS, [M+H]$^{1+}$), 480.06.

Example 10X

1-[(5-chloro-3-methyl-1-benzothien-2-yl)sulfonyl]-4-(2,6-dichlorophenoxy)piperidine The desired product was obtained in 97% yield as white solid. 1H NMR (400 MHz, CHLOROFORM-D) δ ppm 1.95-2.18 (m, 4H) 2.65-2.74 (m, 3H) 3.17-3.31 (m, 2H) 3.55-3.77 (m, 2H) 4.29-4.45 (m, 1H) 6.96 (t, 1H) 7.27 (d, 2H) 7.46 (dd, J=8.59, 2.02 Hz, 1H) 7.76 (d, J=8.59 Hz, 1H) 7.81 (d, J=2.02 Hz, 1H). HRMS: calcd for $C_{20}H_{18}Cl_3NO_3S_2$+H+, 489.98664. found (ESI-FTMS, [M+H]$^{1+}$), 489.9852.

Example 11

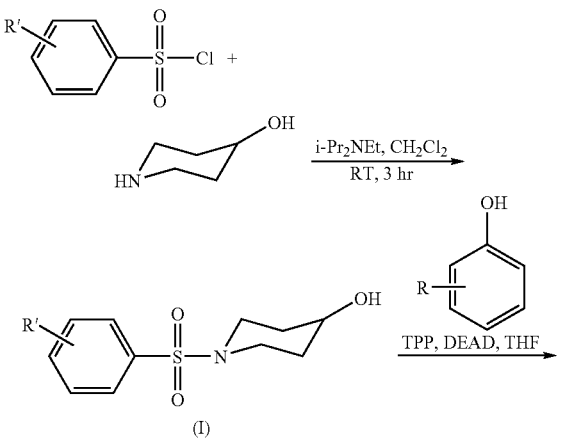

Scheme 11
General procedure of sulfonamide preparation: Mitsunobu Reaction

-continued

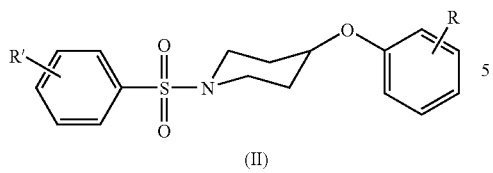

Step 11A: To a stirred solution of p-toluenesulfonyl chloride (39.28 mmol) in dichloromethane (160 mL) was added 4-hydroxypiperidine (40.07 mmol) dropwise, followed by 13.7 ml i-Pr2NEt. The mixture was stirred at room temperature for 3 h. Solvent was removed under vacuum and crude product was purified with flash column chromatography to yield 4-hydroxypiperidin sulfonamide (I).

Step 11B: A solution of aryl alcohol (1.17 mmol) and triphenyl phosphine (0.349 g, 1.33 mmol) in 2 ml THF was mixed in an ice-H$_2$O bath. A solution of diethyl azodicarboxylate (0.232 g, 1.33 mmol) in 2 ml THF was added dropwise, followed by 4-hydroxypiperidin sulfonamide (I) (0.78 mmol). The mixture was warmed up to room temperature and stirred for 22 hr. Solvent was removed under vacuum and crude product was purified with column chromatography. The following compounds were prepared using this procedure.

Example 11A 4-(2,4-dichlorophenoxy)-1-[(4-methylphenyl)sulfonyl]piperidine

The desired product was obtained in 33% yield as white solid. 1H NMR (400 MHz, CHLOROFORM-D) δ ppm 1.87-2.05 (m, 4H) 2.44 (s, 3H) 2.95-3.11 (m, 2H) 3.20-3.35 (m, 2H) 4.34-4.52 (m, 1H) 6.80 (d, J=8.84 Hz, 1H) 7.12 (dd, J=8.84, 2.53 Hz, 2H) 7.22-7.38 (m, 3H) 7.65 (d, J=8.08 Hz, 2H).

Example 11B

1-[(4-methylphenyl)sulfonyl]-4-phenoxypiperidine

The desired product was obtained in 80% yield as white solid. 1H NMR (400 MHz, CHLOROFORM-D) δ ppm 1.83-2.17 (m, 4H) 2.45 (s, 3H) 2.98-3.28 (m, 4H) 4.23-4.45 (m, 1H) 6.80 (d, J=7.58 Hz, 2H) 6.93 (t, J=7.45 Hz, 3H) 7.24 (t, 3H) 7.34 (d, J=8.08 Hz, 2H) 7.66 (d, J=8.34 Hz, 2H).

Example 11C 4-(2-chlorophenoxy)-1-[(4-methylphenyl)sulfonyl]piperidine

The desired product was obtained in 72% yield as white solid. 1H NMR (400 MHz, Acetone) δ ppm 1.82-1.97 (m, 2H) 1.96-2.05 (m, J=10.11 Hz, 2H) 2.47 (s, 3H) 3.06-3.24 (m, 4H) 4.55-4.75 (m, J=3.28 Hz, 1H) 6.89-6.99 (m, 1H) 7.16 (dd, 1H) 7.25 (t, 1H) 7.35 (dd, 1H) 7.48 (d, J=8.59 Hz, 2H) 7.70 (d, 2H).

Example 11D 4-(2-methoxyphenoxy)-1-[(4-methylphenyl)sulfonyl]piperidine

The desired product was obtained in 25% yield as oil-like liquid. 1H NMR (400 MHz, CHLOROFORM-D) δ ppm 1.85-2.08 (m, 4H) 2.44 (s, 3H) 2.97-3.16 (m, 2H) 3.18-3.35 (m, 2H) 3.70 (s, 3H) 4.17-4.38 (m, 1H) 6.80-6.89 (m, 3H) 6.90-7.00 (m, 1H) 7.33 (d, J=8.08 Hz, 2H) 7.67 (d, J=8.08 Hz, 2H).

Example 11D 3-({1-[(4-methylphenyl)sulfonyl]piperidin-4-yl}oxy)pyridine

The desired product was obtained in 44% yield as white solid. 1H NMR (400 MHz, CHLOROFORM-D) δ ppm 1.84-1.99 (m, 2H) 1.98-2.11 (m, 2H) 2.46 (s, 3H) 3.16 (t, J=5.56 Hz, 4H) 4.26-4.53 (m, 1H) 7.07-7.15 (m, 1H) 7.14-7.22 (m, 1H) 7.35 (d, J=8.08 Hz, 2H) 7.67 (d, J=8.34 Hz, 2H) 8.20 (d, J=3.03 Hz, 2H).

Example 11E 4-(2-fluorophenoxy)-1-[(4-methylphenyl)sulfonyl]piperidine

The desired product was obtained in 40% yield as white solid. 1H NMR (400 MHz, CHLOROFORM-D) δ ppm 1.82-2.11 (m, 4H) 2.39-2.52 (m, 3H) 2.95-3.29 (m, 4H) 4.24-4.44 (m, 1H) 6.85-6.97 (m, 2H) 6.96-7.11 (m, 2H) 7.34 (d, J=8.34 Hz, 2H) 7.66 (d, J=8.34 Hz, 2H).

Example 11F 4-(biphenyl-4-yloxy)-1-[(4-methylphenyl)sulfonyl]piperidine

The desired product was obtained in 30% yield as white solid. 1H NMR (400 MHz, CHLOROFORM-D) δ ppm 1.84-2.12 (m, 4H) 2.41-2.53 (m, 3H) 3.03-3.25 (m, 4H) 4.36-4.49 (m, 1H) 6.87 (dd, 2H) 7.30 (t, 1H) 7.35 (d, J=7.83 Hz, 2H) 7.37-7.43 (m, 2H) 7.44-7.54 (m, 4H) 7.67 (d, 2H).

Example 11G 4-(4-methoxyphenoxy)-1-[(4-methylphenyl)sulfonyl]piperidine

The desired product was obtained in 30% yield as white solid. 1H NMR (400 MHz, CHLOROFORM-D) δ ppm 1.82-2.08 (m, 4H) 2.37-2.52 (m, 3H) 3.02-3.27 (m, 4H) 3.71-3.80 (m, 3H) 4.16-4.27 (m, 1H) 6.69-6.81 (m, 4H) 7.34 (d, J=8.08 Hz, 2H) 7.66 (d, J=8.08 Hz, 2H).

Example 11H

1-[(4-methylphenyl)sulfonyl]-4-[2-(trifluoromethyl)phenoxy]piperidine

The desired product was obtained in 44% yield as white solid. 1H NMR (400 MHz, CHLOROFORM-D) δ ppm 1.90-2.11 (m, 4H) 2.45 (s, 3H) 2.80-2.99 (m, 2H) 3.28-3.49 (m, 2H) 4.54-4.72 (m, 1H) 6.89 (d, 1H) 6.96 (t, 1H) 7.33 (d, 2H) 7.42 (t, 1H) 7.51 (t, 1H) 7.64 (d, 2H).

Example 11I

4-(2,6-dichlorophenoxy)-1-[(4-methylphenyl)sulfonyl]piperidine

The desired product was obtained in 40% yield as white solid. 1H NMR (400 MHz, CHLOROFORM-D) δ ppm 1.87-2.19 (m, 4H) 2.44 (s, 3H) 2.88-3.05 (m, 2H) 3.29-3.54 (m, 2H) 4.17-4.43 (m, 1H) 6.96 (t, 1H) 7.26 (d, 2H) 7.33 (d, J=8.08 Hz, 2H) 7.67 (d, 2H), HRMS: calcd for $C_{18}H_{19}Cl_2NO_3S+H+$, 400.05354. found (ESI-FTMS, [M+H]$^{1+}$), 400.0534.

Example 11J

4-(2-methylphenoxy)-1-[(4-methylphenyl)sulfonyl]piperidine

The desired product was obtained in 35% yield as white solid. 1H NMR (400 MHz, CHLOROFORM-D) δ ppm 1.88-2.07 (m, 7H) 2.45 (s, 3H) 2.98-3.11 (m, 2H) 3.12-3.25 (m, 2H) 4.35-4.47 (m, 1H) 6.72 (d, 1H) 6.84 (t, 1H) 7.03-7.15 (m, 2H) 7.34 (d, 2H) 7.66 (d, 2H)

Example 11K

2-({1-[(4-methylphenyl)sulfonyl]piperidin-4-yl}oxy)benzonitrile

The desired product was obtained in 27% yield as white solid. 1H NMR (400 MHz, CHLOROFORM-D) δ ppm 1.93-2.16 (m, 4H) 2.44 (s, 3H) 3.04-3.20 (m, 2H) 3.25-3.41 (m, 2H) 4.47-4.62 (m, 1H) 6.90 (d, J=8.34 Hz, 1H) 6.99 (t, 3H) 7.34 (d, J=7.83 Hz, 2H) 7.43-7.56 (m, 2H) 7.66 (d, J=8.34 Hz, 2H).

Example 11L

1-[(4-methylphenyl)sulfonyl]-4-(2-nitrophenoxy)piperidine

The desired product was obtained in 43% yield as white solid. 1H NMR (400 MHz, CHLOROFORM-D) δ ppm 1.90-2.10 (m, 4H) 2.46 (s, 3H) 2.88-3.07 (m, 2H) 3.26-3.50 (m, 2H) 4.57-4.74 (m, 1H) 7.01 (t, 3H) 7.35 (d, 2H) 7.47 (t, 1H) 7.64 (d, 2H) 7.76 (dd, 1H).

Example 11M

4-[(2-methoxybenzyl)oxy]-1-[(4-methylphenyl)sulfonyl]piperidine

The desired product was obtained in 65% yield as white solid. 1H NMR (400 MHz, CHLOROFORM-D) δ ppm 1.72-1.86 (m, 2H) 1.86-1.97 (m, 2H) 2.43 (s, 3H) 2.88-3.01 (m, 2H) 3.14-3.28 (m, 2H) 3.45-3.52 (m, 1H) 3.76 (s, 3H) 4.48 (s, 2H) 6.83 (d, J=8.34 Hz, 1H) 6.89 (t, 1H) 7.15-7.35 (m, 4H) 7.64 (d, J=8.34 Hz, 2H).

Example 11N

4-(2-bromophenoxy)-1-[(4-methylphenyl)sulfonyl]piperidine

The desired product was obtained in % yield as white solid. 1H NMR (400 MHz, CHLOROFORM-D) δ ppm 1.92-2.05 (m, 4H) 2.45 (s, 3H) 2.95-3.10 (m, 2H) 3.25-3.41 (m, 2H) 4.44-4.62 (m, J=3.79, 3.79 Hz, 1H) 6.82 (q, 2H) 7.19 (t, 1H) 7.35 (d, 2H) 7.45 (dd, 1H) 7.66 (d, 2H), HRMS: calcd for $C_{18}H_{20}BrNO_3S+H+$, 410.04200. found (ESI-FTMS, [M+H]$^{1+}$), 410.0411.

Example 11O

4-(2,6-dimethylphenoxy)-1-[(4-methylphenyl)sulfonyl]piperidine

The desired product was obtained in 41% yield as white solid. 1H NMR (400 MHz, CHLOROFORM-D) δ ppm 1.79-2.04 (m, 4H) 2.16-2.23 (m, 6H) 2.43 (s, 3H) 2.53-2.68 (m, 2H) 3.54-3.67 (m, J=11.87 Hz, 2H) 3.69-3.87 (m, 1H) 6.82-6.93 (m, 1H) 6.97 (dd, 2H) 7.32 (d, 2H) 7.65 (d, 2H), HRMS: calcd for $C_{20}H_{25}NO_3S+H+$, 360.16279. found (ESI-FTMS, [M+H]$^{1+}$), 360.1617.

Example 11P

4-(2-ethylphenoxy)-1-[(4-methylphenyl)sulfonyl]piperidine

The desired product was obtained in 14% yield as white solid. 1H NMR (400 MHz, CHLOROFORM-D) δ ppm 0.94 (t, J=7.58 Hz, 3H) 1.85-2.10 (m, 4H) 2.36 (q, J=7.58 Hz, 2H) 2.44 (s, 3H) 2.89-3.06 (m, 2H) 3.18-3.41 (m, 2H) 4.37-4.58 (m, 1H) 6.73 (dd, 1H) 6.85 (t, 1H) 7.03-7.15 (m, 2H) 7.33 (d, J=7.83 Hz, 2H) 7.66 (d, 2H), HRMS: calcd for $C_{20}H_{25}NO_3S+H+$, 360.16279. found (ESI-FTMS, [M+H]$^{1+}$), 360.1617.

Example 11Q

1-[(4-methylphenyl)sulfonyl]-4-(2-propylphenoxy)piperidine

The desired product was obtained in 19% yield as white solid. 1H NMR (400 MHz, CHLOROFORM-D) δ ppm 0.73 (t, J=7.33 Hz, 3H) 1.26-1.45 (m, 2H) 1.81-2.06 (m, 4H) 2.19-2.36 (m, 2H) 2.44 (s, 3H) 2.81-3.04 (m, 2H) 3.23-3.40 (m, 2H) 4.47 (t, J=4.04 Hz, 1H) 6.70 (d, 1H) 6.83 (t, 1H) 7.01-7.15 (m, 2H) 7.34 (d, 2H) 7.64 (d, 2H); HRMS: calcd for $C_{21}H_{27}NO_3S+H+$, 374.17844. found (ESI-FTMS, [M+H]$^{1+}$), 374.1785.

Example 11R

4-(2-isopropylphenoxy)-1-[(4-methylphenyl)sulfonyl]piperidine

The desired product was obtained in 36% yield as white solid. 1H NMR (400 MHz, CHLOROFORM-D) δ ppm 1.00 (d, J=7.07 Hz, 6H) 1.91-2.07 (m, 4H) 2.44 (s, 3H) 2.85-3.10 (m, 3H) 3.14-3.38 (m, 2H) 4.30-4.56 (m, 1H) 6.72 (d, J=7.83 Hz, 1H) 6.89 (t, 1H) 7.08 (t, 1H) 7.15 (dd, J=7.45, 1.64 Hz, 1H) 7.33 (d, J=8.08 Hz, 2H) 7.65 (d, 2H); HRMS: calcd for $C_{21}H_{27}NO_3S+H+$, 374.17844. found (ESI-FTMS, [M+H]$^{1+}$), 374.1789.

Example 11S

4-(2-chloro-6-methylphenoxy)-1-[(4-methylphenyl)sulfonyl]piperidine

The desired product was obtained in 35% yield as white solid. 1H NMR (400 MHz, CHLOROFORM-D) δδ ppm 1.89-2.10 (m, 4H) 2.21 (s, 3H) 2.43 (s, 3H) 2.67-2.81 (m, 2H)

3.45-3.66 (m, 2H) 3.99-4.22 (m, 1H) 6.91 (t, J=7.71 Hz, 1H) 7.04 (d, J=7.58 Hz, 1H) 7.16 (dd, J=7.71, 1.39 Hz, 1H) 7.33 (d, J=7.83 Hz, 2H) 7.66 (d, J=8.34 Hz, 2H); HRMS: calcd for $C_{19}H_{22}ClNO_3S+H+$, 380.10817. found (ESI-FTMS, $[M+H]^{1+}$), 380.1085.

Example 11T 2-chloro-3-({1-[(4-methylphenyl)sulfonyl]piperidin-4-yl}oxy)pyridine The desired product was obtained in 30% yield as white solid. 1H NMR (400 MHz, CHLOROFORM-D) δ ppm 1.96-2.02 (m, 4H) 2.45 (s, 3H) 2.93-3.07 (m, 2H) 3.29-3.40 (m, 2H) 4.48-4.58 (m, 1H) 7.16 (d, J=3.03 Hz, 2H) 7.35 (d, J=8.08 Hz, 2H) 7.66 (d, 2H) 7.99 (t, J=3.16 Hz, 1H); HRMS: calcd for $C_{17}H_{19}ClN_2O_3S+H+$, 367.08777. found (ESI-FTMS, $[M+H]^{1+}$), 367.0884.

Example 11U 4-(2-bromophenoxy)-1-[(3,4-dimethoxyphenyl)sulfonyl]piperidine

The desired product was obtained in 49% yield as white solid. 1H NMR (400 MHz, CHLOROFORM-D) δ ppm 1.88-2.06 (m, 4H) 2.94-3.15 (m, 2H) 3.26-3.43 (m, 2H) 3.95 (d, J=8.59 Hz, 6H) 4.48-4.62 (m, J=3.54, 3.54 Hz, 1H) 6.79-6.89 (m, 4H) 6.97 (d, J=8.34 Hz, 1 H) 7.18-7.25 (m, 2H) 7.40 (dd, J=8.46, 2.15 Hz, 1H) 7.47 (dd, J=7.96, 1.64 Hz, 1H). HRMS: calcd for $C_{19}H_{22}BrNO_5S+H+$, 456.04748. found (ESI-FTMS, $[M+H]^{1+}$), 456.0472.

Example 12

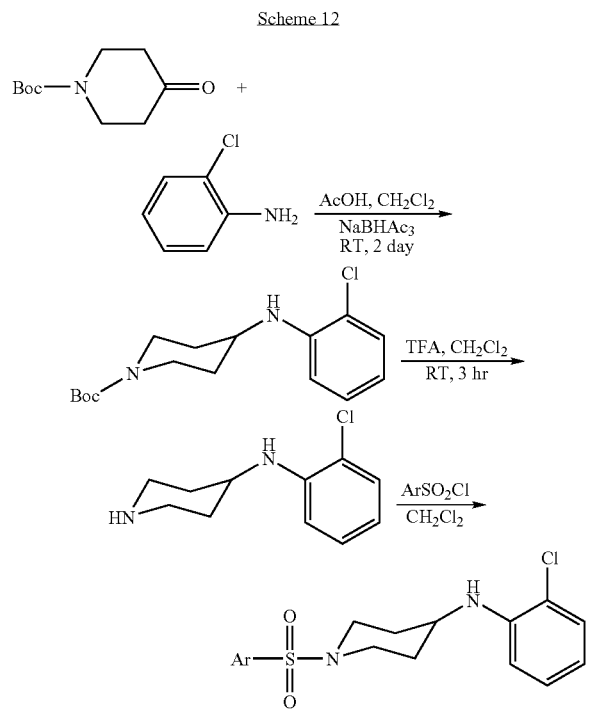

Scheme 12

Step 12A. To a solution of N-(tert-butoxycarbonyl)-4-piperidone (8.01 g, 39.4 mmol), 2-chloroaniline (5.74 g, 44.1 mmol) and acetic acid (2.80 g, 46.6 mmol) in 200 ml ethylene chloride ethane was added sodium triacetoxyborohydride (8.37 g, 78.8 mmol). The mixture was stirred at room temp for 2.5 days. Added 2N NaOH solution to adjust pH to 10. The organic phase was separated and washed with water, then dried over $Na_2SO_4$. Solvent was removed under vacuum and crude product was purified with flash column chromatography to yield tert-butyl-4-(2-chlorophenylamino)piperidine-1-carboxylate in 8.2% yield (1.6 g) as white solid.

Step 12B. tert-butyl-4-(2-chlorophenylamino)piperidine-1-carboxylate (1.54 g, 4.95 mmol) in 20 ml DME was mixed with 20 ml TFA at room temp for 3 hr. Solvent was removed under vacuum to give the desired product (2.2 g).

Step 12C: The product obtained step 12B can then be coupled to the appropriate sulfonyl chloride (e.g., $ArSO_2Cl$) as described elsewhere herein.

Example 12A 1-(1-benzothien-2-ylsulfonyl)-N-(2-chlorophenyl)piperidin-4-amine The desired product was obtained in 99% yield as white solid. 1H NMR (400 MHz, CHLOROFORM-D) δ ppm 1.59-1.75 (m, 2H) 2.09-2.24 (m, 2H) 2.72-2.85 (m, 2H) 3.23-3.45 (m, 1H) 3.75-3.88 (m, 2H) 4.12-4.22 (m, J=7.33, 4.55 Hz, 1H) 6.49-6.68 (m, 2H) 7.07 (t, 1H) 7.26 (t, 1H) 7.44-7.58 (m, 2H) 7.81-7.85 (m, 1H) 7.90 (t, 2H). HRMS: calcd for $C_{19}H_{19}ClN_2O_2S_2+H+$, 407.06492. found (ESI-FTMS, $[M+H]^{1+}$), 407.0645.

Example 12B

N-(2-chlorophenyl)-1-(dibenzo[b,d]furan-3-ylsulfonyl)piperidin-4-amine

The desired product was obtained in 90% yield as white solid. 1H NMR (400 MHz, CHLOROFORM-D) δ ppm 1.61-1.71 (m, 2H) 2.07-2.20 (m, 2H) 2.56-2.72 (m, 2H) 3.22-3.33 (m, 1H) 3.73-3.86 (m, 2H) 4.08-4.19 (m, J=7.07, 7.07, 7.07 Hz, 1H) 6.52 (d, 1H) 6.61 (t, 1H) 7.05 (t, 1H) 7.21 (dd, 1H) 7.45 (t, 1H) 7.59 (t, 1H) 7.67 (d, 1H) 7.79 (dd, 1H) 8.11 (d, 1H). HRMS: calcd for $C_{23}H_{21}ClN_2O_3S+H+$, 441.10342. found (ESI-FTMS, $[M+H]^{1+}$), 441.1031.

Example 12C

N-(2-chlorophenyl)-1-[(2-chlorophenyl)sulfonyl]piperidin-4-amine

The desired product was obtained in 63% yield as white solid. 1H NMR (400 MHz, CHLOROFORM-D) δ ppm 1.51-1.68 (m, 2H) 2.04-2.21 (m, 2H) 2.95-3.09 (m, 2H) 3.35-3.52 (m, 1H) 3.70-3.92 (m, 2H) 4.10-4.26 (m, J=7.58 Hz, 1H) 6.63 (t, 3H) 7.10 (t, 1H) 7.23-7.26 (m, 1H) 7.36-7.44 (m, 1H) 7.47-7.57 (m, 2H) 8.08 (dd, J=7.71, 1.39 Hz, 1H). HRMS: calcd for $C_{17}H_{18}Cl_2N_2O_2S+H+$, 385.05388. found (ESI-FTMS, $[M+H]^{1+}$), 385.0536.

Example 12D

N-(2-chlorophenyl)-1-[(3-chlorophenyl)sulfonyl]piperidin-4-amine

The desired product was obtained in 63% yield as white solid. 1H NMR (400 MHz, CHLOROFORM-D) δ ppm 1.57-1.71 (m, 2H) 2.09-2.20 (m, 2H) 2.63 (t, 2H) 3.26-3.40 (m, J=3.79 Hz, 1H) 3.63-3.79 (m, 2H) 4.10-4.20 (m, J=8.08 Hz, 1H) 6.53-6.68 (m, 2H) 7.08 (t, 1H) 7.24 (dd, 1H) 7.51 (t, 1H) 7.57-7.64 (m, 1H) 7.64-7.70 (m, 1H) 7.75-7.81 (m, 1H). HRMS: calcd for $C_{17}H_{18}Cl_2N_2O_2S+H+$, 385.05388. found (ESI-FTMS, $[M+H]^{1+}$), 385.0537.

Example 12E

N-(2-chlorophenyl)-1-[(4-phenoxyphenyl)sulfonyl]piperidin-4-amine

The desired product was obtained in 64% yield as white solid. 1H NMR (400 MHz, CHLOROFORM-D) δ ppm 1.57-1.71 (m, 2H) 2.13 (dd, J=13.01, 3.66 Hz, 2H) 2.55-2.72 (m, 2H) 3.23-3.39 (m, J=8.08 Hz, 1H) 3.60-3.71 (m, 2H) 4.10-4.18 (m, J=7.83 Hz, 1H) 6.54-6.72 (m, 2H) 7.03-7.13 (m, 5H) 7.21-7.26 (m, 2H) 7.39-7.46 (m, 2H) 7.70-7.76 (m, 2H). HRMS: calcd for $C_{23}H_{23}ClN_2O_3S+H+$, 443.11907. found (ESI-FTMS, $[M+H]^{1+}$), 443.1198.

Example 12F 1-(biphenyl-4-ylsulfonyl)-N-(2-chlorophenyl)piperidin-4-amine

The desired product was obtained in 60% yield as white solid. 1H NMR (400 MHz, CHLOROFORM-D) δ ppm 1.57-1.73 (m, 2H) 2.08-2.22 (m, 2H) 2.58-2.72 (m, 2H) 3.26-3.43 (m, 1H) 3.68-3.81 (m, 2H) 4.07-4.20 (m, J=7.83 Hz, 1H) 6.53-6.65 (m, 2H) 7.06 (t, 1H) 7.23 (dd, 1H) 7.40-7.47 (m, 1H) 7.47-7.55 (m, 2H) 7.60-7.66 (m, 2H) 7.73-7.79 (m, 2H) 7.82-7.87 (m, 2H). HRMS: calcd for $C_{23}H_{23}ClN_2O_2S+H+$, 427.12415. found (ESI-FTMS, $[M+H]^{1+}$), 427.1247.

Example 13

Example 13A

1-[(3,4-dichlorophenyl)sulfonyl]-4-(3-fluoropyridin-2-yl)piperazine

The desired product was obtained in 90% yield as white solid. 1H NMR (400 MHz, CHLOROFORM-D) δ ppm 3.07-3.31 (m, 4H) 3.51-3.72 (m, 4H) 6.74-6.84 (m, 1H) 7.22 (t, 1H) 7.58-7.67 (m, 2H) 7.87 (d, J=1.52 Hz, 1H) 7.98 (d, 1H).

Example 13B

2-{4-[(3,4-dichlorophenyl)sulfonyl]piperazin-1-yl}nicotinonitrile

The desired product was obtained in 70% yield as white solid. 1H NMR (400 MHz, CHLOROFORM-D) δ ppm 3.09-3.31 (m, 4H) 3.63-3.88 (m, 4H) 6.84 (dd, J=7.58, 4.80 Hz, 1H) 7.55-7.70 (m, 2H) 7.79 (dd, J=7.58, 2.02 Hz, 1H) 7.87 (d, J=1.77 Hz, 1H) 8.35 (dd, J=4.93, 1.90 Hz, 1H).

Example 13C

1-[(3,4-dichlorophenyl)sulfonyl]-4-(3-nitropyridin-2-yl)piperazine

The desired product was obtained in 45% yield as white solid. 1H NMR (400 MHz, CHLOROFORM-D) δ ppm 3.11-3.27 (m, 4H) 3.48-3.66 (m, 4H) 6.85 (dd, J=7.96, 4.67 Hz, 1H) 7.54-7.71 (m, 2H) 7.86 (t, J=2.02 Hz, 1H) 8.15 (dd, J=8.08, 1.77 Hz, 1H) 8.34 (dd, J=4.55, 1.77 Hz, 1H).

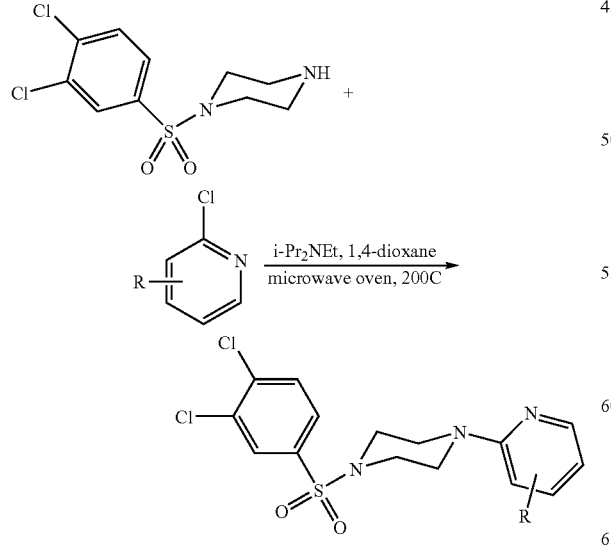

Scheme 13
General procedure of sulfonamide preparation: Substitution on Pyridine

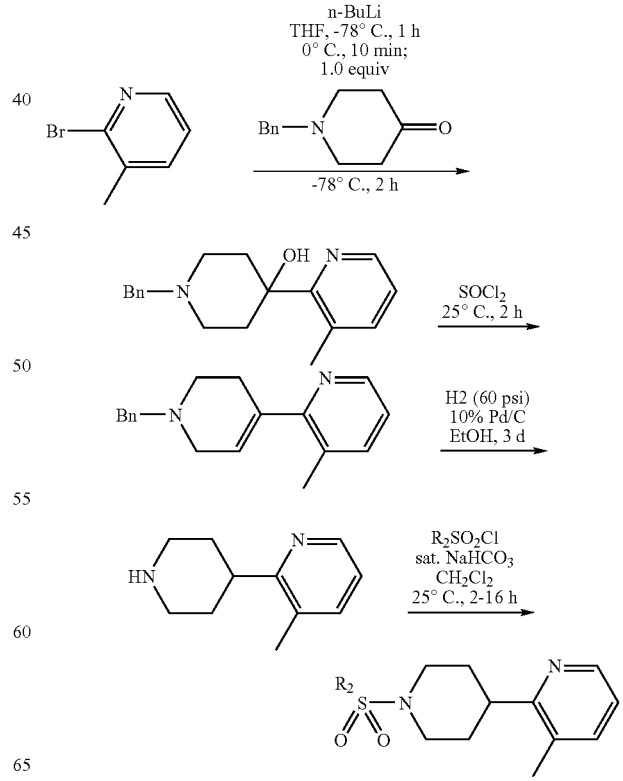

Scheme 13A

Example 13A-1

2-{1-[(2-chlorophenyl)sulfonyl]piperidin-4-yl}-3-methylpyridine

Step 13AA: 1'-Benzyl-3-methyl-2',3',5',6'-tetrahydro-1'H-[2,4']bipyridinyl-4'-ol. Following the procedure of N. I. Carruthers et al. (J. Med. Chem. 2005, 48, 1857-1872), to a −78° C. solution of 2-bromo-3-methylpyridine (10.0 g, 7.1 mL, 57.1 mmol) in THF (150 mL) was added drop wise a solution of n-BuLi (2.5 M in hexanes, 25.1 mL, 62.8 mmol) over 10 min. After 1.5 h a solution of N-benzyl-4-piperidone (10.8 g, 57.1 mmol) in THF (20 mL) was added drop wise over 15 min and the mixture was allowed to slowly warm to room temperature overnight. After 18 h sat. $NH_4Cl$ solution (40 mL) was added and the mixture was concentrated. The resulting residue was diluted with 1N $NaHCO_3$ (100 ml) and extracted with EtOAc. The combined organic phase washed with brine, dried ($MgSO_4$), and concentrated. Flash chromatography afforded the alcohol (8.1 g), an orange viscous oil, in 50% yield.

Step 13AB: 1'-Benzyl-3-methyl-1',2',3',6'-tetrahydro-[2,4']bipyridinyl. Thionyl chloride (10 mL) was added slowly drop wise to the alcohol from Step 13AA (6.34 g, 22.45 mmol). After 20 h, the mixture was concentrated, diluted with $CH_2Cl_2$ (100 mL) and cooled to 0° C. Sat. $NaHCO_3$ (300 mL) was slowly added to the mixture. The aqueous phase was separated and extracted with $CH_2Cl_2$ (2×150 mL). The combined organic extracts were washed with $H_2O$ (2×150 mL) and brine (150 mL), dried ($MgSO_4$), and concentrated to afford the olefin (3.54 g), a brown viscous oil, in 60% yield.

1H NMR (400 MHz, MeOD) δ ppm 2.59 (s, 3H), 2.69-2.76 (m, 2H), 3.04 (t, J=5.7 Hz, 2H), 3.44 (q, J=2.8 Hz, 2H), 3.95 (s, 2H), 5.94-5.99 (m, 1H), 7.42 (dd, J=7.7, 4.9 Hz, 1H), 7.49-7.54 (m, 1H), 7.55-7.61 (m, 2H), 7.61-7.66 (m, 2H), 7.88 (d, J=8.6 Hz, 1H), 8.51 (dd, J=4.8, 1.0 Hz, 1H).

Step 13AC: 3-Methyl-1',2',3',4',5',6'-hexahydro-[2,4']bipyridinyl. The olefin from Step 13AB (2.97 g, 11.23 mmol) was dissolved in EtOH (100 mL) and transferred to a Parr shaker bottle. 20% $Pd(OH)_2$ (1.48 g) was added, and the mixture was hydrogenated at 60 psi for 20 h. The mixture was filtered and concentrated. The residue was re-dissolved in MeOH (176 ml). 20% $Pd(OH)_2$ (2.0 g) and Acetyl Chloride (1.44 g, 1.3 ml, 18.32 mmol) was added, and the mixture was hydrogenated at 60 psi for 2 d. The mixture was filtered and concentrated and adhered to silica. Purification by flash chromatography (elution with 0 to 20% MeOH—$CH_2Cl_2$) to afford the amine (1.51 g), an off-white 76% yield.

1H NMR (400 MHz, MeOD) δ ppm 2.36-2.61 (m, 4H), 2.87 (s, 3H), 3.47-3.58 (m, 3H), 3.77-3.87 (m, 2H), 3.89-4.03 (m, 1H), 8.12 (dd, J=8.1, 5.8 Hz, 1H), 8.69 (d, J=7.1 Hz, 1H), 8.86 (d, J=4.5 Hz, 1H).

Step 13AD: 2-{1-[(2-chlorophenyl)sulfonyl]piperidin-4-yl}-3-methylpyridine. To a solution of the amine from Step 13AC (100 mg, 0.57 mmol) in $CH_2Cl_2$ (2.9 mL) was added 2-chlorobenzenesulfonyl chloride (150 mg, 0.097 mL, 0.69 mmol) and sat. $NaHCO_3$ (1.4 mL). The biphasic mixture was stirred at room temperature overnight. The reaction mixture was diluted with $CH_2Cl_2$ (3 mL) and poured into a Phase Separator cartridge. The organic phase was concentrated and purified by flash chromatography (elution with 0-30% EtOAc-hex). Lyophilization then afforded the title compound (26 mg), a white solid, in 13% yield.

1H NMR (400 MHz, CHLOROFORM-D) δ ppm 1.79 (d, J=14.1 Hz, 2H), 1.97-2.11 (m, 2H), 2.31 (s, 3H), 2.87-2.96 (m, 3H), 3.99 (dd, J=12.1 Hz, 2H), 7.03 (dd, J=7.6, 4.8 Hz, 1 H), 7.36-7.42 (m, 2H), 7.46-7.56 (m, 2H), 8.10 (dd, J=8.0, 1.6 Hz, 1H), 8.39 (d, J=4.8 Hz, 1 H). HRMS: calcd for $C_{17}H_{19}ClN_2O_2S+H+$, 351.09285. found (ESI-FTMS, $[M+H]^{1+}$), 351.0934.

Example 13A-2

2-{1-[(4-chlorophenyl)sulfonyl]piperidin-4-yl}-3-methylpyridine

Using the procedure from Example 13A-1, the title compound was prepared and isolated as a white solid in 33% yield.

1H NMR (400 MHz, CHLOROFORM-D) δ ppm 1.80 (d, J=14.4 Hz, 2H), 2.03-2.16 (m, 2H), 2.26 (s, 3H), 2.38-2.49 (m, 2H), 2.73-2.81 (m, 1H), 3.93 (d, J=11.4 Hz, 2H), 7.03 (dd, J=7.6, 4.8 Hz, 1H), 7.39 (d, J=6.6 Hz, 1H), 7.53 (d, J=8.6 Hz, 2H), 7.75 (d, J=8.8 Hz, 2H), 8.38 (d, J=4.8 Hz, 1H). HRMS: calcd for $C_{17}H_{19}ClN_2O_2S+H+$, 351.09285. found (ESI-FTMS, $[M+H]^{1+}$), 351.0935.

Example 13A-3

2-{1-[(2,6-dichlorophenyl)sulfonyl]piperidin-4-yl}-3-methylpyridine

Using the procedure from Example 13A-1, the title compound was isolated as a white solid (82 mg) in 31% yield.

1H NMR (400 MHz, CHLOROFORM-D) δ ppm 1.81 (d, J=14.7 Hz, 2H), 1.94-2.11 (m, 2H), 2.32 (s, 3H), 2.90-2.99 (m, 1H), 2.99-3.09 (m, 2H), 4.07 (d, J=12.4 Hz, 2H), 7.03 (dd, J=7.6, 4.8 Hz, 1H), 7.29-7.35 (m, 1H), 7.41 (d, J=7.6 Hz, 1H), 7.44-7.50 (m, 2H), 8.38 (d, J=6.3 Hz, 1H). HRMS: calcd for $C_{17}H_{18}Cl_2N_2O_2S+H+$, 385.05388. found (ESI-FTMS, $[M+H]^{1+}$), 385.0543.

Example 13A-4

2-{1-[(3,4-dichlorophenyl)sulfonyl]piperidin-4-yl}-3-methylpyridine

Using the procedure from Example 13A-1, the title compound (35 mg) was isolated as a white solid in 13% yield.

1H NMR (400 MHz, CHLOROFORM-D) δ ppm 1.76-1.86 (m, J=16.2, 1.3 Hz, 2H), 2.04-2.18 (m, 2H), 2.27 (s, 3H), 2.43-2.55 (m, 2H), 2.74-2.84 (m, 1H), 3.94 (d, J=11.4 Hz, 2H), 7.03 (dd, J=7.7, 4.7 Hz, 1H), 7.39 (d, J=7.6 Hz, 1H), 7.64 (d, J=1.3 Hz, 2H), 7.90 (s, 1H), 8.39 (d, J=6.3 Hz, 1H). HRMS: calcd for $C_{17}H_{18}Cl_2N_2O_2S+H+$, 385.05388. found (ESI-FTMS, $[M+H]^{1+}$), 385.0545.

Example 13A-5

2-{1-[(4-tert-butylphenyl)sulfonyl]piperidin-4-yl}-3-methylpyridine

Using the procedure from Example 13A-1, the title compound (105 mg) was isolated as a white solid in 41% yield.

1H NMR (400 MHz, CHLOROFORM-D) δ ppm 1.37 (s, 9H), 1.79 (d, J=14.9 Hz, 2H), 2.02-2.17 (m, 2H), 2.26 (s, 3H), 2.40-2.51 (m, 2H), 2.71-2.84 (m, 1H), 3.95 (d, J=11.4 Hz, 2H), 7.02 (dd, J=7.6, 4.8 Hz, 1H), 7.38 (d, J=8.6 Hz, 1H), 7.55 (d, J=8.8 Hz, 2H), 7.73 (d, J=8.8 Hz, 2H), 8.38 (d, J=6.3 Hz,

Example 13A-6

2-{1-[(4-bromophenyl)sulfonyl]piperidin-4-yl}-3-methylpyridine

Using the procedure from Example 13A-1, the title compound (51 mg) was isolated as a white solid in 27% yield.

1H NMR (400 MHz, CHLOROFORM-D) δ ppm 1.80 (d, J=13.4 Hz, 2H), 2.04-2.16 (m, 2H), 2.26 (s, 3H), 2.39-2.48 (m, 2H), 2.70-2.83 (m, 1H), 3.93 (d, J=11.6 Hz, 2H), 7.03 (dd, J=7.6, 4.8 Hz, 1H), 7.39 (d, J=7.6 Hz, 1H), 7.64-7.73 (m, 4H), 8.39 (d, J=6.1 Hz, 1H). HRMS: calcd for $C_{17}H_{19}BrN_2O_2S$+H+, 395.04233. found (ESI-FTMS, [M+H]$^{1+}$), 395.0432.

Example 13A-7

3-methyl-2-[1-(2-naphthylsulfonyl)piperidin-4-yl]pyridine

Using the procedure from Example 13A-1, the title compound (92 mg) was isolated as a white solid in 36% yield.

1H NMR (400 MHz, CHLOROFORM-D) δ ppm 1.79 (d, J=15.9 Hz, 2H), 2.05-2.18 (m, 2H), 2.21 (s, 3H), 2.42-2.51 (m, 2H), 2.68-2.77 (m, 1H), 4.02 (d, J=11.4 Hz, 2H), 7.01 (dd, J=7.6, 4.8 Hz, 1H), 7.36 (d, J=7.6 Hz, 1H), 7.60-7.71 (m, 2H), 7.82 (dd, J=8.6, 1.8 Hz, 1 H), 7.95 (d, J=8.1 Hz, 1H), 8.00 (d, J=8.1 Hz, 2H), 8.35-8.40 (m, 2H). HRMS: calcd for $C_{21}H_{22}N_2O_2S$+H+, 367.14747. found (ESI-FTMS, [M+H]$^{1+}$), 367.1479.

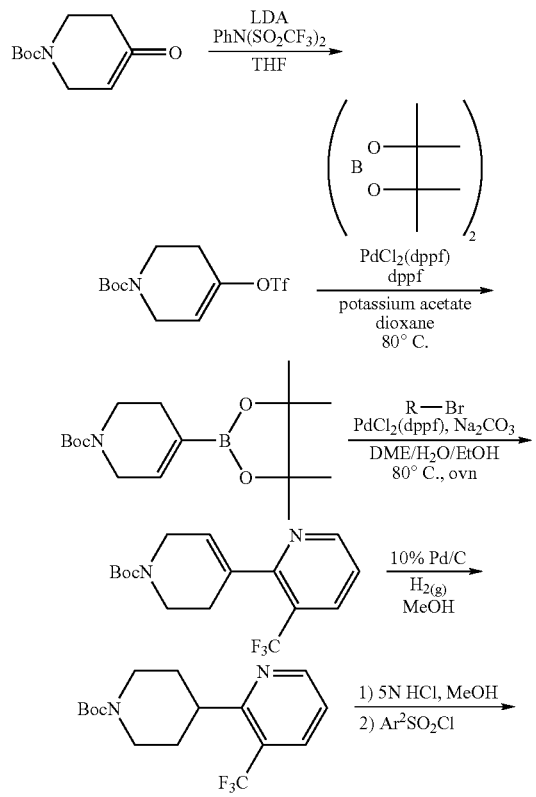

Scheme 13B

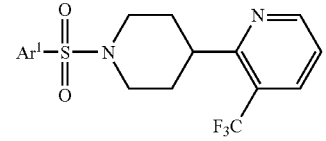

Example 13B-1

2-{1-[(2-chlorophenyl)sulfonyl]piperidin-4-yl}-3-(trifluoromethyl)pyridine

Step 13BA: 4-Trifluoromethanesulfonyloxy-3,6-dihydro-2H-pyridine-1 carboxylic acid tert-butyl ester. The vinyl triflate was prepared from tert-butyl-4-oxopiperidine-1-carboxylate using the procedure from WO 2004/036649. To a −78° C. solution of diisopropylamine (6.0 mL, 42.1 mmol) in THF (59 mL) was added drop wise a solution of n-BuLi (2.5 M in hexanes, 16.8 mL, 42.1 mmol) over 15 min. After 2 h a solution of the piperidone (7.13 g, 35.1 mmol) in THF (59 mL) was added drop wise over 30 min. After 40 min at −78° C. a solution of N-phenyltrifluoromethanesulfonimide (15.2 g, 42.1 mmol) in THF (59 ml) was added over 25 min. After 2.5 hr at −78° C. the mixture was allowed to slowly warm to room temperature. After 16 h the mixture was diluted with a 1:1 solution of THF and H$_2$O (140 ml). The aqueous phase was extracted with EtOAc. The combined organic phase washed with brine, dried (MgSO$_4$), and concentrated to give 29.6 g of a brown solid. The crude product was adhered to silica and eluted with 15% EtOAc/Hex to give 18.3 g of a yellow oil. Purification by flash chromatography (elution with 0 to 15% EtOAc-Hex) afforded 13.26 g of a yellow viscous oil, a mixture of the vinyl triflate and phenyl amine. The oil was dissolved in EtOAc washed with 5% Citric acid, 1N NaOH and brine dried (MgSO$_4$), and concentrated to afford the vinyl triflate (6.06 g), a yellow oil, in 52% yield. 1H NMR (400 MHz, CHLOROFORM-D) δ ppm 1.48 (s, 9H), 2.40-2.52 (m, J=2.9, 1.4 Hz, 2H), 3.63 (t, J=5.6 Hz, 2H), 4.05 (d, J=2.8 Hz, 2H), 5.77 (s, 1H).

Step 13BB: 4-(4,4,5,5-Tetramethyl-[1,3,2]dioxaborolan-2-yl)-3,6-dihydro-2H-pyridine-1-carboxylic acid tert-butyl ester. A mixture of the vinyl triflate from Step 13BA (3.0 g, 9.05 mmol), bis(pinacolato)diboron (2.53 g, 9.96 mmol), Dichloro[1-1'-bis(diphenylphosphino)ferrocene]palladium (II) dichloromethane adduct (0.020 g, 0.27 mmol), bis(diphenylphosphino)ferrocene (0.15 g, 0.27 mmol) and potassium acetate (2.66 g, 27.15 mmol) in 1,4-dioxane (53 ml) was degassed with N$_2$ and heated to 80° C. After 17 h, the mixture was cooled to room temperature, filtered through celite eluting with EtOAc. The filtrate was concentrated, adhered to silica and chromatographed (elution with 5 to 20% EtOAc-Hex) to afford the boronate (1.91 g), a white solid, in 68% yield. 1H NMR (400 MHz, CHLOROFORM-D) δ ppm 1.26 (s, 12H), 1.46 (s, 9H), 2.22 (s, 2H), 3.44 (t, J=5.3 Hz, 2H), 3.95 (d, J=2.3 Hz, 2H), 6.46 (s, 1H).

Step 13BC: 3-Trifluoromethyl-3',6'-dihydro-2'H-[2,4']bipyridinyl-1'-carboxylic acid tert-butyl ester. A mixture of the boronate from Step 13BB (1.49 g, 4.82 mmol), Dichloro[1-1'-bis(diphenylphosphino)ferrocene]palladium (II) dichloromethane adduct (703 mg, 0.96 mmol), 2-Bromo-3-(trifluoromethyl)pyridine (1.33 g, 5.78 mmol) and sodium carbonate (2.04 g, 19.28 mmol) in a 7:3:2 solution of dimethoxyethane/H$_2$O/EtOH (30 ml) was degassed with N$_2$ and heated at 80° C. After 20 h the mixture was cooled to room temperature and diluted with equal portions of EtOAc and H₂O, the aqueous phase was then extracted with EtOAc. The combined organic phase washed with brine, dried (MgSO₄) and concentrated. Purification by flash chromatography (elution with 0 to 30% EtOAc-Hex) afforded the desired product (1.24 g), an orange oil, in 78% yield. 1H NMR (400 MHz, CHLOROFORM-D) δ ppm 1.50 (s, 9H), 2.51 (s, 2H), 3.67 (s, 2H), 4.07 (s, 2H), 5.76 (s, 1H), 7.34 (dd, J=8.1, 4.8 Hz, 1H), 7.99 (d, J=8.1 Hz, 1H), 8.75 (d, J=4.8 Hz, 1H).

Step 13BD: 3-Trifluoromethyl-3',4',5',6'-tetrahydro-2'H-[2,4']bipyridinyl-1'-carboxylic acid tert-butyl ester. The olefin from Step 13BC (1.23 g, 3.75 mmol) was dissolved in EtOH (100 mL) and transferred to a Parr shaker bottle. 10% Pd/C (1.0 g) was added, and the mixture was hydrogenated at 60 psi for 16 h. The mixture was filtered, fresh Pd/C (3.0 g) was added, and the mixture was hydrogenated at 60 psi for 2 d. The mixture was filtered and concentrated to afford the piperidine (1.22 g), brown viscous oil, in 98% yield. 1H NMR (400 MHz, CHLOROFORM-D) δ ppm 1.48 (s, 9H), 1.71 (d, J=12.9 Hz, 2H), 1.86-2.08 (m, 2H), 2.83 (broad, s, 2H), 3.05-3.24 (m, 1H), 4.25 (broad, s, 2H), 7.24 (dd, J=8.1, 4.8 Hz, 1H), 7.91 (d, J=8.1 Hz, 1H), 8.73 (d, J=4.3 Hz, 1H).

Step 13BE: 3-Trifluoromethyl-1',2',3',4',5',6'-hexahydro-[2,4']bipyridinyl. A mixture of the piperidine from Step 13BD (1.22 g, 3.69 mmol), MeOH (15 mL), and 6N HCl (2.2 mL) was heated to reflux for 3 h. The mixture was cooled to room temperature and diluted with sat. Na₂CO₃ solution (30 mL). The mixture was extracted with CH₂Cl₂ (2×50 mL). The organic phase washed with H₂O and brine, dried (MgSO₄) and concentrated to afford the amine (608 mg), an off-white solid, 72% yield. 1H NMR (400 MHz, CHLOROFORM-D) δ ppm 1.75 (d, J=13.4 Hz, 2H), 1.90-2.05 (m, 2H), 2.38 (s, 1H), 2.75-2.85 (m, 2H), 3.19 (t, J=12.1 Hz, 1H), 3.22-3.29 (m, 2H), 7.23 (dd, J=7.8, 4.8 Hz, 1H), 7.90 (d, J=6.8 Hz, 1H), 8.74 (d, J=3.8 Hz, 1 H).

Step 13BF: 2-{1-[(2-chlorophenyl)sulfonyl]piperidin-4-yl}-3-(trifluoromethyl)pyridine. To a solution of the amine from Step 13BE (100 mg, 0.43 mmol) in CH₂Cl₂ (2.9 mL) was added 2-chlorobenzenesulfonyl chloride (113 mg, 73 μl, 0.52 mmol) and sat. NaHCO₃ (1.4 mL). The biphasic mixture was stirred at room temperature overnight. The reaction mixture was diluted with CH₂Cl₂ (3 mL) and poured into a Phase Separator cartridge. The organic phase was concentrated and purified by flash chromatography (elution with 0-20% EtOAc-hex). Lyophilization then afforded the title compound (121 mg), a white solid, in 70% yield. 1H NMR (400 MHz, CHLOROFORM-D) δ ppm 1.79 (d, J=13.6 Hz, 2H), 2.09-2.23 (m, 2H), 2.82-2.92 (m, 2H), 3.08 (t, J=11.9 Hz, 1H), 4.02 (d, J=12.4 Hz, 2H), 7.21-7.27 (m, 1H), 7.37-7.44 (m, 1H), 7.46-7.52 (m, 1H), 7.53-7.59 (m, 1H), 7.89 (dd, J=8.0, 1.6 Hz, 1H), 8.09 (d, J=6.3 Hz, 1 H), 8.73 (d, J=3.5 Hz, 1H). HRMS: calcd for $C_{17}H_{16}ClF_3N_2O_2S+H+$, 405.06458. found (ESI-FTMS, $[M+H]^{1+}$), 405.0652.

Example 13B-2

2-{1-[(4-chlorophenyl)sulfonyl]piperidin-4-yl}-3-(trifluoromethyl)pyridine

Using the procedure from Example 13B-1, the title compound (168 mg) was prepared and isolated as a white solid in 97% yield.

1H NMR (400 MHz, CHLOROFORM-D) δ ppm 1.80 (d, J=12.6 Hz, 2H), 2.13-2.27 (m, 2H), 2.34-2.45 (m, 2H), 2.94 (t, J=11.4 Hz, 1H), 3.95 (d, J=11.6 Hz, 2H), 7.21-7.28 (m, 1H), 7.54 (d, J=8.3 Hz, 2H), 7.74 (d, J=8.6 Hz, 2H), 7.89 (d, J=7.8 Hz, 1H), 8.73 (d, J=4.8 Hz, 1H). HRMS: calcd for $C_{17}H_{16}ClF_3N_2O_2S+H+$, 405.06458. found (ESI-FTMS, $[M+H]^{1+}$), 405.065.

Example 13B-3

2-{1-[(3,4-dichlorophenyl)sulfonyl]piperidin-4-yl}-3-(trifluoromethyl)pyridine

Using the procedure from Example 13B-1, the title compound (178 mg) was prepared and isolated as a white solid in 94% yield.

1H NMR (400 MHz, CHLOROFORM-D) δ ppm 1.82 (d, J=14.1 Hz, 2H), 2.13-2.28 (m, 2H), 2.39-2.50 (m, 2H), 2.89-3.02 (m, 1H), 3.96 (d, J=11.6 Hz, 2H), 7.22-7.29 (m, 1H), 7.59-7.68 (m, 2H), 7.86-7.93 (m, 2H), 8.73 (d, J=4.8 Hz, 1H). HRMS: calcd for $C_{17}H_{15}Cl_2F_3N_2O_2S+H+$, 439.02561. found (ESI-FTMS, $[M+H]^{1+}$), 439.0256.

Example 13B-4

2-{1-[(4-tert-butylphenyl)sulfonyl]piperidin-4-yl}-3-(trifluoromethyl)pyridine

Using the procedure from Example 13AA, the title compound (172 mg) was prepared and isolated as a white solid in 94% yield.

1H NMR (400 MHz, CHLOROFORM-D) δ ppm 1.38 (s, 9H), 1.79 (d, J=12.9 Hz, 2H), 2.13-2.30 (m, 2H), 2.35-2.45 (m, 2H), 2.94 (t, J=11.6 Hz, 1H), 3.96 (d, J=9.6 Hz, 2H), 7.24 (dd, J=8.1, 4.8 Hz, 1H), 7.56 (d, J=8.6 Hz, 2H), 7.67-7.76 (m, 2H), 7.88 (d, J=8.1 Hz, 1H), 8.73 (d, J=3.5 Hz, 1H). HRMS: calcd for $C_{21}H_{25}F_3N_2O_2S+H+$, 427.16616. found (ESI-FTMS, $[M+H]^{1+}$), 427.1662.

Example 13B-5

2-[1-(2-naphthylsulfonyl)piperidin-4-yl]-3-(trifluoromethyl)pyridine

Using the procedure from Example 13AA, the title compound (168 mg) was isolated as a white solid in 93% yield.

1H NMR (400 MHz, CHLOROFORM-D) δ ppm 1.79 (d, J=13.1 Hz, 2H), 2.16-2.29 (m, 2H), 2.38-2.48 (m, 2H), 2.89 (t, J=11.2 Hz, 1H), 4.04 (d, J=11.4 Hz, 2H), 7.23 (dd, J=8.0, 4.7 Hz, 1H), 7.59-7.70 (m, 2H), 7.80 (dd, J=8.6, 1.8 Hz, 1H), 7.86 (d, J=8.1 Hz, 1H), 7.95 (d, J=7.8 Hz, 1H), 7.98-8.04 (m, 2H), 8.38 (s, 1H), 8.72 (d, J=4.8 Hz, 1H). HRMS: calcd for $C_{21}H_{19}F_3N_2O_2S+H+$, 421.11921. found (ESI-FTMS, $[M+H]^{1+}$), 421.1189.

Example 13B-6

2-{1-[(2,6-dichlorophenyl)sulfonyl]piperidin-4-yl}-3-(trifluoromethyl)pyridine

Using the procedure from Example 13AA, the title compound (126 mg) was isolated as a white solid in 67% yield.

1H NMR (400 MHz, CHLOROFORM-D) δ ppm 1.81 (d, J=13.1 Hz, 2H), 2.08-2.22 (m, 2H), 2.92-3.05 (m, 2H), 3.13 (t, J=11.9 Hz, 1H), 4.11 (d, J=12.4 Hz, 2H), 7.20-7.28 (m, 1H), 7.29-7.36 (m, 1H), 7.44-7.52 (m, 2H), 7.90 (d, J=7.8 Hz, 1H), 8.72 (d, J=4.5 Hz, 1H). HRMS: calcd for $C_{17}H_{15}Cl_2F_3N_2O_2S+H+$, 439.02561. found (ESI-FTMS, $[M+H]^{1+}$), 439.0255.

Example 14

Scheme 14

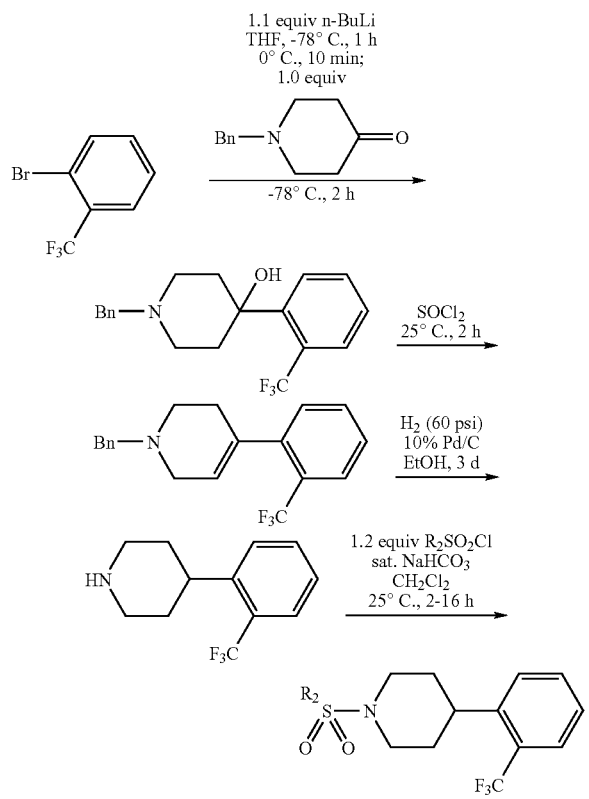

Example 14A

1-[(3-chlorophenyl)sulfonyl]-4-[2-(trifluoromethyl)phenyl]piperidine

Step 14A: 1-Benzyl-4-[2-(trifluoromethyl)phenyl]piperidin-4-ol. Following the procedure of N. I. Carruthers et al. (J. Med. Chem. 2005, 48, 1857-1872), to a −78° C. solution of 2-bromobenzotrifluoride (12.9 g, 7.8 mL, 57 mmol) in THF (225 mL) was added dropwise a solution of n-BuLi (2.5 M in hexanes, 26 mL, 65 mmol) over 10 min. After 1 h, the reaction mixture was stirred at 0° C. for 10 min, recooled to −78° C., and a solution of N-benzyl-4-piperidone (10.7 g, 57 mmol) in THF (40 mL) was added dropwise via addition funnel over 10 min. After 2 h at −78° C., sat. NH₄Cl solution (200 mL) was added and the mixture was warmed to room temperature. The aqueous phase was extracted with EtOAc (2×200 mL). The organic phase washed with H2O (200 mL) and brine (150 mL), dried (MgSO₄), and concentrated. Flash chromatography afforded the alcohol (2.7 g), a yellow oil, slightly contaminated with piperidone starting material, in ~15% yield.

Step 14B: 1-Benzyl-4-[2-(trifluoromethyl)phenyl]-1,2,3,6-tetrahydropyridine. Thionyl chloride (10 mL) was added slowly dropwise to the alcohol from Step 14A (4.9 g, 14.6 mmol). After 2 h, the mixture was concentrated, diluted with $CH_2Cl_2$ (50 mL), and added slowly to a stirred solution of sat. $NaHCO_3$ (200 mL). The aqueous phase was separated and extracted with $CH_2Cl_2$ (2×150 mL). The combined organic extracts were washed with $H_2O$ (2×150 mL) and brine (150 mL), dried ($MgSO_4$), and concentrated. Flash chromatography (elution with 10-30% EtOAc-hexanes) afforded the olefin (2.75 g), a yellow oil, in 59% yield. 1H NMR (400 MHz, $CDCl_3$) δ 2.38 (dd, J=4.5, 2.8 Hz, 2H), 2.70 (t, J=5.7 Hz, 2H), 3.14 (q, J=2.9 Hz, 2H), 3.66 (s, 2H), 5.57 (s, 1H), 7.22-7.30 (m, 2H), 7.31-7.42 (m, 5H), 7.47 (t, J=7.6 Hz, 1H), 7.63 (d, J=7.1 Hz, 1H).

Step 14C: Following the procedure of N. I. Carruthers et al. (J. Med. Chem. 2005, 48, 1857-1872), the olefin from Step 14B (2.99 g, 9.4 mmol) was dissolved in EtOH (50 mL) and transferred to a Parr shaker bottle. 10% Pd/C (wet Degussa, 3.0 g) was added, and the mixture was hydrogenated at 50 psi for 16 h. The mixture was filtered, fresh Pd/C (3.0 g) was added, and the mixture was hydrogenated at 50 psi for 2 d. The mixture was filtered and concentrated to afford a beige solid that was purified by flash chromatography (elution with 10% MeOH—$CH_2Cl_2$ to 0.1% $Et_3N$-10% MeOH—$CH_2Cl_2$) to afford the amine (1.24 g), a yellow oil, contaminated with $Et_3N$, in 57% yield. $^1H$ NMR (400 MHz, $CDCl_3$) δ 1.62-1.87 (m, 4H), 2.70-2.84 (m, 2H), 2.97-3.10 (m, 1H), 3.19 (d, J=11.6 Hz, 2H), 7.18-7.35 (m, 1H), 7.44-7.56 (m, 2H), 7.61 (d, J=7.8 Hz, 1H).

Step 14D: To a solution of the amine from Step 14C (150 mg, 0.65 mmol) in $CH_2Cl_2$ (4 mL) was added 3-chlorobenzenesulfonyl chloride (165 mg, 0.11 mL, 0.78 mmol) and saturated $NaHCO_3$ (2 mL). The biphasic mixture was stirred for 6 h. The reaction mixture was diluted with $CH_2Cl_2$ (3 mL) and poured into a Phase Separator cartridge. The organic phase was concentrated and purified by flash chromatography (elution with 2-10% EtOAc-hex). Lyophilization then afforded the title compound (176 mg), a white solid, in 67% yield.

$^1H$ NMR (400 MHz, $CDCl_3$) δ 1.80-2.01 (m, 4H), 2.26-2.49 (m, 2H), 2.69-2.94 (m, 1H), 3.98 (d, J=11.9 Hz, 2H), 7.31 (t, J=7.7 Hz, 1H), 7.41 (d, J=7.8 Hz, 1H), 7.48-7.58 (m, 2H), 7.58-7.65 (m, 2H), 7.66-7.72 (m, 1H), 7.79 (t, J=1.9 Hz, 1H). HRMS: calcd for $C_{18}H_{17}ClF_3NO_2S+H+$, 404.06934. found (ESI-FTMS, $[M+H]^{1+}$), 404.0692. HPLC Method 1: room temperature, 6.99 min, 99.2%. HPLC Method 2: room temperature, 7.54 min, 97.7%.

Example 14B

1-[(4-chlorophenyl)sulfonyl]-4-[2-(trifluoromethyl)phenyl]piperidine

Using the procedure from Example 14A, Step 14D, 1-benzyl-4-[2-(trifluoromethyl)phenyl]-1,2,3,6-tetrahydropyridine (Example 14A, Step 14C, 150 mg, 0.65 mmol) was reacted with 4-chlorobenzenesulfonyl chloride (165 mg, 0.78 mmol) to afford the title compound (219 mg), a white solid, in 84% yield.

$^1H$ NMR (400 MHz, $CDCl_3$) δ 1.74-1.98 (m, 4H), 2.26-2.43 (m, 2H), 2.68-2.95 (m, 1H), 3.96 (d, J=11.9 Hz, 2H), 7.31 (t, J=7.6 Hz, 1H), 7.41 (d, J=7.8 Hz, 1H), 7.48-7.57 (m, 3H), 7.61 (d, J=7.8 Hz, 1H), 7.74 (d, J=8.8 Hz, 2H). HRMS: calcd for $C_{18}H_{17}ClF_3NO_2S+H+$, 404.06934. found (ESI-

Example 14C

1-[(3,4-dichlorophenyl)sulfonyl]-4-[2-(trifluoromethyl)phenyl]piperidine

Using the procedure from Example 14A, 1-benzyl-4-[2-(trifluoromethyl)phenyl]-1,2,3,6-tetrahydropyridine (Example 14A, Step 14C, 150 mg, 0.65 mmol) was reacted with 3,4-dichlorobenzenesulfonyl chloride (191 mg, 0.12 mL, 0.78 mmol) to afford the title compound (211 mg), a white solid, in 74% yield.

$^1$H NMR (400 MHz, CDCl$_3$) δ 1.77-1.96 (m, 4H), 2.29-2.58 (m, 2H), 2.72-3.00 (m, 1H), 3.97 (d, J=12.1 Hz, 2H), 7.32 (t, J=7.7 Hz, 1H), 7.41 (d, J=7.8 Hz, 1H), 7.54 (t, J=7.5 Hz, 1H), 7.58-7.69 (m, 3H), 7.88 (d, J=1.8 Hz, 1H). HRMS: calcd for C$_{18}$H$_{16}$Cl$_2$F$_3$NO$_2$S+H+, 438.03036. found (ESI-FTMS, [M+H]$^{1+}$), 438.0303. HPLC Method 1: room temperature, 7.31 min, 99.3%. HPLC Method 2: room temperature, 7.84 min, 99.4%.

Example 14D

1-[(4-tert-butylphenyl)sulfonyl]-4-[2-(trifluoromethyl)phenyl]piperidine

Using the procedure from Example 14A, Step 14D, 1-benzyl-4-[2-(trifluoromethyl)phenyl]-1,2,3,6-tetrahydropyridine (Example 14A, Step 14C, 150 mg, 0.65 mmol) was reacted with 4-tert-butylbenzenesulfonyl chloride (182 mg, 0.78 mmol) to afford the title compound (135 mg), a white solid, in 49% yield.

$^1$H NMR (400 MHz, CDCl$_3$) δ 1.71-1.97 (m, 4H), 2.24-2.53 (m, 2H), 2.69-2.99 (m, 1H), 3.97 (d, J=11.9 Hz, 2H), 7.30 (t, J=7.7 Hz, 1H), 7.40 (d, J=7.8 Hz, 1H), 7.48-7.63 (m, 4H), 7.72 (d, J=8.6 Hz, 2H). HRMS: calcd for C$_{22}$H$_{26}$F$_3$NO$_2$S+H+, 426.17091. found (ESI-FTMS, [M+H]$^{1+}$), 426.1714. HPLC Method 1: room temperature, 7.52 min, 99.5%. HPLC Method 2: room temperature, 7.85 min, 99.3%.

Example 14E 1-(2-naphthylsulfonyl)-4-[2-(trifluoromethyl)phenyl]piperidine

Using the procedure from Example 14A, the title compound (235 mg) was isolated as a white solid, in 86% yield.

$^1$H NMR (400 MHz, CDCl$_3$) δ 1.68-2.09 (m, 4H), 2.26-2.62 (m, 2H), 2.52-3.04 (m, 1H), 4.05 (d, J=11.6 Hz, 2H), 7.29 (t, J=7.6 Hz, 1H), 7.40 (d, J=7.8 Hz, 1H), 7.51 (t, J=7.6 Hz, 1H), 7.58 (d, J=8.1 Hz, 1H), 7.61-7.74 (m, 2H), 7.80 (dd, J=8.6, 1.8 Hz, 1H), 7.96 (d, J=8.1 Hz, 1H), 7.98-8.12 (m, 2H), 8.37 (d, J=1.5 Hz, 1H). HRMS: calcd for C$_{22}$H$_{20}$F$_3$NO$_2$S+H+, 420.12396. found (ESI-FTMS, [M+H]$^{1+}$), 420.1244. HPLC Method 1: room temperature, 7.12 min, 99.4%. HPLC Method 2: room temperature, 7.66 min, 99.3%.

Example 14F

1-[(2,6-dichlorophenyl)sulfonyl]-4-[2-(trifluoromethyl)phenyl]piperidine

Using the procedure from Example 14A, the title compound (236 mg) was isolated as a white solid, in 83% yield.

$^1$H NMR (400 MHz, CDCl$_3$) δ 1.79-1.96 (m, 4H), 2.86-3.01 (m, 2H), 3.02-3.13 (m, 1H), 4.12 (d, J=12.9 Hz, 2H), 7.28-7.38 (m, 2H), 7.42 (d, J=7.8 Hz, 1H), 7.46-7.57 (m, 3H), 7.62 (d, J=8.1 Hz, 1H). HRMS: calcd for C$_{18}$H$_{16}$Cl$_2$F$_3$NO$_2$S+H+, 438.03036. found (ESI-FTMS, [M+H]$^{1+}$), 438.0307. HPLC Method 1: room temperature, 7.03 min, 99.2%. HPLC Method 2: room temperature, 7.53 min, 99.1%.

Example 14G

1-[(4-bromophenyl)sulfonyl]4-[2-(trifluoromethyl)phenyl]piperidine

Using the procedure from Example 14A, the title compound (209 mg) was isolated as a white solid, in 72% yield.

$^1$H NMR (400 MHz, CDCl$_3$) δ 1.78-1.97 (m, 4H), 2.28-2.41 (m, 2H), 2.75-2.92 (m, 1H), 3.96 (d, J=12.1 Hz, 2H), 7.31 (t, J=7.7 Hz, 1H), 7.41 (d, J=7.8 Hz, 1H), 7.53 (t, J=7.7 Hz, 1H), 7.61 (d, J=7.8 Hz, 1H), 7.66 (d, J=8.7 Hz, 2H), 7.72 (d, J=8.7 Hz, 2H). HRMS: calcd for C$_{18}$H$_{17}$BrF$_3$NO$_2$S+H+, 448.01882. found (ESI-FTMS, [M+H]$^{1+}$), 448.0192. HPLC Method 1: room temperature, 7.06 min, 99.7%. HPLC Method 2: room temperature, 7.58 min, 99.4%.

Example 14H

1-[(2-fluorophenyl)sulfonyl]4-[2-(trifluoromethyl)phenyl]piperidine

Using the procedure from Example 14A, the title compound (25 mg) was isolated as a white solid, in 15% yield.

$^1$H NMR (400 MHz, CDCl$_3$) δ 1.80-1.96 (m, 4H), 2.54-2.71 (m, 2H), 2.87-3.03 (m, 1H), 4.04 (d, J=12.1 Hz, 2H), 7.18-7.37 (m, 3H), 7.42 (d, J=8.1 Hz, 1H), 7.53 (t, J=7.7 Hz, 1H), 7.57-7.66 (m, 2H), 7.82-7.96 (m, 1H). HRMS: calcd for C$_{18}$H$_{17}$F$_4$NO$_2$S+H+, 388.09889. found (ESI-FTMS, [M+H]$^{1+}$), 388.0991. HPLC Method 1: room temperature, 6.64 min, 98.1%. HPLC Method 2: room temperature, 7.22 min, 97.0%.

Example 14I

1-[(3-fluorophenyl)sulfonyl]-4-[2-(trifluoromethyl)phenyl]piperidine

Using the procedure from Example 14A, the title compound (93 mg) was isolated as a white solid, in 55% yield.

$^1$H NMR (400 MHz, CDCl$_3$) δ 1.73-2.02 (m, 4H), 2.28-2.55 (m, 2H), 2.75-3.07 (m, 1H), 3.98 (d, J=11.9 Hz, 2H), 7.28-7.39 (m, 2H), 7.41 (d, J=8.1 Hz, 1H), 7.46-7.65 (m, 5H). HRMS: calcd for C$_{18}$H$_{17}$F$_4$NO$_2$S+H+, 388.09889. found (ESI-FTMS, [M+H]$^{1+}$), 388.0991. HPLC Method 1: room temperature, 6.71 min, 98.7%. HPLC Method 2: room temperature, 7.32 min, 100%.

Example 14J

4-[2-(trifluoromethyl)phenyl]-1-{[2-(trifluoromethyl)phenyl]sulfonyl}piperidine

Using the procedure from Example 14A, the title compound (110 mg) was isolated as a white solid, in 57% yield.

$^1$H NMR (400 MHz, CDCl$_3$) δ 1.75-2.00 (m, 4H), 2.60-2.90 (m, 2H), 2.94-3.14 (m, 1H), 4.00 (d, J=12.9 Hz, 2H), 7.31 (t, J=7.7 Hz, 1H), 7.43 (d, J=7.8 Hz, 1H), 7.53 (t, J=7.5 Hz, 1H), 7.62 (d, J=7.8 Hz, 1H), 7.66-7.81 (m, 2H), 7.86-8.00 (m, 1H), 8.07-8.24 (m, 1H). HRMS: calcd for C$_{19}$H$_{17}$F$_6$NO$_2$S+H+, 438.09569. found (ESI-FTMS, [M+H]$^{1+}$), 438.0958. HPLC Method 1: room temperature, 6.89 min, 99.1%. HPLC Method 2: room temperature, 7.37 min, 100%.

Example 14K

4-[2-(trifluoromethyl)phenyl]-1-{[3-(trifluoromethyl)phenyl]sulfonyl}piperidine

Using the procedure from Example 14A, the title compound (92 mg) was isolated as a white solid, in 48% yield.
$^1$H NMR (400 MHz, CDCl$_3$) δ 1.78-2.13 (m, 4H), 2.26-2.50 (m, 2H), 2.78-3.11 (m, 1H), 4.01 (d, J=12.1 Hz, 2H), 7.32 (t, J=7.7 Hz, 1H), 7.41 (d, J=8.1 Hz, 1H), 7.54 (t, J=7.6 Hz, 1H), 7.61 (d, J=7.8 Hz, 1H), 7.74 (t, J=7.8 Hz, 1H), 7.91 (d, J=7.8 Hz, 1H), 7.99 (d, J=7.8 Hz, 1H), 8.06 (s, 1H). HRMS: calcd for C$_{19}$H$_{17}$F$_6$NO$_2$S+H+, 438.09569. found (ESI-FTMS, [M+H]$^{1+}$), 438.0959. HPLC Method 1: room temperature, 6.98 min, 98.4%. HPLC Method 2: room temperature, 7.52 min, 98.9%.

Example 14L

4-[2-(trifluoromethyl)phenyl]-1-{[4-(trifluoromethyl)phenyl]sulfonyl}piperidine

Using the procedure from Example 14A, the title compound (90 mg) was isolated as a white solid, in 47% yield.
$^1$H NMR (400 MHz, CDCl$_3$) δ 1.74-2.00 (m, 4H), 2.21-2.53 (m, 2H), 2.67-3.27 (m, 1H), 4.00 (d, J=11.4 Hz, 2H), 7.32 (t, J=7.7 Hz, 1H), 7.40 (d, J=7.6 Hz, 1H), 7.53 (t, J=7.6 Hz, 1H), 7.61 (d, J=7.8 Hz, 1H), 7.85 (d, J=8.3 Hz, 2H), 7.93 (d, J=8.3 Hz, 2H). HRMS: calcd for C$_{19}$H$_7$F$_6$NO$_2$S+H+, 438.09569. found (ESI-FTMS, [M+H]$^{1+}$), 438.0959. HPLC Method 1: room temperature, 7.03 min, 99.3%. HPLC Method 2: room temperature, 7.53 min, 99.0%.

Example 14M

1-[(4-methoxyphenyl)sulfonyl]-4-[2-(trifluoromethyl)phenyl]piperidine

Using the procedure from Example 14A, the title compound (117 mg) was isolated as a white solid, in 67% yield.
$^1$H NMR (400 MHz, CDCl$_3$) δ 1.66-2.04 (m, 4H), 2.19-2.46 (m, 2H), 2.51-3.09 (m, 1H), 3.90 (s, 3H), 3.94 (d, J=11.4 Hz, 2H), 7.03 (d, J=8.8 Hz, 2H), 7.30 (t, J=7.7 Hz, 1H), 7.42 (d, J=8.1 Hz, 1H), 7.53 (t, J=7.6 Hz, 1H), 7.60 (d, J=7.6 Hz, 1H), 7.73 (d, J=9.1 Hz, 2H). HRMS: calcd for C$_{19}$H$_{20}$F$_3$NO$_3$S+H+, 400.11887. found (ESI-FTMS, [M+H]$^{1+}$), 400.1192. HPLC Method 1: room temperature, 6.63 min, 99.0%. HPLC Method 2: room temperature, 7.27 min, 98.5%.

Example 14N

1-{[4-(trifluoromethoxy)phenyl]sulfonyl}-4-[2-(trifluoromethyl)phenyl]piperidine Using the procedure from Example 14A, the title compound (126 mg) was isolated as a white solid, in 64% yield.
$^1$H NMR (400 MHz, CDCl$_3$) δ 1.72-2.02 (m, 4H), 2.26-2.55 (m, 2H), 2.75-3.01 (m, 1H), 3.98 (t, J=11.9 Hz, 2H), 7.31 (t, J=7.6 Hz, 1H), 7.40 (appar d, J=8.1 Hz, 3H), 7.53 (t, J=7.7 Hz, 1H), 7.61 (d, J=7.8 Hz, 1H), 7.85 (d, J=8.8 Hz, 2H). HRMS: calcd for C$_{19}$H$_{17}$F$_6$NO$_3$S+H+, 454.09061. found (ESI-FTMS, [M+H]$^{1+}$), 454.0909. HPLC Method 1: room temperature, 7.09 min, 89.7%. HPLC Method 2: room temperature, 7.57 min, 89.9%.

Example 14O

1-[(4-bromo-3-fluorophenyl)sulfonyl]-4-[2-(trifluoromethyl)phenyl]piperidine

Using the procedure from Example 14A, the title compound (115 mg) was isolated as a white solid, in 57% yield.
$^1$H NMR (400 MHz, CDCl$_3$) δ 1.70-2.06 (m, 4H), 2.28-2.51 (m, 2H), 2.74-3.07 (m, 1H), 3.96 (d, J=11.1 Hz, 2H), 7.32 (t, J=7.6 Hz, 1H), 7.41 (d, J=7.6 Hz, 1H), 7.46 (dd, J=8.3, 1.3 Hz, 1H), 7.50-7.57 (m, 2H), 7.61 (d, J=7.8 Hz, 1H), 7.78 (dd, J=8.3, 6.6 Hz, 1H). HRMS: calcd for C$_{18}$H$_{16}$BrF$_4$NO$_2$S+H+, 466.00940. found (ESI-FTMS, [M+H]$^{1+}$), 466.0097. HPLC Method 1: room temperature, 7.11 min, 98.7%. HPLC Method 2: room temperature, 7.68 min, 98.2%.

Example 15

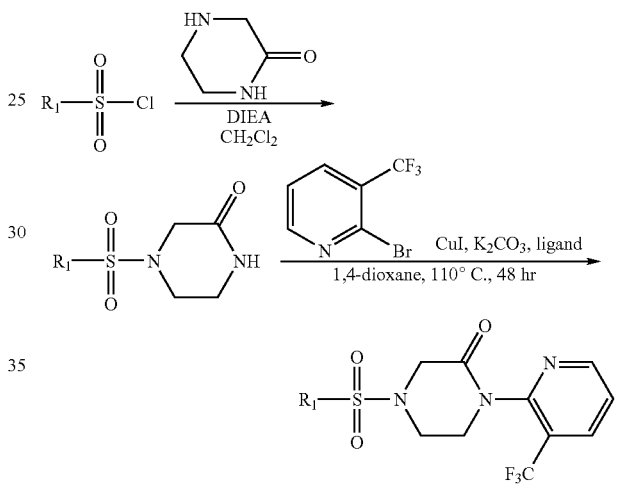

Scheme 15

Example 15A 4-(naphthalene-2-sulfonyl)-1-(3-trifluoromethylpyridin-2-yl)-piperazin-2-one Step 15A: To a stirred solution of piperazine-2-one (353.3 mg, 3.5 mmol) and naphthalene-2-sulfonyl chloride (800 mg, 3.5 mmol) in anhydrous dichloromethane (15 mL) was added diisopropylethylamine (1.54 mL, 8.8 mmol). The mixture was stirred for 30 min. Reaction was complete as determined by TLC. The reaction mixture was filtered, washed with hexane to give a first batch. The mother liquor washed with saturated ammonium chloride, then washed with saturated brine, separated, dried over sodium sulphate. Then hexane was added, lots of precipitate formed. The was filtered, washed with hexane to give a second batch. The two batches were combined to yield 4-(naphthalene-2-sulfonyl)-piperazin-2-one in 92.5% yield (947 mg) as an off-white solid. 1H NMR (400 MHz, CHLOROFORM-D) δ ppm 3.35-3.40 (m, 2H) 3.42-3.48 (m, 2H) 3.79 (s, 2H) 6.11 (s, 1H) 7.63-7.73 (m, 2H) 7.77 (dd, J=8.72, 1.89 Hz, 1 H) 7.94 (d, J=7.83 Hz, 1H) 7.98-8.05 (m, 2H) 8.38 (s, 1H).

Step 15B: An oven-dried microwave vial was charged with of 4-(naphthalene-2-sulfonyl)-piperazin-2-one (100 mg, 0.34 mmol), 2-bromo-3-trifluoromethyl pyridine (115.3 mg, 0.51 mmol), powdered anhydrous potassium carbonate (94 mg, 0.68 mmol), and CuI (6.5 mg, 0.034 mmol). The vial was purged and back-filled with $N_2$. Anhydrous 1,4-dioxane (1.2 mL) was added, followed by 3.7 μL (0.034 mmol) of N,N'-dimethyl-1,2-ethylenediamine. The blue suspension was heated in a 110° C. oil bath for 48 hr. After cooling to room temperature, the brown suspension was diluted with $H_2O$ and EtOAc. The layers were separated, and the aqueous layer washed with EtOAc (2×). The combined organic layers were dried over $Na_2SO_4$, filtered, and concentrated under reduced pressure. The residue was purified by prep HPLC to provide 4.8 mg (3.2%) of 4-(Naphthalene-2-sulfonyl)-1-(3-trifluoromethyl-pyridin-2-yl)-piperazin-2-one as a light yellow solid.

1H NMR (400 MHz, CHLOROFORM-D) δ ppm 3.38-3.46 (m, 1H) 3.57-3.66 (m, 1H) 3.68-3.79 (m, 1H) 3.82-3.91 (m, 1H) 3.98-4.09 (m, 2H) 7.46 (dd, J=7.83, 4.80 Hz, 1H) 7.64-7.74 (m, 2H) 7.81 (dd, J=8.59, 1.77 Hz, 1H) 7.94-8.09 (m, 4H) 8.42 (d, J=1.77 Hz, 1H) 8.71 (dd, J=5.05, 1.77 Hz, 1H). HRMS: calcd for $C_{20}H_{16}F_3N_3O_3S+H+$, 436.09372. found (ESI-FTMS, $[M+H]^{1+}$), 436.0936.

Example 15B 4-(3,4-dichloro-benzenesulfonyl)-1-(3-trifluoromethyl-pyridin-2-yl)-piperazin-2-one Step 15A: Sulfonylation of piperazine-2-one (326.2 mg, 3.3 mmol) with 3,4-dichlorobenzene-sulfonyl chloride (800 mg, 3.3 mmol) was carried out according to a similar procedure described for example 15A using anhydrous dichloromethane (8 mL) as solvent and diisopropylethylamine (1.42 mL, 8.2 mmol) as base. 4-(3,4-dichloro-benzenesulfonyl)-piperazin-2-one was obtained in 90.3% yield (912 mg) as white solid. 1H NMR (400 MHz, DMSO-D6) δ ppm 3.17-3.24 (m, 2H) 3.25-3.30 (m, 2H) 3.59 (s, 2H) 7.79 (dd, J=8.46, 2.15 Hz, 1H) 7.94 (d, J=8.34 Hz, 1H) 8.06 (d, J=2.02 Hz, 1H) 8.08 (s, 1H).

Step 15B: Amidation of 4-(3,4-dichloro-benzenesulfonyl)-piperazin-2-one (150 mg, 0.49 mmol) with 2-bromo-3-trifluoromethyl pyridine (164.5 mg, 0.73 mmol) was carried out according to a similar procedure described for example 15A using powdered anhydrous potassium carbonate (134.1 mg, 0.97 mmol) as base, CuI (9.2 mg, 0.049 mmol) as catalyst, N,N'-dimethyl-1,2-ethylenediamine (5.2 μL, 0.049 mmol) as ligand, and anhydrous 1,4-dioxane (1.8 mL) as solvent. 4-(3,4-dichloro-benzenesulfonyl)-1-(3-trifluoromethyl-pyridin-2-yl)-piperazin-2-one was obtained in 10% yield (21 mg) as an off-white solid.

1H NMR (400 MHz, CHLOROFORM-D) δ ppm 3.38-3.47 (m, 1H) 3.57-3.65 (m, 1H) 3.68-3.76 (m, 1H) 3.82-3.89 (m, 1H) 3.98-4.08 (m, 2H) 7.46-7.53 (m, 1H) 7.64-7.72 (m, 2H) 7.93 (d, J=1.77 Hz, 1H) 8.09 (dd, J=7.96, 1.39 Hz, 1H) 8.75 (dd, J=4.80, 1.26 Hz, 1H); HRMS: calcd for $C_{16}H_{12}Cl_2F_3N_3O_3S+H+$, 454.00013. found (ESI-FTMS, $[M+H]^{1+}$), 454. HPLC Method 1: room temperature, 5.484 min, 100%, HPLC Method 2: room temperature, 6.418 min, 97.52%.

Example 16

Example 16A 1,1,1-trifluoro-2-[4-({(2R)-2-methyl-4-[2-(trifluoromethyl)phenyl]piperazin-1-yl}sulfonyl)phenyl]propan-2-ol Step 16A: A mixture of (R)-2-methyl-piperazine (300 mg, 2.99 mmol), 2-bromo benzotrifluoride (612 mg, 2.72 mmol), tris(dibenzylidineacetone)dipalladium (0) (24.72 mg, 0.027 mmol), rac-2,2'-bis(diphenylphosphino)-1,1'-binaphtyl (51.06 mg, 0.082 mmol) and sodium tert-butoxide (326.77 mg, 3.4 mmol) were charged to a microwave vial. Toluene (3.0 mL) was introduced under nitrogen atmosphere and the reaction mixture was irradiated at 110° C. for 30 minutes. Reaction was complete as determined by TLC. The reaction was repeated at (R)-2-methyl-piperazine (1.0 g, 9.98 mmol). Reaction mixtures were combined, diluted with dichloromethane, washed with water, saturated brine then dried over $Na_2SO_4$ and concentrated. The crude product was purified via flash column chromatography to yield (R)-3-methyl-1-(2-trifluoromethyl-phenyl)-piperazine as yellow oil (1.23 g, 39.6% yield). 1H NMR (400 MHz, CHLOROFORM-D) δ ppm 1.07 (d, J=6.32 Hz, 3H) 2.41-2.51 (m, 1H) 2.74-2.84 (m, 1H) 2.90-2.98 (m, 2H) 3.00-3.13 (m, 3H) 7.18-7.25 (m, 1H) 7.35 (d, J=8.08 Hz, 1H) 7.47-7.55 (m, 1H) 7.62 (d, J=7.83 Hz, 1H).

Step 16B: To a stirred solution of (R)-3-methyl-1-(2-trifluoromethyl-phenyl)-piperazine (500 mg, 2.05 mmol) and 4-acetylbenzenesulfonyl chloride (448.23 mg, 2.05 mmol) in anhydrous dichloromethane (6 mL) was added diisopropylethylamine (0.71 mL, 4.1 mmol). The mixture was stirred at room temperature for over night. Reaction was complete as determined by TLC. The reaction mixture was purified via flash column chromatography to yield (R)-1-{4-[2-methyl-4-(2-trifluoromethyl-phenyl)-piperazine-1-sulfonyl]-phenyl}-ethanone in 74.0% yield (646.7 mg) as a light yellow solid. 1H NMR (400 MHz, CHLOROFORM-D) δ ppm 1.20 (d, J=6.57 Hz, 3H) 2.67 (s, 3H) 2.75-2.83 (m, 2H) 2.98 (d, J=10.11 Hz, 1H) 3.06 (d, J=10.11 Hz, 1H) 3.33-3.43 (m, 1H) 3.76 (d, J=10.61 Hz, 1H) 4.26 (d, J=6.82 Hz, 1H) 7.23-7.30 (m, 2H) 7.52 (t, J=7.71 Hz, 1H) 7.62 (d, J=8.08 Hz, 1H) 7.89-7.99 (m, 2H) 8.07-8.14 (m, 2H).

Step 16C: To a 50 mL flask containing (R)-1-{4-[2-methyl-4-(2-trifluoromethyl-phenyl)-piperazine-1-sulfonyl]-phenyl}-ethanone (200 mg, 0.47 mmol) and 2.34 mL of 0.5 M TMS-$CF_3$, was added 0.47 mL of 1.0 M tetrabutylammonium fluoride in THF at 0° C. After stirring for 4 h, the solution was diluted with saturated $NaHCO_3$, extracted (2×$CH_2Cl_2$), washed with brine and dried over $Na_2SO_4$, and concentrated under reduced pressure. Purification by flash column chromatography to yield 1,1,1-trifluoro-2-[4-({(2R)-2-methyl-4-[2-(trifluoromethyl)phenyl]piperazin-1-yl}sulfonyl)phenyl]propan-2-ol in 31.8% yield (74.1 mg) as a colorless oil.

1H NMR (400 MHz, CHLOROFORM-D) δ ppm 1.19-1.29 (m, 3H) 1.84 (s, 3H) 2.56 (s, 1H) 2.72-2.82 (m, 2H) 2.92-2.98 (m, 1H) 3.03 (dd, J=11.12, 3.54 Hz, 1H) 3.32-3.45 (m, 1H) 3.74 (d, J=13.14 Hz, 1H) 4.26 (dd, J=6.44, 3.41 Hz, 1H) 7.21-7.30 (m, 2H) 7.48-7.55 (m, 1H) 7.59-7.65 (m, 1H) 7.77 (d, J=8.34 Hz, 2H) 7.85-7.92 (m, 2H). HPLC Method 1: room temperature, 6.486 min, 99.56%, HPLC Method 2: room temperature, 7.222 min, 98.64%.

Example 16B (2R)-1-[(2-chlorophenyl)sulfonyl]-2-methyl-4-[2-(trifluoromethyl)phenyl]piperazine The title compound was prepared according to a similar procedure for Example 16A, step 16B. Yield 86%.

1H NMR (400 MHz, CHLOROFORM-D) δ ppm 1.35 (d, J=6.82 Hz, 3H) 2.75-2.84 (m, 2H) 2.96 (dd, J=11.24, 2.91 Hz, 1H) 3.12 (dd, J=11.12, 3.54 Hz, 1H) 3.53-3.63 (m, 1H) 3.73 (d, J=13.14 Hz, 1H) 4.11-4.20 (m, 1H) 7.22-7.28 (m, 1H) 7.32 (d, J=7.83 Hz, 1H) 7.38-7.43 (m, 1H) 7.47-7.57 (m, 3H) 7.64 (dd, J=7.83, 1.26 Hz, 1H) 8.15 (dd, J=7.96, 1.64 Hz, 1

Example 16C (2R)-1-[(3,4-dichlorophenyl)sulfonyl]-2-methyl-4-[2-(trifluoromethyl)phenyl]piperazine

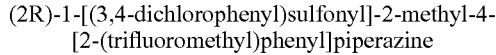

The title compound was prepared according to a similar procedure for Example 16A, step 16B. Yield 92.3%.

1H NMR (400 MHz, CHLOROFORM-D) δ ppm 1.20-1.29 (m, 3H) 2.74-2.86 (m, 2H) 2.93-3.12 (m, 2H) 3.32-3.43 (m, 1H) 3.71 (d, J=12.63 Hz, 1H) 4.18-4.27 (m, 1H) 7.23-7.32 (m, 3H) 7.53 (t, J=7.83 Hz, 1H) 7.59-7.70 (m, 3H) 7.94 (d, J=2.02 Hz, 1H). HPLC Method 1: room temperature, 7.363 min, 96.36%, HPLC Method 2: room temperature, 7.845 min, 96.64%.

Example 16D (2R)-1-[(4-chlorophenyl)sulfonyl]-2-methyl-4-[2-(trifluoromethyl)phenyl]piperazine

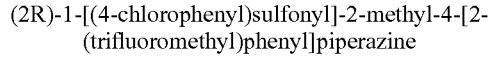

The title compound was prepared according to a similar procedure for Example 16A, step 16B. Yield 90.5%.

1H NMR (400 MHz, CHLOROFORM-D) δ ppm 1.21 (d, J=6.57 Hz, 3H) 2.74-2.83 (m, 2H) 2.97 (d, J=10.86 Hz, 1H) 3.06 (dd, J=11.12, 3.54 Hz, 1H) 3.31-3.41 (m, 1H) 3.71 (d, J=12.63 Hz, 1H) 4.17-4.27 (m, 1H) 7.22-7.31 (m, 2H) 7.46-7.56 (m, 3H) 7.63 (d, J=7.83 Hz, 1H) 7.75-7.83 (m, 2H). HPLC Method 1: room temperature, 7.044 min, 97.87%, HPLC Method 2: room temperature, 7.541 min, 98.11%.

Example 16E (2R)-1-[(5-chloro-2-thienyl)sulfonyl]-2-methyl-4-[2-(trifluoromethyl)phenyl]piperazine

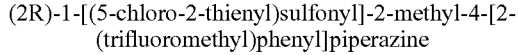

The title compound was prepared according to a similar procedure for Example 16A, step 16B. Yield 70.7%.

1H NMR (400 MHz, CHLOROFORM-D) δ ppm 1.30 (d, J=6.82 Hz, 3H) 2.76-2.87 (m, 2H) 2.96-3.03 (m, 1H) 3.09 (dd, J=11.12, 3.54 Hz, 1H) 3.35-3.48 (m, 1H) 3.70 (d, J=12.63 Hz, 1H) 4.24 (d, J=6.82 Hz, 1H) 6.95 (d, J=4.04 Hz, 1H) 7.24-7.34 (m, 2H) 7.38 (d, J=4.04 Hz, 1H) 7.54 (t, J=7.71 Hz, 1H) 7.61-7.68 (m, 1H). HPLC Method 1: room temperature, 7.162 min, 99.59%, HPLC Method 2: room temperature, 7.621 min, 99.80%.

Example 16F (2R)-1-[(5-chloro-3-methyl-1-benzothien-2-yl)sulfonyl]-2-methyl-4-[2-(trifluoromethyl)phenyl]piperazine

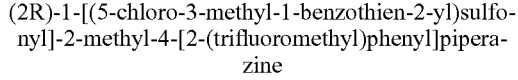

The title compound was prepared according to a similar procedure for Example 16A, step 16B. Yield 86.1%.

1H NMR (400 MHz, CHLOROFORM-D) δ ppm 1.33 (d, J=6.82 Hz, 3H) 2.69 (s, 3H) 2.78-2.89 (m, 2H) 2.94-3.04 (m, 1H) 3.12 (d, J=10.86 Hz, 1H) 3.45-3.57 (m, 1H) 3.82 (d, J=12.88 Hz, 1H) 4.31 (d, J=6.82 Hz, 1H) 7.22-7.31 (m, 2H) 7.46 (dd, J=8.59, 2.02 Hz, 1H) 7.49-7.54 (m, 1H) 7.62-7.66 (m, 1H) 7.77 (d, J=8.59 Hz, 1H) 7.80 (d, J=2.02 Hz, 1H). HPLC Method 1: room temperature, 7.710 min, 99.78%, HPLC Method 2: room temperature, 8.038 min, 99.77%.

Example 16G (2R)-1-[(5-chloro-2-naphthyl)sulfonyl]-2-methyl-4-[2-(trifluoromethyl)phenyl]piperazine

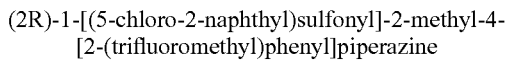

The title compound was prepared according to a similar procedure for Example 16A, step 16B. Yield 88.8%.

1H NMR (400 MHz, CHLOROFORM-D) δ ppm 1.22 (d, J=6.82 Hz, 3H) 2.76-2.84 (m, 2H) 2.98 (d, J=12.63 Hz, 1H) 3.05-3.11 (m, 1H) 3.38-3.47 (m, 1H) 3.78-3.84 (m, 1H) 4.30 (s, 1H) 7.21-7.30 (m, 2H) 7.47-7.57 (m, 2H) 7.62 (dd, J=7.83, 1.26 Hz, 1H) 7.74 (dd, J=7.58, 1.01 Hz, 1H) 7.88-7.96 (m, 2H) 8.41-8.46 (m, 2H). HPLC Method 1: room temperature, 7.566 min, 99.33%, HPLC Method 2: room temperature, 7.951 min, 99.11%.

Example 17

Scheme 17

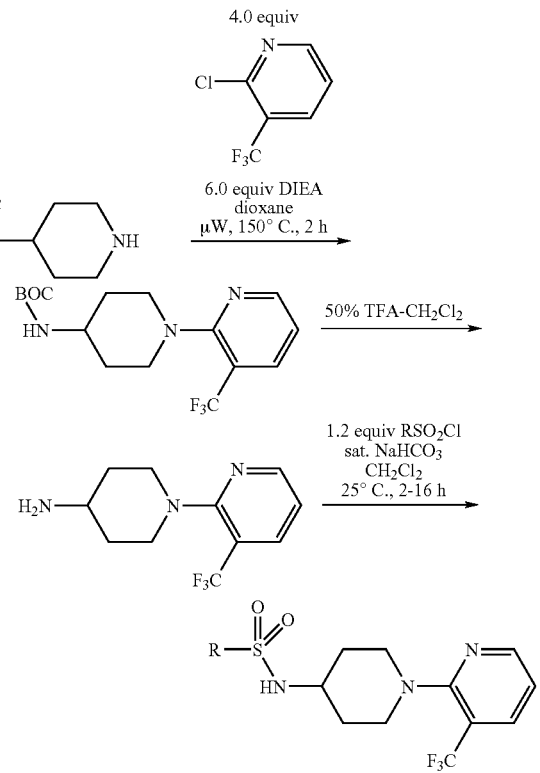

Example 17A 2-chloro-N-{1-[3-(trifluoromethyl)pyridin-2-yl]piperidin-4-yl}benzenesulfonamide

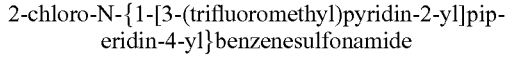

Step 17A: tert-Butyl {1-[3-(trifluoromethyl)pyridin-2-yl]piperidin-4-yl}carbamate. A mixture of 4-(tertbutoxycarbonylamino)piperidine (1.0 g, 5.0 mmol), 2-chloro-4-trifluoromethylpiperidine (3.6 g, 20.0 mmol), DIEA (6.0 mL, 30.0 mmol), and dioxane (2.0 mL) was heated in a microwave reactor at 150° C. for 2 h. the mixture was cooled, diluted with CH₂Cl₂ (50 mL), and poured in 1N HCl (100 mL). The aqueous phase was extracted with CH₂Cl₂ (2×100 mL). The combined organic extracts were washed with H₂O and brine, dried (MgSO₄), and concentrated. Purification by SiO₂ chromatography afforded the tert-butyl carbamate (1.39 g), a pale yellow oil, in 80% yield.

$^1$H NMR (400 MHz, CDCl₃) δ 1.46 (s, 9H), 1.48-1.68 (m, 2H), 2.04 (d, J=12.4 Hz, 2H), 2.80-3.10 (m, 2H), 3.54 (d, J=13.1 Hz, 2H), 3.65 (br s, 1H), 4.52 (br s, 1H), 6.98 (dd, J=7.7, 4.7 Hz, 1H), 7.85 (dd, J=7.7, 1.9 Hz, 1H), 8.42 (dd, J=4.8, 2.0 Hz, 1H).

Step 17B: 1-[3-(Trifluoromethyl)pyridin-2-yl]piperidin-4-amine. A solution of TFA (10 mL) and CH₂Cl₂ (10 mL) was added to a flask containing the tert-butyl carbamate from Step 17A (1.39 g, 4.0 mmol). After 1 h, the mixture was concentrated, diluted with CH₂Cl₂ (100 mL), washed with 1N NaOH (100 mL), H₂O (100 mL) and brine (100 mL), dried (MgSO₄), and concentrated to afford the amine (0.57 g, 57%), a pale yellow oil. 1H NMR (400 MHz, CDCl₃) δ 1.38-1.70 (m, 2H), 1.75-2.08 (m, 2H), 2.44 (br s, 2H), 2.71-3.21 (m, 3H), 3.59 (d, J=13.4 Hz, 2H), 6.76-7.13 (m, 1H), 7.85 (dd, J=7.7, 1.9 Hz, 1H), 8.41 (dd, J=4.8, 1.3 Hz, 1H).

Step 17C: 1-[3-(trifluoromethyl)pyridin-2-yl]piperidin-4-amine (100 mg, 0.42 mmol) was reacted with 2-chlorobenzenesulfonyl chloride (106 mg, 0.50 mmol) to afford the title compound (73 mg), a white solid, in 41% yield.

$^1$H NMR (400 MHz, CDCl₃) δ 1.46-1.72 (m, 2H), 1.76-1.93 (m, 2H), 2.70-3.07 (m, 2H), 3.27-3.39 (m, 1H), 3.40-3.61 (m, 2H), 5.04 (d, J=7.6 Hz, 1H), 6.99 (dd, J=7.5, 4.4 Hz, 1H), 7.37-7.49 (m, 1H), 7.49-7.64 (m, 2H), 7.84 (dd, J=7.7, 1.9 Hz, 1H), 8.14 (dd, J=7.6, 1.3 Hz, 1H), 8.40 (dd, J=4.8, 1.5 Hz, 1H). HRMS: calcd for $C_{17}H_{17}ClF_3N_3O_2S$+H+, 420.07548. found (ESI-FTMS, [M+H]$^{1+}$), 420.0756. HPLC Method 1: room temperature, 6.69 min, 97.0%. HPLC Method 2: room temperature, 6.18 min, 97.0%.

Example 17B 3-chloro-N-{1-[3-(trifluoromethyl)pyridin-2-yl]piperidin-4-yl}benzenesulfonamide Step 17C: Using the procedure from Example 17A, Step 17C, 1-[3-(trifluoromethyl)pyridin-2-yl]piperidin-4-amine (100 mg, 0.42 mmol) was reacted with 3-chlorobenzenesulfonyl chloride (106 mg, 0.50 mmol) to afford the title compound (71 mg), a white solid, in 40% yield.

$^1$H NMR (400 MHz, CDCl₃) δ 1.51-1.70 (m, 2H), 1.79-1.97 (m, 2H), 2.81-2.99 (m, 2H), 3.21-3.56 (m, 3H), 4.64 (d, J=7.8 Hz, 1H), 7.00 (dd, J=8.2, 5.2 Hz, 1H), 7.48 (t, J=8.1 Hz, 1H), 7.54-7.62 (m, 1H), 7.73-7.82 (m, 1H), 7.85 (dd, J=8.0, 1.6 Hz, 1H), 7.91 (t, J=1.8 Hz, 1H), 8.41 (dd, J=4.8, 1.3 Hz, 1H). HRMS: calcd for $C_{17}H_{17}ClF_3N_3O_2S$+H+, 420.07548. found (ESI-FTMS, [M+H]$^{1+}$), 420.0759. HPLC Method 1: room temperature, 6.18 min, 95.9%. HPLC Method 2: room temperature, 6.94 min, 96.2%.

Example 17C 4-chloro-N-{1-[3-(trifluoromethyl)pyridin-2-yl]piperidin-4-yl}benzenesulfonamide Using the procedure from Example 17A, the title compound (142 mg) was isolated as a white solid, in 81% yield.

$^1$H NMR (400 MHz, CDCl₃) δ 1.51-1.70 (m, 2H), 1.75-1.95 (m, 2H), 2.86-3.02 (m, 2H), 3.28-3.41 (m, 1H), 3.41-3.57 (m, 2H), 4.61 (d, J=7.8 Hz, 1H), 6.86-7.07 (m, 1H), 7.50 (d, J=8.8 Hz, 1H), 7.67 (d, J=8.8 Hz, 2H), 7.78 (d, J=8.8 Hz, 1H), 7.81-7.93 (m, 2H), 8.41 (dd, J=4.7, 1.4 Hz, 1H). HRMS: calcd for $C_{17}H_{17}ClF_3N_3O_2S$+H+, 420.07548. found (ESI-FTMS, [M+H]$^{1+}$), 420.0761. HPLC Method 1: room temperature, 6.26 min, 98.5%. HPLC Method 2: room temperature, 6.95 min, 98.5%.

Example 17D 4-bromo-N-{1-[3-(trifluoromethyl)pyridin-2-yl]piperidin-4-yl}benzenesulfonamide Step 17C: Using the procedure from Example 17A, the title compound (47 mg) was isolated as a white solid, in 24% yield.

$^1$H NMR (400 MHz, CDCl₃) δ 1.45-1.73 (m, 2H), 1.77-1.96 (m, 2H), 2.64-3.09 (m, 2H), 3.21-3.73 (m, 3H), 4.57 (d, J=7.8 Hz, 1H), 7.00 (dd, J=6.8, 4.8 Hz, 1H), 7.67 (d, J=8.8 Hz, 2H), 7.78 (d, J=8.8 Hz, 2H), 7.85 (dd, J=8.0, 1.9 Hz, 1H), 8.41 (dd, J=4.8, 1.3 Hz, 1H). HRMS: calcd for $C_{17}H_{17}BrF_3N_3O_2S$+H+, 464.02497. found (ESI-FTMS, [M+H]$^{1+}$), 464.0258. HPLC Method 1: room temperature, 6.26 min, 95.4%. HPLC Method 2: room temperature, 7.02 min, 95.1%.

Example 17E 3-fluoro-N-{1-[3-(trifluoromethyl)pyridin-2-yl]piperidin-4-yl}benzenesulfonamide Step 17C: Using the procedure from Example 17A, the title compound (73 mg) was isolated as a white solid, in 43% yield.

$^1$H NMR (400 MHz, CDCl₃) δ 1.48-1.71 (m, 2H), 1.82-1.99 (m, 2H), 2.69-3.09 (m, 2H), 3.20-3.59 (m, 3H), 4.63 (d, J=7.8 Hz, 1H), 7.00 (dd, J=7.8, 4.8 Hz, 1H), 7.27-7.39 (m, 1H), 7.42-7.59 (m, 1H), 7.57-7.67 (m, 1H), 7.67-7.79 (m, 1H), 7.85 (dd, J=7.8, 1.8 Hz, 1H), 8.41 (dd, J=4.8, 1.3 Hz, 1H). HRMS: calcd for $C_{17}H_{17}F_4N_3O_2S$+H+, 404.10503. found (ESI-FTMS, [M+H]$^{1+}$), 404.1056. HPLC Method 1: room temperature, 5.90 min, 97.8%. HPLC Method 2: room temperature, 6.67 min, 97.7%.

Example 17F 4-bromo-3-fluoro-N-{1-[3-(trifluoromethyl)pyridin-2-yl]piperidin-4-yl}benzenesulfonamide Step 17C: Using the procedure from Example 17A, the title compound (137 mg) was isolated as a white solid, in 68% yield.

$^1$H NMR (400 MHz, CDCl₃) δ 1.49-1.70 (m, 2H), 1.90 (dd, J=12.5, 3.9 Hz, 2H), 2.82-3.05 (m, 2H), 3.18-3.56 (m, 3H), 4.57 (d, J=8.1 Hz, 1H), 7.01 (dd, J=7.3, 5.1 Hz, 1H), 7.58 (dd, J=8.3, 1.5 Hz, 1H), 7.66 (dd, J=7.8, 2.0 Hz, 1H), 7.74 (dd, J=8.3, 6.6 Hz, 1H), 7.85 (dd, J=7.8, 1.8 Hz, 1H), 8.41 (dd, J=4.7, 1.4 Hz, 1H). HRMS: calcd for $C_{17}H_{16}BrF_4N_3O_2S$+H+, 482.01555. found (ESI-FTMS, [M+H]$^{1+}$), 482.0164. HPLC Method 1: room temperature, 6.35 min, 98.0%. HPLC Method 2: room temperature, 7.14 min, 97.6%.

Example 17G 3,4-dichloro-N-{1-[3-(trifluoromethyl)pyridin-2-yl]piperidin-4-yl}benzenesulfonamide Step 17C: Using the procedure from Example 17A, the title compound (95 mg) was isolated as a white solid, in 50% yield.

¹H NMR (400 MHz, CDCl₃) δ 1.50-1.70 (m, 2H), 1.82-1.99 (m, 2H), 2.82-3.10 (m, 2H), 3.19-3.57 (m, 3H), 4.65 (d, J=7.8 Hz, 1H), 7.01 (dd, J=7.1, 4.8 Hz, 1H), 7.61 (d, J=8.3 Hz, 1H), 7.73 (dd, J=8.3, 2.0 Hz, 1H), 7.85 (dd, J=7.8, 1.8 Hz, 1H), 8.00 (d, J=2.3 Hz, 1H), 8.41 (dd, J=4.8, 1.8 Hz, 1H). HRMS: calcd for $C_{17}H_{16}Cl_2F_3N_3O_2S+H+$, 454.03651. found (ESI-FTMS, $[M+H]^{1+}$), 454.0372. HPLC Method 1: room temperature, 6.55 min, 96.6%. HPLC Method 2: room temperature, 7.32 min, 96.8%.

Example 17H

N-{1-[3-(trifluoromethyl)pyridin-2-yl]piperidin-4-yl}naphthalene-2-sulfonamide

Step 17C: Using the procedure from Example 17A, the title compound (114 mg) was isolated as a white solid, in 62% yield.

¹H NMR (400 MHz, CDCl₃) δ 1.59 (dd, 3H), 1.79-1.96 (m, 2H), 2.76-2.99 (m, 2H), 3.26-3.62 (m, 3H), 4.58 (d, J=8.1 Hz, 1H), 6.98 (dd, J=8.1, 5.1 Hz, 1H), 7.59-7.71 (m, 2H), 7.82 (dd, J=7.8, 2.0 Hz, 1H), 7.87 (dd, J=8.7, 1.9 Hz, 1H), 7.90-7.96 (m, 1H), 7.99 (d, J=8.8 Hz, 2H), 8.38 (dd, J=4.8, 1.8 Hz, 1H), 8.49 (d, J=1.3 Hz, 1H). HRMS: calcd for $C_{21}H_{20}F_3N_3O_2S+H+$, 436.13011. found (ESI-FTMS, $[M+H]^{1+}$), 436.1303. HPLC Method 1: room temperature, 6.30 min, 95.0%. HPLC Method 2: room temperature, 7.04 min, 95.5%.

Example 17I 4-tert-butyl-N-{1-[3-(trifluoromethyl)pyridin-2-yl]piperidin-4-yl}benzenesulfonamide Step 17C: Using the procedure from Example 17A, the title compound (107 mg) was isolated as a white solid, in 58% yield.

¹H NMR (400 MHz, CDCl₃) δ 1.35 (s, 9H), 1.55-1.67 (m, 2H), 1.89 (dd, J=12.5, 4.2 Hz, 2H), 2.82-2.97 (m, 2H), 3.26-3.41 (m, 1H), 3.41-3.57 (m, 2H), 4.41 (d, J=7.6 Hz, 1H), 6.91-7.03 (m, 1H), 7.52 (d, J=8.8 Hz, 2H), 7.73-7.90 (m, 3H), 8.40 (dd, J=4.8, 1.3 Hz, 1H). HRMS: calcd for $C_{21}H_{26}F_3N_3O_2S+H+$, 442.17706. found (ESI-FTMS, $[M+H]^{1+}$), 442.1773. HPLC Method 1: room temperature, 6.74 min, 88.8%. HPLC Method 2: room temperature, 7.34 min, 92.4%.

Example 18

Scheme 18
General Procedure for the preparation of amides via acid chlorides

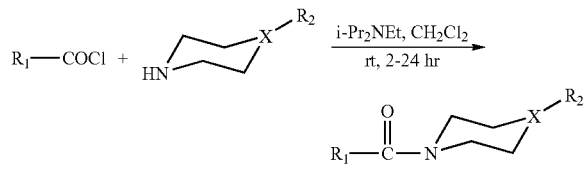

The piperazine or piperidine derivative (1.0 mmol) was mixed with 5 ml of CH₂Cl₂ and diisopropylethyl amine (2.4 mmol), aryl or alkyl acid chloride (1.2 mmol) or alkyl or aryl chloroformate (1.2 mmol) was added in one portion. The reaction mixture was stirred at room temperature and monitored by TLC (2-24 hrs). When the reaction was completed, the reaction mixture was loaded onto a silica gel column to remove high polar impurities. The product was isolated and purified by column chromatography. The following compounds were prepared using this general procedure.

Example 18A 1-(1-adamantylcarbonyl)-4-[3-(trifluoromethyl)pyridin-2-yl]piperazine The desired product was obtained in 90% yield as a oil. 1H NMR (400 MHz, CHLOROFORM-D) δ ppm 1.59-1.88 (m, 6H) 2.01-2.13 (m, 9H) 3.24-3.32 (m, 4H) 3.78-3.93 (m, 4H) 7.02-7.11 (m, 1H) 7.92 (dd, J=7.71, 1.89 Hz, 1H) 8.46 (dd, J=4.93, 1.89 Hz, 1H). HRMS: calcd for $C_{21}H_{26}F_3N_3O+H+$, 394.21007. found (ESI-FTMS, $[M+H]^{1+}$), 394.2097.

Example 18B 1-(cyclohexylcarbonyl)-4-[3-(trifluoromethyl)pyridin-2-yl]piperazine The desired product was obtained in 75% yield as a colorless oil. 1H NMR (400 MHz, CHLOROFORM-D) δ ppm 1.19-1.40 (m, 3H) 1.48-1.65 (m, J=11.87, 2.78 Hz, 2H) 1.64-1.94 (m, 5H) 2.46-2.57 (m, 1H) 3.19-3.37 (m, 4H) 3.60-3.83 (m, 4H) 7.02-7.12 (m, J=7.83, 4.80 Hz, 1H) 7.92 (dd, J=7.71, 1.89 Hz, 1H) 8.47 (dd, J=4.80, 1.26 Hz, 1H). HRMS: calcd for $C_{17}H_{22}F_3N_3O+H+$, 342.17877. found (ESI-FTMS, $[M+H]^{1+}$), 342.1784.

Example 18C

1-[(4-chlorophenyl)acetyl]-4-[3-(trifluoromethyl)pyridin-2-yl]piperazine

The desired product was obtained in 68% yield as a colorless oil. 1H NMR (400 MHz, CHLOROFORM-D) δ ppm 3.11-3.18 (m, 2H) 3.19-3.27 (m, 2H) 3.55-3.65 (m, 2H) 3.73 (s, 2H) 3.76-3.82 (m, 2H) 7.00-7.09 (m, J=7.83, 4.80 Hz, 1H) 7.17-7.23 (m, 2H) 7.28-7.33 (m, 2H) 7.85-7.93 (m, J=7.58, 1.77 Hz, 1H) 8.44 (dd, J=4.93, 1.39 Hz, 1H). HRMS: calcd for $C_{18}H_{17}ClF_3N_3O+H+$, 384.10850. found (ESI-FTMS, $[M+H]^{1+}$), 384.108.

Example 18D

Adamantan-1-yl-[4-(2,6-dichloro-phenoxy)-piperidin-1-yl]-methanone

The desired product was obtained in 85% yield as a colorless oil. mp 191-199, 1H NMR (400 MHz, CHLOROFORM-D) δ ppm 1.68-1.82 (m, 9H) 1.83-1.98 (m, 6H) 1.97-2.13 (m, 4H) 3.29-3.49 (m, 2H) 4.09-4.28 (m, 2H) 4.43-4.54 (m, 1H) 6.99 (t, 1H) 7.29-7.31 (m, 1H) 7.31-7.33 (m, 1H).

Example 18E

1-[(4-chlorophenyl)acetyl]-4-(2,6-dichlorophenoxy)piperidine

The desired product was obtained in 70% yield as a oil. 1H NMR (400 MHz, CHLOROFORM-D) δ ppm 1.68-1.83 (m, 2H) 1.86-2.00 (m, 2H) 3.22-3.39 (m, 1H) 3.42-3.56 (m, 1H) 3.73 (s, 2H) 3.77-3.91 (m, 1H) 4.01-4.14 (m, 1H) 4.36-4.49 (m, 1H) 6.98 (t, 1H) 7.18-7.23 (m, 2H) 7.27-7.34 (m, 4H).

HRMS: calcd for $C_{19}H_{18}Cl_3NO_2$+H+, 398.04759. found (ESI-FTMS, [M+H]$^{1+}$), 398.0492.

Example 18F 1-(cyclohexylcarbonyl)-4-(2,6-dichlorophenoxy)piperidine

The desired product was obtained in 85% yield as a colorless oil. 1H NMR (400 MHz, CHLOROFORM-D) δ ppm 1.16-1.40 (m, 3H) 1.42-1.64 (m, 2H) 1.62-1.87 (m, 5H) 1.87-2.09 (m, J=14.15, 14.15 Hz, 4H) 2.43-2.58 (m, 1H) 3.25-3.41 (m, 2H) 3.79-3.98 (m, J=13.39 Hz, 1H) 4.06-4.21 (m, 1H) 4.40-4.55 (m, 1H) 6.99 (t, 1H) 7.29-7.31 (m, 1H) 7.30-7.33 (m, 1H). HRMS: calcd for $C_{19}H_{23}Cl_2NO_2$+H+, 356.11786. found (ESI-FTMS, [M+H]$^{1+}$), 356.1197.

Example 18G tert-butyl 4-[(3,4-dichlorophenyl)sulfonyl]piperazine-1-carboxylate The desired product was obtained in 80% yield as a white solid. 1H NMR (400 MHz, CHLOROFORM-D) δ ppm 1.33-1.52 (m, 9H) 2.91-3.09 (m, 4H) 3.45-3.64 (m, 4H) 7.57 (dd, 1H) 7.63 (d, 1H) 7.84 (d, J=2.02 Hz, 1H).

Example 19

Scheme 19

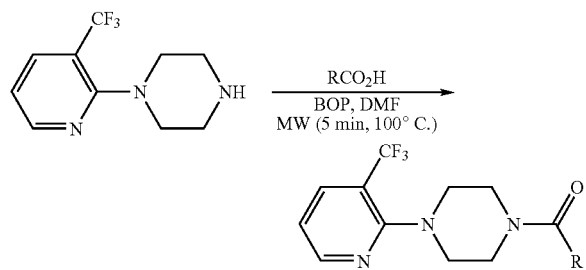

Example 19A

1-[(3-isopropyl-1-methylcyclopentyl)carbonyl]-4-[3-(trifluoromethyl)pyridin-2-yl]piperazine Step 19A: To a stirred solution of 3-isopropyl-1-methylcyclopentanecarboxylic acid (89 mg, 0.52 mmol) and 1-(3-(trifluoromethyl)pyridin-2-yl)piperazine (242 mg, 1.04 mmol) in N,N-dimethylformamide (1 mL) was added benzotriazole-1 yl-oxy-tris-(dimethylamino)-phosphonium hexafluorophosphate (700 mg, 1.56 mmol). The reaction was heated in a microwave at 150° C. for 5 minutes. The reaction mixture was purified with HPLC to yield 1-[(3-isopropyl-1-methylcyclopentyl)carbonyl]-4-[3-(trifluoromethyl)pyridin-2-yl]piperazine in 42% yield (83.3 mg) as off-white solid.

1H NMR (400 MHz, CHLOROFORM-d) δ ppm 0.90 (t, J=6.57 Hz, 6H) 1.12-1.45 (m, 5H) 1.47-1.69 (m, 3H) 1.76-1.90 (m, 2H) 2.20-2.43 (m, 1H) 3.12-3.35 (m, 4H) 3.59-3.87 (m, 4H) 7.06 (dd, J=7.83, 4.80 Hz, 1H) 7.90 (dd, J=7.83, 1.77 Hz, 1H) 8.46 (dd, J=4.67, 1.39 Hz, 1H). HRMS: calcd for $C_{20}H_{28}F_3N_3O$+H+, 384.22572. found (ESI-FTMS, [M+H]$^{1+}$), 384.2253. HPLC Method 1: room temperature, 7.177 min, 97.88%. HPLC Method 2: room temperature, 7.801 min, 99.06%.

Example 19B

1-[(2,2-dichloro-1-methylcyclopropyl)carbonyl]-4-[3-(trifluoromethyl)pyridin-2-yl]piperazine Step 19A: Coupling of 1-(3-(trifluoromethyl)pyridin-2-yl)piperazine (271 mg, 1.17 mmol) with 2,2-dichloro-1-methylcyclopropanecarboxylic acid (100 mg, 0.59 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-[(2,2-dichloro-1-methylcyclopropyl)carbonyl]-4-[3-(trifluoromethyl)pyridin-2-yl]piperazine was obtained in 56% yield (127 mg) as colorless oil.

1H NMR (400 MHz, CHLOROFORM-d) δ ppm 1.42 (d, J=7.58 Hz, 1H) 1.57 (s, 3H) 2.11 (d, J=7.58 Hz, 1H) 3.13-3.34 (m, 2H) 3.35-3.47 (m, 2H) 3.63-3.81 (m, 3H) 3.81-4.20 (m, 1H) 6.94-7.21 (m, 1H) 7.93 (dd, J=7.83, 1.77 Hz, 1H) 8.48 (dd, J=4.80, 1.26 Hz, 1H). HRMS: calcd for $C_{15}H_{16}Cl_2F_3N_3O$+H+, 382.06953. found (ESI-FTMS, [M+H]$^{1+}$), 382.069. HPLC Method 1: room temperature, 6.036 min, 100.00%. HPLC Method 2: room temperature, 7.073 min, 99.71%.

Example 19C 1-(cyclohexylacetyl)-4-[3-(trifluoromethyl)pyridin-2-yl]piperazine Step 19A: Coupling of 1-(3-(trifluoromethyl)pyridin-2-yl)piperazine (271 mg, 1.17 mmol) with 2-cyclohexylacetic acid (100 mg, 0.70 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-(cyclohexylacetyl)-4-[3-(trifluoromethyl)pyridin-2-yl]piperazine was obtained in 56% yield (140 mg) as colorless oil.

1H NMR (400 MHz, CHLOROFORM-d) δ ppm 0.90-1.37 (m, 5H) 1.59-1.89 (m, 6H) 2.27 (d, J=6.82 Hz, 2H) 3.15-3.36 (m, 4H) 3.56-3.71 (m, 2H) 3.70-3.86 (m, 2H) 7.07 (dd, J=7.33, 5.05 Hz, 1H) 7.90 (dd, J=7.71, 1.89 Hz, 1H) 8.46 (dd, J=4.80, 1.26 Hz, 1H). HRMS: calcd for $C_{18}H_{24}F_3N_3O$+H+, 356.19442. found (ESI-FTMS, [M+H]$^{1+}$), 356.1942. HPLC Method 1: room temperature, 6.253 min, 98.75%. HPLC Method 2: room temperature, 7.279 min, 97.47%.

Example 19D 1-(cyclopentylacetyl)-4-[3-(trifluoromethyl)pyridin-2-yl]piperazine Step 19A: Coupling of 1-(3-(trifluoromethyl)pyridin-2-yl)piperazine (271 mg, 1.17 mmol) with 2-cyclopentylacetic acid (100 mg, 0.78 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-(cyclopentylacetyl)-4-[3-(trifluoromethyl)pyridin-2-yl]piperazine was obtained in 43% yield (114 mg) as colorless oil.

1H NMR (400 MHz, CHLOROFORM-d) δ ppm 1.03-1.36 (m, 2H) 1.41-1.79 (m, 4H) 1.72-1.97 (m, 2H) 2.10-2.32 (m, 1H) 2.42 (d, J=7.33 Hz, 2H) 3.06-3.37 (m, 4H) 3.48-3.77 (m, 2H) 3.71-4.06 (m, 2H) 7.07 (dd, J=7.33, 4.80 Hz, 1H) 7.91 (dd, J=7.83, 1.77 Hz, 1H) 8.46 (dd, J=4.67, 1.39 Hz, 1H). HRMS: calcd for $C_{17}H_{22}F_3N_3O+H+$, 342.17877. found (ESI-FTMS, [M+H]$^{1+}$), 342.1784. HPLC Method 1: room temperature, 6.082 min, 100.00%. HPLC Method 2: room temperature, 7.121 min, 99.55%.

Example 19E

1-[(2,2,3,3-tetramethylcyclopropyl)carbonyl]-4-[3-(trifluoromethyl)pyridin-2-yl]piperazine Step 19A: Coupling of 1-(3-(trifluoromethyl)pyridin-2-yl)piperazine (271 mg, 1.17 mmol) with 2,2,3,3-tetramethylcyclopropanecarboxylic acid (100 mg, 0.70 mmol) was carried out according to a similar procedure described for example 1A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-[(2,2,3,3-tetramethylcyclopropyl)carbonyl]-4-[3-(trifluoromethyl)pyridin-2-yl]piperazine was obtained in 67% yield (166 mg) as colorless oil.

HRMS: calcd for $C_{18}H_{24}F_3N_3O+H+$, 356.19442. found (ESI-FTMS, [M+H]$^{1+}$), 356.1942. HPLC Method 1: room temperature, 6.399 min, 99.04%. HPLC Method 2: room temperature, 7.328 min, 98.59%.

Example 19F

1-[(4-methylcyclohexyl)acetyl]-4-[3-(trifluoromethyl)pyridin-2-yl]piperazine

Step 19A: Coupling of 1-(3-(trifluoromethyl)pyridin-2-yl)piperazine (271 mg, 1.17 mmol) with 2-(4-methylcyclohexyl)acetic acid (100 mg, 0.64 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-[(4-methylcyclohexyl)acetyl]-4-[3-(trifluoromethyl)pyridin-2-yl]piperazine was obtained in 43% yield (102 mg) as colorless oil.

1H NMR (400 MHz, CHLOROFORM-d) δ ppm 1.08 (s, 1H) 1.19 (d, J=2.27 Hz, 12H) 2.79-3.52 (m, 4H) 3.50-3.99 (m, 4H) 7.06 (dd, J=7.45, 5.18 Hz, 1H) 7.90 (dd, J=7.83, 1.77 Hz, 1H) 8.46 (dd, J=4.80, 1.52 Hz, 1H). HRMS: calcd for $C_{19}H_{26}F_3N_3O+H+$, 370.21007. found (ESI-FTMS, [M+H]$^{1+}$), 370.2097. HPLC Method 1: room temperature, 6.761 min, 100.00%. HPLC Method 2: room temperature, 7.578 min, 100.00%.

Example 19G 1-(bicyclo[2.2.1]hept-2-ylacetyl)-4-[3-(trifluoromethyl)pyridin-2-yl]piperazine Step 19A: Coupling of 1-(3-(trifluoromethyl)pyridin-2-yl)piperazine (271 mg, 1.17 mmol) with 2-(bicyclo[2.2.1]heptan-2-yl)acetic acid (100 mg, 0.65 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-(bicyclo[2.2.1]hept-2-ylacetyl)-4-[3-(trifluoromethyl)pyridin-2-yl]piperazine was obtained in 82% yield (195 mg) as colorless oil.

1H NMR (400 MHz, CHLOROFORM-d) δ ppm 0.56-0.83 (m, 1H) 0.98-1.67 (m, 6H) 1.75-1.98 (m, 1H) 2.07-2.61 (m, 5H) 3.10-3.38 (m, 4H) 3.56-3.69 (m, 2H) 3.70-3.84 (m, 2H) 7.06 (dd, J=7.83, 4.80 Hz, 1H) 7.90 (dd, J=7.71, 1.89 Hz, 1H) 8.46 (dd, J=4.80, 1.52 Hz, 1H). HRMS: calcd for $C_{19}H_{24}F_3N_3O+H+$, 368.19442. found (ESI-FTMS, [M+H]$^{1+}$), 368.1941. HPLC Method 1: room temperature, 6.489 min, 99.72%. HPLC Method 2: room temperature, 7.421 min, 99.63%.

Example 19H

1-[(3-methylcyclohexyl)carbonyl]-4-[3-(trifluoromethyl)pyridin-2-yl]piperazine

Step 19A: Coupling of 1-(3-(trifluoromethyl)pyridin-2-yl)piperazine (271 mg, 1.17 mmol) with 3-methylcyclohexanecarboxylic acid (100 mg, 0.70 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-[(3-methylcyclohexyl)carbonyl]-4-[3-(trifluoromethyl)pyridin-2-yl]piperazine was obtained in 45% yield (112 mg) as colorless oil.

1H NMR (400 MHz, CHLOROFORM-d) δ ppm 0.87-1.06 (m, 3H) 1.12-1.92 (m, 7H) 1.93-2.13 (m, 1H) 2.46-2.64 (m, 1H) 2.70-2.90 (m, 1H) 3.10-3.39 (m, 4H) 3.55-3.84 (m, 4H) 7.06 (dd, J=7.07, 4.80 Hz, 1H) 7.90 (dd, J=7.83, 1.77 Hz, 1H) 8.46 (dd, J=4.80, 1.26 Hz, 1H). HRMS: calcd for $C_{18}H_{24}F_3N_3O+H+$, 356.19442. found (ESI-FTMS, [M+H]$^{1+}$), 356.1942. HPLC Method 1: room temperature, 6.420 min, 98.80%. HPLC Method 2: room temperature, 7.354 min, 98.10%.

Example 19I

1-[(2-methylcyclohexyl)carbonyl]-4-[3-(trifluoromethyl)pyridin-2-yl]piperazine

Step 19A: Coupling of 1-(3-(trifluoromethyl)pyridin-2-yl)piperazine (271 mg, 1.17 mmol) with 2-methylcyclohexanecarboxylic acid (100 mg, 0.70 mmol) was carried out according to a similar procedure described for example 19A using N,N-dimethylformamide (1 mL) as solvent and benzotriazole-1 yl-oxy-tris-(dimethylamino)-phosphonium hexafluorophosphate (700 mg, 1.56 mmol) as coupling agent. 1-[(2-methylcyclohexyl)carbonyl]-4-[3-(trifluoromethyl)pyridin-2-yl]piperazine was obtained in 45% yield (112 mg) as colorless oil.

1H NMR (400 MHz, CHLOROFORM-d) δ ppm 0.95 (d, J=7.07 Hz, 3H) 1.13-2.17 (m, 9H) 2.65-2.83 (m, 1H) 3.06-3.41 (m, 4H) 3.51-3.74 (m, 3H) 3.80-3.98 (m, 1H) 7.06 (dd, J=7.83, 4.80 Hz, 1H) 7.90 (dd, J=7.58, 1.77 Hz, 1H) 8.46 (dd, J=4.80, 1.26 Hz, 1H). HRMS: calcd for $C_{18}H_{24}F_3N_3O+H+$, 356.19442. found (ESI-FTMS, [M+H]$^{1+}$), 356.1942. HPLC Method 1: room temperature, 6.388 min, 99.03%. HPLC Method 2: room temperature, 7.333 min, 99.27%.

Example 20

Scheme 20

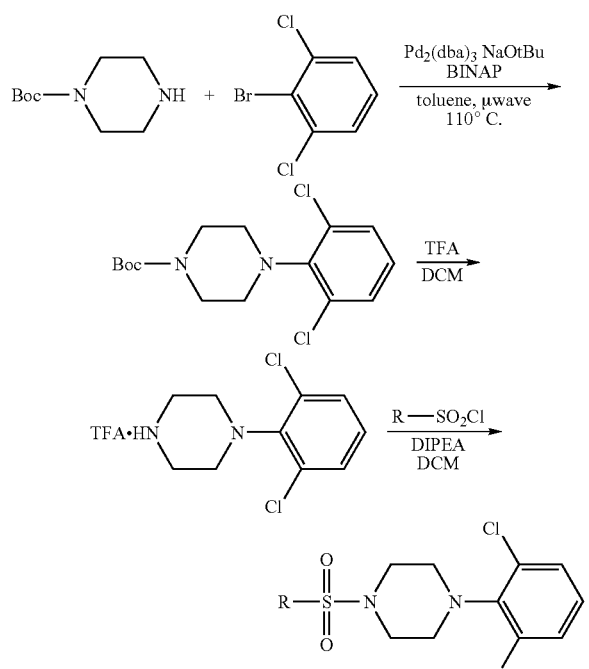

Example 20A

1-[(2-chlorophenyl)sulfonyl]-4-(2,6-dichlorophenyl) piperazine

Step 20A: 2,6-dichlorobromobenzene (2.26 g, 10 mmole), N-Boc-piperazine (2.05 g, 11 mmole), $Pd_2(dba)_3$ (92 mg, 1 mol %), BINAP (187 mg, 3 mol %), and sodium tert-butoxide (1.15 g, 12 mmole) were charged in a microwave vessel. The vessel was capped, purged with nitrogen, and 20 mL toluene added. The reaction mixture was heated to 110° C. for 30 minutes in the microwave and then the mixture was filtered through celite, rinsing with EtOAc. The filtrate was evaporated and then filtered through a pad of silica gel, eluting with dichloromethane. Evaporation gave crude 4-(2,6-Dichloro-phenyl)-piperazine-1-carboxylic acid tert-butyl ester as an orange oil that was taken on to the next step without further purification.

Step 20B: 4-(2,6-Dichloro-phenyl)-piperazine-1-carboxylic acid tert-butyl ester (crude material from Step 20A) was dissolved in 50 mL dichloromethane and TFA (25 mL) was added and the mixture stirred at room temperature for 1 hour. The solvent was evaporated, then co-evaporated 3 times with dichloromethane. Obtain 1-(2,6-Dichloro-phenyl)-piperazine, trifluoroacetic acid salt, as a yellow crystalline solid. ESI-MS: m/e=231 [M+H]+.

Step 20C: 1-(2,6-Dichloro-phenyl)-piperazine, trifluoroacetic acid salt (207 mg, 0.6 mmole) and DIPEA (0.32 mL, 1.8 mmole) were dissolved in 2.5 mL dichloromethane and 2-chlorophenylsulfonyl chloride (152 mg, 0.72 mmole) was added and stirred at room temperature for 1 hour. The reaction mixture was partitioned between water and dichloromethane and the organic layer dried over $Na_2SO_4$ and evaporated. The crude product was purified by flash chromatography using a gradient of 2% EtOAc/Hex to 10% EtOAc/Hex. Obtain the title compound in 37% yield as a white crystalline solid.

1H NMR (400 MHz, CHLOROFORM-D) δ ppm 3.23-3.29 (m, 4H) 3.41-3.48 (m, 4H) 7.00 (t, J=8.08 Hz, 1H) 7.23-7.28 (m, 1H) 7.38-7.45 (m, 2H) 7.48-7.59 (m, 2H) 8.09 (dd, J=7.96, 1.64 Hz, 1H). HRMS: calcd for $C_{16}H_{15}Cl_3N_2O_2S+H+$, 404.99925. found (ESI-FTMS, [M+H]$^{1+}$), 404.9992. HPLC Method 1: room temperature, 7.013 min, 98.61%, HPLC Method 2: room temperature, 7.531 min, 98.77%.

Example 20B

1-[(4-chlorophenyl)sulfonyl]-4-(2,6-dichlorophenyl) piperazine

The title compound was obtained in 42% yield as a white crystalline solid according to a similar procedure described for example 20A.

1H NMR (400 MHz, CHLOROFORM-D) δ ppm 3.15-3.21 (m, 4H) 3.28-3.33 (m, 4H) 6.97-7.03 (m, 1H) 7.23-7.28 (m, 4H) 7.53-7.57 (m, 1H) 7.72-7.77 (m, 1H). HRMS: calcd for $C_{16}H_{15}Cl_3N_2O_2S+H+$, 404.99925. found (ESI-FTMS, [M+H]$^{1+}$), 404.9991. HPLC Method 1: room temperature, 7.104 min, 100.00%, HPLC Method 2: room temperature, 7.624 min, 100.00%.

Example 20C 1-(2,6-dichlorophenyl)-4-[(3,4-dichlorophenyl)sulfonyl]piperazine The title compound was obtained in 40% yield as a white crystalline solid according to a similar procedure described for example 20A.

1H NMR (400 MHz, CHLOROFORM-D) δ ppm 3.17-3.22 (m, 4H) 3.28-3.33 (m, 4H) 7.01 (t, J=7.96 Hz, 1H) 7.22-7.28 (m, 2H) 7.60-7.67 (m, 2H) 7.89 (d, J=1.77 Hz, 1H). HRMS: calcd for $C_{16}H_{14}Cl_4N_2O_2S+H+$, 438.96028. found (ESI-FTMS, [M+H]$^{1+}$), 438.96. HPLC Method 1: room temperature, 7.440 min, 100.00%, HPLC Method 2: room temperature, 7.935 min, 100.00%.

Example 21

Scheme 21

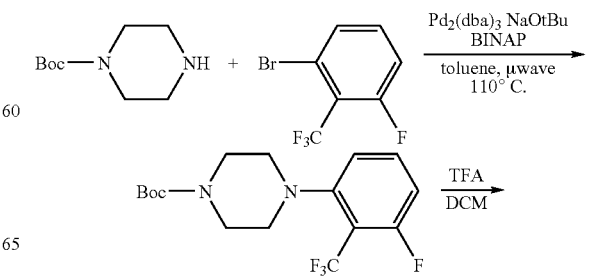

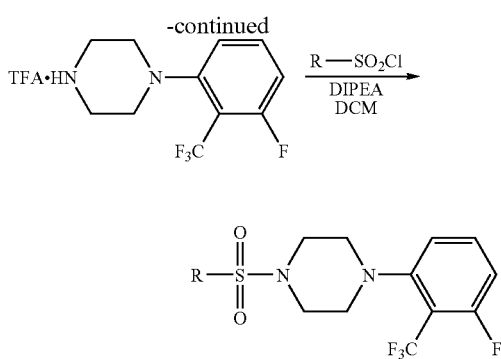

Example 21A

1-[(2-chlorophenyl)sulfonyl]-4-[3-fluoro-2-(trifluoromethyl)phenyl]piperazine Step 21A: 3-fluoro-2-(trifluoromethylbromobenzene (2.43 g, 10 mmole), N-Boc-piperazine (2.05 g, 11 mmole), $Pd_2(dba)_3$ (92 mg, 1 mol %), BINAP (187 mg, 3 mol %), and sodium tert-butoxide (1.15 g, 12 mmole) were charged in a microwave vessel. The vessel was capped, purged with nitrogen, and 20 mL toluene added. The reaction mixture was heated to 110° C. for 30 minutes in the microwave and then the mixture was filtered through celite, rinsing with EtOAc. The filtrate was evaporated and then filtered through a pad of silica gel, eluting with dichloromethane. Evaporation gave crude 4-(3-fluoro-2-(trifluoromethyl)-piperazine-1-carboxylic acid tert-butyl ester as a red oil that was taken on to the next step without further purification. ESI-MS: m/e=293 [M-tBu]$^+$.

Step 21B: 4-(3-fluoro-2-(trifluoromethyl)-piperazine-1-carboxylic acid tert-butyl ester (crude material from Step 21A) was dissolved in 50 mL dichloromethane and TFA (25 mL) was added and the mixture stirred at room temperature for 1 hour. The solvent was evaporated, then co-evaporated 3 times with dichloromethane. Obtain 1-(3-Fluoro-2-trifluoromethyl-phenyl)-piperazine, trifluoroacetic acid salt, as a low-melting red solid. ESI-MS: m/e=249 [M+H]$^+$.

Step 21C: 1-(3-Fluoro-2-trifluoromethyl-phenyl)-piperazine, trifluoroacetic acid salt (217 mg, 0.6 mmole) and DIPEA (0.32 mL, 1.8 mmole) were dissolved in 2.5 mL dichloromethane and 2-chlorophenylsulfonyl chloride (152 mg, 0.72 mmole) was added and stirred at room temperature overnight. The reaction mixture was partitioned between water and dichloromethane and the organic layer dried over $Na_2SO_4$ and evaporated. The crude product was purified by flash chromatography using a gradient of 5% EtOAc/Hex to 25% EtOAc/Hex. The title compound was obtained in 54% yield as a white solid.

1H NMR (400 MHz, CHLOROFORM-D) δ ppm 3.01 (t, J=4.80 Hz, 4H) 3.46 (br.s, 4H) 6.90-7.03 (m, 2H) 7.25-7.27 (m, 1H) 7.40-7.59 (m, 3H) 8.07 (dd, J=7.83, 1.77 Hz, 1H). HRMS: calcd for $C_{17}H_{15}ClF_4N_2O_2S+H+$, 423.05516. found (ESI-FTMS, [M+H]$^{1+}$), 423.0555. HPLC Method 1: room temperature, 6.625 min, 100.00%, HPLC Method 2: room temperature, 7.202 min, 100.00%.

Example 21B

1-[(4-chlorophenyl)sulfonyl]-4-[3-fluoro-2-(trifluoromethyl)phenyl]piperazine The title compound was obtained in 56% yield as a white solid according to a similar procedure described for example 21A.

1H NMR (400 MHz, CHLOROFORM-D) δ ppm 3.04 (t, J=4.42 Hz, 4H) 3.17 (br.s, 4H) 6.90-7.04 (m, 2H) 7.41-7.50 (m, 1H) 7.52-7.59 (m, 2H) 7.69-7.76 (m, 2H). HRMS: calcd for $C_{17}H_{15}ClF_4N_2O_2S+H+$, 423.05516. found (ESI-FTMS, [M+H]$^{1+}$), 423.0555. HPLC Method 1: room temperature, 6.786 min, 86.35%, HPLC Method 2: room temperature, 7.317 min, 82.80%.

Example 21C

1-[(3,4-dichlorophenyl)sulfonyl]-4-[3-fluoro-2-(trifluoromethyl)phenyl]piperazine The title compound was obtained in 52% yield as a white solid according to a similar procedure described for example 21A.

1H NMR (400 MHz, CHLOROFORM-D) δ ppm 3.05 (t, J=4.55 Hz, 4H) 3.20 (br.s, 4H) 6.92-7.03 (m, 1H) 7.25-7.27 (m, 1H) 7.42-7.50 (m, 1H) 7.58-7.63 (m, 1H) 7.64-7.68 (m, 1H) 7.88 (d, J=2.02 Hz, 1H). HRMS: calcd for $C_{17}H_{14}Cl_2F_4N_2O_2S+H+$, 457.01619. found (ESI-FTMS, [M+H]1+), 457.0166. HPLC Method 1: room temperature, 7.105 min, 100.00%, HPLC Method 2: room temperature, 7.635 min, 99.39%.

Example 21D

1-[(4-tert-butylphenyl)sulfonyl]-4-[3-fluoro-2-(trifluoromethyl)phenyl]piperazine The title compound was obtained in 30% yield as a white solid according to a similar procedure described for example 21A.

1H NMR (400 MHz, CHLOROFORM-D) δ ppm 1.38 (s, 9H) 3.03 (t, J=4.55 Hz, 4H) 3.20 (br.s, 4H) 6.93 (dd, J=10.86, 8.34 Hz, 1H) 6.98-7.03 (m, 1H) 7.41-7.49 (m, 1H) 7.55-7.60 (m, 2H) 7.68-7.73 (m, 2H). HRMS: calcd for $C_{21}H_{24}F_4N_2O_2S+H+$, 445.15674. found (ESI-FTMS, [M+H]$^{1+}$), 445.1571. HPLC Method 1: room temperature, 7.28 min, 99.04%, HPLC Method 2: room temperature, 7.66 min, 99.34%.

Example 21E

1-[3-fluoro-2-(trifluoromethyl)phenyl]-4-(2-naphthylsulfonyl)piperazine

The title compound was obtained in 62% yield as a white solid according to a similar procedure described for example 21A.

1H NMR (400 MHz, CHLOROFORM-D) δ ppm 3.04 (t, J=4.42 Hz, 4H) 3.23 (br.s, 4H) 6.88-6.96 (m, 1H) 7.00 (d, J=8.34 Hz, 1H) 7.39-7.49 (m, 1H) 7.60-7.73 (m, 2H) 7.75-7.81 (m, 1H) 7.92-8.06 (m, 3H) 8.37 (s, 1H). HRMS: calcd for $C_{21}H_{18}F_4N_2O_2S+H+$, 439.10979. found (ESI-FTMS,

Example 22

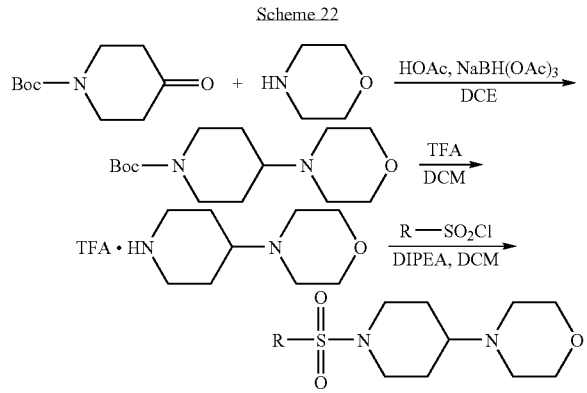

Representative Procedure

Step 22A: 4-Oxo-piperidine-1-carboxylic acid tert-butyl ester (2.99 g, 15 mmole), morpholine (1.4 mL, 15.8 mmole), acetic acid (11.0 mL, 18 mmole) were dissolved in 30 mL dichloroethane and sodium triacetoxyborohydride (6.36 g, 30 mmole) was added and the reaction mixture was stirred at room temperature for 2 hours. The mixture was diluted with dichloromethane and then washed with 2N NaOH, water, and dried (MgSO$_4$). Filtration and evaporation gave 3.84 g (95%) 4-morpholin-4-yl-piperidine-1-carboxylic acid tert-butyl ester as a colorless oil that solidified on standing.

Step 22B: 4-morpholin-4-yl-piperidine-1-carboxylic acid tert-butyl ester (3.85 g, 14.2) was dissolved in 25 mL dichloromethane and 20 mL trifluoroacetic acid was added and stirred at room temperature for 90 minutes. The reaction mixture was then evaporated then co-evaporated twice with dichloromethane. The semisolid residue was triturated with 75 mL ether, stirred at room temperature 1 hour, then filtered to give 5.03 g of 4-piperidin-4-yl-morpholine, bis-trifluoroacetic acid salt (89%) as a white solid.

Step 22C: 4-piperidin-4-yl-morpholine, bis-trifluoroacetic acid salt (299 mg, 0.75 mmole) and DIPEA (0.54 mL, 3 mmole) were dissolved in 2 mL dichloromethane and 2-chlorophenylsulfonyl chloride (189 mg, 0.9 mmole) was added and the reaction mixture stirred at room temperature overnight. The reaction was diluted with dichloromethane, washed with water and dried over Na$_2$SO$_4$. The organic layer was evaporated then dissolved in ~5 mL EtOAc then 2-3 mL 1M HCl/EtOAc was added and stirred at room temperature. The resulting solid was filtered to give 225 mg (75%) of 4-{1-[(2-chlorophenyl)sulfonyl]piperidin-4-yl}morpholine, hydrochloric acid salt as a white solid.

1H NMR (400 MHz, DMSO-D6) δ ppm 1.61-1.75 (m, 2H) 2.19 (d, J=11.87 Hz, 2H) 2.69-2.82 (m, 2H) 2.97-3.10 (m, 2H) 3.26-3.43 (m, 3H) 3.77-3.89 (m, 4H) 3.92-3.99 (m, 2H) 7.55-7.61 (m, 1H) 7.67-7.75 (m, 2H) 7.99 (dd, J=7.96, 1.39 Hz, 1H). HPLC Method 1: room temperature, 3.297 min, 100.00%, HPLC Method 2: room temperature, 2.869 min, 100.00%.

Example 22A

4-{1-[(3,4-dichlorophenyl)sulfonyl]piperidin-4-yl}morpholine

The title compound was obtained in 53% yield as a white solid according to a similar procedure described for example 22A.

1H NMR (400 MHz, DMSO-D6) δ ppm 1.66-1.80 (m, 2H) 2.16 (d, J=12.63 Hz, 2H) 2.29-2.39 (m, 2H) 2.96-3.08 (m, 2H) 3.15-3.24 (m, 1H) 3.29-3.39 (m, 2H) 3.73-3.85 (m, 4H) 3.96 (d, J=13.89 Hz, 2H) 7.74 (dd, J=8.34, 2.02 Hz, 1H) 7.95 (d, J=8.34 Hz, 1H) 8.00 (d, J=2.02 Hz, 1H). HPLC Method 1: room temperature, 4.046 min, 100.00%, HPLC Method 2: room temperature, 3.978 min, 100.00%.

Example 23

The following compounds can be prepared according to the following scheme.

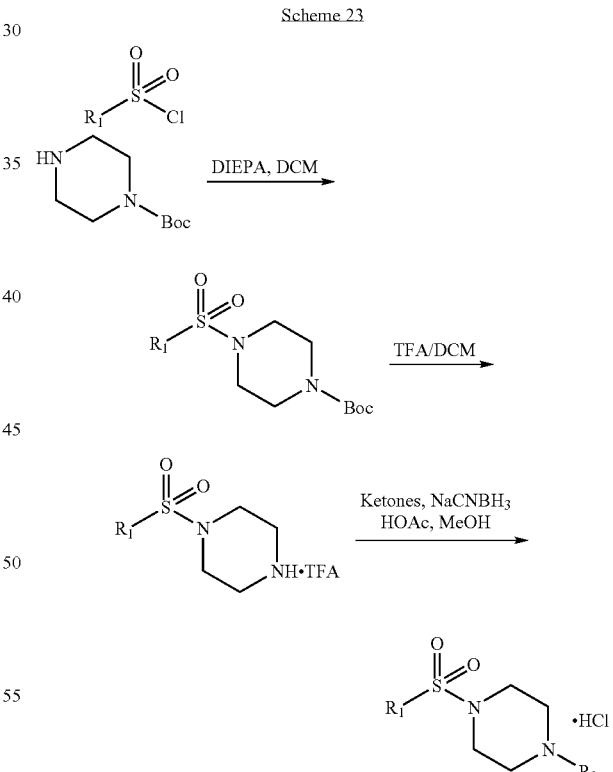

Example 23A 1-bicyclo[2.2.1]hept-2-yl-4-[(3,4-dichlorophenyl)sulfonyl]piperazine

ESI-MS, [M+H]$^{1+}$: 389.02.

Example 23B 1-bicyclo[2.2.1]hept-2-yl-4-[(5-chloro-3-methyl-1-benzothien-2-yl)sulfonyl]piperazine

ESI-MS, [M+H]$^{1+}$: 425.02.

Example 23C 1-(3,4-dichlorophenylsulfonyl)-4-(tetrahydro-2H-pyran-4-yl)piperazine

ESI-MS, [M+H]$^{1+}$: 378.97.

Example 24

The following compounds can be prepared according to the following scheme.

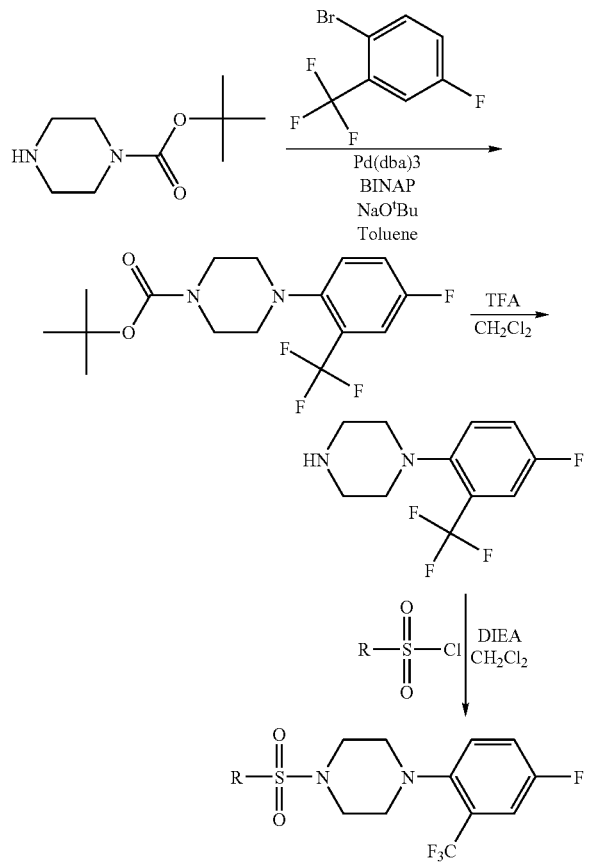

Scheme 24

Example 24A

4-[5-({4-[4-fluoro-2-(trifluoromethyl)phenyl]piperazin-1-yl}sulfonyl)pyridin-2-yl]morpholine Yield 41.5%. 1H NMR (400 MHz, CHLOROFORM-D) δ ppm 2.94-3.02 (m, 4H) 3.07-3.23 (m, 4H) 3.67-3.74 (m, 4H) 3.80-3.89 (m, 4H) 6.66 (d, J=9.09 Hz, 1H) 7.18-7.43 (m, 3H) 7.77 (dd, J=9.09, 2.53 Hz, 1H) 8.54 (d, J=2.53 Hz, 1H). HPLC Method 1: room temperature, 6.215 min, 99.73%, HPLC Method 2: room temperature, 7.042 min, 100%.

Example 24B

N-[4-({4-[4-fluoro-2-(trifluoromethyl)phenyl]piperazin-1-yl}sulfonyl)phenyl]pyrrolidine-1-carboxamide Yield 81.02%. 1H NMR (400 MHz, CHLOROFORM-D) δ ppm 1.93-2.12 (m, 4H) 2.95 (t, J=4.67 Hz, 4H) 3.14 (s, 4H) 3.51 (t, J=6.69 Hz, 4H) 6.44 (s, 1H) 7.17-7.42 (m, 3H) 7.60-7.75 (m, 4H). HPLC Method 1: room temperature, 6.059 min, 100%, HPLC Method 2: room temperature, 6.941 min, 100%.

Example 24C

N-[3-chloro-4-({4-[4-fluoro-2-(trifluoromethyl)phenyl]piperazin-1-yl}sulfonyl)phenyl]azepane-1-carboxamide Yield 90.72%. 1H NMR (400 MHz, CHLOROFORM-D) δ ppm 1.61-1.67 (m, 4H) 1.81 (s, 4H) 2.91 (t, J=4.67 Hz, 4H) 3.39 (s, 4H) 3.48-3.57 (m, 4H) 6.55 (s, 1H) 7.19-7.40 (m, 4H) 7.80 (d, J=2.27 Hz, 1H) 7.94 (d, J=8.84 Hz, 1H). HPLC Method 1: room temperature, 6.963 min, 99.43%, HPLC Method 2: room temperature, 7.575 min, 99.58%.

Example 24D 4-(5-{[4-(4-fluorophenyl)piperazin-1-yl]sulfonyl}pyridin-2-yl)morpholine Yield 39.3%. 1H NMR (400 MHz, CHLOROFORM-D) δ ppm 3.17 (s, 8H) 3.63-3.74 (m, 4H) 3.75-3.90 (m, 4H) 6.63 (d, J=9.09 Hz, 1H) 6.78-6.90 (m, 2H) 6.88-7.03 (m, 2H) 7.78 (dd, J=9.09, 2.53 Hz, 1H) 8.54 (d, J=1.77 Hz, 1H). HPLC Method 1: room temperature, 5.506 min, 100%, HPLC Method 2: room temperature, 6.343 min, 100%.

Example 24E

N-(4-{[4-(4-fluorophenyl)piperazin-1-yl]sulfonyl}phenyl)pyrrolidine-1-carboxamide Yield 73.1%. 1H NMR (400 MHz, CHLOROFORM-D) δ ppm 1.97-2.06 (m, 4H) 3.15 (s, 8H) 3.49 (t, J=6.57 Hz, 4H) 6.41 (s, 1H) 6.79-6.87 (m, 2H) 6.95 (dd, J=9.09, 8.08 Hz, 2H) 7.59-7.65 (m, 2H) 7.66-7.73 (m, 2H). HPLC Method 1: room temperature, 5.469 min, 100%, HPLC Method 2: room temperature, 6.325 min, 100%.

Example 24F

N-(3-chloro-4-{[4-(4-fluorophenyl)piperazin-1-yl]sulfonyl}phenyl)azepane-1-carboxamide Yield 60.8%. 1H NMR (400 MHz, CHLOROFORM-D) δ ppm 1.59-1.67 (m, 4H) 1.74-1.84 (m, 4H) 3.07-3.16 (m, 4H) 3.37-3.45 (m, 4H) 3.47-3.56 (m, 4H) 6.56 (s, 1H) 6.81-6.89 (m, 2H) 6.91-7.02 (m, 2H) 7.38 (dd, J=8.72, 2.15 Hz, 1H) 7.76 (d, J=2.27 Hz, 1H) 7.94 (d, J=8.59 Hz, 1H). HPLC Method 1: room temperature, 6.382 min, 98.96%, HPLC Method 2: room temperature, 7.144 min, 99.00%.

Example 25

The following compounds can be prepared according to the following scheme.

Scheme 25

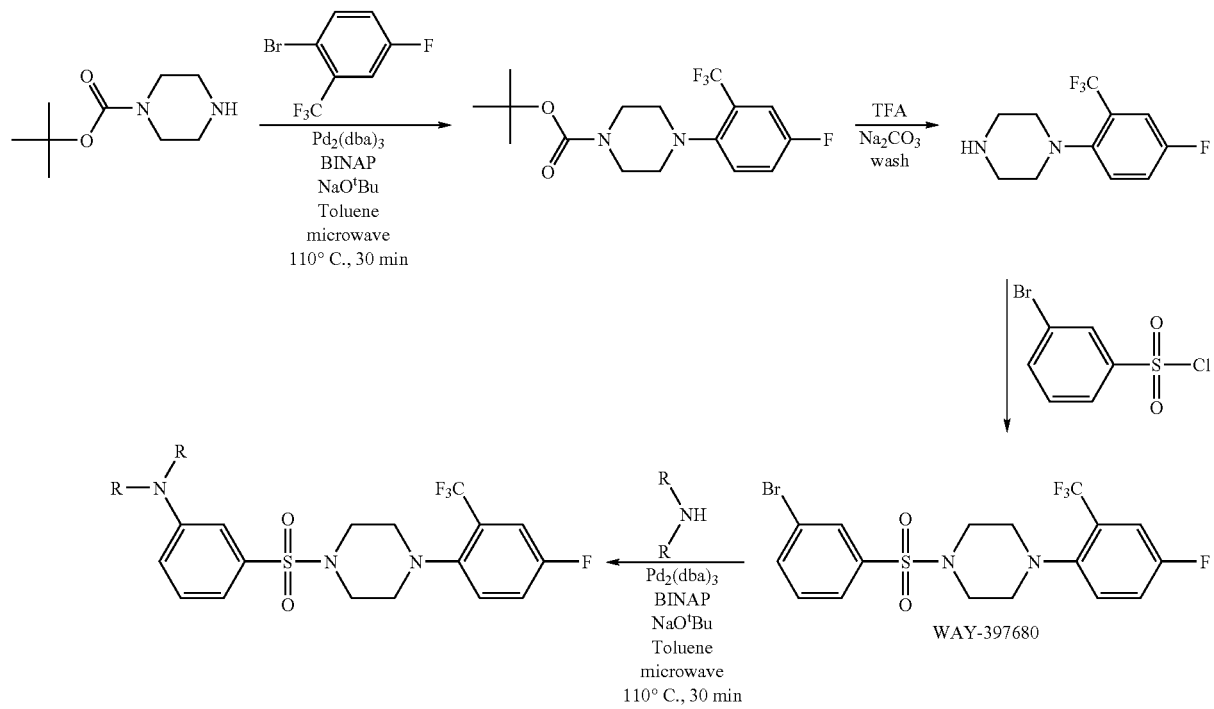

Example 25A

1-[4-fluoro-2-(trifluoromethyl)phenyl]-4-[(3-piperidin-1-ylphenyl)sulfonyl]piperazine 1H NMR (400 MHz, DMSO-D6) δ ppm 1.50-1.69 (m, 6H) 2.91 (d, J=4.29 Hz, 4H) 2.99 (s, 4H) 3.20-3.29 (m, 4H) 7.07 (d, J=8.08 Hz, 1H) 7.14 (s, 1H) 7.29 (d, J=8.34 Hz, 1H) 7.40-7.61 (m, 3H) 7.65-7.77 (m, 1H). HRMS: calcd for $C_{22}H_{25}F_4N_3O_2S+H+$, 472.16763. found (ESI-FTMS, $[M+H]^{1+}$), 472.1681. HPLC Method 1: room temperature, 7.301 min, 98.52%. HPLC Method 2: room temperature, 7.746 min, 98.54%.

Example 25B

4-[3-({4-[4-fluoro-2-(trifluoromethyl)phenyl]piperazin-1-yl}sulfonyl)phenyl]morpholine 1H NMR (400 MHz, DMSO-D6) δ ppm 2.91 (t, J=4.29 Hz, 4H) 3.00 (s, 4H) 3.16-3.26 (m, 4H) 3.70-3.81 (m, 4H) 7.10-7.21 (m, 2H) 7.26-7.36 (m, 1H) 7.44-7.61 (m, 3H) 7.73 (d, J=5.05 Hz, 1H). HRMS: calcd for $C_{21}H_{23}F_4N_3O_3S+H+$, 474.14690. found (ESI-FTMS, $[M+H]^{1+}$), 474.1464. HPLC Method 1: room temperature, 7.157 min, 98.07%. HPLC Method 2: room temperature, 6.452 min, 97.21%.

Example 25C

1-[4-fluoro-2-(trifluoromethyl)phenyl]-4-[(3-pyrrolidin-1 ylphenyl)sulfonyl]piperazine 1H NMR (400 MHz, CHLOROFORM-D) δ ppm 2.03-2.09 (m, 4H) 2.95 (t, J=4.80 Hz, 4H) 3.19 (s, 4H) 3.29-3.39 (m, 4H) 6.75 (dd, J=8.08, 2.27 Hz, 1H) 6.84-6.90 (m, 1H) 7.00 (d, J=8.59 Hz, 1H) 7.19-7.26 (m, 1H) 7.27-7.39 (m, 3H). HRMS: calcd for $C_{21}H_{23}F_4N_3O_2S+H+$, 458.15198. found (ESI-FTMS, $[M+H]^{1+}$), 458.1525. HPLC Method 1: room temperature, 7.221 min, 97.78%. HPLC Method 2: room temperature, 7.718 min, 97.61%.

Example 26

The following compounds can be prepared according to the following scheme.

Scheme 26

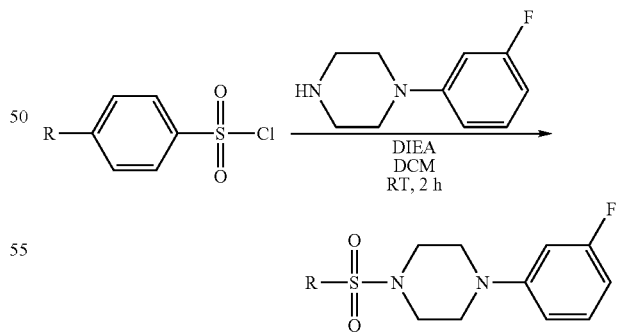

Example 26A

1-[(5-chloro-3-methyl-1-benzothien-2-yl)sulfonyl]-4-(3-fluorophenyl)piperazine

1H NMR (400 MHz, CHLOROFORM-D) δ ppm 2.71 (s, 3H) 3.24-3.31 (m, 4H) 3.37 (d, J=4.29 Hz, 4H) 6.48-6.67 (m, 3H) 7.12-7.23 (m, 1H) 7.47 (dd, J=8.59, 2.02 Hz, 1H) 7.76 (dd, J=8.59, 0.51 Hz, 1H) 7.82 (dd, J=2.02, 0.51 Hz, 1H). HRMS: calcd for $C_{19}H_{18}ClFN_2O_2S_2$+H+, 425.05550. found (ESI-FTMS, [M+H]$^{1+}$), 425.0557. HPLC Method 1: room temperature, 7.123 min, 99.58%. HPLC Method 2: room temperature, 7.698 min, 99.75%.

Example 26B

1-[(5-chloro-2-naphthyl)sulfonyl]-4-(3-fluorophenyl)piperazine

1H NMR (400 MHz, CHLOROFORM-D) δ ppm 3.25 (d, J=3.54 Hz, 8H) 6.45-6.66 (m, 3H) 7.07-7.22 (m, 1H) 7.49-7.60 (m, 1H) 7.76 (dd, J=7.45, 1.14 Hz, 1H) 7.82-7.98 (m, 2H) 8.38 (d, J=2.02 Hz, 1H) 8.44 (d, J=8.84 Hz, 1H). HRMS: calcd for $C_{20}H_{18}ClFN_2O_2S$+H+, 405.08343. found (ESI-FTMS, [M+H]$^{1+}$), 405.0838. HPLC Method 1: room temperature, 7.571 min, 99.44%. HPLC Method 2: room temperature, 6.963 min, 99.64%.

Example 27

The following compounds can be prepared according to the following scheme.

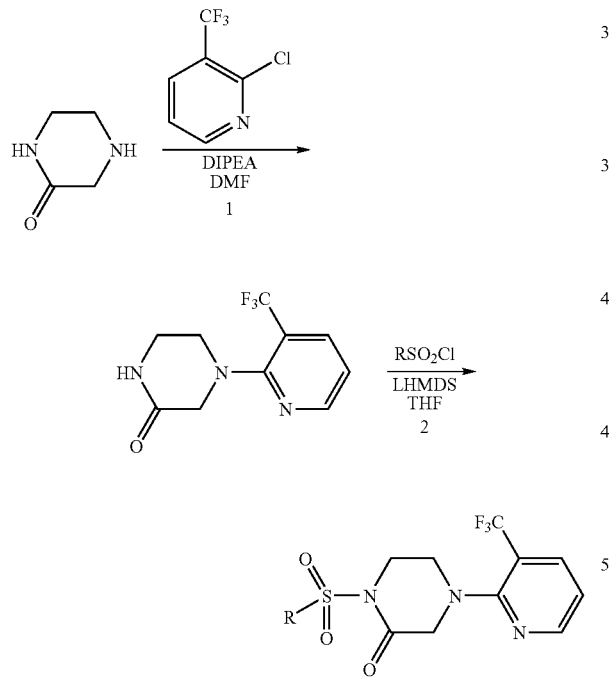

Example 27A

1-[(5-chloro-3-methyl-1-benzothien-2-yl)sulfonyl]-4-[3-(trifluoromethyl)pyridin-2-yl]piperazin-2-one Step 27A): To a solution of piperazin-2-one (1.0 g, 10.0 mmol) in DMF (1.0 mL) was added 2-chloro-3-trifluoromethyl pyridine (2.0 g, 11.0 mmol) and DIPEA (2.0 mL, 12.0 mmol). The reaction mixture was heated to 150° C. under microwave conditions for one hour, after which maximum attainable conversion to desired product was judged complete by LCMS. The crude reaction mixture was quenched with $H_2O$ (5 mL), resulting in precipitation of the desired product, in >75% purity. The crude solid was then dissolved in ethyl acetate (25 mL) and washed with brine (2×10 mL). The organic layer was dried over $Na_2SO_4$, decanted, and concentrated in vacuo, and the resultant crude oil was purified via normal phase $SiO_2$ column chromatography using a 50%-100% ethyl acetate/hexanes solvent gradient. The desired product was isolated in >99% purity, 30% yield (720 mg).

1H NMR (400 MHz, DMSO-D6) δ ppm 3.21-3.28 (m, 2H) 3.39-3.46 (m, 2H) 3.76 (s, 2H) 7.23 (dd, J=7.58, 5.05 Hz, 1H) 7.96 (s, 1H) 8.11 (dd, J=7.83, 1.77 Hz, 1H) 8.54 (dd, J=4.80, 1.52 Hz, 1H); LCMS: calcd for $C_{10}H_{10}F_3N_3O$+H+, 246.08. found ([M+H]$^{1+}$), 246.19. HPLC Method 1: room temperature, 4.16 min, 89.3%. HPLC Method 2: room temperature, 4.1214 min, 95.92%.

Step 27B: A solution of 4-(3-(trifluoromethyl)pyridin-2-yl)piperazin-2-one (150 mg, 0.61 mmol) in anhydrous THF (2.0 mL) was cooled to −78° C., followed by drop-wise addition of LHMDS (0.92 mL, 0.92 mmol (1.0 Min THF)). The reaction was allowed to stir five minutes after which a solution of 5-chloro-3-methyl-2-benzothiophene sulfonyl chloride in anhydrous THF (221 mg, 0.79 mmol in 1 mL) was added drop-wise. The reaction mixture was allowed to stir at −78° C. for approximately two hours, after which it was judged complete by TLC. The reaction was quenched with excess $H_2O$ (10 mL), extracted into ethyl acetate (3×10 mL), and finally washed with aqueous $NaHCO_3$ (2×10 mL). The organic layers were combined and dried over $Na_2SO_4$, decanted, and concentrated in vacuo. The resultant crude oil was purified via normal phase $SiO_2$ column chromatography using a 5%-20% EA/Hex solvent gradient. The desired product, was isolated in >95% purity, 3.5% yield (10 mg).

1H NMR (400 MHz, CHLOROFORM-D) δ ppm 2.77 (s, 3H) 3.62-3.68 (m, 2H) 3.99 (s, 2H) 4.02-4.08 (m, 2H) 7.12 (dd, J=7.96, 4.93 Hz, 1H) 7.49 (d, J=8.72, 1.89 Hz, 1H) 7.85 (d, J=1.77 Hz, 1H) 7.94 (dd, J=7.96, 1.64 Hz, 1H) 8.33 (dd, J=4.80, 1.26 Hz, 1H); LCMS: calcd for $C_{198}H_{15}ClF_3N_3O_3S_2$+H+, 490.02. found ([M+H]$^{1+}$), 490.05. HPLC Method 1: room temperature, 6.771 min, 97.56%. HPLC Method 2: room temperature, 3.375 min, 97.92%.

Example 27B 3-(2-(naphthalen-2-yl)ethylsulfonyl)-1-(3-(trifluoromethyl)pyridin-2-yl)imidazolidin-4-one Step 27A: Prepared according to the procedure for example 27A, affording 50 mg of the desired sulfonamide in >95% purity (21% yield).

1H NMR (400 MHz, CHLOROFORM-D) δ ppm 3.49-3.54 (m, 2H) 3.57-3.64 (m, 2H) 3.73-3.78 (m, 2H) 3.99 (s, 2H) 4.04-4.09 (m, 2H) 7.10 (dd, J=7.83, 4.80 Hz, 1H) 7.39-7.44 (m, 2H) 7.49-7.55 (m, 1H) 7.55-7.62 (m, 1H) 7.79 (dd, J=6.82, 2.78 Hz, 1H) 7.88 (dd, J=8.08, 0.76 Hz, 1H) 7.94 (dd, J=7.71, 1.89 Hz, 1H) 8.04 (d, J=8.59 Hz, 1H) 8.37 (dd, J=4.80, 1.77 Hz, 1H); LCMS: calcd for $C_{21}H_{18}F_3N_3O_3S$+H+, 450.10. found ([M+H]$^{1+}$), 450.23. HPLC Method 1: room temperature, 6.448 min, 98.49%. HPLC Method 2: room temperature, 7.151 min, 99.25%.

Example 28

The following compounds can be prepared according to the following scheme.

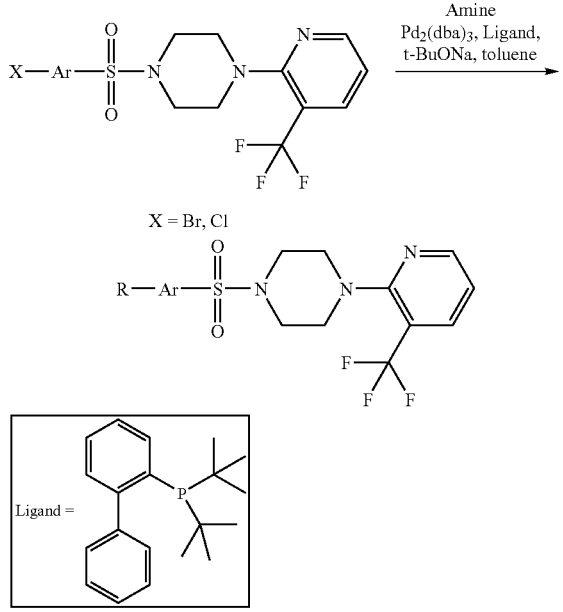

Scheme 28

Example 28A

4-{3-Methyl-2-[4-(3-trifluoromethyl-pyridin-2-yl)-piperazine-1-sulfonyl]-benzo[b]thiophen-5-yl}-morpholine Step 28A: 1-(5-chloro-3-methyl-benzo[b]thiophene-2-sulfonyl)-4-(3-trifluoromethyl-pyridin-2-yl)-piperazine (142.5 mg, 0.3 mmol), Pd$_2$(dba)$_3$ (13.7 mg, 0.015 mmol), t-BuONa (82.7 mg, 0.84 mmol) and the ligand (9 mg, 0.03 mmol) were mixed in a sealed tube which was flushed with N$_2$. To this was added tolene (2 mL) and then morpholine (21 µL, 0.24 mmol). The resultant mixture was heated at 80° C. for 4 hours. The solvent was removed under vacuum and the crude product was purified with flash column chromatography to yield 4-{3-Methyl-2-[4-(3-trifluoromethyl-pyridin-2-yl)-piperazine-1-sulfonyl]-benzo[b]thiophen-5-yl}-morpholine in 52% yield (82 mg) as white solid. HRMS: calcd for C$_{23}$H$_{25}$F$_3$N$_4$O$_3$S$_2$+H+, 527.13929. found (ESI-FTMS, [M+H]$^{1+}$), 527.1392.

Example 28B 1-(3-Methyl-5-piperazin-1-yl-benzo[b]thiophene-2-sulfonyl)-4-(3-trifluoromethyl-pyridin-2-yl)-piperazine Step 28A: 1-(5-chloro-3-methyl-benzo[b]thiophene-2-sulfonyl)-4-(3-trifluoromethyl-pyridin-2-yl)-piperazine (142.5 mg, 0.3 mmol), Pd$_2$(dba)$_3$ (13.7 mg, 0.015 mmol), t-BuONa (82.7 mg, 0.84 mmol) and the ligand (9 mg, 0.03 mmol) were mixed in a sealed tube which was flushed with N$_2$. To this was added tolene (2 mL) and then 1-BOC-piperazine (67.1 mg, 0.36 mmol). The resultant mixture was heated at 80° C. for 3 hours. The solvent was removed under vacuum and the crude product was purified with flash column chromatography to yield 4-{3-methyl-2-[4-(3-trifluoromethyl-pyridin-2-yl)-piperazine-1-sulfonyl]-benzo[b]thiophen-5-yl}-piperazine-1-carboxylic acid tert-butyl ester 68% yield (128 mg) as white solid.

Step 28B: To a solution of 4-{3-methyl-2-[4-(3-trifluoromethyl-pyridin-2-yl)-piperazine-1-sulfonyl]-benzo[b]thiophen-5-yl}-piperazine-1-carboxylic acid tert-butyl ester (95 mg, 0.18 mmol) in DCM (4 mL) was added TFA (1 mL). The resultant mixture was stirred at ambient temperature for 3 hours. The solvent was removed under vacuum. The crude product was triturated with ether then water to give 1-(3-Methyl-5-piperazin-1-yl-benzo[b]thiophene-2-sulfonyl)-4-(3-trifluoromethyl-pyridin-2-yl)-piperazine as a light yellow solid (51 mg, 66%).

Example 28C 1-(4-Piperidin-1-yl-benzenesulfonyl)-4-(3-trifluoromethyl-pyridin-2-yl)-piperazine Step 28A: 4-bromobenzenesulfonyl)-4-(3-trifluoromethyl-pyridin-2-yl)-piperazine (135.5 mg, 0.3 mmol), Pd$_2$(dba)$_3$ (13.7 mg, 0.015 mmol), t-BuONa (82.7 mg, 0.84 mmol) and the ligand (9 mg, 0.03 mmol) were mixed in a sealed tube which was flushed with N$_2$. To this was added tolene (2 mL) and then piperidine (35 µL, 0.36 mmol). The resultant mixture was heated at 80° C. for 2 hours. The solvent was removed under vacuum and the crude product was purified with flash column chromatography to yield 1-(4-Piperidin-1-yl-benzenesulfonyl)-4-(3-trifluoromethyl-pyridin-2-yl)-piperazine in 85% yield (116 mg) as white solid.

Example 28D

4-{4-[4-(3-Trifluoromethyl-pyridin-2-yl)-piperazine-1-sulfonyl]-phenyl}-morpholine Step 28A: 4-bromobenzenesulfonyl)-4-(3-trifluoromethyl-pyridin-2-yl)-piperazine (135.5 mg, 0.3 mmol), Pd$_2$(dba)$_3$ (13.7 mg, 0.015 mmol), t-BuONa (82.7 mg, 0.84 mmol) and the ligand (9 mg, 0.03 mmol) were mixed in a sealed tube which was flushed with N$_2$. To this was added tolene (2 mL) and then morpholine (31.5 µL, 0.36 mmol). The resultant mixture was heated at 80° C. for 2 hours. The solvent was removed under vacuum and the crude product was purified with flash column chromatography to yield 4-{4-[4-(3-trifluoromethyl-pyridin-2-yl)-piperazine-1-sulfonyl]-phenyl}-morpholine in 78% yield (106 mg) as a white solid.

Example 28E

1-Methyl-{4-{4-[4-(3-trifluoromethyl-pyridin-2-yl)-piperazine-1-sulfonyl]-phenyl}}-piperazine Step 28A: 4-bromobenzenesulfonyl)-4-(3-trifluoromethyl-pyridin-2-yl)-piperazine (135.5 mg, 0.3 mmol), Pd$_2$(dba)$_3$ (13.7 mg, 0.015 mmol), t-BuONa (82.7 mg, 0.84 mmol) and the ligand (9 mg, 0.03 mmol) were mixed in a sealed tube which was flushed with N$_2$. To this was added tolene (2 mL) and then morpholine (31.5 µL, 0.36 mmol). The resultant mixture was heated at 80° C. for 2 hours. The solvent was removed under vacuum and the crude product was purified with flash column chromatography to yield 1-Methyl-{4-{4-[4-(3-trifluoromethyl-pyridin-2-yl)-piperazine-1-sulfonyl]-phenyl}}-piperazine in 67% yield (93 mg) as a yellow solid.

Example 29

Example 29A

Step 1: (R)-2-methyl-piperazine (3.5 g, 34.9 mmol), 2-bromo-5-fluoro benzotrifluoride (7.74 g, 31.7 mmol), BINAP (0.59 g, 0.95 mmol), tBuONa (4.58 g, 47.65 mmol) and $Pd_2(dba)_3$ (0.29 g, 0.32 mmol) were mixed in the flask and purged with $N_2$. Anhydrous toluene (50 mL) was added and purged with $N_2$ again. The resulting mixture was heated in an oil bath at 100° C. under $N_2$ for 3 hours. The mixture was cooled to room temperature, diluted with dichloromethane (150 mL), washed with $H_2O$ (30 mL) first, then washed with saturated brine (30 mL). The combined organic layer was dried over $Na_2SO_4$, concentrated down under reduced pressure to give a brown color liquid as crude. The crude product was purified on silica gel column eluted with 5-10% MeOH in DCM to give (3R)-1-[4-fluoro-2-(trifluoromethyl)phenyl]-3-methylpiperazine as a light yellow oil (6.85 g, 82%).

Step 2: To a solution of (3R)-1-[4-fluoro-2-(trifluoromethyl)phenyl]-3-methylpiperazine (2.5 g, 9.53 mmol) in DCM (50 mL) at 0° C. was added 3-acetyl benzenelsulfonyl chloride (2.08 g, 9.53 mmol) and DIPEA (3.32 mL, 19.06 mmol). The resultant mixture was stirred at room temperature overnight, then washed with $H_2O$ first, the aqueous layer was extracted with DCM (2×50 mL). The combined organic layer was dried over $Na_2SO_4$. The crude product was purified on SiO2 gel column eluted with 30-40% EtOAc in hexanes to give 1-[3-({(2R)$_4$-[4-fluoro-2-(trifluoromethyl)phenyl]-2-methylpiperazin-1-yl}sulfonyl)phenyl]ethanone as an off white solid (3.7 g, 90%). Step 3: To 1-[3-({(2R)$_4$-[4-fluoro-2-(trifluoromethyl)phenyl]-2-methylpiperazin-1-yl}sulfonyl)phenyl]ethanone (3.7 g, 8.33 mmol) was added TMS-CF$_3$ (50 mL, 25 mmol, 0.5 M in THF) at room temperature. This was cooled down to 0° C. in an ice bath, then TBAF (8.33 mL, 8.33 mmol, 1.0 M in THF) was added slowly. The resultant mixture was stirred at 0° C. for 30 min, then stirred at room temperature for 5 hours. The resultant mixture was diluted with saturated NaHCO$_3$ (40 mL), washed with DCM (100 mL). This was separated, the organic layer washed with saturated brine, dried over $Na_2SO_4$. The crude product was purified on SiO$_2$ gel column eluted with 30-50% EtOAc in Hexanes first, then purified again on SiO$_2$ gel column eluted with 2.5% MeOH in DCM to give 1,1,1-trifluoro-2-[3-({(2R)$_4$-[4-fluoro-2-(trifluoromethyl)phenyl]-2-methylpiperazin-1-yl}sulfonyl)phenyl]propan-2-ol as a white solid (2.76 g, 64%).

1H NMR (400 MHz, CHLOROFORM-d) δ ppm 1.15-1.23 (m, 3H) 1.85 (s, 3H) 2.55 (s, 1H) 2.66-2.76 (m, 2H) 2.87 (d, J=9.85 Hz, 1H) 2.92-3.00 (m, 1H) 3.32-3.41 (m, 1H) 3.75 (d, J=13.14 Hz, 1H) 4.22-4.24 (m, 1H) 7.18-7.23 (m, 2H) 7.32 (dd, J=8.59, 2.02 Hz, 1H) 7.58 (t, J=7.83 Hz, 1H) 7.79-7.89 (m, 2H) 8.10 (d, J=5.56 Hz, 1H). HRMS: calcd for $C_{21}H_{21}F_7N_2O_3S+H+$, 515.12339. found (ESI-FTMS, [M+H]$^{1+}$), 515.123. HPLC Method 1: room temperature, 6.882 min, 99.13%, HPLC Method 2: room temperature, 7.550 min, 100%.

Step 4: The product of step 3 (2.97 g 5.78 mmol) was separated by chiral column. The diastereomers were separated using prep SFC (15% IPA/85% CO$_2$, chiralpak AS-H) to provide:

(2R)-1,1,1-trifluoro-2-[3-({(2R)-4-[4-fluoro-2-(trifluoromethyl)phenyl]-2-methylpiperazin-1-yl}sulfonyl)phenyl]propan-2-ol as a white solid (1.32 g). 1H NMR (400 MHz, CHLOROFORM-d) δ ppm 1.21 (dd, J=6.44, 5.18 Hz, 3H) 1.84 (s, 3H) 2.63 (s, 1H) 2.67-2.75 (m, 2H) 2.84-2.90 (m, 1H) 2.95 (dd, J=10.99, 3.41 Hz, 1H) 3.31-3.41 (m, 1H) 3.75 (d, J=12.88 Hz, 1H) 4.18-4.27 (m, 1H) 7.19-7.23 (m, 2H) 7.32 (dd, J=8.59, 2.02 Hz, 1H) 7.58 (t, J=7.83 Hz, 1H) 7.81 (d, J=7.83 Hz, 1H) 7.85-7.88 (m, 1H) 8.11 (s, 1H); HRMS: calcd for $C_{21}H_{21}F_7N_2O_3S+H+$, 515.12339. found (ESI-FTMS, [M+H]$^{1+}$), 515.12488; and (2S)-1,1,1-trifluoro-2-[3-({(2R)-4-[4-fluoro-2-(trifluoromethyl)phenyl]-2-methylpiperazin-1-yl}sulfonyl)phenyl]propan-2-ol as a white solid (1.26 g). 1H NMR (400 MHz, CHLOROFORM-d) δ ppm 1.17-1.23 (m, 3H) 1.85 (d, J=1.01 Hz, 3H) 2.54 (s, 1H) 2.66-2.73 (m, 2H) 2.87 (d, J=8.34 Hz, 1H) 2.97 (dd, J=11.24, 3.41 Hz, 1H) 3.32-3.41 (m, 1H) 3.75 (d, J=12.88 Hz, 1H) 4.24 (s, 1H) 7.18-7.24 (m, 2H) 7.29-7.35 (m, 1H) 7.58 (t, J=8.08 Hz, 1H) 7.80-7.88 (m, 2H) 8.10 (s, 1H); HRMS: calcd for $C_{21}H_{21}F_7N_2O_3S+H+$, 515.12339. found (ESI-FTMS, [M+H]$^{1+}$), 515.12492.

Example 29B 1-(3-bromo-benzenesulfonyl)-4-(4-fluoro-2-(trifluoromethyl-phenyl)-2-methyl-piperazine was prepared from the corresponding sulfonyl chloride and piperazine according to the sulfonation methods described above (diisopropylethylamine/CH$_2$Cl$_2$). A dry sample 1-(3-bromo-benzenesulfonyl)-4-(4-fluoro-2-(trifluoromethyl-phenyl)-2-methyl-piperazine (Compound B, 3.43 g, 7.14 mmol) was dissolved in 50 mL dry THF at 25° C. under nitrogen. The solution was cooled to −78° C. n-BuLi (2.59 M in hexane, 2.89 mL, 7.49 mmol) was added in 20 seconds. The resulting yellow solution was stirred at −78° C. for 30 seconds, and 1,1,1-trifluoropropan-2-one (0.70 mL, 7.49 mmol) was added in less than 5 seconds. After the reaction mixture was stirred at −78° C. for 30 min, water (0.5 mL) was added. The cooling bath was removed. The reaction mixture was warmed to 25° C. and concentrated to yield a yellow oily residue, which was dissolved in 10 mL toluene. Combiflash of the toluene solution (40 g silica gel column, ethyl acetate:hexane=5:95 to 30:70 in 50 min) afforded 1,1,1-trifluoro-2-[3-({(2R)-4-[4-fluoro-2-(trifluoromethyl)phenyl]-2-methylpiperazin-1-yl}sulfonyl)phenyl]propan-2-ol (3.05 g, 82%) as a white solid.

The following compounds were prepared using a procedures similar to those described in Example 29A.

Example 29C 1,1,1-trifluoro-2-[4-({(2R)-4-[4-fluoro-2-(trifluoromethyl)phenyl]-2-methylpiperazin-1-yl}sulfonyl) phenyl]propan-2-ol The title compound was obtained in 51.4% yield (166.6 mg) as a light yellow solid. HRMS: calcd for $C_{21}H_{21}F_7N_2O_3S+H+$, 515.12339. found (ESI-FTMS, [M+H]$^{1+}$), 515.1227. HPLC Method 1: room temperature, 6.580 min, 99.41%, HPLC Method 2: room temperature, 7.307 min, 98.12%.

Example 29D 1,1,1-trifluoro-2-[4-({(2R)-4-[3-fluoro-2-(trifluoromethyl)phenyl]-2-methylpiperazin-1-yl}sulfonyl)phenyl]propan-2-ol Yield 85.1%. HRMS: calcd for $C_{21}H_{21}F_7N_2O_3S+H+$, 515.12339. found (ESI-FTMS, [M+H]$^{1+}$), 515.1247. HPLC Method 1: room temperature, 6.679 min, 99.48%, HPLC
Method 2: room temperature, 7.333 min, 99.0%.

Example 29E 3-({(2R)-4-[4-fluoro-2-(trifluoromethyl)phenyl]-2-methylpiperazin-1-yl}sulfonyl)benzoic acid Yield 12.1%. HRMS: calcd for $C_{19}H_{18}F_4N_2O_4S+H+$, 447.09962. found (ESI-FTMS, $[M+H]^{1+}$), 447.1008. HPLC Method 1: room temperature, 6.210 min, 90.00%, HPLC Method 2: room temperature, 7.226 min, 95.84%.

Example 29F (2R)-1-[(5-bromo-2-methoxyphenyl)sulfonyl]-4-[4-fluoro-2-(trifluoromethyl)phenyl]-2-methylpiperazine Yield 72.9%. HRMS: calcd for $C_{19}H_{19}BrF_4N_2O_3S+H+$, 511.03086. found (ESI-FTMS, $[M+H]^{1+}$), 511.0293.

Example 29G 1,1,1-trifluoro-2-[4-({(2R)-2-methyl-4-[3-(trifluoromethyl)pyridin-4-yl]piperazin-1-yl}sulfonyl)phenyl]propan-2-ol Yield 87.5%. HRMS: calcd for $C_{20}H_{21}F_6N_3O_3S+H+$, 498.12806. found (ESI-FTMS, $[M+H]^{1+}$), 498.1289.

Example 29H 1,1,1-trifluoro-2-(4-{[(2R)-4-(4-fluoro-2-methylphenyl)-2-methylpiperazin-1-yl]sulfonyl}phenyl)propan-2-ol Yield 42.9%. HRMS: calcd for $C_{21}H_{24}F_4N_2O_3S+H+$, 461.15165. found (ESI-FTMS, $[M+H]^{1+}$), 461.1519.

Example 29I 2-(4-{[(2R)-4-(2-chloro-4-fluorophenyl)-2-methylpiperazin-1-yl]sulfonyl}phenyl)-1,1,1-trifluoropropan-2-ol Yield 63.6%. HRMS: calcd for $C_{20}H_{21}ClF_4N_2O_3S+H+$, 481.09703. found (ESI-FTMS, $[M+H]^{1+}$), 481.0975.

Example 29J 5-fluoro-2-((3R)-3-methyl-4-{[4-(2,2,2-trifluoro-1-hydroxy-1-methylethyl)phenyl]sulfonyl}piperazin-1-yl)benzonitrile Yield 83.8%. HRMS: calcd for $C_{21}H_{21}F_4N_3O_3S+H+$, 472.13125. found (ESI-FTMS, $[M+H]^{1+}$), 472.1316.

Example 29K 2-(3-{[(2R)-4-(2-chloro-4-fluorophenyl)-2-methylpiperazin-1-yl]sulfonyl}phenyl)-1,1,1-trifluoropropan-2-ol Yield 63.6%. HRMS: calcd for $C_{20}H_{21}ClF_4N_2O_3S+H+$, 481.09703. found (ESI-FTMS, $[M+H]^{1+}$), 481.09623.

Example 29L 1,1,1-trifluoro-2-(4-{[(2R)-4-(4-fluoro-2-methoxyphenyl)-2-methylpiperazin-1-yl]sulfonyl}phenyl)propan-2-ol Yield 76.6%. HRMS: calcd for $C_{21}H_{24}F_4N_2O_4S+H+$, 477.14657. found (ESI-FTMS, $[M+H]^{1+}$), 477.14454.

Example 29M 1,1,1-trifluoro-2-(3-{[(2R)-4-(4-fluoro-2-methylphenyl)-2-methylpiperazin-1-yl]sulfonyl}phenyl)propan-2-ol Yield 82.2%. HRMS: calcd for $C_{21}H_{24}F_4N_2O_3S+H+$, 461.15165. found (ESI-FTMS, $[M+H]^{1+}$), 461.15059.

Example 29N 2-(3-{[(2R)-4-(2-chloro-4-fluorophenyl)-2-methylpiperazin-1-yl]sulfonyl}phenyl)propan-2-ol Yield 88%. HRMS: calcd for $C_{21}H_{21}ClF_6N_2O_3S+H+$, 531.09383. found (ESI-FTMS, $[M+H]^{1+}$), 531.09359.

Example 29O 1,1,1-trifluoro-2-[4-({(2R)-2-methyl-4-[2-(trifluoromethoxy)phenyl]piperazin-1-yl}sulfonyl)phenyl]propan-2-ol Yield 88%. HRMS: calcd for $C_{21}H_{22}F_6N_2O_4S+H+$, 513.12772. found (ESI-FTMS, $[M+H]^{1+}$), 513.12786.

Example 29P 4-((3R)-3-methyl-4-{[4-(2,2,2-trifluoro-1-hydroxy-1-methylethyl)phenyl]sulfonyl}piperazin-1-yl)-3-(trifluoromethyl)benzonitrile Yield 46.7%. HRMS: calcd for $C_{22}H_{21}F_6N_3O_3S+H+$, 522.12806. found (ESI-FTMS, $[M+H]^{1+}$), 522.12846.

Example 29Q 2-(4-{[(2R)-4-(2,4-dichlorophenyl)-2-methylpiperazin-1-yl]sulfonyl}phenyl)-1,1,1-trifluoropropan-2-ol Yield 82.6%. HRMS: calcd for $C_{20}H_{21}Cl_2F_3N_2O_3S+H+$, 497.06748. found (ESI-FTMS, $[M+H]^{1+}$), 497.06732.

Example 29R 2-(4-{[(2R)-4-(2-chloro-4-methylphenyl)-2-methylpiperazin-1-yl]sulfonyl}phenyl)-1,1,1-trifluoropropan-2-ol Yield 86.9%. HRMS: calcd for $C_{21}H_{24}ClF_3N_2O_3S+H+$, 477.12210. found (ESI-FTMS, $[M+H]^{1+}$), 477.12206.

Example 29S

2-[3-({(2R)-4-[4-chloro-2-(trifluoromethyl)phenyl]-2-methylpiperazin-1-yl}sulfonyl)phenyl]-1,1,1-trifluoropropan-2-ol Yield 86.2%. HRMS: calcd for $C_{21}H_{21}ClF_6N_2O_3S+H+$, 531.09383. found (ESI-FTMS, $[M+H]^{1+}$), 531.09365.

Example 29T 1,1,1-trifluoro-2-[3-({(2R)-2-methyl-4-[2-(trifluoromethoxy)phenyl]piperazin-1-yl}sulfonyl)phenyl]

propan-2-ol

Yield 89.9%. HRMS: calcd for $C_{21}H_{22}F_6N_2O_4S+H+$, 513.12772. found (ESI-FTMS, $[M+H]^{1+}$), 513.12744.

Example 29U 4-((3R)-3-methyl-4-{[3-(2,2,2-trifluoro-1-hydroxy-1-methylethyl)phenyl]sulfonyl}piperazin-1-yl)-3-(trifluoromethyl)benzonitrile Yield 43.9%. HRMS: calcd for $C_{22}H_{21}F_6N_3O_3S+H+$, 522.12806. found (ESI-FTMS, $[M+H]^{1+}$), 522.12844.

Example 29T'

2-(3-{[(2R)-4-(2,4-dichlorophenyl)-2-methylpiperazin-1-yl]sulfonyl}phenyl)-1,1,1-trifluoropropan-2-ol Yield 84.5%. HRMS: calcd for $C_{20}H_{21}Cl_2F_3N_2O_3S+H+$, 497.06748. found (ESI-FTMS, $[M+H]^{1+}$), 497.0673.

Example 29U'

2-(3-{[(2R)-4-(2-chloro-4-methylphenyl)-2-methylpiperazin-1-yl]sulfonyl}phenyl)-1,1,1-trifluoropropan-2-ol Yield 86.9%. HRMS: calcd for $C_{21}H_{24}ClF_3N_2O_3S+H+$, 477.12210. found (ESI-FTMS, $[M+H]^{1+}$), 477.12238.

Example 29V 2-(3-{[(2R)-4-{6-[1-amino-2,2,2-trifluoro-1-(trifluoromethyl)ethyl]pyridin-3-yl}-2-methylpiperazin-1-yl]sulfonyl}phenyl)-1,1,1-trifluoropropan-2-ol Step A: A mixture of (R)-2-methyl-piperazine (1.0 g, 9.98 mmol), 5-bromo 2-cyanopyridine (1.66 g, 9.08 mmol), tris(dibenzylidineacetone)dipalladium (0) (83.15 mg, 0.0908 mmol), rac-2,2'-bis(diphenylphosphino)-1,1'-binaphtyl (169.37 mg, 0.272 mmol) and sodium tert-butoxide (1.09 g, 11.35 mmol) were charged to a microwave vial. Toluene (10.0 mL) was introduced under nitrogen atmosphere and the reaction mixture was irradiated at 110° C. for 35 minutes. Reaction was complete as determined by TLC. Reaction mixtures was diluted with dichloromethane, washed with water, saturated brine then dried over $Na_2SO_4$ and concentrated. The crude product was purified via flash column chromatography to yield 5-[(3R)-3-methylpiperazin-1-yl]pyridine-2-carbonitrile as brown color oil (1.15 g, 39.1% yield).

Step B: To a stirred solution of 5-[(3R)-3-methylpiperazin-1-yl]pyridine-2-carbonitrile (250 mg, 1.24 mmol) and 3-acetylbenzenesulfonyl chloride (270.3 mg, 1.24 mmol) in anhydrous dichloromethane (4 mL) was added diisopropylethylamine (0.43 mL, 2.48 mmol). The mixture was stirred at room temperature for over night. Reaction was complete as determined by TLC. The reaction mixture was purified via flash column chromatography to yield 5-{(3R)-4-[(3-acetylphenyl)sulfonyl]-3-methylpiperazin-1-yl}pyridine-2-carbonitrile in 80.3% yield (383 mg) as a light yellow solid.

Step C: To a 50 mL flask containing 5-{(3R)-4-[(3-acetylphenyl)sulfonyl]-3-methylpiperazin-1-yl}pyridine-2-carbonitrile (383 mg, 0.996 mmol) and 6.0 mL of 0.5 M TMS-$CF_3$, was added 0.996 mL of 1.0 M tetrabutylammonium fluoride in THF at 0° C. After stirring for 2 h, the solution was diluted with saturated $NaHCO_3$, extracted ($2 \times CH_2Cl_2$), washed with brine and dried over $Na_2SO_4$, and concentrated under reduced pressure. Purification by flash column chromatography to yield 2-(3-{[(2R)-4-{6-[1-amino-2,2,2-trifluoro-1-(trifluoromethyl)ethyl]pyridin-3-yl}-2-methylpiperazin-1-yl]sulfonyl}phenyl)-1,1,1-trifluoropropan-2-ol as a light yellow solid. HRMS: calcd for $C_{22}H_{23}F_9N_4O_3S+H+$, 595.14199. found (ESI-FTMS, $[M+H]^{1+}$), 595.14231.

Example 29W 2-(3-{[(2R)-4-(2,4-difluorophenyl)-2-methylpiperazin-1-yl]sulfonyl}phenyl)-1,1,1-trifluoropropan-2-ol Yield 67.8%. HRMS: calcd for $C_{20}H_{21}F_5N_2O_3S+H+$, 465.12658. found (ESI-FTMS, $[M+H]^{1+}$), 465.12772.

Example 29X 1,1,1-trifluoro-2-[3-({(2R)-2-methyl-4-[4-(1H-tetrazol-5-yl)-2-(trifluoromethyl)phenyl]piperazin-1-yl}sulfonyl)phenyl]propan-2-ol The compound of Example 29U, 4-((3R)-3-methyl-4-{[3-(2,2,2-trifluoro-1-hydroxy-1-methylethyl)phenyl]sulfonyl}piperazin-1-yl)-3-(trifluoromethyl)benzonitrile, was used as starting material to make the title compound. A mixture of 4-((3R)-3-methyl-4-{[3-(2,2,2-trifluoro-1-hydroxy-1-methylethyl)phenyl]sulfonyl}piperazin-1-yl)-3-(trifluoromethyl)benzonitrile (300 mg, 0.58 mmol), $NaN_3$ (112.5 mg, 1.73 mmol), $Et_3NHCl$ (238.1 mg, 1.73 mmol) were charged to a microwave vial. Toluene (3 mL) was introduced under nitrogen atmosphere and the reaction mixture was heated at 100° C. over night in an oil bath. Reaction was complete as determined by TLC. Reaction mixtures was diluted with EtoAc, washed with 10% HCl until pH=6-7. The organic layer was dried over $Na_2SO_4$ and concentrated. The crude product was purified via prep HPLC under acidic condition to yield 1,1,1-trifluoro-2-[3-({(2R)-2-methyl-4-[4-(1H-tetrazol-5-yl)-2-(trifluoromethyl)phenyl]piperazin-1-yl}sulfonyl)phenyl]propan-2-ol as a white solid (111.2 mg, 34.3 yield %). HRMS: calcd for $C_{22}H_{22}F_6N_6O_3S+H+$, 565.14510. found (ESI-FTMS, $[M+H]^{1+}$), 565.14524.

Example 29Y 1,1,1,3,3,3-hexafluoro-2-[4-({(2R)-4-[4-fluoro-2-(trifluoromethyl)phenyl]-2-methylpiperazin-1-yl}sulfonyl)phenyl]propan-2-amine The title compound was prepared in a manner similar to that described in Example 29V. In step B, 4-cyanobenzenesulfonyl chloride was used as starting material to make intermediate. Yield 5.3%. HRMS: calcd for $C_{21}H_{19}F_{10}N_3O_2S+H+$, 568.11110. found (ESI-FTMS, $[M+H]^{1+}$), 568.11129.

Example 29Z 4-({(2R)-4-[4-fluoro-2-(trifluoromethyl)phenyl]-2-methylpiperazin-1-yl}sulfonyl)benzamide Yield 31.9%. HRMS: calcd for $C_{19}H_{19}F_4N_3O_3S+H+$, 446.11560. found (ESI-FTMS, $[M+H]^{1+}$), 446.11559.

Example 29AA 1,1,1,3,3,3-hexafluoro-2-[3-({(2R)-4-[4-fluoro-2-(trifluoromethyl)phenyl]-2-methylpiperazin-1-yl}sulfonyl)phenyl]propan-2-amine The title compound was prepared in a manner similar to that described in Example 29V. In step B, 3-cyanobenzenesulfonyl chloride was used as starting material to make intermediate. Yield 24.1%. HRMS: calcd for $C_{21}H_{19}F_{10}N_3O_2S$+H+, 568.11110. found (ESI-FTMS, $[M+H]^{1+}$), 568.11142.

Example 29AB 3-({(2R)-4-[4-fluoro-2-(trifluoromethyl)phenyl]-2-methylpiperazin-1-yl}sulfonyl)benzamide Yield 18.8%. HRMS: calcd for $C_{19}H_{19}F_4N_3O_3S$+H+, 446.11560. found (ESI-FTMS, $[M+H]^{1+}$), 446.11556.

Example 29AC

5-[(3R)-3-methyl-4-{[3-(2,2,2-trifluoro-1-hydroxy-1-methylethyl)phenyl]sulfonyl}piperazin-1-yl]pyridine-2-carbonitrile Yield 82.2%. HRMS: calcd for $C_{20}H_{21}F_3N_4O_3S$+H+, 455.13592. found (ESI-FTMS, $[M+H]^{1+}$), 455.13594.

Example 29AD

2-[4-({(2R)-4-[4-[1-amino-2,2,2-trifluoro-1-(trifluoromethyl)ethyl]-2-(trifluoromethyl)phenyl]-2-methylpiperazin-1-yl}sulfonyl)phenyl]-1,1,1-trifluoropropan-2-ol The title compound was prepared in a manner similar to that described in Example 29V. HRMS: calcd for $C_{24}H_{23}F_{12}N_3O_3S$+H+, 662.13412. found (ESI-FTMS, $[M+H]^{1+}$), 662.13495.

Example 29AD'

2-(3-{[(2R)-4-{4-[1-amino-2,2,2-trifluoro-1-(trifluoromethyl)ethyl]-2-(trifluoromethyl)phenyl}-2-methylpiperazin-1-yl]sulfonyl}phenyl)-1,1,1-trifluoropropan-2-ol The title compound was prepared in a manner similar to that described in Example 29V. HRMS: calcd for $C_{24}H_{23}F_{12}N_3O_3S$+H+, 662.13412. found (ESI-FTMS, $[M+H]^{1+}$), 662.13513.

Example 29AE (2R)-4-[4-fluoro-2-(trifluoromethyl)phenyl]-2-methyl-1-({5-[5-(trifluoromethyl)isoxazol-3-yl]-2-thienyl}sulfonyl)piperazine Yield 70-80%. HRMS: calcd for $C_{20}H_{16}F_7N_3O_3S_2$+H+, 544.05940. found (ESI-FTMS, $[M+H]^{1+}$), 544.05847.

Example 29AF

4-[5-({(2R)-4-[4-fluoro-2-(trifluoromethyl)phenyl]-2-methylpiperazin-1-yl}sulfonyl)pyridin-2-yl]morpholine Yield 54.8%. HRMS: calcd for $C_{21}H_{24}F_4N_4O_3S$+H+, 489.15780. found (ESI-FTMS, $[M+H]^{1+}$), 489.15913.

Example 29AG

N-[3-chloro-4-({(2R)-4-[4-fluoro-2-(trifluoromethyl)phenyl]-2-methylpiperazin-1-yl}sulfonyl)phenyl]morpholine-4-carboxamide Yield 85.0%. HRMS: calcd for $C_{23}H_{25}ClF_4N_4O_4S$+H+, 565.12939. found (ESI-FTMS, $[M+H]^{1+}$), 565.1304.

Example 29AH

4-[(3R)-4-{[3-(1-hydroxy-1-methylethyl)phenyl]sulfonyl}-3-methylpiperazin-1-yl]-3-(trifluoromethyl)benzonitrile Yield 65%. HRMS: calcd for $C_{22}H_{24}F_3N_3O_3S$+H+, 468.15632. found (ESI-FTMS, $[M+H]^{1+}$), 468.15712.

Example 29AI 1,1,1-trifluoro-2-[4-({(2R)-2-methyl-4-[2-(trifluoromethyl)phenyl]piperazin-1-yl}sulfonyl)phenyl]propan-2-ol HRMS: calcd for $C_{21}H_{22}F_6N_2O_3S$+H+, 497.13281. found (ESI-FTMS, $[M+H]^{1+}$), 497.1322.

Example 29AJ (S)-1,1,1-trifluoro-2-(4-((R)-2-methyl-4-(2-(trifluoromethyl)phenyl)piperazin-1-ylsulfonyl)phenyl)propan-2-ol The title compound was prepared by resolving the enantiomeric mixture of Example 29AI, (1,1,1-trifluoro-2-[4-({(2R)-2-methyl-4-[2-(trifluoromethyl)phenyl]piperazin-1-yl}sulfonyl)phenyl]propan-2-ol), using preparative SPC. Solvent evaporation afforded (S)-1,1,1-trifluoro-2-(4-((R)-2-methyl-4-(2-(trifluoromethyl)phenyl)piperazin-1-ylsulfonyl)phenyl)propan-2-ol as a white solid (80.4 mg).

Example 29AK (R)-1,1,1-trifluoro-2-(4-((R)-2-methyl-4-(2-(trifluoromethyl)phenyl)piperazin-1-ylsulfonyl)phenyl)propan-2-ol The title compound was prepared by resolving the enantiomeric mixture of Example 29AI, (1,1,1-trifluoro-2-[4-({(2R)-2-methyl-4-[2-(trifluoromethyl)phenyl]piperazin-1-yl}sulfonyl)phenyl]propan-2-ol), using preparative SPC. Solvent evaporation afforded (R)-1,1,1-trifluoro-2-(4-((R)-2-methyl-4-(2-(trifluoromethyl)phenyl)piperazin-1-ylsulfonyl)phenyl)propan-2-ol as a white solid (70.2 mg).

Example 29AL (2R)-1-[(3-bromophenyl)sulfonyl]-4-(2-chloro-4-fluorophenyl)-2-methylpiperazine HRMS: calcd for $C_{17}H_{17}BrClFN_2O_2S+H+$, 446.99394. found (ESI-FTMS, [M+H]$^{1+}$), 446.99325.

Example 29AM (2R)-4-[4-fluoro-2-(trifluoromethyl)phenyl]-2-methyl-1-[(4-piperazin-1-yl-1-naphthyl)sulfonyl]piperazine Step 2A and 2B: The intermediate (2R)-1-[(4-bromo-1-naphthyl)sulfonyl]-4-[4-fluoro-2-(trifluoromethyl)phenyl]-2-methylpiperazine was prepared according to a similar procedure for Example II-1A, step 1A and step 1B.

Step 2C: A mixture of (2R)-1-[(4-bromo-1-naphthyl)sulfonyl]-4-[4-fluoro-2-(trifluoromethyl)phenyl]-2-methylpiperazine (250 mg, 0.47 mmol), 4-methyl-piperazine-1-carboxylic acid tert-butyl ester (175.1 mg, 0.94 mmol), tris(dibenzylidineacetone)dipalladium (0) (4.3 mg, 0.0047 mmol), rac-2,2'-bis(diphenylphosphino)-1,1'-binaphtyl (8.78 mg, 0.014 mmol) and sodium tert-butoxide (56.5 mg, 0.59 mmol) were charged to a microwave vial. Toluene (3.0 mL) was introduced under nitrogen atmosphere and the reaction mixture was irradiated at 110° C. for 35 minutes. Reaction was complete as determined by TLC. Reaction mixtures was diluted with dichloromethane, washed with water, saturated brine then dried over $Na_2SO_4$ and concentrated. The crude product was purified via flash column chromatography to yield tert-butyl 4-[4-({(2R)-4-[4-fluoro-2-(trifluoromethyl)phenyl]-2-methylpiperazin-1-yl}sulfonyl)-1-naphthyl]piperazine-1-carboxylate as yellow gum (200.1 mg, 66.9% yield).

Step 2D: To a 50 mL flask containing tert-butyl 4-[4-({(2R)-4-[4-fluoro-2-(trifluoromethyl)phenyl]-2-methylpiperazin-1-yl}sulfonyl)-1-naphthyl]piperazine-1-carboxylate (185.2 mg) and 5 mL of $CH_2Cl_2$ was added 3 mL of TFA. This was stirred at room temperature for 4.5 hr. Reaction was complete as determined by TLC. Solvent and TFA was removed under vacuum. The resulting residue was dissolved in $CH_2Cl_2$, washed with sat. $K_2CO_3$ until pH=8, then washed with saturated brine, dried over $Na_2SO_4$ and concentrated down to yield (2R)-4-[4-fluoro-2-(trifluoromethyl)phenyl]-2-methyl-1-[(4-piperazin-1-yl-1-naphthyl)sulfonyl]piperazine as a yellow solid (136.3 mg, 87.3% yield). HRMS: calcd for $C_{26}H_{28}F_4N_4O_2S+H+$, 537.19418. found (ESI-FTMS, [M+H]$^{1+}$), 537.1968. HPLC Method 1: room temperature, 5.003 min, 94.44%, HPLC Method 2: room temperature, 6.254 min, 93.74%.

Example 29AN (2R)-4-[4-fluoro-2-(trifluoromethyl)phenyl]-2-methyl-1-{[4-(4-methylpiperazin-1-yl)-1-naphthyl]sulfonyl}piperazine The title compound was prepared according to a similar procedure for Example II-4A Yield 71.3%. HRMS: calcd for $C_{27}H_{30}F_4N_4O_2S+H+$, 551.20983. found (ESI-FTMS, [M+H]$^{1+}$), 551.2119. HPLC Method 1: room temperature, 5.058 min, 92.54%, HPLC Method 2: room temperature, 6.187 min, 92.23%.

Example 29AO

2-[4-({(2R)-4-[4-fluoro-2-(trifluoromethyl)phenyl]-2-methylpiperazin-1-yl}sulfonyl)phenyl]propan-2-ol 41.5% yield. HRMS: calcd for $C_{21}H_{24}F_4N_2O_3S+H+$, 461.15165. found (ESI-FTMS, [M+H]$^{1+}$), 461.1517.

Example 29AP 2-(4-{[(2R)-4-(2-chloro-4-fluorophenyl)-2-methylpiperazin-1-yl]sulfonyl}phenyl)propan-2-ol Yield 72.5%. HRMS: calcd for $C_{20}H_{24}ClFN_2O_3S+H+$, 427.12529. found (ESI-FTMS, [M+H]$^{1+}$), 427.12476.

Example 29AQ 2-(3-{[(2R)-4-(2-chloro-4-fluorophenyl)-2-methylpiperazin-1-yl]sulfonyl}phenyl)propan-2-ol Yield 81.5%. HRMS: calcd for $C_{20}H_{24}ClFN_2O_3S+H+$, 427.12529. found (ESI-FTMS, [M+H]$^{1+}$), 427.12517.

Example 29AR 4-((3R)-3-methyl-4-{[3-(4-methylpiperazin-1-yl)phenyl]sulfonyl}piperazin-1-yl)-3-(trifluoromethyl)benzonitrile Yield 59.8%. HRMS: calcd for $C_{24}H_{28}F_3N_5O_2S+H+$, 508.19885. found (ESI-FTMS, [M+H]$^{1+}$), 508.20129.

Example 29AS

4-{(3R)-4-[(3-bromophenyl)sulfonyl]-3-methylpiperazin-1-yl}-3-(trifluoromethyl)benzonitrile Yield 85.2%. HRMS: calcd for $C_{19}H_{17}BrF_3N_3O_2S+H+$, 488.02497. found (ESI-FTMS, [M+H]$^{1+}$), 488.02487.

Example 29AT (2R)-1-[(3-bromophenyl)sulfonyl]-4-(2,4-dichlorophenyl)-2-methylpiperazine Yield 98.6%. HRMS: calcd for $C_{17}H_{17}BrCl_2N_2O_2S+H+$, 462.96439. found (ESI-FTMS, [M+H]$^{1+}$), 462.9633.

Example 29AU (2R)-4-(2,4-dichlorophenyl)-2-methyl-1-{[3-(4-methylpiperazin-1-yl)phenyl]sulfonyl}piperazine Yield 78%. HRMS: calcd for $C_{22}H_{28}Cl_2N_4O_2S+H+$, 483.13828. found (ESI-FTMS, [M+H]$^{1+}$), 483.13912.

Example 29AV (2R)-1-[(3-bromophenyl)sulfonyl]-2-methyl-4-(2,4,5-trifluorophenyl)piperazine Yield 95.6%. HRMS: calcd for $C_{17}H_{16}BrF_3N_2O_2S+H+$, 449.01407. found (ESI-FTMS, $[M+H]^{1+}$), 449.0139.

Example 29AW (2R)-2-methyl-1-{[3-(4-methylpiperazin-1-yl)phenyl]sulfonyl}-4-(2,4,5-trifluorophenyl)piperazine Yield 80%. HRMS: calcd for $C_{22}H_{27}F_3N_4O_2S+H+$, 469.18796. found (ESI-FTMS, $[M+H]^{1+}$), 469.1891.

Example 29AX 3-({(2R)-4-[4-fluoro-2-(trifluoromethyl)phenyl]-2-methylpiperazin-1-yl}sulfonyl)phenol Step A: (R)-2-methyl-piperazine (3.88 g, 38.70 mmol), 2-bromo, 5-fluoro benzotrifluoride (8.55 g, 35.18 mmol), tris(dibenzylidineacetone)dipalladium (0) (32.0 mg g, 0.35 mmol), rac-2,2'-bis(diphenylphosphino)-1,1'-binaphthyl (657.0 mg, 1.06 mmol) and sodium tert-butoxide (5.07 g, 52.77 mmol) were charged to a reaction flask. Toluene (40 mL) was introduced under nitrogen atmosphere and the reaction mixture was heated up at 110° C. for 5.0 hours. Reaction was complete as determined by TLC. The reaction mixture was diluted with dichloromethane, washed with water, saturated brine then dried over $MgSO_4$ and concentrated. The crude product was purified via flash column chromatography to yield (R)-1-(4-fluoro-2-(trifluoromethyl)phenyl)-3-methylpiperazine as a light brown oil (3.1 g, 33.6% yield).

Step B: To a stirred solution of (R)-1-(4-fluoro-2-(trifluoromethyl)phenyl)-3-methylpiperazine (5.34 g, 21.86 mmol) in anhydrous dichloromethane (20 mL) was added diisopropylethylamine (10.3 mL, 59.1 mmol) at 0° C. The reaction mixture was stirred at room temperature for 15 minutes then 3-Methoxy benzene sulfonyl chloride (2.44 g, 11.82 mmol) dissolved in dichloromethane (10 mL) was introduced dropwise. The cooling bath was removed and the mixture was stirred at room temperature for 0.5 hour. Reaction was complete as determined by TLC. The reaction mixture was diluted with dichloromethane washed with saturated $NaHCO_3$ (aqueous), dried over $MgSO_4$ and concentrated. The crude product was purified via flash column chromatography to yield (R)-4-(4-fluoro-2-(trifluoromethyl)phenyl)-1-(3-methoxyphenylsulfonyl)-2-methylpiperazine in quantitative yield (5.10 g) as a white solid.

Step C: A stirred solution of (R)-4-(4-fluoro-2-(trifluoromethyl)phenyl)-1-(3-methoxyphenylsulfonyl)-2-methylpiperazine (2.22 g, 5.13 mmol) in anhydrous dichloromethane (60 mL) was cooled down to −50° C. (acetone+dry ice bath). $BBr_3$ (1M in $CH_2Cl_2$) was added dropwise via addition funnel while keeping the temperature between −50° C. and −55° C. Then the reaction mixture was stirred at −50° C. to −20° C. for 3 hours. Reaction was complete as determined by TLC. The reaction mixture was quenched with water and diluted with dichloromethane. pH was adjusted to 7 using saturated $NaHCO_3$ (aqueous) and it was allowed to stir for 20 minutes. The layers were separated; the organic layer was dried over $MgSO_4$ and concentrated. The reaction was repeated at 2.85 g scale. The combined crud products were purified via flash column chromatography to yield 3-({(2R)-4-[4-fluoro-2-(trifluoromethyl)phenyl]-2-methylpiperazin-1-yl}sulfonyl)phenol in 96% yield (4.07 g) as a white solid. HRMS: calcd for $C_{18}H_{18}F_4N_2O_3S+H+$, 419.10470. found (ESI-FTMS, $[M+H]^{1+}$), 419.104. HPLC Method 1: room temperature, 6.318 min, 100%, HPLC Method 2: room temperature, 7.220 min, 99.48%.

Example 29AY

2-[3-({(2R)-4-[4-fluoro-2-(trifluoromethyl)phenyl]-2-methylpiperazin-1-yl}sulfonyl)phenoxy]-N,N-dimethylethanamine Yield 98.75%. HRMS: calcd for $C_{22}H_{27}F_4N_3O_3S+H+$, 490.17820. found (ESI-FTMS, $[M+H]^{1+}$), 490.17796. HPLC Method 1: room temperature, 5.899 min, 98.23%, HPLC Method 2: room temperature, 4.828 min, 98.75%.

Example 29AZ

3-[3-({(2R)-4-[4-fluoro-2-(trifluoromethyl)phenyl]-2-methylpiperazin-1-yl}sulfonyl)phenoxy]-N,N-dimethylpropan-1-amine Yield 57.2%. HRMS: calcd for $C_{23}H_{29}F_4N_3O_3S+H+$, 504.19385. found (ESI-FTMS, $[M+H]^{1+}$), 504.19386. HPLC Method 1: room temperature, 5.970 min, 97.87%, HPLC Method 2: room temperature, 4.881 min, 98.31%.

Example 29BA

4-{(3R)-4-[(3-hydroxyphenyl)sulfonyl]-3-methylpiperazin-1-yl}-3-(trifluoromethyl)benzonitrile A light yellow solid (615 mg, 96.4 yield %). HRMS: calcd for $C_{19}H_{18}F_3N_3O_3S+H+$, 426.10937. found (ESI-FTMS, $[M+H]^{1+}$), 426.10931.

Example 29BB

4-{(3R)-4-[(3-methoxyphenyl)sulfonyl]-3-methylpiperazin-1-yl}-3-(trifluoromethyl)benzonitrile Yield 92.7%. HRMS: calcd for $C_{20}H_{20}F_3N_3O_3S+H+$, 440.12502. found (ESI-FTMS, $[M+H]^{1+}$), 440.12536.

Example 29BC 4-((3R)-3-methyl-4-{[3-(1H-1,2,4-triazol-1-yl)phenyl]sulfonyl}piperazin-1-yl)-3-(trifluoromethyl)benzonitrile Step 8A: 4-[(3R)-3-methylpiperazin-1-yl]-3-(trifluoromethyl)benzonitrile was prepared according to procedures similar to those described above.

Step 8B: 4-{(3R)-4-[(3-fluorophenyl)sulfonyl]-3-methylpiperazin-1-yl}-3-(trifluoromethyl)benzonitrile was prepared according to procedures similar to those described above.

Step 8C: A mixture of 4-{(3R)-4-[(3-fluorophenyl)sulfonyl]-3-methylpiperazin-1-yl}-3-(trifluoromethyl)benzonitrile (349 mg, 0.82 mmol), 1,2,4-triazole (112.6 mg, 1.64 mmol), $K_2CO_3$ (226.7 mg, 1.64 mmol), and CuI (15.6 mg, 0.082 mmol) were charged to a microwave vial. NMP (3 mL) was introduced under nitrogen atmosphere and the reaction mixture was heated at 166° C. for 3 hr in an oil bath. Reaction was complete as determined by TLC. Reaction mixtures was diluted with dichloromethane, washed with water, saturated brine then dried over $Na_2SO_4$ and concentrated. The crude product was purified via prep HPLC under neutral condition to yield 4-((3R)-3-methyl-4-{[3-(1H-1,2,4-triazol-1-yl)phenyl]sulfonyl}piperazin-1-yl)-3-(trifluoromethyl)benzonitrile as a light tan color solid (176.8 mg, 45.3% yield). HRMS: calcd for $C_{21}H_{19}F_3N_6O_2S$+H+, 477.13150. found (ESI-FTMS, $[M+H]^{1+}$), 477.13303.

Example 29BD

4-{(3R)-4-[(3-fluorophenyl)sulfonyl]-3-methylpiperazin-1-yl}-3-(trifluoromethyl)benzonitrile Yield 92.1%. HRMS: calcd for $C_{19}H_{17}F_4N_3O_2S$+H+, 428.10503. found (ESI-FTMS, $[M+H]^{1+}$), 428.1049.

Example 29BE 4-((3R)-3-methyl-4-{[3-(4H-1,2,4-triazol-4-yl)phenyl]sulfonyl}piperazin-1-yl)-3-(trifluoromethyl)benzonitrile HRMS: calcd for $C_{21}H_{19}F_3N_6O_2S$+H+, 477.13150. found (ESI-FTMS, $[M+H]^{1+}$), 477.13273.

Example 29BF (2R)-4-(2,4-dichlorophenyl)-2-methyl-1-{[3-(1H-1,2,4-triazol-1-yl)phenyl]sulfonyl}piperazine Yield 48.5%. HRMS: calcd for $C_{19}H_{19}Cl_2N_5O_2S$+H+, 452.07092. found (ESI-FTMS, $[M+H]^{1+}$), 452.07066.

Example 29BG (2R)-2-methyl-1-{[3-(1H-1,2,4-triazol-1-yl)phenyl]sulfonyl}-4-(2,4,5-trifluorophenyl)piperazine Yield 11.3%. HRMS: calcd for $C_{19}H_{18}F_3N_5O_2S$+H+, 438.12060. found (ESI-FTMS, $[M+H]^{1+}$), 438.12062.

Example 29BH (2R)-1-[(3-bromophenyl)sulfonyl]-4-[2,5-difluoro-4-(1H-1,2,4-triazol-1-yl)phenyl]-2-methylpiperazine HRMS: calcd for $C_{19}H_{18}BrF_2N_5O_2S$+H+, 498.04054. found (ESI-FTMS, $[M+H]^{1+}$), 498.04153.

Example 29BI

4-[(3R)-3-methyl-4-{[3-(1H-1,2,4-triazol-1-yl)phenyl]sulfonyl}piperazin-1-yl]benzonitrile Yield 40.7%. HRMS: calcd for $C_{20}H_{20}N_6O_2S$+H+, 409.14412. found (ESI-FTMS, $[M+H]^{1+}$), 409.14386.

Example 29BJ

5-[(3R)-3-methyl-4-{[3-(1H-1,2,4-triazol-1-yl)phenyl]sulfonyl}piperazin-1-yl]pyridine-2-carbonitrile Yield 59.0%. HRMS: calcd for $C_{19}H_{19}N_7O_2S$+H+, 410.13937. found (ESI-FTMS, $[M+H]^{1+}$), 410.13914.

Example 29BK

2-[3-({(2R)-4-[4-(aminomethyl)-2-(trifluoromethyl)phenyl]-2-methylpiperazin-1-yl}sulfonyl)phenyl]-1,1,1-trifluoropropan-2-ol Step 9A: To a flask containing 4-((3R)-3-methyl-4-{[3-(2,2,2-trifluoro-1-hydroxy-1-methylethyl)phenyl]sulfonyl}piperazin-1-yl)-3-(trifluoromethyl)benzonitrile (50 mg, 0.10 mmol) and 2 mL of THF was added $CoCl_2$ (32.5 mg, 0.25 mmol) at 0° C., then $NaBH_4$ (28.4 mg, 0.75 mmol) was added, followed by adding 1 mL of MeOH. The reaction mixture was stirred at 0° C. for 0.5 hr. Reaction was complete as determined by TLC. The reaction mixture was filtered, washed with EtoAc. The filtrate washed with $H_2O$, then washed with sat. brine and dried over $Na_2SO_4$, and concentrated under reduced pressure. Purification by flash column chromatography to yield 2-[3-({(2R)-4-[4-(aminomethyl)-2-(trifluoromethyl)phenyl]-2-methylpiperazin-1-yl}sulfonyl)phenyl]-1,1,1-trifluoropropan-2-ol as a white solid. Yield 29%. HRMS: calcd for $C_{22}H_{25}F_6N_3O_3S$+H+, 526.15936. found (ESI-FTMS, $[M+H]^{1+}$), 526.15985.

Example 29BL

2-[3-({(2R)-4-[4-(aminomethyl)-2-(trifluoromethyl)phenyl]-2-methylpiperazin-1-yl}sulfonyl)phenyl]propan-2-ol The title compound was prepared according to a similar procedure for Example II-9A. Yield 41.0% HRMS: calcd for $C_{22}H_{28}F_3N_3O_3S$+H+, 472.18762. found (ESI-FTMS, $[M+H]^{1+}$), 472.18899.

Example 29BM 4-chloro-2-fluoro-5-({(2R)-4-[4-fluoro-2-(trifluoromethyl)phenyl]-2-methylpiperazin-1-yl}sulfonyl)benzamide Step A: The intermediate (3R)-1-[4-fluoro-2-(trifluoromethyl)phenyl]-3-methylpiperazine was prepared according to procedures similar to those described herein.

Step B: To a stirred solution of 4-chloro-5-chlorosulfonyl-2-fluoro-benzoic acid (306.4 mg, 1.20 mmol) in anhydrous dichloromethane (5 mL) was added TMSCl (0.43 mL, 3.42 mmol). This was stirred at room temperature for 30 min. Then added a solution of (3R)-1-[4-fluoro-2-(trifluoromethyl)phenyl]-3-methylpiperazine (300 mg, 1.14 mmol) in anhydrous dichloromethane (3 mL), followed by adding diisopropylethylamine (1.19 mL, 6.84 mmol) slowly. The mixture was stirred at room temperature for 3 hr. Reaction was complete as determined by TLC. The reaction mixture was diluted with $H_2O$, extracted (2×$CH_2Cl_2$), washed with brine and dried over $Na_2SO_4$, and concentrated under reduced pressure. Purification by flash column chromatography to yield 4-chloro-2-fluoro-5-[4-(4-fluoro-2-(trifluoromethyl-phenyl)-2-methyl-piperazine-1-sulfonyl]-benzoic acid as a dark yellow solid.

Step C: To a flask containing 4-chloro-2-fluoro-5-[4-(4-fluoro-2-(trifluoromethyl-phenyl)-2-methyl-piperazine-1-sulfonyl]-benzoic acid (645 mg, 1.29 mmol) and 10 mL of anhydrous THF was added CDI (628.97 mg, 3.88 mmol). The reaction mixture was refluxed under $N_2$ for 2.5 hr. The reaction mixture was cooled down to room temperature, then 15 mL of $NH_3H_2O$ was added, this was stirred at room temperature for 2 hr. Acidified the reaction mixture with 6N HCl until pH=4-5, extracted (2× EtoAc), washed with brine and dried over Na$_2$SO$_4$, and concentrated under reduced pressure. Purification by prep HPLC under neutral condition to yield 4-chloro-2-fluoro-5-({(2R)-4-[4-fluoro-2-(trifluoromethyl)phenyl]-2-methylpiperazin-1-yl}sulfonyl)benzamide as an off-white solid (6.0 mg, 0.9% yield). HRMS: calcd for C$_{19}$H$_{17}$ClF$_5$N$_3$O$_3$S+H+, 498.06720. found (ESI-FTMS, [M+H]$^{1+}$), 498.06793.

Example 29BN 2-chloro-4-fluoro-5-({(2R)-4-[4-fluoro-2-(trifluoromethyl)phenyl]-2-methylpiperazin-1-yl}sulfonyl)benzoic acid Yield 19.3%. HRMS: calcd for C$_{19}$H$_{16}$ClF$_5$N$_2$O$_4$S+H+, 499.05122. found (ESI-FTMS, [M+H]$^{1+}$), 499.05277.

Example 29BO 3-({(2R)-4-[4-fluoro-2-(trifluoromethyl)phenyl]-2-methylpiperazin-1-yl}sulfonyl)-4-methoxybenzamide Yield 75.6%. HRMS: calcd for C$_{20}$H$_{21}$F$_4$N$_3$O$_4$S+H+, 476.12617. found (ESI-FTMS, [M+H]$^{1+}$), 476.12811.

Example 29BP 4-chloro-3-({(2R)-4-[4-fluoro-2-(trifluoromethyl)phenyl]-2-methylpiperazin-1-yl}sulfonyl)benzamide Yield 32.5%. HRMS: calcd for C$_{19}$H$_{18}$ClF$_4$N$_3$O$_3$S+H+, 480.07663. found (ESI-FTMS, [M+H]$^{1+}$), 480.07798.

Example 29BQ 1,1,1-trifluoro-2-[4-({(2R)-2-methyl-4-[1-oxido-3-(trifluoromethyl)pyridin-4-yl]piperazin-1-yl}sulfonyl)phenyl]propan-2-ol To a flask containing 1,1,1-trifluoro-2-[4-({(2R)-2-methyl-4-[3-(trifluoromethyl)pyridin-4-yl]piperazin-1-yl}sulfonyl)phenyl]propan-2-ol (60 mg, 0.12 mmol) and 1.5 mL of DCM/MeOH (9/1, v/v) was added MMPP (74.6 mg, 0.15 mmol). The resulting slurry was stirred at room temperature over night. Reaction was complete as determined by TLC. This was filtered, washed with DCM. The filtrate was concentrated under reduced pressure. Purification by flash column chromatography to yield 1,1,1-trifluoro-2-[4-({(2R)-2-methyl-4-[1-oxido-3-(trifluoromethyl)pyridin-4-yl]piperazin-1-yl}sulfonyl)phenyl]propan-2-ol as a white solid (13.5 mg, 21.9 yield). HRMS: calcd for C$_{20}$H$_{21}$F$_6$N$_3$O$_4$S+H+, 514.12297. found (ESI-FTMS, [M+H]$^{1+}$), 514.12174.

Example 29BR 1,1,1-trifluoro-2-[3-({4-[4-fluoro-2-(trifluoromethyl)phenyl]piperidin-1-yl}sulfonyl)phenyl]propan-2-ol Prepared according to scheme II-12. HRMS: calcd for C$_{21}$H$_{20}$F$_7$NO$_3$S+H+, 500.11249. found (ESI-FTMS, [M+H]$^{1+}$), 500.11256.

Example 29BR

N-[3-({(2R)$_4$-[4-fluoro-2-(trifluoromethyl)phenyl]-2-methylpiperazin-1-yl}sulfonyl)phenyl]-N,1-dimethylpyrrolidin-3-amine Step A: (R)-1-(4-fluoro-2-(trifluoromethyl)phenyl)-3-methylpiperazine was prepared according to procedures similar to those described above using 2-bromo, 5-fluorobenzotrifluoride was used as starting material. Yield 57.4%.

Step B: (R)-1-(3-bromophenylsulfonyl)-4-(4-fluoro-2-(trifluoromethyl)phenyl)-2-methylpiperazine was prepared according to procedures similar to those described above using 2-Bromobenzene sulfonyl chloride as starting material. Yield 93.6%.

Step 5C: N-[3-({(2R)-4-[4-fluoro-2-(trifluoromethyl)phenyl]-2-methylpiperazin-1-yl}sulfonyl)phenyl]-N, 1-dimethylpyrrolidin-3-amine was prepared according to procedures similar to those described above except instead of conventional heating, microwave irradiation was used at 110° C., for 30 minutes and N,N'-dimethyl-3-aminopyrrolidine was used as starting material. Yield 36.8%. HRMS: calcd for C$_{24}$H$_{30}$F$_4$N$_4$O$_2$S+H+, 515.20983. found (ESI-FTMS, [M+H]$^{1+}$), 515.2104. HPLC Method 1: room temperature, 4.854 min, 99.40%, HPLC Method 2: room temperature, 5.969 min, 99.20%.

Example 29BS (2R)-4-[4-fluoro-2-(trifluoromethyl)phenyl]-2-methyl-1-{[3-(4-methylpiperazin-1-yl)phenyl]sulfonyl}piperazine Yield 27.9%. HRMS: calcd for C$_{23}$H$_{27}$F$_4$N$_3$O$_2$S+H+, 486.18328. found (ESI-FTMS, [M+H]$^{1+}$), 486.18327.

Example 29BT

N-{1-[3-({(2R)-4-[4-fluoro-2-(trifluoromethyl)phenyl]-2-methylpiperazin-1-yl}sulfonyl)phenyl]pyrrolidin-3-yl}-N-methylacetamide Yield 25.3%. HRMS: calcd for C$_{25}$H$_{30}$F$_4$N$_4$O$_3$S+H+, 543.20475. found (ESI-FTMS, [M+H]$^{1+}$), 543.20336. HPLC Method 1: room temperature, 6.629 min, 96.40%, HPLC Method 2: room temperature, 7.462 min, 96.06%.

Example 29BU

{(2S)-1-[3-({(2R)-4-[4-fluoro-2-(trifluoromethyl)phenyl]-2-methylpiperazin-1-yl}sulfonyl)phenyl]pyrrolidin-2-yl}methanol Yield 54.4%. HRMS: calcd for C$_{23}$H$_{27}$F$_4$N$_3$O$_3$S+H+, 502.17820. found (ESI-FTMS, [M+H]$^{1+}$), 502.17748.

Example 29BV (3R)-1-[3-({(2R)-4-[4-fluoro-2-(trifluoromethyl)phenyl]-2-methylpiperazin-1-yl}sulfonyl)phenyl]pyrrolidin-3-ol Yield 76.6%. HRMS: calcd for C$_{22}$H$_{25}$F$_4$N$_3$O$_3$S+H+, 488.16255. found (ESI-FTMS, [M+H]$^{1+}$), 488.16359.

Example 29BW

{(2R)-1-[3-({(2R)-4-[4-fluoro-2-(trifluoromethyl)phenyl]-2-methylpiperazin-1-yl}sulfonyl)phenyl]pyrrolidin-2-yl}methyl acetate Yield 54.0%. HRMS: calcd for $C_{25}H_{29}F_4N_3O_4S$+H+, 544.18877. found (ESI-FTMS, [M+H]$^{1+}$), 544.18921.

Example 29BX (methyl 1-[3-({(2R)-4-[4-fluoro-2-(trifluoromethyl)phenyl]-2-methylpiperazin 1-yl}sulfonyl)phenyl]pyrrolidine-3-carboxylate HRMS: calcd for $C_{24}H_{27}F_4N_3O_4S$+H+, 530.17312. found (ESI-FTMS, [M+H]$^{1+}$), 530.17135

Example 29BY

1-[3-({(2R)$_4$-[4-fluoro-2-(trifluoromethyl)phenyl]-2-methylpiperazin-1-yl}sulfonyl)phenyl]pyrrolidine-3-carboxylic acid The title compound was obtained by hydrolyzing (1-(3-((R)-4-(4-fluoro-2-(trifluoromethyl)phenyl)-2-methylpiperazin-1-ylsulfonyl)phenyl)pyrrolidin-2-yl)methyl acetate using 1N NaOH. Yield 90%. HRMS: calcd for $C_{23}H_{25}F_4N_3O_4S$+H+, 516.15747. found (ESI-FTMS, [M+H]$^{1+}$), 516.15646.

Example 29BZ

{(2R)-1-[3-({(2R)-4-[4-fluoro-2-(trifluoromethyl)phenyl]-2-methylpiperazin-1-yl}sulfonyl)phenyl]pyrrolidin-2-yl}methanol Yield 29.0%. HRMS: calcd for $C_{23}H_{27}F_4N_3O_3S$+H+, 502.17820. found (ESI-FTMS, [M+H]$^{1+}$), 502.17972.

Example 29CA

1-[3-({(2R)-4-[4-fluoro-2-(trifluoromethyl)phenyl]-2-methylpiperazin-1-yl}sulfonyl)phenyl]pyrrolidin-3-ol HRMS: calcd for $C_{22}H_{25}F_4N_3O_3S$+H+, 488.16255. found (ESI-FTMS, [M+H]$^{1+}$), 488.1636.

Example 29CB 1-(3-{[(2R)-4-(2-chloro-4-fluorophenyl)-2-methylpiperazin-1-yl]sulfonyl}phenyl)pyrrolidin-3-ol HRMS: calcd for $C_{21}H_{25}ClFN_3O_3S$+H+, 454.13619. found (ESI-FTMS, [M+H]$^{1+}$), 454.13559.

Example 29CC (2R)-4-(2-chloro-4-fluorophenyl)-2-methyl-1-({3-[4-(2-oxo-2-pyrrolidin-1 ylethyl)piperazin-1-yl]phenyl}sulfonyl)piperazine HRMS: calcd for $C_{27}H_{35}ClFN_5O_3S$+H+, 564.22059. found (ESI-FTMS, [M+H]$^{1+}$), 564.22189.

Example 29CD (2R)-4-[4-fluoro-2-(trifluoromethyl)phenyl]-1-({3-[(2S)-2-(methoxymethyl)pyrrolidin-1-yl]phenyl}sulfonyl)-2-methylpiperazine HRMS: calcd for $C_{24}H_{29}F_4N_3O_3S$+H+, 516.19385. found (ESI-FTMS, [M+H]$^{1+}$), 516.19562.

Example 29CE (2R)-4-[4-fluoro-2-(trifluoromethyl)phenyl]-2-methyl-1-{[3-(4-pyrrolidin-1-ylpiperidin-1-yl)phenyl]sulfonyl}piperazine HRMS: calcd for $C_{27}H_{34}F_4N_4O_2S$+H+, 555.24113. found (ESI-FTMS, [M+H]$^{1+}$), 555.24346.

Example 29CF (2R)$_4$-[4-fluoro-2-(trifluoromethyl)phenyl]-2-methyl-1-({3-[4-(2-oxo-2-pyrrolidin-1-ylethyl)piperazin-1-yl]phenyl}sulfonyl)piperazine HRMS: calcd for $C_{28}H_{35}F_4N_5O_3S$+H+, 598.24695. found (ESI-FTMS, [M+H]$^{1+}$), 598.2501.

Example 29CG (3S)-1-[3-({(2R)-4-[4-fluoro-2-(trifluoromethyl)phenyl]-2-methylpiperazin-1-yl}sulfonyl)phenyl]pyrrolidin-3-ol HRMS: calcd for $C_{22}H_{25}F_4N_3O_3S$+H+, 488.16255. found (ESI-FTMS, [M+H]$^{1+}$), 488.16074.

Example 29CH (2R)-4-[4-fluoro-2-(trifluoromethyl)phenyl]-2-methyl-1-[(3-pyrrolidin-1-ylphenyl)sulfonyl]piperazine HRMS: calcd for $C_{22}H_{25}F_4N_3O_2S$+H+, 472.16763. found (ESI-FTMS, [M+H]$^{1+}$), 472.16822.

Example 29CI

1-[3-({(2R)-4-[4-fluoro-2-(trifluoromethyl)phenyl]-2-methylpiperazin-1-yl}sulfonyl)phenyl]pyrrolidin-3-amine HRMS: calcd for $C_{22}H_{26}F_4N_4O_2S$+H+, 487.17853. found (ESI-FTMS, [M+H]$^{1+}$), 487.18047.

Example 29CJ 4-({1-[3-({(2R)-4-[4-fluoro-2-(trifluoromethyl)phenyl]-2-methylpiperazin-1-yl}sulfonyl)phenyl]pyrrolidin-3-yl}carbonyl)morpholine Yield 31.6%. HRMS: calcd for $C_{27}H_{32}F_4N_4O_4S$+H+, 585.21531. found (ESI-FTMS, [M+H]$^{1+}$), 585.21414. HPLC Method 1: room temperature, 6.641 min, 97.09%, HPLC Method 2: room temperature, 7.428 min, 95.08%.

Example 29CK

N-cyclohexyl-1-[3-({(2R)-4-[4-fluoro-2-(trifluoromethyl)phenyl]-2-methylpiperazin-1-yl}sulfonyl)phenyl]pyrrolidine-3-carboxamide Yield 16.8%. HRMS: calcd for $C_{29}H_{36}F_4N_4O_3S+H+$, 597.25170. found (ESI-FTMS, $[M+H]^{1+}$), 597.25049. HPLC Method 1: room temperature, 7.319 min, 96.16%, HPLC Method 2: room temperature, 7.893 min, 98.77%.

Example 29CL

N,N-diethyl-1-[3-({(2R)-4-[4-fluoro-2-(trifluoromethyl)pheny]-2-methylpiperazin-1-yl}sulfonyl)phenyl]pyrrolidine-3-carboxamide Yield 39.4%. HRMS: calcd for $C_{27}H_{34}F_4N_4O_3S+H+$, 571.23605. found (ESI-FTMS, $[M+H]^{1+}$), 571.23575. HPLC Method 1: room temperature, 7.171 min, 100%, HPLC Method 2: room temperature, 7.710 min, 100%.

Example 29CM 1-(5-((R)-4-(4-fluoro-2-(trifluoromethyl)phenyl)-2-methylpiperazin-1-ylsulfonyl)thiophen-2-yl)pyrrolidine-2-carboxamide Step 15C: tert-butyl 1-(5-((R)-4-(4-fluoro-2-(trifluoromethyl)phenyl)-2-methylpiperazin-1-ylsulfonyl)thiophen-2-yl)pyrrolidine-2-carboxylate was prepared according to for a procedure similar to the Buchwald couplings described herein. Yield 19%.

Step 15D: tert-butyl 1-(5-((R)-4-(4-fluoro-2-(trifluoromethyl)phenyl)-2-methylpiperazin-1-ylsulfonyl)thiophen-2-yl)pyrrolidine-2-carboxylate (316.0 mg, 0.547 mmol), $CeCl_3 \cdot 7H_2O$ (815.0 mg, 2.19 mmol) and KI (363.0 mg, 2.19 mmol) charged to a microwave vial were added with $CH_3CN$ (12 mL) and water (0.2 mL). The reaction mixture was subjected to microwave irradiation at 110° C. for 1 hour. This reaction was repeated twice. Both reaction mixtures were then combined and the supernatant clear solution was transferred into a flask, added with $CH_2Cl_2$ and stirred at room temperature. Solid was filtered off, filtrate concentrated, dried under high vacuum to yield crude 1-(5-((R)-4-(4-fluoro-2-(trifluoromethyl)phenyl)-2-methylpiperazin-1-ylsulfonyl)thiophen-2-yl)pyrrolidine-2-carboxylic acid which will be used as it is for the next step.

Step 15E: Crude 1-(5-((R)-4-(4-fluoro-2-(trifluoromethyl)phenyl)-2-methylpiperazin-1-ylsulfonyl)thiophen-2-yl)pyrrolidine-2-carboxylic acid (570 mg, 1.094 mmol) charged to a reaction flask was dissolved in THF (23 mL). To it was added CDI (649 mg, 4.38 mmol) and the reaction mixture was heated to reflux for 1 hour. After cooling down to room temperature excess $NH_4OH$ (28% $NH_3$)(23 ml) was added dropwise via addition funnel. The reaction mixture was left to stir at room temperature for 10 minutes, then it was diluted with ethyl acetate, acidified (pH acidic) using 10% HCl (aqueous) and stirred for 5 minutes. The layers were separated, and the organic layer washed with saturated brine, dried over $MgSO_4$, concentrated. Crude product containing a significant amount of starting acid by TLC was subjected to the same reaction and work up conditions. After reaction completation crude was purified via flash column chromatography to yield 1-(5-((R)-4-(4-fluoro-2-(trifluoromethyl)phenyl)-2-methylpiperazin-1-ylsulfonyl)thiophen-2-yl)pyrrolidine-2-carboxamide as white solid (180 mg, 31% yield). HRMS: calcd for $C_{21}H_{24}F_4N_4O_3S_2+H+$, 521.12987. found (ESI-FTMS, $[M+H]^{1+}$), 521.13026.

Example 29CN (R)-2-chloro-3-(4-(4-fluoro-2-(trifluoromethyl)phenyl)-2-methylpiperazin-1-ylsulfonyl)benzamide The title compound was prepared in a manner similar to that described in Example 29CM. Yield 24.8%. HRMS: calcd for $C_{23}H_{25}ClF_4N_4O_3S+H+$, 549.13448. found (ESI-FTMS, $[M+H]^{1+}$), 549.13507.

Example 29CO

1-[3-({(2R)-4-[4-fluoro-2-(trifluoromethyl)phenyl]-2-methylpiperazin-1-yl}sulfonyl)phenyl]pyrrolidine-3-carboxamide HRMS: calcd for $C_{23}H_{26}F_4N_4O_3S+H+$, 515.17345. found (ESI-FTMS, $[M+H]^{1+}$), 515.17243.

Example 29CP

1-[2-chloro-3-({(2R)-4-[4-cyano-2-(trifluoromethyl)phenyl]-2-methylpiperazin-1-yl}sulfonyl)phenyl] prolinamide Yield 52.0%. HRMS: calcd for $C_{24}H_{25}ClF_3N_5O_3S+H+$, 556.13915. found (ESI-FTMS, $[M+H]^{1+}$), 556.13923.

Example 29CQ

1-[3-({(2R)-4-[4-cyano-2-(trifluoromethyl)phenyl]-2-methylpiperazin-1-yl}sulfonyl)phenyl]prolinamide HRMS: calcd for $C_{24}H_{26}F_3N_5O_3S+H+$, 522.17812. found (ESI-FTMS, $[M+H]^{1+}$), 522.17711.

Example 29CR 1-(3-((R)-4-(4-fluoro-2-(trifluoromethyl)phenyl)-2-methylpiperazin-1-ylsulfonyl)phenyl)pyrrolidine-2-carboxamide HRMS: calcd for $C_{23}H_{26}F_4N_4O_3S+H+$, 515.17345. found (ESI-FTMS, $[M+H]^{1+}$), 515.17506.

Example 29CS 1-(3-((R)-4-(4-fluoro-2-(trifluoromethyl)phenyl)-2-methylpiperazin-1-ylsulfonyl)phenyl)pyrrolidine-2-carboxylic acid HRMS: calcd for $C_{23}H_{25}F_4N_3O_4S+H+$, 516.15747. found (ESI-FTMS, $[M+H]^{1+}$), 516.15865.

Example 29CT 2-fluoro-5-({(2R)-4-[4-fluoro-2-(trifluoromethyl)phenyl]-2-methylpiperazin-1-yl}sulfonyl)benzamide Step 16A and 16B: The intermediate 2-fluoro-5-({(2R)-4-[4-fluoro-2-(trifluoromethyl)phenyl]-2-methylpiperazin-1-yl}sulfonyl)benzonitrile was prepared according to procedures similar to those described in Example 29A.

Step 16C: To a flask containing 2-fluoro-5-({(2R)-4-[4-fluoro-2-(trifluoromethyl)phenyl]-2-methylpiperazin-1-yl}sulfonyl)benzonitrile (399 mg, 0.90 mmol) was added a mixture of TFA/$H_2SO_4$ (4 mL, 2/2 v/v). The reaction mixture was stirred at room temperature for 5 days. Reaction was complete as determined by TLC. Slowly poured the reaction mixture to the ice, then neutralized the reaction mixture with 3N NaOH until pH=7-8, extracted with EtOAc (2×150 mL). The combined organic layer washed with sat. brine and dried over $Na_2SO_4$, and concentrated under reduced pressure. Purification by prep HPLC under neutral condition to yield 2-fluoro-5-({(2R)-4-[4-fluoro-2-(trifluoromethyl)phenyl]-2-methylpiperazin-1-yl}sulfonyl)benzamide as a white solid (243.7 mg, 58.4%). HRMS: calcd for $C_{19}H_{18}F_5N_3O_3S$+H+, 464.10618. found (ESI-FTMS, [M+H]$^{1+}$), 464.10639.

Example 29CU 1,1,1-trifluoro-2-(3-((2R,6S)-4-(4-fluoro-2-(trifluoromethyl)phenyl)-2,6-dimethylpiperazin-1-ylsulfonyl)phenyl)propan-2-ol A white solid (2.76 g, 66%). 1H NMR (400 MHz, CHLOROFORM-d) δ ppm 1.49 (d, 6H) 1.78-1.89 (m, 3H) 2.43-2.78 (m, 5H) 4.08-4.26 (m, 2H) 7.07-7.15 (m, 1H) 7.16-7.22 (m, 1H) 7.29-7.37 (m, 1H) 7.51-7.63 (m, 1H) 7.77-7.84 (m, 1H) 7.88-7.95 (m, 1H) 8.08-8.15 (m, 1H). HPLC Method 1: room temperature, 6.955 min, 99.23%, HPLC Method 2: room temperature, 7.574 min, 97.80%.

Example 29CV

4-{(3R)-3-methyl-4-[(5-piperazin-1-yl-2-thienyl)sulfonyl]piperazin-1-yl}benzonitrile Yield 59.9%. HRMS: calcd for $C_{20}H_{25}N_5O_2S_2$+H+, 432.15224. found (ESI-FTMS, [M+H]$^{1+}$), 432.15278.

Example 29CW (2R)-1-[(3-bromophenyl)sulfonyl]-4-[4-fluoro-2-(trifluoromethyl)phenyl]-2-methylpiperazine Step 1A: A mixture of 1 (7.92 g, 79.07 mmol), 2 (18.3 g, 75.3 mmol), BINAP (2.81 g, 4.52 mmol), tBuONa (10.86 g, 112.95 mmol) and $Pd_2(dba)_3$ (2.07 g, 2.259 mmol) was mixed and purged with $N_2$. Anhydrous toluene (200 mL) was added and purged with $N_2$ again. The resultant mixture was heated in an oil bath at 100° C. under $N_2$ for 5 hours. After cooling, diluted with EtOAc (200 mL), filtered through a pad of Celite and washed with EtOAc (200 mL). The combined organic layer washed with aq. $NaHCO_3$. The aqueous layer was back extracted with EtOAc (2×100 mL). The combined organic layer was dried over $Na_2SO_4$. The crude product was purified on $SiO_2$ gel column eluted with 0-25% MeOH in EtOAc to give 3 as a light yellow oil (14.5 g, 73%).

Step 1B: To a solution of (R)-1-(4-fluoro-2-(trifluoromethyl)phenyl)-3-methylpiperazine (5 g, 19 mmol) in DCM (50 mL) at 0° C. was added DIPEA (6.62 mL, 38 mmol) 3-bromophenylsulfonyl chloride (3.29 mL, 22.8 mmol). The resultant mixture was stirred at room temperature overnight, then washed with aq. $NaHCO_3$. The aqueous layer was extracted with DCM (2×50 mL). The combined organic layer was dried over Na2SO4. The crude product was purified on SiO2 gel column eluted with 5-15% EtOAc in hexanes to give 4 as a white solid (7.9 g, 86%). HRMS: calcd for $C_{18}H_{17}BrF_4N_2O_2S$+H+, 481.02030. found (ESI-FTMS, [M+H]$^{1+}$), 481.0208.

Example 29CX (2R)-4-[4-fluoro-2-(trifluoromethyl)phenyl]-2-methyl-1-{[3-(4-methylpiperazin-1-yl)phenyl]sulfonyl}piperazine Step 1C: A mixture of (2R)-1-[(3-bromophenyl)sulfonyl]-4-[4-fluoro-2-(trifluoromethyl)phenyl]-2-methylpiperazine (8 g, 16.667 mmol), N-Me-piperazine (2.22 mL, 20 mmol), bis-t-Bu-biphenylphosphine (298.2 mg, 1.0 mmol), tBuONa (2.4 g, 25 mmol) and $Pd_2(dba)_3$ (305.2 mg, 0.333 mmol) was mixed and purged with $N_2$. Anhydrous toluene (80 mL) was added and purged with $N_2$ again. The resultant mixture was heated in an oil bath at 110° C. under $N_2$ for 5 hours. After cooling, diluted with EtOAc (100 mL), filtered through a pad of Celite and washed with EtOAc (100 mL). The combined organic layer washed with aq. $NaHCO_3$. The aqueous layer was back extracted with EtOAc (2×50 mL). The combined organic layer was dried over $Na_2SO_4$. The crude product was purified on $SiO_2$ gel column eluted with 0-25% MeOH in EtOAc to give the desired product as a light yellow solid (6.5 g, 78%). HRMS: calcd for $C_{23}H_{28}F_4N_4O_2S$+H+, 501.19418. found (ESI-FTMS, [M+H]$^{1+}$), 501.1944.

Example 29CY (2R)-4-[4-fluoro-2-(trifluoromethyl)phenyl]-2-methyl-1-[(3-piperazin-1-ylphenyl)sulfonyl]piperazine Step 1D: To a solution of (R)-tert-butyl 4-(3-(4-(4-fluoro-2-(trifluoromethyl)phenyl)-2-methylpiperazin-1-ylsulfonyl)phenyl)piperazine-1-carboxylate (970 mg, 1.655 mmol) in DCM (15 mL) was added TFA (5 mL) at room temperature. The resultant mixture was stirred for 4 h then basified with 5% aq. NH3. The precipitate was collected and washed with water to give the desired product as a light yellow solid (795 mg, 99%). HRMS: calcd for $C_{22}H_{26}F_4N_4O_2S$+H+, 487.17853. found (ESI-FTMS, [M+H]$^{1+}$), 487.17747.

Example 29CZ (2R)-1-{[3-(4-ethylpiperazin-1-yl)phenyl]sulfonyl}-4-[4-fluoro-2-(trifluoromethyl)phenyl]-2-methylpiperazine Step 1E: To a solution of (2R)-4-[4-fluoro-2-(trifluoromethyl)phenyl]-2-methyl-1-[(3-piperazin-1-ylphenyl)sulfonyl]piperazine (120 mg, 0.247 mmol) in MeOH (2 mL) was added $CH_3CHO$ (12 mg, 0.27 mmol), HOAc (17.7 μL, 0.3 mmol) and $NaBH_3CN$ (8 mg, 0.125 mmol) at room temperature. The resultant mixture was stirred till disappearance of starting material as monitored by LCMS. The solvent was removed. The crude product was purified by SiO2 column eluted with DCM/MeOH to give the desired product as a light yellow solid (116 mg, 100%). HRMS: calcd for $C_{24}H_{30}F_4N_4O_2S$+H+, 515.20983. found (ESI-FTMS, [M+H]$^{1+}$), 515.20891.

The following examples (Examples 29DA to 29EK) were prepared using procedures similar to those described in Examples 29CW-29CZ.

Example 29DA (2R)-4-[4-fluoro-2-(trifluoromethyl)phenyl]-1-{[3-(4-isopropylpiperazin-1-yl)phenyl]sulfonyl}-2-methylpiperazine Yield 100%. HRMS: calcd for $C_{25}H_{32}F_4N_4O_2S$+H+, 529.22548. found (ESI-FTMS, $[M+H]^{1+}$), 529.22456.

Example 29 DB (2R)-4-[4-fluoro-2-(trifluoromethyl)phenyl]-1-{[3-(4-isobutylpiperazin-1-yl)phenyl]sulfonyl}-2-methylpiperazine Yield 65%. HRMS: calcd for $C_{26}H_{34}F_4N_4O_2S$+H+, 543.24113. found (ESI-FTMS, $[M+H]^{1+}$), 543.2412.

Example 29DC (2R)-1-{[3-(4-cyclohexylpiperazin-1-yl)phenyl]sulfonyl}-4-[4-fluoro-2-(trifluoromethyl)phenyl]-2-methylpiperazine Yield 56%. HRMS: calcd for $C_{28}H_{36}F_4N_4O_2S$+H+, 569.25678. found (ESI-FTMS, $[M+H]^{1+}$), 569.25578.

Example 29DD (2R)-4-[4-fluoro-2-(trifluoromethyl)phenyl]-2-methyl-1-({3-[4-(tetrahydro-2H-pyran-4-yl)piperazin-1-yl]phenyl}sulfonyl)piperazine Yield 63%. HRMS: calcd for $C_{27}H_{34}F_4N_4O_3S$+H+, 571.23605. found (ESI-FTMS, $[M+H]^{1+}$), 571.23507.

Example 29DE (2R)-1-{[3-(4-acetylpiperazin-1-yl)phenyl]sulfonyl}-4-[4-fluoro-2-(trifluoromethyl)phenyl]-2-methylpiperazine Yield 58%. HRMS: calcd for $C_{24}H_{28}F_4N_4O_3S$+H+, 529.18910. found (ESI-FTMS, $[M+H]^{1+}$), 529.1879.

Example 29DF

Methyl 4-[3-({(2R)-4-[4-fluoro-2-(trifluoromethyl)phenyl]-2-methylpiperazin-1-yl}sulfonyl)phenyl]piperazine-1-carboxylate Yield 97%. HRMS: calcd for $C_{24}H_{28}F_4N_4O_4S$+H+, 545.18401. found (ESI-FTMS, $[M+H]^{1+}$), 545.1827.

Example 29DG

N-ethyl-4-[3-({(2R)-4-[4-fluoro-2-(trifluoromethyl)phenyl]-2-methylpiperazin-1-yl}sulfonyl)phenyl]piperazine-1-carboxamide Yield 71%. HRMS: calcd for $C_{24}H_{28}F_4N_4O_4S$+H+, 545.18401. found (ESI-FTMS, $[M+H]^{1+}$), 545.1827.

Example 29DH (2R)-1-[(5-bromo-2-thienyl)sulfonyl]-4-[4-fluoro-2-(trifluoromethyl)phenyl]-2-methylpiperazine Yield 95%. HRMS: calcd for $C_{16}H_{15}BrF_4N_2O_2S_2$+H+, 486.97672. found (ESI-FTMS, $[M+H]^{1+}$), 486.9753.

Example 29DI (2R)-4-[4-fluoro-2-(trifluoromethyl)phenyl]-2-methyl-1-[(5-pyridin-2-yl-2-thienyl)sulfonyl]piperazine Yield 77%. HRMS: calcd for $C_{21}H_{19}F_4N_3O_2S_2$+H+, 486.09276. found (ESI-FTMS, $[M+H]^{1+}$), 486.09151.

Example 29DJ (2R)-4-[4-fluoro-2-(trifluoromethyl)phenyl]-2-methyl-1-{[5-(1,3-oxazol-5-yl)-2-thienyl]sulfonyl}piperazine Yield 58%. HRMS: calcd for $C_{19}H_{17}F_4N_3O_3S_2$+H+, 476.07202. found (ESI-FTMS, $[M+H]^{1+}$), 476.07045.

Example 29DK (2R)-1-[(4-bromo-5-chloro-2-thienyl)sulfonyl]-4-[4-fluoro-2-(trifluoromethyl)phenyl]-2-methylpiperazine HRMS: calcd for $C_{16}H_{14}BrClF_4N_2O_2S_2$+H+, 520.93774. found (ESI-FTMS, $[M+H]^{1+}$), 520.93796.

Example 29DM (2R)-1-[(5-chloro-2-thienyl)sulfonyl]-4-[4-fluoro-2-(trifluoromethyl)phenyl]-2-methylpiperazine HRMS: calcd for $C_{16}H_{15}ClF_4N_2O_2S_2$+H+, 443.02723. found (ESI-FTMS, $[M+H]^{1+}$), 443.02752.

Example 29DN (2R)-4-[4-fluoro-2-(trifluoromethyl)phenyl]-2-methyl-1-{[3-(5-methyl-2-furyl)phenyl]sulfonyl}piperazine HRMS: calcd for $C_{23}H_{22}F_4N_2O_3S$+H+, 483.13600. found (ESI-FTMS, $[M+H]^{1+}$), 483.13551.

Example 29DO

4-[(3R)-4-{[3-(2,4-dimethyl-1,3-thiazol-5-yl)phenyl]sulfonyl}-3-methylpiperazin-1-yl]-3-(trifluoromethyl)benzonitrile HRMS: calcd for $C_{24}H_{23}F_3N_4O_2S_2$+H+, 521.12873. found (ESI-FTMS, $[M+H]^{1+}$), 521.12984.

Example 29DP (2R)-4-[4-fluoro-2-(trifluoromethyl)phenyl]-2-methyl-1-{[3-(trifluoromethoxy)phenyl]sulfonyl}piperazine Yield 84%. HRMS: calcd for $C_{19}H_{17}F_7N_2O_3S+H+$, 487.09208. found (ESI-FTMS, [M+H]$^{1+}$), 487.09309.

Example 29DQ (2R)-1-{[3-(difluoromethoxy)phenyl]sulfonyl}-4-[4-fluoro-2-(trifluoromethyl)phenyl]-2-methylpiperazine Yield 84%. HRMS: calcd for $C_{19}H_{18}F_6N_2O_3S+H+$, 469.10151. found (ESI-FTMS, [M+H]$^{1+}$), 469.10142.

Example 29DR (2R)-4-[4-fluoro-2-(trifluoromethyl)phenyl]-2-methyl-1-{[5-(4-methylpiperazin-1-yl)-2-thienyl]sulfonyl}piperazine Yield 54%. MS (LC-ESIMS) m/z 507.2.

Example 29DS

4-[5-({(2R)-4-[4-fluoro-2-(trifluoromethyl)phenyl]-2-methylpiperazin-1-yl}sulfonyl)-2-thienyl]morpholine Yield 59%. MS (LC-ESIMS) m/z 494.0

Example 29DT (2R)-4-[4-fluoro-2-(trifluoromethyl)phenyl]-2-methyl-1-[(5-piperidin-1-yl-2-thienyl)sulfonyl]piperazine Yield 50%. MS (LC-ESIMS) m/z 492.1.

Example 29DT (2R)-4-[4-fluoro-2-(trifluoromethyl)phenyl]-2-methyl-1-[(5-piperidin-1-yl-2-thienyl)sulfonyl]piperazine Yield 81%. HRMS: calcd for $C_{20}H_{24}F_4N_4O_2S_2+H+$, 493.13495. found (ESI-FTMS, [M+H]$^{1+}$), 493.13585.

Example 29DU (2R)-4-[4-fluoro-2-(trifluoromethyl)phenyl]-2-methyl-1-({5-[(3R)-3-methylpiperazin-1-yl]-2-thienyl}sulfonyl)piperazine Yield 82%. HRMS: calcd for $C_{21}H_{26}F_4N_4O_2S_2+H+$, 507.15060. found (ESI-FTMS, [M+H]$^{1+}$), 507.15115.

Example 29DV (2R)-4-[4-fluoro-2-(trifluoromethyl)phenyl]-2-methyl-1-({5-[(3S)-3-methylpiperazin-1-yl]-2-thienyl}sulfonyl)piperazine Yield 59%. HRMS: calcd for $C_{21}H_{26}F_4N_4O_2S_2+H+$, 507.15060. found (ESI-FTMS, [M+H]$^{1+}$), 507.1505.

Example 29DW

1-[5-({(2R)-4-[4-fluoro-2-(trifluoromethyl)phenyl]-2-methylpiperazin-1-yl}sulfonyl)-2-thienyl]-N,N-dimethylpiperidin-4-amine Yield 70%. MS (LC-ESIMS) m/z 535.1.

Example 29DX

4-[5-({(2R)-4-[4-fluoro-2-(trifluoromethyl)phenyl]-2-methylpiperazin-1-yl}sulfonyl)-2-thienyl]-2,6-cis-dimethylmorpholine Yield 67%. HRMS: calcd for $C_{22}H_{27}F_4N_3O_3S_2+H+$, 522.15027. found (ESI-FTMS, [M+H]$^{1+}$), 522.14978.

Example 29DY

4-[5-({(2R)-4-[4-fluoro-2-(trifluoromethyl)phenyl]-2-methylpiperazin-1-yl}sulfonyl)-2-thienyl]piperazin-2-one Yield 77%. MS (LC-ESI-MS) m/z 507.3.

Example 29DZ

1-[5-({(2R)-4-[4-fluoro-2-(trifluoromethyl)phenyl]-2-methylpiperazin-1-yl}sulfonyl)-2-thienyl]piperidine-4-carboxamide Yield 37%. HRMS: calcd for $C_{22}H_{26}F_4N_4O_3S_2+H+$, 535.14552. found (ESI-FTMS, [M+H]$^{1+}$), 535.14646.

Example 29EA (2R)-1-({5-[3,5-cis-dimethylpiperazin-1-yl]-2-thienyl}sulfonyl)-4-[4-fluoro-2-(trifluoromethyl)phenyl]-2-methylpiperazine Yield 52.2%. HRMS: calcd for $C_{22}H_{28}F_4N_4O_2S_2+H+$, 521.16625. found (ESI-FTMS, [M+H]$^{1+}$), 521.16822.

Example 29EA

1-[5-({(2R)-4-[4-fluoro-2-(trifluoromethyl)phenyl]-2-methylpiperazin-1-yl}sulfonyl)-2-thienyl]piperidine-4-carboxylic acid HRMS: calcd for $C_{22}H_{25}F_4N_3O_4S_2+H+$, 536.12954. found (ESI-FTMS, [M+H]$^{1+}$), 536.13032.

Example 29EB (2R)-1-{[5-(4-acetylpiperazin-1-yl)-2-thienyl]sulfonyl}-4-[4-fluoro-2-(trifluoromethyl)phenyl]-2-methylpiperazine Yield 85%. HRMS: calcd for $C_{22}H_{26}F_4N_4O_3S_2$+H+, 535.14552. found (ESI-FTMS, [M+H]$^{1+}$), 535.14534.

Example 29EC (2R)-4-[4-fluoro-2-(trifluoromethyl)phenyl]-1-{[5-(4-isobutyrylpiperazin-1-yl)-2-thienyl]sulfonyl}-2-methylpiperazine Yield 56%. HRMS: calcd for $C_{24}H_{30}F_4N_4O_3S_2$+H+, 563.17682. found (ESI-FTMS, [M+H]$^{1+}$), 563.17644.

Example 29ED

Methyl 4-[5-({(2R)-4-[4-fluoro-2-(trifluoromethyl)phenyl]-2-methylpiperazin-1-yl}sulfonyl)-2-thienyl]piperazine-1-carboxylate Yield 78%. HRMS: calcd for $C_{22}H_{26}F_4N_4O_4S_2$+H+, 551.14043. found (ESI-FTMS, [M+H]$^{1+}$), 551.14026.

Example 29EE

Isopropyl 4-[5-({(2R)-4-[4-fluoro-2-(trifluoromethyl)phenyl]-2-methylpiperazin-1-yl}sulfonyl)-2-thienyl]piperazine-1-carboxylate Yield 84%. HRMS: calcd for $C_{24}H_{30}F_4N_4O_4S_2$+H+, 579.17173. found (ESI-FTMS, [M+H]$^{1+}$), 579.17159.

Example 29EF

4-[5-({(2R)-4-[4-fluoro-2-(trifluoromethyl)phenyl]-2-methylpiperazin-1-yl}sulfonyl)-2-thienyl]-N-isopropylpiperazine-1-carboxamide Yield 91%. HRMS: calcd for $C_{24}H_{31}F_4N_5O_3S_2$+H+, 578.18772. found (ESI-FTMS, [M+H]$^{1+}$), 578.18767.

Example 29EG (2R)-4-[4-fluoro-2-(trifluoromethyl)phenyl]-1-{[5-(4-isopropylpiperazin-1-yl)-2-thienyl]sulfonyl}-2-methylpiperazine Yield 73%. HRMS: calcd for $C_{23}H_{30}F_4N_4O_2S_2$+H+, 535.18190. found (ESI-FTMS, [M+H]$^{1+}$), 535.18259.

Example 29EH (2R)-1-{[5-(4-cyclohexylpiperazin-1-yl)-2-thienyl]sulfonyl}-4-[4-fluoro-2-(trifluoromethyl)phenyl]-2-methylpiperazine Yield 77%. HRMS: calcd for $C_{26}H_{34}F_4N_4O_2S_2$+H+, 575.21320. found (ESI-FTMS, [M+H]$^{1+}$), 575.21408.

Example 29EI (2R)-4-[4-fluoro-2-(trifluoromethyl)phenyl]-2-methyl-1-({5-[4-(tetrahydro-2H-pyran-4-yl)piperazin-1-yl]-2-thienyl}sulfonyl)piperazine Yield 69%. HRMS: calcd for $C_{25}H_{32}F_4N_4O_3S_2$+H+, 577.19247. found (ESI-FTMS, [M+H]$^{1+}$), 577.19308.

Example 29EJ

2-{4-[5-({(2R)-4-[4-fluoro-2-(trifluoromethyl)phenyl]-2-methylpiperazin-1-yl}sulfonyl)-2-thienyl]piperazin-1-yl}ethanol Yield 69%. HRMS: calcd for $C_{22}H_{28}F_4N_4O_3S_2$+H+, 537.16117. found (ESI-FTMS, [M+H]$^{1+}$), 537.16153.

Example 29EK

1-[3-({(2R)-4-[4-fluoro-2-(trifluoromethyl)phenyl]-2-methylpiperazin-1-yl}sulfonyl)phenyl]piperidin-4-ol Yield 36%. HRMS: calcd for $C_{23}H_{27}F_4N_3O_3S$+H+, 502.17820. found (ESI-FTMS, [M+H]$^{1+}$), 502.17957.

Example 29EL 1,1,1,3,3,3-hexafluoro-2-[4-({(2R)-4-[4-fluoro-2-(trifluoromethyl)phenyl]-2-methylpiperazin-1-yl}sulfonyl)phenyl]propan-2-ol Step 2A: To a solution of (R)-1-(4-bromophenylsulfonyl)-4-(4-fluoro-2-(trifluoromethyl)phenyl)-2-methylpiperazine (265 mg, 0.55 mmol) in dry THF (2.5 mL) was added tBuLi (0.65 mL, 1.7 M in pentane, 1.1 mmol) at −78° C. The resultant mixture was stirred for 5 min then $CF_3COCF_3$ was bubbled into the solution and stirred another 30 min before quenched by addition of aq. NH4Cl. The aq. layer was extracted with DCM and combined organic layer was dried over MgSO4. The crude product was purified on SiO2 gel column eluted with hexanes/EtOAc to give the desired product as a white solid (125 mg, 40%). HRMS: calcd for $C_{21}H_{18}F_{10}N_2O_3S$+H+, 569.09512. found (ESI-FTMS, [M+H]$^{1+}$), 569.0967.

The following examples (29EM to 29EU) were prepared using procedures similar to those in Scheme III-2.

Example 29EM

4-[3-({(2R)-4-[4-fluoro-2-(trifluoromethyl)phenyl]-2-methylpiperazin-1-yl}sulfonyl)phenyl]-1-methylpiperidin-4-ol Yield 34%. HRMS: calcd for $C_{24}H_{29}F_4N_3O_3S$+H+, 516.19385. found (ESI-FTMS, [M+H]$^{1+}$), 516.19400.

Example 29EN

4-[4-({(2R)-4-[4-fluoro-2-(trifluoromethyl)phenyl]-2-methylpiperazin-1-yl}sulfonyl)phenyl]-1-methylpiperidin-4-ol Yield 26%. HRMS: calcd for $C_{24}H_{29}F_4N_3O_3S$+H+, 516.19385. found (ESI-FTMS, [M+H]$^{1+}$), 516.1939.

Example 29EO 2,2,2-trifluoro-1-[5-({(2R)-4-[4-fluoro-2-(trifluoromethyl)phenyl]-2-methylpiperazin-1-yl}sulfonyl)-2-thienyl]ethanone

Example 29EP

2-[5-({(2R)-4-[4-fluoro-2-(trifluoromethyl)phenyl]-2-methylpiperazin-1-yl}sulfonyl)-2-thienyl]propan-2-ol Yield 70%. HRMS: calcd for $C_{19}H_{22}F_4N_2O_3S_2$+H+, 467.10807. found (ESI-FTMS, [M+H]$^{1+}$), 467.10824.

Example 29EQ 1,1,1-trifluoro-2-[5-({(2R)-4-[4-fluoro-2-(trifluoromethyl)phenyl]-2-methylpiperazin-1-yl}sulfonyl)-2-thienyl]propan-2-ol Yield 86%. HRMS: calcd for $C_{19}H_{19}F_7N_2O_3S_2$+H+, 521.07980. found (ESI-FTMS, [M+H]$^{1+}$), 521.07991.

Example 29ER 5-({(2R)-4-[4-fluoro-2-(trifluoromethyl)phenyl]-2-methylpiperazin-1-yl}sulfonyl)thiophene-2-carboxylic acid Yield 86%. HRMS: calcd for $C_{17}H_{16}F_4N_2O_4S_2$+H+, 453.05604. found (ESI-FTMS, [M+H]$^{1+}$), 453.05652.

Example 29ES 3,3,3-trifluoro-2-[5-({(2R)-4-[4-fluoro-2-(trifluoromethyl)phenyl]-2-methylpiperazin-1-yl}sulfonyl)-2-thienyl]-2-hydroxypropanoic acid HRMS: calcd for $C_{17}H_{16}F_4N_2O_4S_2$+H+, 453.05604. found (ESI-FTMS, [M+H]$^{1+}$), 453.05652.

Example 29ET (2S)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol Prepared by chiral HPLC separation of Example 29EQ. MS (LC-ESIMS) m/z 521.1. MS (LC-ESIMS) m/z 519.2.

Example 29EU (2R)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol Prepared by chiral HPLC separation of Example 29EQ. MS (LC-ESIMS) m/z 520.7. MS (LC-ESIMS) m/z 519.0.

Example 29EV 5-({(2R)-4-[4-fluoro-2-(trifluoromethyl)phenyl]-2-methylpiperazin-1-yl}sulfonyl)-N,N-dimethylthiophene-2-carboxamide Step 3A: To a solution of 5-({(2R)-4-[4-fluoro-2-(trifluoromethyl)phenyl]-2-methylpiperazin-1-yl}sulfonyl)thiophene-2-carboxylic acid (260 mg, 0.575 mmol) in DCM (5 mL) was added (COCl)$_2$ (150.5 μL, 1.726 mmol) and DMF (1 small drop). The resultant mixture was stirred for 3 h. The solvent was evaporated and the crude residue was redissolved in dioxane (5 mL). To this was added 2N NH3 in EtOH (2 mL). The reaction mixture was stirred for 6 h then concentrated. The crude product was purified on SiO2 column eluted with hexanes/EtOAc to give the titled compound (less polar fraction, a side product) as a light yellow solid (48 mg, 17%). HRMS: calcd for $C_{19}H_{21}F_4N_3O_3S_2$+H+, 480.10332. found (ESI-FTMS, [M+H]$^{1+}$), 480.1042.

Example 29EW 5-({(2R)-4-[4-fluoro-2-(trifluoromethyl)phenyl]-2-methylpiperazin-1-yl}sulfonyl)thiophene-2-carboxamide Method 1: Prepared according to Step 3A in Example 29EV as the major product, as a white solid (180 mg, 69%).
Method 2: To a solution of 5-({(2R)-4-[4-fluoro-2-(trifluoromethyl)phenyl]-2-methylpiperazin-1-yl}sulfonyl)thiophene-2-carboxylic acid (1.15 g, 2.54 mmol) in THF (10 mL) was added Im$_2$CO (825.1 mg, 5.08 mmol). The resultant mixture was stirred for 4 h. To this was added 2N NH3 in EtOH (6.3 mL). The reaction mixture was stirred overnight then concentrated. The crude product was purified by HPLC to give the titled compound as a white solid (789 mg, 69%). HRMS: calcd for $C_{17}H_{17}F_4N_3O_3S_2$+H+, 452.07202. found (ESI-FTMS, [M+H]$^{1+}$), 452.07369.

Example 29EX tert-butyl 4-[3-({(2R)-4-[4-fluoro-2-(trifluoromethyl)phenyl]-2-methylpiperazin-1-yl}sulfonyl)phenyl]piperidine-1-carboxylate Step 4A: A reaction mixture of (R)-1-(3-bromophenylsulfonyl)-4-(4-fluoro-2-(trifluoromethyl)phenyl)-2-methylpiperazine (1.008 g, 2.1 mmol), boronate ester (620 mg, 2 mmol), PdCl$_2$(dppf) (43.9 mg, 0.06 mmol), dppf (33.3 mg, 0.06 mmol) and KOAc (589 mg, 6 mmol) in dioxane (8 mL) was degassed and sealed. The reaction mixture was heated to 80° C. for 3 h then 100° C. for 2 h. It was diluted with DCM after cooling and washed with brine. The crude product was purified on SiO2 gel column eluted with hexanes/EtOAc to give (R)-tert-butyl 4-(3-(4-(4-fluoro-2-(trifluoromethyl)phenyl)-2-methylpiperazin-1-ylsulfonyl)phenyl)-5,6-dihydropyridine-1(2H)-carboxylate as a light yellow solid (628 mg, 54%).

Step 4B: To a solution of (R)-tert-butyl 4-(3-(4-(4-fluoro-2-(trifluoromethyl)phenyl)-2-methylpiperazin-1-ylsulfonyl)phenyl)-5,6-dihydropyridine-1(2H)-carboxylate (620 mg, 1.06 mmol) in MeOH (50 mL) was added Pd/C (~100 mg). The mixture was purged with nitrogen and then stirred under H2 balloon at room temperature for 2 h. The reaction mixture was filtered through Celite and concentrated. The crude product was purified by SiO2 gel column eluted with hexanes/EtOAc to give the titled compound as a light yellow solid (569 mg, 92%). HRMS: calcd for $C_{28}H_{35}F_4N_3O_4S$+H+, 586.23572. found (ESI-FTMS, [M+H]$^{1+}$), 586.23585.

Example 29EY (2R)-4-[4-fluoro-2-(trifluoromethyl)phenyl]-2-methyl-1-[(3-piperidin-4-ylphenyl)sulfonyl]piperazine Step 4C: To a solution of tert-butyl 4-[3-({(2R)-4-[4-fluoro-2-(trifluoromethyl)phenyl]-2-methylpiperazin-1-yl}sulfonyl)phenyl]piperidine-1-carboxylate (540 mg, 0.923 mmol) in DCM (15 mL) was added TFA (5 mL). The reaction mixture was stirred at room temperature for 2 h and washed with aq. $Na_2CO_3$. The organic layer was dried over Na2SO4, concentrated and redissolved in Et2O and acidified with 1N HCl in Et2O to give the titled compound as a white solid (427 mg, 89%). HRMS: calcd for $C_{23}H_{27}F_4N_3O_2S$+H+, 486.18328. found (ESI-FTMS, [M+H]$^{1+}$), 486.18382.

Example 29EZ (2R)-4-[4-fluoro-2-(trifluoromethyl)phenyl]-2-methyl-1-{[3-(1-methylpiperidin-4-yl)phenyl]sulfonyl}piperazine Step 4D: To a solution of (2R)-4-[4-fluoro-2-(trifluoromethyl)phenyl]-2-methyl-1-[(3-piperidin-4-ylphenyl)sulfonyl]piperazine (81 mg, 0.155 mmol) in MeOH (2 mL) was added (CHO)n 27 mg, 0.93 mmol), HOAc (13.7 µL, 0.23 mmol) and NaBH3CN (6 mg, 0.093 mmol). The reaction mixture was stirred at room temperature overnight then 50° C. till disappearance of starting material. The reaction was diluted with DCM and quenched with aq. NaHCO3. The organic layer was separated and dried over Na2SO4 and purified on SiO2 gel column eluted with hexanes/EtOAc to give the desired product as a sticky oil (65 mg, 84%). It was redissolved in Et2O and acidified with 1N HCl in Et2O and triturated with hexanes/Et2O to give the titled compound as a white solid. HRMS: calcd for $C_{24}H_{29}F_4N_3O_2S$+H+, 500.19893. found (ESI-FTMS, [M+H]$^{1+}$), 500.19765.

Example 29FA (2R)-4-[4-fluoro-2-(trifluoromethyl)phenyl]-1-{[3-(1-isopropylpiperidin-4-yl)phenyl]sulfonyl}-2-methylpiperazine Prepared according to the synthesis of Example 29EZ in Step 4D from (2R)-4-[4-fluoro-2-(trifluoromethyl)phenyl]-2-methyl-1-[(3-piperidin-4-ylphenyl)sulfonyl]piperazine (81 mg, 0.155 mmol) and acetone (23 µL, 0.31 mmol) as a sticky oil (75 mg, 92%). It was redissolved in $Et_2O$ and acidified with 1N HCl in Et2O and triturated with hexanes/$Et_2O$ to give the titled compound as a white solid. HRMS: calcd for $C_{26}H_{33}F_4N_3O_2S$+H+, 528.23023. found (ESI-FTMS, [M+H]$^{1+}$), 528.22834.

Example 29FB (2R)-4-[4-fluoro-2-(trifluoromethyl)phenyl]-2-methyl-1-[(5-piperidin-4-yl-2-thienyl)sulfonyl]piperazine Prepared according to the synthesis of Example 29EY in Step 4C from (R)-tert-butyl 4-(5-(4-(4-fluoro-2-(trifluoromethyl)phenyl)-2-methylpiperazin-1-ylsulfonyl)thiophen-2-yl)piperidine-1-carboxylate (150 mg, 0.253 mmol) in DCM (3 mL) and TFA (1 mL), purified by SiO2 column eluted with EtOAc/MeOH to give the titled compound as a white solid (75 mg, 60%). HRMS: calcd for $C_{21}H_{25}F_4N_3O_2S_2$+H+, 492.13970. found (ESI-FTMS, [M+H]$^{1+}$), 492.14043.

Example 29FC 2-(4-{[(2R)-4-(2,4-difluorophenyl)-2-methylpiperazin-1-yl]sulfonyl}phenyl)-1,1,1-trifluoropropan-2-ol Step 5A: To a solution of (R)-1-(4-(4-(2,4-difluorophenyl)-2-methylpiperazin-1-ylsulfonyl)phenyl)ethanone (360 mg, 0.87 mmol, prepared according to procedures similar to those described in Example 29A) was added $TMSCF_3$ (5.2 mL, 0.5 M in THF, 2.6 mmol) and TBAF (0.87 mL, 1 M in THF, 1.0 mmol) at 0° C. The resultant mixture was stirred for 6 h then rt overnight. It washed with aq. NH4Cl and aq. layer was extracted with DCM. The organic layer was dried over Na2SO4. The crude product was purified on SiO2 column eluted with hexanes/EtOAc to give the desired product as a white solid (329 mg, 81%). HRMS: calcd for $C_{20}H_{21}F_5N_2O_3S$+H+, 465.12658. found (ESI-FTMS, [M+H]$^{1+}$), 465.12565.

Example 29FD 2-(4-{[(2R)-4-(2,4-difluorophenyl)-2-methylpiperazin-1-yl]sulfonyl}phenyl)propan-2-ol Step 5B: To a solution of (R)-1-(4-(4-(2,4-difluorophenyl)-2-methylpiperazin-1-ylsulfonyl)phenyl)ethanone (220 mg, 0.558 mmol, prepared according to procedures similar to those described in Example 29A in THF (3 mL) was added MeLi (0.42 mL, 1.6 M in THF, 0.67 mmol) at −78° C. The resultant mixture was stirred for 6 h then quenched with aq. NH4Cl and aq. layer. It was extracted with DCM. The organic layer was dried over Na2SO4. The crude product was purified on SiO2 column eluted with hexanes/EtOAc to give the desired product as a white solid (167 mg, 73%). HRMS: calcd for $C_{20}H_{24}F_2N_2O_3S$+H+, 411.15484. found (ESI-FTMS, [M+H]$^{1+}$), 411.15477.

Example 29FE 1,1,1-trifluoro-2-[4-({(2R)-2-methyl-4-[4-(4-methylpiperazin-1-yl)-2-(trifluoromethyl)phenyl]piperazin-1-yl}sulfonyl)phenyl]propan-2-ol Prepared according to procedures similar those described in Example 29FC from (R)-1-(4-(2-methyl-4-(4-(4-methylpiperazin-1-yl)-2-(trifluoromethyl)phenyl)piperazin-1-ylsulfonyl)phenyl)ethanone (180 mg, 0.344 mmol), as a white solid (87.6 mg, 43%). HRMS: calcd for $C_{26}H_{32}F_6N_4O_3S$+ H+, 595.21721. found (ESI-FTMS, [M+H]$^{1+}$), 595.21453.

Example 29FF (R)-2-(3-(4-(4-fluoro-2-(trifluoromethyl)phenyl)-2-methylpiperazin-1-ylsulfonyl)phenyl)propan-2-ol Prepared according to procedures similar those described in Example 29FD from (R)-1-(3-(4-(4-fluoro-2-(trifluoromethyl)phenyl)-2-methylpiperazin-1-ylsulfonyl)phenyl)ethanone, as a white solid. HRMS: calcd for $C_{21}H_{24}F_4N_2O_3S$+ H+, 461.15165. found (ESI-FTMS, [M+H]$^{1+}$), 461.1523.

Example 29FG 1,1,1-trifluoro-2-[4-({(2R)-2-methyl-4-[3-(1H-1,2,4-triazol-1-yl)-2-(trifluoromethyl)phenyl]piperazin-1-yl}sulfonyl)phenyl]propan-2-ol Prepared according to procedures similar those described in Example 29FC from (R)-1-(4-(4-(3-(1H-1,2,4-triazol-1-yl)-2-(trifluoromethyl)phenyl)-2-methylpiperazin-1-ylsulfonyl)phenyl)ethanone, as a white solid. HRMS: calcd for $C_{23}H_{23}F_6N_5O_3S+H+$, 564.14985. found (ESI-FTMS, $[M+H]^{1+}$), 564.14965.

Example 29FH (2R)-4-[4-fluoro-2-(trifluoromethyl)phenyl]-2-methyl-1-{[3-(1H-imidazol-1-yl)phenyl]sulfonyl}piperazine Step 6A: A suspension of (R)-1-(3-bromophenylsulfonyl)-4-(4-fluoro-2-(trifluoromethyl)phenyl)-2-methylpiperazine (168 mg, 0.35 mmol), 1,2-trans-diaminomethylcyclohexane (2.9 mg, 0.015 mmol), K3PO4 (8.5 mmg, 0.06 mmol) and Imidazole (41 mg, 0.6 mmol) in dioxane (0.6 mL) was degassed and heated to 120° C. in a sealed tube till disappearance of starting material as monitored by LCMS. The crude reaction mixture was filtered through a pad of Celite and washed with EtOAc. The crude product was purified on SiO2 column eluted with hexanes/EtOAc to give the desired product as a white solid (123 mg, 75%). HRMS: calcd for $C_{21}H_{20}F_4N_4O_2S+H+$, 469.13158. found (ESI-FTMS, $[M+H]^{1+}$), 469.13336.

Example 29FI (2R)-4-[4-fluoro-2-(trifluoromethyl)phenyl]-2-methyl-1-{[3-(1H-pyrazol-1-yl)phenyl]sulfonyl}piperazine Prepared according to procedures similar to those described in Example 29FH from (R)-1-(3-bromophenylsulfonyl)-4-(4-fluoro-2-(trifluoromethyl)phenyl)-2-methylpiperazine (168 mg, 0.35 mmol), and Imidazole (41 mg, 0.6 mmol) as a white solid (152.3 mg, 93%). HRMS: calcd for $C_{21}H_{20}F_4N_4O_2S+H+$, 469.13158. found (ESI-FTMS, $[M+H]^{1+}$), 469.13318.

Example 29FJ (2R)-2-methyl-1-{[3-(1H-1,2,4-triazol-1-yl)phenyl]sulfonyl}-4-[4-(1H-1,2,4-triazol-1-yl)-2-(trifluoromethyl)phenyl]piperazine Prepared according to procedures similar to those described in Example 29FH from (R)-1-(3-bromophenylsulfonyl)-4-(4-fluoro-2-(trifluoromethyl)phenyl)-2-methylpiperazine (96 mg, 0.2 mmol), salicylaldoxime (2.8 mg, 0.02 mmol), K3PO4 (8.5 mmg, 0.06 mmol) and triazole (27.6 mg, 0.4 mmol) in DMF (0.4 mL) as a white solid (major product, 89.4 mg, 86%). HRMS: calcd for $C_{22}H_{21}F_3N_8O_2S+H+$, 519.15330. found (ESI-FTMS, $[M+H]^{1+}$), 519.15377.

Example 29FK

1-[5-({(2R)-4-[4-fluoro-2-(trifluoromethyl)phenyl]-2-methylpiperazin-1-yl}sulfonyl)-2-thienyl]piperazin-2-one Prepared by acid treatment (1N HCl in EtOAc) of tert-butyl 4-(5-((R)-4-(4-fluoro-2-(trifluoromethyl)phenyl)-2-methylpiperazin-1-ylsulfonyl)thiophen-2-yl)-3-oxopiperidine-1-carboxylate, as a white solid [tert-butyl 4-(5-((R)-4-(4-fluoro-2-(trifluoromethyl)phenyl)-2-methylpiperazin-1-ylsulfonyl)thiophen-2-yl)-3-oxopiperidine-1-carboxylate was prepared according to procedures similar to those described in Example 29FH from (R)-1-(5-bromothiophen-2-ylsulfonyl)-4-(4-fluoro-2-(trifluoromethyl)phenyl)-2-methylpiperazine (292 mg, 0.6 mmol), and tert-butyl 3-oxopiperazine-1-carboxylate (181 mg, 0.9 mmol) as a white solid (major product, 89.4 mg, 86%)]. HRMS: calcd for $C_{20}H_{22}F_4N_4O_3S_2+H+$, 507.11422. found (ESI-FTMS, $[M+H]^{1+}$), 507.11461.

Example 29FL (2R)-4-[4-fluoro-2-(trifluoromethyl)phenyl]-2-methyl-2-{[3-(1H-1,2,4-triazol-1-yl)phenyl]sulfonyl}piperazine Prepared according to procedures similar to those described in Example 29FH from (R)-1-(3-bromophenylsulfonyl)-4-(4-fluoro-2-(trifluoromethyl)phenyl)-2-methylpiperazine, without using ligand, as a white solid. HRMS: calcd for $C_{20}H_{19}F_4N_5O_2S+H+$, 470.12683. found (ESI-FTMS, $[M+H]^{1+}$), 470.1276.

Example 29FM (2R)-1-{[2-chloro-4-(1H-1,2,4-triazol-1-yl)phenyl]sulfonyl}-4-[4-fluoro-2-(trifluoromethyl)phenyl]-2-methylpiperazine Prepared according to procedures similar to those described in Example 29FH from (R)-1-(2-chloro-4-fluorophenylsulfonyl)-4-(4-fluoro-2-(trifluoromethyl)phenyl)-2-methylpiperazine, without using ligand, as a white solid. HRMS: calcd for $C_{20}H_{18}ClF_4N_5O_2S+H+$, 504.08786. found (ESI-FTMS, $[M+H]^{1+}$), 504.08778.

Example 29FN (2R)-1-{[3-chloro-4-(1H-1,2,4-triazol-1-yl)phenyl]sulfonyl}-4-[4-fluoro-2-(trifluoromethyl)phenyl]-2-methylpiperazine Prepared according to procedures similar to those described in Example 29FH from (R)-1-(3-chloro-4-fluorophenylsulfonyl)-4-(4-fluoro-2-(trifluoromethyl)phenyl)-2-methylpiperazine, without using ligand, as a white solid. HRMS: calcd for $C_{20}H_{18}ClF_4N_5O_2S+H+$, 504.08786. found (ESI-FTMS, $[M+H]^{1+}$), 504.08934.

Example 29FO

3-[5-({(2R)-4-[4-fluoro-2-(trifluoromethyl)phenyl]-2-methylpiperazin-1-yl}sulfonyl)-2-thienyl]-2-methylpropanoic acid Step 7A: To a solution of (R)-1-(5-bromothiophen-2-ylsulfonyl)-4-(4-fluoro-2-(trifluoromethyl)phenyl)-2-methylpiperazine (389 mg, 0.8 mmol), Pd2(dba)3 (22 mg, 0.024 mmol), ZnF2 (41.6 mg, 0.4 mmol) and P(tBu$_3$)HBF$_4$ (13.9 mg, 0.048 mmol) in DMF (1 mL) was added ketene acetal (0.256 mL, 1.2 mmol) under nitrogen. The resultant mixture was stirred at 100° C. for 3 h. After cooling, it was diluted with EtOAc and washed with brine. Dried over MgSO4. The crude product was purified on SiO2 gel column eluted with hexanes/EtOAc to give 3-[5-({(2R)-4-[4-fluoro-2-(trifluoromethyl)phenyl]-2-methylpiperazin-1-yl}sulfonyl)-2-thienyl]-2-methylpropanoic acid methyl ester as a light yellow sticky oil (285 mg, 70%).

Step 7B: To a solution of 3-[5-({(2R)-4-[4-fluoro-2-(trifluoromethyl)phenyl]-2-methylpiperazin-1-yl}sulfonyl)-2-thienyl]-2-methylpropanoic acid methyl ester (115 mg, 0.2 mmol) in THF (3 mL) was added LiOH (excess) and water (3 mL). The reaction mixture was stirred at rt overnight and acidified with 1N aq. HCl, then extracted with EtOAc. The organic layer was dried over Na2SO4. The crude product was purified on SiO2 column eluted with hexanes/EtOAc to give the titled compounds as a light yellow solid (94 mg, 95%). HRMS: calcd for $C_{20}H_{22}F_4N_2O_4S_2$+H+, 495.10299. found (ESI-FTMS, [M+H]$^{1+}$), 495.10293.

Example 29FP

2-[3-({(2R)-4-[4-fluoro-2-(trifluoromethyl)phenyl]-2-methylpiperazin-1-yl}sulfonyl)phenyl]-2-methylpropanoic acid Prepared according to procedures similar to those described in Example 29FO. Yield 87%. HRMS: calcd for $C_{22}H_{24}F_4N_2O_4S$+H+, 489.14657. found (ESI-FTMS, [M+H]$^{1+}$), 489.14748.

Example 29FQ

2-[3-({(2R)-4-[4-fluoro-2-(trifluoromethyl)phenyl]-2-methylpiperazin-1-yl}sulfonyl)phenyl]-2-methylpropanamide Prepared according to the procedures similar to those described in Example 29FO. Yield 73%. HRMS: calcd for $C_{22}H_{25}F_4N_3O_3S$+H+, 488.16255. found (ESI-FTMS, [M+H]$^{1+}$), 488.164.

Example 29FR 3-chloro-4-({(2R)-4-[4-fluoro-2-(trifluoromethyl)phenyl]-2-methylpiperazin-1-yl}sulfonyl)benzamide Step 9A: A mixture of (R)-3-chloro-4-(4-(4-fluoro-2-(trifluoromethyl)phenyl)-2-methylpiperazin-1-ylsulfonyl)benzonitrile (290 mg, 0.626 mmol) in H2SO4 (3 mL) and TFA (6 mL) was stirred at rt overnight. To this was added ice-water. The precipitate was collected by filtration and washed with water to give the desired product as a white solid (267.5 mg, 89%). HRMS: calcd for $C_{19}H_{18}ClF_4N_3O_3S$+H+, 480.07663. found (ESI-FTMS, [M+H]$^{1+}$), 480.07642.

Example 29FS (2S)-3,3,3-trifluoro-2-[3-({(2R)-4-[4-fluoro-2-(trifluoromethyl)phenyl]-2-methylpiperazin-1-yl}sulfonyl)phenyl]propane-1,2-diol Step A: (2R)-1-[(3-bromophenyl)sulfonyl]-4-[4-fluoro-2-(trifluoromethyl)phenyl]-2-methylpiperazine (960 mg, 2.0 mmol), 4,4,4',4',5,5,5',5'-octamethyl-2,2'-bi(1,3,2-dioxaborolane) (559 mg, 2.2 mmol), PdCl$_2$(dppf)$_2$ (82 mg, 0.1 mmol) and KOAc (588 mg, 6 mmol) in DMSO (5 mL) was degassed and heated in a sealed tube in an oil bath at 60° C. for 12 hours. After cooling, diluted with Et$_2$O and washed with brine and extracted with Et$_2$O. The combined organic layer was dried over Na$_2$SO$_4$. The crude product was purified on SiO$_2$ gel column eluted with hexanes/EtOAc to give the desired product (R)-4-(4-fluoro-2-(trifluoromethyl)phenyl)-2-methyl-1-(3-(4,4,5,5-tetramethyl-1,3,2-dioxaborolan-2-yl)phenylsulfonyl)piperazine (916 mg, 87%).

Step B: A solution of (R)-4-(4-fluoro-2-(trifluoromethyl)phenyl)-2-methyl-1-(3-(4,4,5,5-tetramethyl-1,3,2-dioxaborolan-2-yl)phenylsulfonyl)piperazine (106 mg, 0.2 mmol) and Pd(PPh$_3$) (12 mg, 0.01 mmol) in THF (2 mL) was degassed and then added Na$_2$CO$_3$ (0.6 mL, 1.0 M in water, 0.6 mmol) and 2-bromo-3,3,3-trifluoroprop-1-ene (105 mg, 0.6 mmol) under N$_2$. The resultant mixture was heated in a sealed tube in an oil bath at 60° C. overnight. After cooling, diluted with Et$_2$O (10 mL), washed with brine and extracted with Et$_2$O. The combined organic layer was dried over Na$_2$SO$_4$. The crude product was purified on SiO$_2$ gel column eluted with hexanes/EtOAc to give (R)-4-(4-fluoro-2-(trifluoromethyl)phenyl)-2-methyl-1-(3-(3,3,3-trifluoroprop-1-en-2-yl)phenylsulfonyl)piperazine as a colorless oil (83 mg, 85%).

Step C: A slurry of (R)-4-(4-fluoro-2-(trifluoromethyl)phenyl)-2-methyl-1-(3-(3,3,3-trifluoroprop-1-en-2-yl)phenylsulfonyl)piperazine was dissolved in aqueous tBuOH (1:1 vol) with slight heating via heat gun, under continuous stirring until ~75% of the solid was in solution. The solution was allowed to cool slightly, (T=40-50° C. max), and then slowly added to a flask containing 5 mol % (DHQ)Phal ligand, and 1.0 eq. MeSO$_2$NH$_2$ at 0° C. Immediately following, AD mix α (1.5 g/mmol of substrate) was added to the solution, and it was allowed to stir at 0° C., never exceeding 2-3° C. for 48 hours, after which it can be judged complete by TLC (EtOAc/Hexanes 1/5 vol). Workup: Add excess saturated aqueous Na$_2$S$_2$O$_3$ and allow the reaction to stir for 20-30 minutes, warming to room temperature, and extract into DCM. The organic layer was dried over Na$_2$SO$_4$ and washed with brine. The crude product was purified on SiO$_2$ gel column eluted with hexanes/EtOAc to give the desired product as a white solid. HRMS: calcd for $C_{21}H_{21}F_7N_2O_4S$+H+, 531.11830. found (ESI-FTMS, [M+H]$^{1+}$), 531.11699.

Example 29FT (2S)-3,3,3-trifluoro-2-[3-({(2R)-4-[4-fluoro-2-(trifluoromethyl)phenyl]-2-methylpiperazin-1-yl}sulfonyl)phenyl]propane-1,2-diol The title compound was according to the procedure described in Example 29FS except that AD mix α was replaced with AD mix β. HRMS: calcd for $C_{21}H_{21}F_7N_2O_4S$+H+, 531.11830. found (ESI-FTMS, [M+H]$^{1+}$), 531.11675.

Example 29FU (2S,4S)-1-[(3-bromophenyl)sulfonyl]-4-[4-fluoro-2-(trifluoromethyl)phenyl]-2-methylpiperidine Step 11A: A reaction mixture of 4-fluoro-2-(trifluoromethyl)benzoyl fluoride (1.36 mL, 10 mmol), dimethyl 2-oxopropylphosphonate (1.366 mL, 10 mmol) and $K_2CO_3$ (1.65 g, 12 mmol) in MeCN (20 mL) was stirred at room temperature for 26 h. It was then diluted with EtOAc and washed with brine. The organic layer was dried over $Na_2SO_4$ and crude product was purified on $SiO_2$ gel column eluted with hexanes/EtOAc to give the desired product (E)-4-(4-fluoro-2-(trifluoromethyl)phenyl)but-3-en-2-one (2.3 g, 99%).

Step B: A solution of (E)-4-(4-fluoro-2-(trifluoromethyl)phenyl)but-3-en-2-one (696 mg, 3.0 mmol), and Jacobsen [(s,s)-(salen)]2Al (69.2 mg, 0.045 mmol) and ethyl cyanoacetate (383.8 mL, 3.6 mmol) in cyclohexane (13 mL) was stirred at room temperature for 24 h. The solvent was removed, and the crude product was purified on $SiO_2$ gel column eluted with hexanes/EtOAc to give the desired product (2R,3R)-ethyl 2-cyano-3-(4-fluoro-2-(trifluoromethyl)phenyl)-5-oxohexanoate (750 mg, 72%).

Step C: A solution of (2R,3R)-ethyl 2-cyano-3-(4-fluoro-2-(trifluoromethyl)phenyl)-5-oxohexanoate (750 mg, 2.17 mmol) in DMSO (20 mL) and water (10 mL) was heated to 130° C. in microwave oven for 1.5 h. It was diluted with water (80 mL) and extracted with $Et_2O$ (3×80 mL). The organic layer was dried over $MgSO_4$. The crude product was purified on SiO2 gel column eluted with hexanes/EtOAc to give the desired product (S)-3-(4-fluoro-2-(trifluoromethyl)phenyl)-5-oxohexanenitrile (500 mg, 84%).

Step D: To a solution of (S)-3-(4-fluoro-2-(trifluoromethyl)phenyl)-5-oxohexanenitrile (482 mg, 1.76 mmol) was added $NaBH_4$ in MeOH (10 mL) at 0° C. The reaction was stirred for 20 minutes and quenched with aq. NH4Cl and then extracted with DCM. The organic layer was dried over $MgSO_4$ and the crude product mixture was purified on $SiO_2$ gel column eluted with hexanes/EtOAC to give the desired product (3S)-3-(4-fluoro-2-(trifluoromethyl)phenyl)-5-hydroxyhexanenitrile (390 mg, 81%, 3.5:1 mixture).

Step E: To a solution of (3S)-3-(4-fluoro-2-(trifluoromethyl)phenyl)-5-hydroxyhexanenitrile (340 mg, 1.23 mmol) in DCE (6 mL) was added TEA (516 mL, 3.9 mmol) and then MsCl (124.4 mL, 1.61 mmol) at 0° C. It was stirred at room temperature overnight and washed with brine. The crude reaction product was purified on $SiO_2$ gel column eluted with hexanes/EtOAc to give the desired mesylate (420 mg, 97%).

Step F: To a solution of mesylate, obtained from Step E, in MeOH was added Pd/C (~60 mg). The reaction mixture was stirred under $H_2$ at 50 psi for 4 days. It was then filtered through a pad of Celite. The resultanted methanol solution was concentrated (~5 mL). To this was added DIPEA (436 mL, 2.5 mmol). The reaction mixture was then heated in microwave oven at 100° C. for 30 minutes. The solvent was removed under vacuum. The crude product was purified on $SiO_2$ column eluted with EtOAc/MeOH to give the desired product (2S,4S)-4-(4-fluoro-2-(trifluoromethyl)phenyl)-2-methylpiperidine as single diastereomer (150 mg, 51%).

Step G: Prepared from (2S,4S)-4-(4-fluoro-2-(trifluoromethyl)phenyl)-2-methylpiperidine (120 mg, 0.46 mmol) and 3-bromophenylsulfonyl chloride (99.4 mL, 0.69 mmol) according to scheme III-11 in 97% yield. HRMS: calcd for $C_{19}H_{18}BrF_4NO_2S$+H+, 480.02505. found (ESI-FTMS, [M+H]$^{1+}$), 480.02396.

Example 29FV

1-[3-({(2S,4S)-4-[4-fluoro-2-(trifluoromethyl)phenyl]-2-methylpiperidin-1-yl}sulfonyl)phenyl]-4-methylpiperazine The title compound was prepared in a manner similar to that described in Example 29FU. Yield 24%. HRMS: calcd for $C_{24}H_{29}F_4N_3O_2S$+H+, 500.19893. found (ESI-FTMS, [M+H]$^{1+}$), 500.19814.

Example 29FW (2R)-4-[4-fluoro-2-(trifluoromethyl)phenyl]-1-[(4-methoxyphenyl)sulfonyl]-2-methylpiperazine Step 1. A 1 L round bottom flask was charged with a stirbar, (R)-2-Methylpiperazine (20.0 g, 200.0 mmol), Sodium tert-butoxide (28.0 g, 300 mmol), BINAP (12.4 g, 20 mmol), and $Pd_2(dba)_3$. The flask was sealed and vacuum-purged with $N_2$ three times. Toluene (500.0 mL) was then added under $N_2$, followed by 2-Bromo-5-Fluorobenzotrifluoride (31.4 mL, 220.0 mmol). The reaction mixture was heated to 105° C. under thermal conditions for three hours, upon which the reaction cooled to room temperature, and diluted with diethyl ether (2.0 L) and filtered through celite, to remove inorganics and excess BINAP. The filtrate was collected and the product was extracted into 10% HCl (2×500 mL). The organic layers were then discarded and the aqueous layer was basified to pH 10 using 3M NaOH (~300 mL). Product was then extracted into ether (3×500 mL). The organic layers were combined and dried over $Na_2SO_4$, decanted, and concentrated in vacuo, and the resultant crude oil (>95% purity by $^1$H-NMR) was taken on to the next step without further purification. 90% yield (51 g).

Step 2: To solution of 1-(4-Fluoro-2-trifluoromethyl-phenyl)-3-methyl-piperazine (200 mg, 0.76 mmol) and DIPEA (0.33 mL, 1.90 mmol) in DCM (8.0 mL) was added 4-Methoxybenzenesulfonyl chloride. The reaction was allowed to stir over a 12-16 hr period, after which it was judged complete by TLC. The reaction mixture was concentrated in-vacuo, and the resultant crude oil was purified via normal phase $SiO_2$ column chromatography using a 2%-10% EtOAc/Hex solvent gradient. The desired product, was isolated in >95% purity. HRMS: calcd for $C_{19}H_{20}F_4N_2O_3S$+H+, 433.12035. found ([M+H]$^{1+}$), 433.12037.

Example 29FX 4-({(2R)-4-[4-fluoro-2-(trifluoromethyl)phenyl]-2-methylpiperazin-1-yl}sulfonyl)benzonitrile Step 2: Prepared according to the procedure for Example 29FW, step 2, with the exception of a slightly more polar solvent system for purification (2%-20% EtOAc/Hex) affording 230 mg of the desired sulfonamide in >95% purity (65% yield). HRMS: calcd for $C_{19}H_{17}F_4N_3O_2S$+H+, 428.10503. found ([M+H]$^+$), 428.1057. HPLC Method 1: room temperature, 6.822 min, 92.14%. HPLC Method 2: room temperature, 7.395 min, 90.74%.

Example 29FY (2R)-1-[(4-bromo-2-chlorophenyl)sulfonyl]-4-[4-fluoro-2-(trifluoromethyl)phenyl]-2-methylpiperazine Step 2: Prepared according to the procedure for Example 29FW, step 2, affording 850 mg of the desired sulfonamide in >95% purity (72% yield). HRMS: calcd for $C_{18}H_{16}BrClF_4N_2O_2S+H+$, 514.98132. found ([M+H]$^+$), 514.98153. HPLC Method 1: room temperature, 7.704 min, 99.20%. HPLC Method 2: room temperature, 8.125 min, 98.12%.

Example 29FZ (2R)-1-[(4,5-dichloro-2-thienyl)sulfonyl]-4-[4-fluoro-2-(trifluoromethyl)phenyl]-2-methylpiperazine Step 2: Prepared according to the procedure for Example 29FW, step 2, affording 900 mg of the desired sulfonamide in >95% purity (83% yield). HRMS: calcd for $C_{16}H_{14}Cl_2F_4N_2O_2S_2+H+$, 476.98826. found ([M+H]$^+$), 476.9865. HPLC Method 1: room temperature, 7.771 min, 96.52%. HPLC Method 2: room temperature, 8.194 min, 97.28%.

Example 29GA (2R)-1-[(3-chloro-2-methylphenyl)sulfonyl]-4-[4-fluoro-2-(trifluoromethyl)phenyl]-2-methylpiperazine Step 2: Prepared according to the procedure for Example 29FW, step 2, affording 876 mg of the desired sulfonamide in >95% purity (80% yield). HRMS: calcd for $C_{19}H_{19}ClF_4N_2O_2S+H+$, 451.08646. found ([M+H]$^+$), 451.0849. HPLC Method 1: room temperature, 7.623 min, 96.58%. HPLC Method 2: room temperature, 8.050 min, 96.36%.

Example 29 GB (2R)-1-[(2,3-dichlorophenyl)sulfonyl]-4-[4-fluoro-2-(trifluoromethyl)phenyl]-2-methylpiperazine Step 2: Prepared according to the procedure for Example 29FW, step 2, affording 876 mg of the desired sulfonamide in >95% purity (83% yield). HRMS: calcd for $C_{18}H_{16}Cl_2F_4N_2O_2S+H+$, 471.03184. found ([M+H]$^+$), 471.0303. HPLC Method 1: room temperature, 7.529 min, 100%. HPLC Method 2: room temperature, 7.972 min, 99.21%.

Example 29GC (2R)-1-[(3-fluorophenyl)sulfonyl]-4-[4-fluoro-2-(trifluoromethyl)phenyl]-2-methylpiperazine Step 2: Prepared according to the procedure for Example 29FW, step 2, affording 1.1 g of the desired sulfonamide in >95% purity (87% yield). HRMS: calcd for $C_{18}H_{17}F_5N_2O_2S+H+$, 421.10036. found ([M+H]$^+$), 421.0991.

Example 29GD 3-({(2R)-4-[4-fluoro-2-(trifluoromethyl)phenyl]-2-methylpiperazin-1-yl}sulfonyl)aniline Step 2: Prepared according to the procedure for Example 29FW, step 2, affording 330 mg of 4-(4-Fluoro-2-trifluoromethyl-phenyl)-2-methyl-1-(3-nitro-benzenesulfonyl)-piperazine in >95% purity (47% yield).

Step 3: A solution of 4-(4-Fluoro-2-trifluoromethyl-phenyl)-2-methyl-1-(3-nitro-benzenesulfonyl)-piperazine (330 mg, 0.8 mmol) and a catalytic amount of 10% Pd/C in EtOAc (25 mL) was stirred under $H_2$ (1 atm) at ambient temperature for two hours, after which the reduction was judged complete by TLC. The $H_2$ removed under vacuum, and the reaction mixture was filtered through celite, and rinsed with EtOAc (3×25 mL), and the filtrate was concentrated in vacuo, affording 180 mg of the desired sulfonamide in >95% purity (62% yield). HRMS: calcd for $C_{18}H_{19}F_4N_3O_2S+H+$, 418.12068. found ([M+H]$^+$), 418.12119.

Example 29GE (2R)-4-[4-fluoro-2-(trifluoromethyl)phenyl]-2-methyl-1-(2-thienylsulfonyl)piperazine Step 2: Prepared according to the procedure for Example 29FW, step 2, affording 330 mg of the desired sulfonamide in >95% purity (98% yield). HRMS: calcd for $C_{16}H_{16}F_4N_2O_2S_2+H+$, 409.06621. found ([M+H]$^+$), 409.06656. HPLC Method 1: room temperature, 7.382 min, 88.19%. HPLC Method 2: room temperature, 6.871 min, 78.28%.

Example 29GF

4-{(3R)-4-[(4-bromo-2-chlorophenyl)sulfonyl]-3-methylpiperazin-1-yl}-3-(trifluoromethyl)benzonitrile Step 2: Prepared according to the procedure for Example 29FW, step 2, with the exception of a slightly more polar solvent system for purification (2%-30% EtOAc/Hex) affording 150 mg of the desired sulfonamide in >95% purity (33% yield). HRMS: calcd for $C_{19}H_{16}BrClF_3N_3O_2S+H+$, 521.98600. found ([M+H]$^+$), 521.98688.

Example 29GG

4-{(3R)-4-[(4-bromo-2-fluorophenyl)sulfonyl]-3-methylpiperazin-1-yl}-3-(trifluoromethyl)benzonitrile Step 2: Prepared according to the procedure for Example 29FW, step 2, with the exception of a slightly more polar solvent system for purification (2%-30% EtOAc/Hex) affording 200 mg of the desired sulfonamide in >95% purity (45% yield). HRMS: calcd for $C_{19}H_{16}BrF_4N_3O_2S+H+$, 506.01555. found ([M+H]$^+$), 506.01605.

Example 29 GH (2R)-4-[4-fluoro-2-(trifluoromethyl)phenyl]-2-methyl-1-{[4-(trifluoromethoxy)phenyl]sulfonyl}piperazine

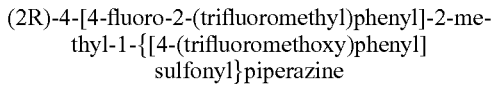

Step 2: Prepared according to the procedure for Example 29FW, step 2, affording the desired sulfonamide in >95% purity. HRMS: calcd for $C_{19}H_{17}F_7N_2O_3S+H+$, 487.09208. found ([M+H]$^+$), 487.09215. HPLC Method 1: room temperature, 7.660 min, 92.30%. HPLC Method 2: room temperature, 7.797 min, 83.08%.

Example 29GI

4-[3-chloro-4-({(2R)-4-[4-fluoro-2-(trifluoromethyl)phenyl]-2-methylpiperazin-1-yl}sulfonyl)phenyl]morpholine

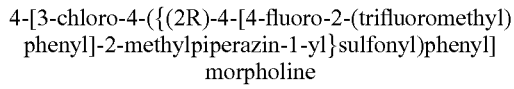

A 5-mL microwave vial was charged with a stirbar, (2R)-1-[(4-bromo-2-chlorophenyl)sulfonyl]-4-[4-fluoro-2-(trifluoromethyl)phenyl]-2-methylpiperazine (250 mg, 0.49 mmol), Sodium tert-butoxide (77 mg, 0.74 mmol), BINAP (31 mg, 0.05 mmol), and $Pd_2(dba)_3$ (25 mg, 0.03 mmol). The vial was sealed and vacuum-purged with $N_2$ three times. Toluene (2.0 mL) was then added under $N_2$, followed by morpholine (0.05 mL, 0.53 mmol). The reaction mixture was heated to 75° C. under thermal conditions for 30 minutes, upon which the reaction was judged complete by LCMS. The reaction mixture was diluted with EtOAc (100 mL), and filtered through celite to remove inorganics. The filtrate was concentrated in vacuo and the crude product was directly loaded onto a $SiO_2$ column and purified via normal phase chromatography (5%-50% EtOAc/Hexanes gradient), affording the desired compound in >95% purity. HRMS: calcd for $C_{22}H_{24}ClF_4N_3O_3S+H+$, 522.12358. found ([M+H]$^+$), 522.12358. HPLC Method 1: room temperature, 7.125 min, 100%. HPLC Method 2: room temperature, 7.664 min, 100%.

Example 29GJ (2R)-1-[(2-chloro-4-piperidin-1-ylphenyl)sulfonyl]-4-[4-fluoro-2-(trifluoromethyl)phenyl]-2-methylpiperazine Prepared according to the procedure for Example 29GI, affording the desired compound in >95% purity. HRMS: calcd for $C_{23}H_{26}ClF_4N_3O_2S+H+$, 520.14431. found ([M+H]$^+$), 520.1445. HPLC Method 1: room temperature, 7.914 min, 79.25%. HPLC Method 2: room temperature, 8.209 min, 78.92%.

Example 29GK (2R)-1-{[2-chloro-4-(4-methylpiperazin-1-yl)phenyl]sulfonyl}-4-[4-fluoro-2-(trifluoromethyl)phenyl]-2-methylpiperazine

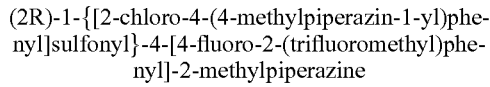

Prepared according to the procedure for Example 29GI, with the exception of purification which was done on reversed phase HPLC, under acidic conditions, (10%-90% ACN/H$_2$O gradient), affording the desired compound in >95% purity. HRMS: calcd for $C_{23}H_{27}ClF_4N_4O_2S+H+$, 535.15521. found ([M+H]$^+$), 535.1576. HPLC Method 1: room temperature, 4.647 min, 89.88%. HPLC Method 2: room temperature, 5.774 min, 93.13%.

Example 29GL (2R)-1-[(4-tert-butoxy-2-chlorophenyl)sulfonyl]-4-[4-fluoro-2-(trifluoromethyl)phenyl]-2-methylpiperazine

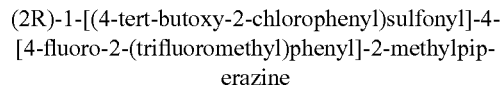

Buchwald Reaction: Prepared according to the procedure for Example 29GI, without an amine, (excess NaOtBu as nucleophile), affording the desired compound in >95% purity. HPLC Method 1: room temperature, 8.041 min, 97.87%. HPLC Method 2: room temperature, 8.296 min, 98.22%.

Example 29GM (2R)-1-[(4-tert-butoxy-2-fluorophenyl)sulfonyl]-4-[4-fluoro-2-(trifluoromethyl)phenyl]-2-methylpiperazine

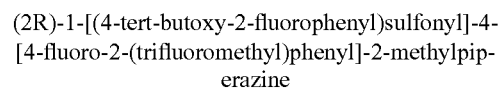

Buchwald Reaction: Prepared according to the procedure for Example 29GI, affording the desired compound in >95% purity. HRMS: calcd for $C_{23}H_{27}F_5N_4O_2S+H+$, 493.15788. found ([M+H]$^+$), 493.15802.

Example 29GN 3-chloro-4-({(2R)-4-[4-fluoro-2-(trifluoromethyl)phenyl]-2-methylpiperazin-1-yl}sulfonyl)-N,N-dimethylaniline

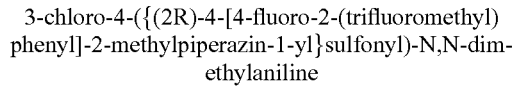

Buchwald Amination: Prepared according to the procedure for Example 29GI, affording the desired compound in >95% purity. HRMS: calcd for $C_{20}H_{22}ClF_4N_3O_2S+H+$, 480.11301. found ([M+H]$^+$), 480.1129. HPLC Method 1: room temperature, 7.390 min, 82.15%. HPLC Method 2: room temperature, 7.824 min, 76.87%.

Example 29GO (2R)-1-[(2-chloro-4-pyrrolidin-1-ylphenyl)sulfonyl]-4-[4-fluoro-2-(trifluoromethyl)phenyl]-2-methylpiperazine

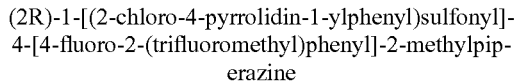

Buchwald Amination: Prepared according to the procedure for Example 29GI, affording the desired compound in >95% purity. HRMS: calcd for $C_{22}H_{24}ClF_4N_3O_2S+H+$, 506.12866. found ([M+H]$^+$), 506.12849. HPLC Method 1: room temperature, 7.786 min, 87.96%. HPLC Method 2: room temperature, 8.019 min, 86.35%.

Example 29GP

N-tert-butyl-3-chloro-4-({(2R)-4-[4-fluoro-2-(trifluoromethyl)phenyl]-2-methylpiperazin-1-yl}sulfonyl)aniline

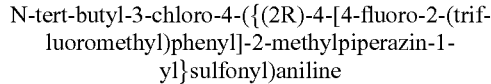

Buchwald Amination: Prepared according to the procedure for Example 29GI, affording the desired compound in >95% purity. HRMS: calcd for $C_{22}H_{26}ClF_4N_3O_2S+H+$, 508.14431. found ([M+H]$^+$), 508.14549. HPLC Method 1: room temperature, 7.622 min, 95.55%. HPLC Method 2: room temperature, 7.963 min, 72.56%.

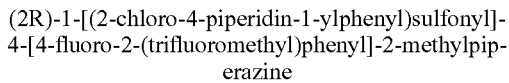

Example 29GQ 3-chloro-4-({(2R)-4-[4-fluoro-2-(trifluoromethyl)phenyl]-2-methylpiperazin-1-yl}sulfonyl)-N-isobutylaniline Buchwald Amination: Prepared according to the procedure for Example 29GI, affording the desired compound in >95% purity. HRMS: calcd for $C_{22}H_{26}ClF_4N_3O_2S$+H+, 508.14431. found ([M+H]$^+$), 508.1442. HPLC Method 1: room temperature, 7.692 min, 88.44%. HPLC Method 2: room temperature, 8.035 min, 81.22%.

Example 29GR

1-[3-chloro-4-({(2R)-4-[4-fluoro-2-(trifluoromethyl)phenyl]-2-methylpiperazin-1-yl}sulfonyl)phenyl]piperidin-4-ol Buchwald Amination: Prepared according to the procedure for Example 29GI, with the exception of the use of a more polar solvent system for purification (20%-100% EtOAc/Hexanes) affording the desired compound in >95% purity. HPLC Method 1: room temperature, 6.637 min, 84.22%. HPLC Method 2: room temperature, 7.517 min, 83.74%.

Example 29GS (2R)-1-({2-chloro-4-[(3S)-3-methylpiperazin-1-yl]phenyl}sulfonyl)-4-[4-fluoro-2-(trifluoromethyl)phenyl]-2-methylpiperazine Buchwald Amination: Prepared according to the procedure for Example 29GI, with the exception of purification protocol; product precipitated out of the organic layer as it was being concentrated in vacuo, and upon filtration, it was afforded in >95% purity. HRMS: calcd for $C_{23}H_{27}ClF_4N_4O_2S$+H+, 535.15521. found ([M+H]$^+$), 535.15532. HPLC Method 1: room temperature, 5.139 min, 92.40%. HPLC Method 2: room temperature, 6.299 min, 100%.

Example 29GT

1-[3-chloro-4-({(2R)-4-[4-fluoro-2-(trifluoromethyl)phenyl]-2-methylpiperazin-1-yl}sulfonyl)phenyl]-N,N-dimethylpiperidin-4-amine Buchwald Amination: Prepared according to the procedure for Example 29GI, with the exception of purification using a more polar solvent system (0%-10% MeOH/EtOAc) affording the desired compound in >95% purity. HRMS: calcd for $C_{25}H_{31}ClF_4N_4O_2S$+H+, 563.18651. found ([M+H]$^+$), 563.18857. HPLC Method 1: room temperature, 5.258 min, 85.99%. HPLC Method 2: room temperature, 6.356 min, 100%.

Example 29GU

4-[3-chloro-4-({(2R)-4-[4-fluoro-2-(trifluoromethyl)phenyl]-2-methylpiperazin-1-yl}sulfonyl)phenyl]thiomorpholine 1,1-dioxide Prepared according to the procedure for Example 29GI, with the exception of purification using a more polar solvent system (5%-40% EtOAc/Hexanes) affording the desired compound in >95% purity. HRMS: calcd for $C_{22}H_{24}ClF_4N_3O_4S_2$+H+, 570.09056. found ([M+H]$^+$), 570.09181. HPLC Method 1: room temperature, 6.908 min, 89.31%. HPLC Method 2: room temperature, 7.186 min, 60.60%.

Example 29GV

4-[3-fluoro-4-({(2R)-4-[4-fluoro-2-(trifluoromethyl)phenyl]-2-methylpiperazin-1-yl}sulfonyl)phenyl]morpholine Prepared according to the procedure for Example 29GI, affording 100 mg of the desired compound in >95% purity (49% yield). HRMS: calcd for $C_{22}H_{24}F_5N_3O_3S$+H+, 506.15313. found ([M+H]$^+$), 506.15321.

Example 29GW

4-[3-chloro-4-({(2R)-4-[4-fluoro-2-(trifluoromethyl)phenyl]-2-methylpiperazin-1-yl}sulfonyl)phenyl]-2,6-cis-dimethylmorpholine Prepared according to the procedure for Example 29GI, affording the desired compound in >95% purity. HRMS: calcd for $C_{24}H_{28}ClF_4N_3O_3S$+H+, 550.15488. found ([M+H]$^+$), 550.15497. HPLC Method 1: room temperature, 7.454 min, 98.89%. HPLC Method 2: room temperature, 6.334 min, 87.84%.

Example 29GX

1-[3-chloro-4-({(2R)-4-[4-fluoro-2-(trifluoromethyl)phenyl]-2-methylpiperazin-1-yl}sulfonyl)phenyl]piperidine-4-carboxylic acid Prepared according to the procedure for Example 29GI, with the ethyl ester of the amine, affording the ethyl ester of the desired compound in >95% purity. Removal of the ester group was achieved under basic conditions (KOH$_{(aq)}$/THF), yielding the desired acid compound. HRMS: calcd for $C_{24}H_{26}ClF_4N_3O_4S$+H+, 564.13414. found ([M+H]$^+$), 564.13421. HPLC Method 1: room temperature, 7.942 min, 92.23%. HPLC Method 2: room temperature, 7.591 min, 92.35%.

Example 29GY

4-[3-chloro-4-({(2R)-4-[4-fluoro-2-(trifluoromethyl)phenyl]-2-methylpiperazin-1-yl}sulfonyl)phenyl]piperazin-2-one Prepared according to the procedure for Example 29GI, with the exception of purification protocol; the crude solid afforded after workup was triturated with EtOAc, yielding the desired compound in >95% purity. HRMS: calcd for $C_{22}H_{23}ClF_4N_4O_3S$+H+, 535.11883. found ([M+H]$^+$), 535.11947.

Example 29GZ

1-[3-chloro-4-({(2R)-4-[4-fluoro-2-(trifluoromethyl)phenyl]-2-methylpiperazin-1-yl}sulfonyl)phenyl]piperidine-4-carboxamide Prepared according to the procedure for Example 29GI, affording the desired compound in >95% purity. HRMS: calcd for $C_{24}H_{27}ClF_4N_4O_3S$+H+, 563.15013. found ([M+

H]+), 563.15087. HPLC Method 1: room temperature, 7.358 min, 87.78%. HPLC Method 2: room temperature, 6.165 min, 86.98%.

Example 29HA (2R)-1-({2-chloro-4-[(3R)-3-methylpiperazin-1-yl] phenyl}sulfonyl)-4-[4-fluoro-2-(trifluoromethyl) phenyl]-2-methylpiperazine Buchwald Amination: Prepared according to the procedure for Example 29GI, affording the desired compound in >95% purity. HRMS: calcd for $C_{23}H_{27}ClF_4N_4O_2S+H+$, 535.15521. found ([M+H]+), 535.15631. HPLC Method 1: room temperature, 5.209 min, 85.44%. HPLC Method 2: room temperature, 6.358 min, 84.83%.

Example 29HB

1-[3-chloro-4-({(2R)-4-[4-fluoro-2-(trifluoromethyl) phenyl]-2-methylpiperazin-1-yl}sulfonyl)phenyl] piperazin-2-one Buchwald Amination: Prepared according to the procedure for Example 29GI, with the 4-Boc-protected amine, affording the Boc-protected analog of the desired compound in >95% purity. Removal of the Boc group was achieved under acidic conditions (TFA/DCM), yielding the desired free amine. HRMS: calcd for $C_{22}H_{23}ClF_4N_4O_3S+H+$, 535.11883. found ([M+H]+), 535.11947.

Example 29HC (2R)-1-{[2-chloro-4-(4-fluoropiperidin-1-yl)phenyl] sulfonyl}-4-[4-fluoro-2-(trifluoromethyl)phenyl]-2-methylpiperazine Prepared according to the procedure for Example 29GI, affording the desired compound in >95% purity. HRMS: calcd for $C_{21}H_{24}F_5N_3O_2S_2+H+$, 510.13028. found ([M+H]+), 510.12968.

Example 29HD (2R)-1-{[3-(4,4-difluoropiperidin-1-yl)phenyl]sulfonyl}-4-[4-fluoro-2-(trifluoromethyl)phenyl]-2-methylpiperazine Prepared according to the procedure for Example 29GI, affording the desired compound in >95% purity. HRMS: calcd for $C_{21}H_{23}F_6N_3O_2S_2+H+$, 522.16444. found ([M+H]+), 522.16468.

Example 29HE

4-[3-({(2R)-4-[4-fluoro-2-(trifluoromethyl)phenyl]-2-methylpiperazin-1-yl}sulfonyl)-4-methoxyphenyl] morpholine Prepared from 1-(5-Bromo-2-methoxy-benzenesulfonyl)-4-(4-fluoro-2-(trifluoromethyl-phenyl)-2-methyl-piperazine and morpholine using sodium tert-butoxide, BINAP, $Pd_2 dba_3$ and toluene, affording the desired compound in >95% purity. HRMS: calcd for $C_{23}H_{27}F_4N_3O_4S+H+$, 518.17312. found ([M+H]+), 518.1716.

Example 29HF (2R)-4-[4-fluoro-2-(trifluoromethyl)phenyl]-1-[(2-methoxy-5-piperidin-1-ylphenyl)sulfonyl]-2-methylpiperazine Prepared according to Example 29HE, affording the desired compound in >95% purity. HRMS: calcd for $C_{24}H_{29}F_4N_3O_3S+H+$, 516.19385. found ([M+H]+), 516.1943. HPLC Method 1: room temperature, 6.597 min, 84.34%. HPLC Method 2: room temperature, 7.739 min, 88.94%.

Example 29HG (2R)-4-[4-fluoro-2-(trifluoromethyl)phenyl]-1-{[2-methoxy-5-(4-methylpiperazin-1-yl)phenyl]sulfonyl}-2-methylpiperazine Prepared according to Example 29HE, with the exception of purification by reversed phase HPLC under acidic conditions (10%-90% ACN/$H_2O$), affording the desired compound in >95% purity. HRMS: calcd for $C_{24}H_{30}F_4N_4O_3S+H+$, 531.20475. found ([M+H]+), 531.2064. HPLC Method 1: room temperature, 4.514 min, 87.19%. HPLC Method 2: room temperature, 5.435 min, 89.27%.

Example 29HH

4-[2-chloro-3-({(2R)-4-[4-fluoro-2-(trifluoromethyl) phenyl]-2-methylpiperazin-1-yl}sulfonyl)phenyl] morpholine HRMS: calcd for $C_{22}H_{24}ClF_4N_3O_3S+H+$, 522.12358. found ([M+H]+), 522.1237.

Example 29HI (2R)-1-[(2-chloro-3-piperidin-1-ylphenyl)sulfonyl]-4-[4-fluoro-2-(trifluoromethyl)phenyl]-2-methylpiperazine HRMS: calcd for $C_{23}H_{26}ClF_4N_3O_2S+H+$, 520.14431. found ([M+H]+), 520.14552.

Example 29HJ

4-[3-({(2R)-4-[4-fluoro-2-(trifluoromethyl)phenyl]-2-methylpiperazin-1-ylphenyl}sulfonyl)-2-methylphenyl]morpholine HRMS: calcd for $C_{23}H_{27}F_4N_3O_3S+H+$, 502.17820. found ([M+H]+), 502.1787.

Example 29HK

4-[3-chloro-5-({(2R)-4-[4-fluoro-2-(trifluoromethyl) phenyl]-2-methylpiperazin-1-ylphenyl}sulfonyl)-2-thienyl]morpholine HRMS: calcd for $C_{20}H_{22}ClF_4N_3O_3S_2+H+$, 528.08000. found ([M+H]+), 528.0800.

Example 29HL (2R)-1-{[3-(4-fluoropiperidin-1-yl)phenyl]sulfonyl}-4-[4-fluoro-2-(trifluoromethyl)phenyl]-2-methylpiperazine HRMS: calcd for $C_{23}H_{26}F_5N_3O_2S+H+$, 504.17386. found ([M+H]+), 504.17263.

Example 29HM (2R)-1-{[3-(4,4-difluoropiperidin-1-yl)phenyl]sulfonyl}-4-[4-fluoro-2-(trifluoromethyl)phenyl]-2-methylpiperazine HRMS: calcd for $C_{23}H_{25}F_6N_3O_2S+H+$, 522.16444. found ([M+H]+), 522.16468.

Example 29HN

4-[4-({(2R)-4-[4-fluoro-2-(trifluoromethyl)phenyl]-2-methylpiperazin-1-yl}sulfonyl)phenyl]morpholine HPLC Method 1: room temperature, 6.8951 min, 75.92%.
HPLC Method 2: room temperature, 7.523 min, 78.91%.

Example 29HO

Ethyl 1-[3-({(2R)-4-[4-fluoro-2-(trifluoromethyl)phenyl]-2-methylpiperazin-1-yl}sulfonyl)phenyl]piperidine-4-carboxylate HRMS: calcd for $C_{20}H_{19}F_4N_5O_2S+H+$, 470.12683. found ([M+H]+), 470.12538.

Example 29HP

4-{(3R)-4-[(4-tert-butoxy-2-chlorophenyl)sulfonyl]-3-methylpiperazin-1-yl}-3-(trifluoromethyl)benzonitrile HRMS: calcd for $C_{23}H_{25}ClF_3N_3O_3S+H+$, 516.13300. found ([M+H]+), 516.13467.

Example 29HQ

4-{(3R)-4-[(4-tert-butoxy-2-fluorophenyl)sulfonyl]-3-methylpiperazin-1-yl}-3-(trifluoromethyl)benzonitrile

Example 29HR

1-[3-({(2R)-4-[4-fluoro-2-(trifluoromethyl)phenyl]-2-methylpiperazin-1-yl}sulfonyl)phenyl]-N,N-dimethylpiperidine-4-carboxamide Step 1: To a solution of ethyl 1-[3-({(2R)-4-[4-fluoro-2-(trifluoromethyl)phenyl]-2-methylpiperazin-1-yl}sulfonyl)phenyl]piperidine-4-carboxylate (100 mg, 0.18 mmol) in THF (5.0 mL) was added 2.0M KOH (0.5 mL, 1.0 mmol). The reaction was allowed to stir at ambient temperature over a 16 hour period, after which it was judged complete by LCMS. THF was removed in vacuo, and the remaining aqueous solution was acidified to pH 4 via addition of 10% HCl solution drop-wise. The resultant precipitate was filtered and rinsed with cold $H_2O$ (3×25 mL), yielding the desired carboxy acid compound in >95% purity. HRMS: calcd for $C_{24}H_{27}F_4N_3O_4S+H+$, 530.17312. found ([M+H]+), 530.17463.

Step 2: To a solution of 1-[3-({(2R)-4-[4-fluoro-2-(trifluoromethyl)phenyl]-2-methylpiperazin-1-yl}sulfonyl)phenyl]piperidine-4-carboxylic acid (200 mg, 0.38 mmol) in DMF (4.0 mL) was added BOP (202 mg, 0.46 mmol), DIPEA (0.33 mL, 1.9 mmol), and finally N'N-dimethylamine (0.6 mL, 1.1 mmol). The reaction was allowed to stir at ambient temperature over a 16 hour period, after which it was judged complete by LCMS. The reaction mixture was diluted with EtOAc (50 mL), and washed with saturated $NaHCO_{3(aq)}$ (3×25 mL). The organic layer was dried over $Na_2SO_4$, decanted, and concentrated in vacuo. The resultant crude oil was purified on a normal phase $SiO_2$ column (20%-80% EtOAc/Hexanes) affording the desired amide in >95% purity. HRMS: calcd for $C_{26}H_{32}F_4N_4O_3S+H+$, 557.22040. found ([M+H]+), 557.22195.

Example 29HS (2R)-4-[4-fluoro-2-(trifluoromethyl)phenyl]-2-methyl-1-({3-[4-(pyrrolidin-1-ylcarbonyl)piperidin-1-yl]phenyl}sulfonyl)piperazine Prepared according to the procedures of Example 29HR, affording the desired amide in >95% purity. HRMS: calcd for $C_{28}H_{34}F_4N_4O_3S+H+$, 583.23605. found ([M+H]+), 583.23752.

Example 29HT 4-({1-[3-({(2R)-4-[4-fluoro-2-(trifluoromethyl)phenyl]-2-methylpiperazin-1-yl}sulfonyl)phenyl]piperidin-4-yl}carbonyl)morpholine Prepared according to the procedures of Example 29HR, affording the desired amide in >95% purity. HRMS: calcd for $C_{28}H_{34}F_4N_4O_4S+H+$, 599.23096. found ([M+H]+), 599.23172.

Example 29HU

N-tert-butyl-1-[3-({(2R)-4-[4-fluoro-2-(trifluoromethyl)phenyl]-2-methylpiperazin-1-yl}sulfonyl)phenyl]piperidine-4-carboxamide Prepared according to the procedure of Example 29HR, affording the desired amide in >95% purity. HRMS: calcd for $C_{28}H_{36}F_4N_4O_3S+H+$, 585.25170. found ([M+H]+), 585.25309.

Example 29HV

1-[3-({(2R)-4-[4-fluoro-2-(trifluoromethyl)phenyl]-2-methylpiperazin-1-yl}sulfonyl)phenyl]-N-isobutylpiperidine-4-carboxamide Prepared according to the procedure of Example 29HR, affording the desired amide in >95% purity. HRMS: calcd for $C_{28}H_{36}F_4N_4O_3S+H+$, 585.25170. found ([M+H]+), 585.25262.

Example 29HW (2R)-1-(biphenyl-3-ylsulfonyl)-4-[4-fluoro-2-(trifluoromethyl)phenyl]-2-methylpiperazine A 5 mL microwave vial was charged with a stir bar, 1-(3-Bromo-benzenesulfonyl)-4-(4-fluoro-2-(trifluoromethylphenyl)-2-methyl-piperazine (230 mg, 0.48 mmol), phenylboronic acid (65 mg, 0.53 mmol), potassium fluoride (111 mg, 1.92 mmol), and palladium tetrakis (28 mg, 0.024 mmol). The vial was sealed and vacuum-purged with $N_2$, after which aqueous THF (4 mL 3:1 vol) was added. The reaction was heated to 120° C. under microwave conditions for 10 minutes, after which it was judged complete by LCMS. The aqueous layer was removed using a simple pasteur pipet, and the organic phase was diluted with EtOAc (25 mL), and filtered through celite to remove inorganics. The filtrate was concentrated in vacuo and the resultant crude oil was purified using a normal phase $SiO_2$ column chromatography (5%-35% EtOAc/Hexanes), affording the desired biphenyl compound in >95% purity. HRMS: calcd for $C_{24}H_{22}F_4N_2O_2S+H+$, 479.14109. found ($[M+H]^+$), 479.1394.

Example 29HX (2R)-4-[4-fluoro-2-(trifluoromethyl)phenyl]-2-methyl-1-[(3-pyridin-4-ylphenyl)sulfonyl]piperazine Prepared according to the procedure for Example 29HW, with the exception of a more polar solvent system during purification (50%-100% EtOAc/Hexanes), affording the desired compound in >95% purity. HRMS: calcd for $C_{23}H_{21}F_4N_3O_2S+H+$, 480.13633. found ($[M+H]^+$), 480.1355.

Example 29HY

3'-({(2R)-4-[4-fluoro-2-(trifluoromethyl)phenyl]-2-methylpiperazin-1-yl}sulfonyl)biphenyl-4-carboxylic acid Suzuki Coupling: Prepared according to the procedure for Example 29HW, with the exception of a more polar solvent system during purification (50%-100% EtOAc/Hexanes), followed by trituration of the chromatographed material using 100% EtOAc, affording the desired compound in >95% purity. HRMS: calcd for $C_{25}H_{22}F_4N_2O_4S+H+$, 523.13092. found ($[M+H]^+$), 523.129.

Example 29 HZ 3-fluoro-4-({(2R)-4-[4-fluoro-2-(trifluoromethyl)phenyl]-2-methylpiperazin-1-yl}sulfonyl)phenol Step 1: A solution of (2R)-1-[(4-tert-butoxy-2-fluorophenyl)sulfonyl]-4-[4-fluoro-2-(trifluoromethyl)phenyl]-2-methylpiperazine (375 mg, 0.76 mmol) in DCM (25 mL) was added TFA (5 mL). The reaction was allowed to stir for 1 hour, after which it was judged complete by LCMS. The reaction was concentrated in vacuo to remove excess TFA, and the crude oil was dissolved in DCM (20 mL) and washed with saturated $NaHCO_{3(aq)}$ (3×25 mL). The organic phase was dried over $Na_2SO_4$, and decanted, then concentrated in vacuo affording the desired phenol in >95% purity, which was used in subsequent synthetic steps without purification. HRMS: calcd for $C_{18}H_{17}F_5N_2O_3S+H+$, 437.09528. found ($[M+H]^+$), 437.09527.

Example 29IA 2-chloro-4-({(2R)-4-[4-fluoro-2-(trifluoromethyl)phenyl]-2-methylpiperazin-1-yl}sulfonyl)phenol Step 1: Prepared from (2R)-1-[(4-tert-butoxy-2-chlorophenyl)sulfonyl]-4-[4-fluoro-2-(trifluoromethyl)phenyl]-2-methylpiperazine according to the procedure for example IV-7A, affording the desired phenol in >95% purity. HRMS: calcd for $C_{18}H_{17}ClF_4N_2O_3S+H+$, 453.06573. found ($[M+H]^+$), 453.06635.

Example 29IB (2R)-1-{[2-chloro-4-(2-methoxyethoxy)phenyl]sulfonyl}-4-[4-fluoro-2-(trifluoromethyl)phenyl]-2-methylpiperazine Prepared according to Example 29 HZ. HRMS: calcd for $C_{21}H_{23}ClF_4N_2O_4S+H+$, 511.10759. found ($[M+H]^+$), 511.10791.

Example 29IC (2R)-1-[(2-chloro-4-ethoxyphenyl)sulfonyl]-4-[4-fluoro-2-(trifluoromethyl)phenyl]-2-methylpiperazine Prepared according to the procedure in Example 29 HZ, affording the desired aryl ether in >95% purity. HRMS: calcd for $C_{20}H_{21}ClF_4N_2O_3S+H+$, 481.09703. found ($[M+H]^+$), 481.09732.

Example 29ID

2-[3-chloro-4-({(2R)-4-[4-fluoro-2-(trifluoromethyl)phenyl]-2-methylpiperazin-1-yl}sulfonyl)phenoxy]-N,N-dimethylethanamine Prepared according to the procedure in Example 29 HZ, affording the desired aryl ether in >95% purity. HRMS: calcd for $C_{22}H_{26}ClF_4N_3O_3S+H+$, 524.13923. found ($[M+H]^+$), 524.14061.

Example 29IE (2R)-1-{[2-chloro-4-(difluoromethoxy)phenyl]sulfonyl}-4-[4-fluoro-2-(trifluoromethyl)phenyl]-2-methylpiperazine Purification (5%-50% EtOAc/Hexanes) afforded the desired aryl ether in >95% purity. HRMS: calcd for $C_{19}H_{17}ClF_6N_2O_3S+H+$, 503.06253. found (ESI-FTMS, $[M+H]^{1+}$), 503.06351.

Example 29IF (2R)-4-[4-fluoro-2-(trifluoromethyl)phenyl]-2-methyl-1-{[3-(4H-1,2,4-triazol-4-yl)phenyl]sulfonyl}piperazine Cyclization. A solution of the aniline (400 mg, 0.96 mmol), N'N-dimethyl-formyl-hydrazine (140 mg, 1.15 mmol), and a catalytic amount of pTSA in toluene (20 mL) was heated at reflux (130° C.) under $N_2$ over a 12-16 hour period, after which the reaction was judged complete by LCMS. The reaction was then cooled to ambient temperature and the solvent was concentrated in vacuo, affording a crude oil which was purified by reversed phase HPLC under neutral conditions (30%-90% ACN/H$_2$O), affording the desired 1,3,4-triazole compound in >95% purity. HRMS: calcd for C$_{20}$H$_{19}$F$_4$N$_5$O$_2$S+H+, 470.12683. found ([M+H]$^+$), 470.12538.

Example 29IG (2R)-4-(2,4-dichlorophenyl)-2-methyl-1-{[3-(4H-1,2,4-triazol-4-yl)phenyl]sulfonyl}piperazine Cyclization: Prepared according to the procedure in Example 29IF, affording the desired 1,3,4-triazole compound in >95% purity. HRMS: calcd for C$_{19}$H$_{19}$Cl$_2$N$_5$O$_2$S+H+, 452.07092. found ([M+H]$^+$), 452.07148.

Example 29IH 1,1,1-trifluoro-2-[4-({(2R)-2-methyl-4-[3-(1H-1,2,4-triazol-1-yl)-2-(trifluoromethyl)phenyl]piperazin-1-yl}sulfonyl)phenyl]propan-2-ol Step 1: A solution of the methyl ketone intermediate (550 mg, 1.25 mmol) and CuI (25 mg, 0.125 mmol) in NMP (10 mL), was heated to 170° C. under thermal conditions over a 12-16 hour period, after which the reaction was judged complete by LCMS. The reaction was then cooled to ambient temperature and clear reaction mixture was directly purified by reversed phase HPLC under neutral conditions (40%-95% ACN/H$_2$O), affording the 1,2,4-triazole methyl ketone intermediate in >95% purity.

Step 2. A solution of the 1,2,4-triazole methyl ketone intermediate (200 mg, 0.4 mmol) in 0.5M TMSCF$_3$ in THF (2.4 mL) under N$_2$ was cooled to 0° C. A solution of 1.0M TBAF/THF (0.4 mL) was then added drop-wise and the reaction was allowed to stir, while warming to room temperature. The reaction was judged complete by LCMS after 1 hour, and was diluted with EtOAc (25 mL), and washed with saturated NaHCO$_{3(aq)}$ and dried over Na$_2$SO$_4$. The crude product was then purified by normal phase SiO$_2$ chromatography (10%-60% EtOAc/Hexanes) affording the desired compound in >95% purity. HRMS: calcd for C$_{23}$H$_{23}$F$_6$N$_5$O$_3$S+H+, 564.14985. found ([M+H]$^+$), 564.14965.

Example 29II 1,1,1-trifluoro-2-[4-({(2R)-2-methyl-4-[4-(1H-1,2,4-triazol-1-yl)-2-(trifluoromethyl)phenyl]piperazin-1-yl}sulfonyl)phenyl]propan-2-ol Step 1: Prepared according to the method described above, affording the 1,2,4-triazole methyl ketone intermediate in >95% purity.
Step 2. Prepared according to the method described above, affording the desired compound in >95% purity. HRMS: calcd for C$_{23}$H$_{23}$F$_6$N$_5$O$_3$S+H+, 564.14985. found ([M+H]$^+$), 564.1506.

Example 29IJ 1,1,1-trifluoro-2-[4-({(2R)-2-methyl-4-[5-(1H-1,2,4-triazol-1-yl)-2-(trifluoromethyl)phenyl]piperazin-1-yl}sulfonyl)phenyl]propan-2-ol Step 1. Prepared according to the method described above. HRMS: calcd for C$_{23}$H$_{23}$F$_6$N$_5$O$_3$S+H+, 564.14985. found ([M+H]$^+$), 564.14905.

Example 29IK

4-[3-chloro-4-({(2R)-2-methyl-4-[4-(1H-1,2,4-triazol-1-yl)-2-(trifluoromethyl)phenyl]piperazin-1-yl}sulfonyl)phenyl]morpholine Step 1: Prepared according to the method described above, affording the 1,2,4-triazole morpholino compound in >95% purity.

Example 29IL (2R)-4-[4-fluoro-2-(trifluoromethyl)phenyl]-2-methyl-1-{[4-(1H-tetrazol-5-yl)phenyl]sulfonyl}piperazine Step 1: To a solution of the nitrile compound described herein (150 mg, 0.35 mmol) in toluene (3.5 mL) was added Et$_3$N*HCl (139 mg, 1.05 mmol) and NaN$_3$ (66 mg, 1.05 mmol). The reaction was heated to 100° C. under thermal conditions over a 12-16 hour period, after which the reaction was judged complete by LCMS. The reaction was diluted with EtOAc, and washed 3× with 10% HCl. The organic phase was concentrated and the resultant crude solid was triturated with Et$_2$O, affording the desired tetrazole in >95% purity. HRMS: calcd for C$_{19}$H$_{18}$F$_4$N$_6$O$_2$S+H+, 471.12208. found ([M+H]$^+$), 471.1225.

Example 29IM 1,1,1-trifluoro-2-[3-({(2R)-4-[4-fluoro-2-(trifluoromethyl)phenyl]-2-methylpiperazin-1-yl}sulfonyl)-4-methoxyphenyl]propan-2-ol Step i: To a solution of 1-(5-Bromo-2-methoxy-benzenesulfonyl)-4-(4-fluoro-2-trifluoromethyl-phenyl)-2-methyl-piperazine (100 mg, 0.196 mmol) in anhydrous THF (2.0 mL) at −78° C. was added n-BuLi (0.07 mL, 0.205 mmol) drop-wise. The reaction was allowed to stir at −78° C. for several minutes, after which, the CF$_3$-Weinreb-amide reagent (0.024 mL, 0.205 mmol) was added drop-wise. The reaction was stirred and allowed to warm to room temperature over a 4-5 hour period, after which the reaction was judged complete by LCMS. The reaction concentrated in vacuo and the resultant crude oil was purified via normal phase SiO$_2$ chromatography (5%-35% EtOAc/Hexanes), affording the trifluoroacetylated intermediate in >95% purity.

Step ii: A solution of the trifluoroacetylated intermediate in anhydrous THF was cooled to −78° C. prop-wise, methyl-lithium was added, and the reaction was allowed to stir at −78° C. for 2-3 hours, after which the reaction was judged complete by TLC. The reaction was allowed to warm to ambient temperature, and directly purified by reversed phase HPLC under acidic conditions, affording the desired trifluoropropanol compound in >95% purity. HRMS: calcd for C$_{22}$H$_{23}$F$_7$N$_2$O$_4$S+H+, 545.13395. found ([M+H]$^+$), 545.1341.

Example 29IN

1-[5-({(2R)-4-[4-fluoro-2-(trifluoromethyl)phenyl]-2-methylpiperazin-1-yl}sulfonyl)-2-thienyl]piperidin-4-ol HRMS: calcd for C$_{21}$H$_{25}$F$_4$N$_3$O$_3$S$_2$+H+, 508.13462. found (ESI-FTMS, [M+H]$^{1+}$), 508.13469.

Example 29IO (2R)-4-[4-fluoro-2-(trifluoromethyl)phenyl]-1-{[5-(4-methoxypiperidin-1-yl)-2-thienyl]sulfonyl}-2-methylpiperazine HRMS: calcd for $C_{22}H_{27}F_4N_3O_3S_2$+H+, 522.15027. found ([M+H]+), 522.15046.

Example 29IP (2R)-4-(2,4-dichlorophenyl)-2-methyl-1-[(5-piperazin-1-yl-2-thienyl)sulfonyl]piperazine HRMS: calcd for $C_{19}H_{24}Cl_2N_4O_2S_2$+H+, 475.07905. found ([M+H]+), 475.08118.

Example 29IQ (2R)-1-{[5-(4-fluoropiperidin-1-yl)-2-thienyl]sulfonyl}-4-[4-fluoro-2-(trifluoromethyl)phenyl]-2-methylpiperazine HRMS: calcd for $C_{21}H_{24}F_5N_3O_2S_2$+H+, 510.13028. found (ESI-FTMS, [M+H]1+), 510.12968.

Example 29IR (2R)-1-{[5-(4,4-difluoropiperidin-1-yl)-2-thienyl]sulfonyl}-4-[4-fluoro-2-(trifluoromethyl)phenyl]-2-methylpiperazine MS (LC-ESIMS) m/z 527.83.

Example 29IS

4-[5-({(2R)-4-[4-fluoro-2-(trifluoromethyl)phenyl]-2-methylpiperazin-1-yl}sulfonyl)-2-thienyl]benzoic acid HRMS: calcd for $C_{23}H_{21}F_4N_2O_4S_2$+H+, 529.08734. found ([M+H]+), 529.08803.

Example 29IT

4-[5-({(2R)-4-[4-fluoro-2-(trifluoromethyl)phenyl]-2-methylpiperazin-1-yl}sulfonyl)-2-thienyl]benzamide HRMS: calcd for $C_{23}H_{21}F_4N_3O_3S_2$+H+, 528.10332. found ([M+H]+), 528.10464.

Example 30

Compounds described herein can be tested in a cell-based assay using a stable CHO cell line expressing human 11 b-HSD1. Cells are plated at 20,000 cells/well in 96 well plates and incubated overnight (12-16 hrs) at 37° C./5% $CO_2$. Cells are treated with different concentration of compound in 90 microliter serum-free media and incubated for 30 minutes at 37° C./5% $CO_2$. 10 ul of 5 micromolar cortisone (final concentration 500 nM) is then added to the cells and the plate is incubated at 37° C./5% $CO_2$ for 120 minutes. 15 microliter of media is withdrawn and amount of cortisol in the media is measured using the DiscoverX HitHunter Cortisol Assay (DiscoverX corp, CA).

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

A number of embodiments of the invention have been described. Nevertheless, it will be understood that various modifications may be made without departing from the spirit and scope of the invention. Accordingly, other embodiments are within claims.

What is claimed is:

1. A compound having formula (I):

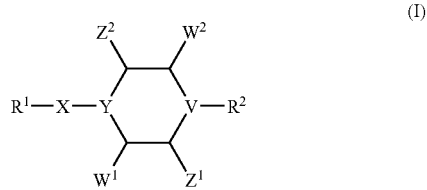

wherein:

$R^1$ is:
(a) phenyl which is monosubstituted at the meta position with $R^a$; or
(b) phenyl which is disubstituted with 2 $R^a$; phenyl which is trisubstituted with 3 $R^a$; phenyl which is tetrasubstituted with 4 $R^a$; or phenyl which is pentasubstituted with 5 $R^a$; or
(c) naphthyl which is optionally substituted with from 1-2 $R^a$; or
(d) heteroaryl including 5-12 atoms, which is optionally substituted with from 1-10 $R^a$;

$R^2$ is $C_6$-$C_{18}$ aryl or heteroaryl including 5-20 atoms, each of which is optionally substituted with from 1-10 $R^c$;

X is S(O)$_n$, wherein n is 1 or 2;

each of V and Y is N;

one, two, three, or four of $W^1$, $Z^1$, $W^2$, and $Z^2$ are each, independently $C_1$-$C_{12}$ alkyl; and the others are hydrogen;

$R^a$ at each occurrence is, independently:
(i) halo; NR$^d$R$^e$; nitro; azido; hydroxy; $C_1$-$C_{12}$ alkoxy or $C_1$-$C_{12}$ thioalkoxy, each of which is optionally substituted with 1-5 R$^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^{a'}$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; —C(O)R$^g$, —C(O)OR$^g$; —OC(O)R$^g$; —C(O)SR$^g$; —SC(O)R$^g$; —C(S)SR$^g$; —SC(S)R$^g$; —C(O)NR$^d$R$^e$; —NR$^h$C(O)R$^i$; —OC(O)NR$^d$R$^e$; or 2 $R^a$ together form $C_1$-$C_3$ alkylenedioxy;
(ii) $C_1$-$C_{12}$ alkyl which is optionally substituted with a hydroxy group; or haloalkyl which is optionally substituted with from 1-5 R$^j$; or
(iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

$R^{a'}$ at each occurrence is, independently, $C_1$-$C_{12}$ alkyl, $C_1$-$C_{12}$ haloalkyl, $C_2$-$C_{12}$ alkenyl; $C_2$-$C_{12}$ alkynyl; $C_3$-$C_{16}$ cycloalkyl; $C_3$-$C_{16}$ cycloalkenyl, heterocyclyl including 3-16 atoms, heterocycloalkenyl including 3-16 atoms; $C_7$-$C_{20}$ aralkyl; $C_6$-$C_{16}$ aryl; heteroaryl including 5-16 atoms; halo; $NR^dR^e$; nitro; azido, hydroxy; $C_1$-$C_{12}$ alkoxy; $C_1$-$C_{12}$ thioalkoxy; $C_1$-$C_{12}$ haloalkoxy; $C_6$-$C_{16}$ aryloxy, $C_6$-$C_{16}$ thioaryloxy; heteroaryloxy including 5-20 atoms; thioaryloxy including 5-20 atoms; $C_2$-$C_{12}$ alkenyloxy; $C_2$-$C_{12}$ alkynyloxy; $C_3$-$C_{16}$ cycloalkyloxy; $C_3$-$C_{16}$ cycloalkenyloxy; heterocyclyloxy including 3-16 atoms; heterocycloalkenyloxy including 3-16 atoms; $C_7$-$C_{20}$ aralkoxy; heteroaralkoxy including 6-20 atoms; mercapto; cyano; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^dR^e$; $NR^hC(O)R^i$; —OC(O)N$R^dR^e$; or 2 $R^{a'}$ together form $C_1$-$C_3$ alkylenedioxy; or 2 $R^{a'}$ together form $C_1$-$C_3$ alkylenedioxy;

$R^b$ at each occurrence is, independently:

(i) halo; $NR^dR^e$; nitro; azido; hydroxy; oxo, thioxo, =$NR^k$, $C_1$-$C_{12}$ alkoxy or thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^a$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^{b'}$; mercapto; cyano; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^dR^e$; —$NR^hC(O)R^i$; —OC(O)N$R^dR^e$; or 2 $R^b$ together form $C_1$-$C_3$ alkylenedioxy; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^{b'}$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

$R^{b'}$ at each occurrence is, independently, $C_1$-$C_{12}$ alkyl or $C_1$-$C_{12}$ haloalkyl, each of which is optionally substituted with 1-5 $R^j$; $C_2$-$C_{12}$ alkenyl; $C_2$-$C_{12}$ alkynyl; $C_3$-$C_{16}$ cycloalkyl; $C_3$-$C_{16}$ cycloalkenyl, heterocyclyl including 3-16 atoms, heterocycloalkenyl including 3-16 atoms; $C_7$-$C_{20}$ aralkyl; $C_6$-$C_{16}$ aryl; heteroaryl including 5-16 atoms; halo; $NR^dR^e$; nitro; azido, hydroxy; oxo, thioxo, =$NR^k$, $C_1$-$C_{12}$ alkoxy; $C_1$-$C_{12}$ thioalkoxy; $C_1$-$C_{12}$ haloalkoxy; $C_6$-$C_{16}$ aryloxy, $C_6$-$C_{16}$ thioaryloxy; heteroaryloxy including 5-20 atoms; thioaryloxy including 5-20 atoms; $C_2$-$C_{12}$ alkenyloxy; $C_2$-$C_{12}$ alkynyloxy; $C_3$-$C_{16}$ cycloalkyloxy; $C_3$-$C_{16}$ cycloalkenyloxy; heterocyclyloxy including 3-16 atoms; heterocycloalkenyloxy including 3-16 atoms; $C_7$-$C_{20}$ aralkoxy; heteroaralkoxy including 6-20 atoms; mercapto; cyano; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^dR^e$; —$NR^hC(O)R^i$; —OC(O)N$R^dR^e$; or 2 $R^{b'}$ together form $C_1$-$C_3$ alkylenedioxy;

$R^c$ at each occurrence is, independently:

(i) halo; nitro; hydroxy; $C_1$-$C_{12}$ alkoxy optionally substituted with 1-5 $R^f$; $C_1$-$C_{12}$ haloalkoxy; cyano; $SO_2R^m$; or 2 $R^c$ together form $C_1$-$C_3$ alkylenedioxy; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

each of $R^d$, $R^e$, $R^g$, $R^h$, and $R^k$, at each occurrence is, independently:

(i) hydrogen; or (ii) $C_1$-$C_{12}$ alkyl or $C_1$-$C_{12}$ haloalkyl; each of which is optionally substituted with from 1-5 $R^j$; or (iii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iv) $C_2$-$C_{20}$ alkenyl or $C_2$-$C_{20}$ alkynyl; or (v) $C_6$-$C_{16}$ aryl or heteroaryl including 5-16 atoms, each of which is optionally substituted with from 1-10 $R^a$;

$R^f$ is $NR^dR^e$; nitro; azido; hydroxy; oxo, thioxo, =$NR^k$, $C_1$-$C_{12}$ alkoxy or thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^a$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^dR^e$; —$NR^hC(O)R^i$; —OC(O)N$R^dR^e$;

$R^i$ is $R^g$; O$R^g$; or $NR^dR^e$;

$R^j$ is $NR^dR^e$; nitro; azido; hydroxy; oxo; thioxo; =$NR^k$; $C_1$-$C_{12}$ alkoxy or $C_1$-$C_{12}$ thioalkoxy, each of which is optionally substituted with 1-5 $R^f$; $C_1$-$C_{12}$ haloalkoxy; $C_6$-$C_{16}$ aryloxy, $C_6$-$C_{16}$ thioaryloxy, heteroaryloxy including 5-20 atoms, or thioaryloxy including 5-20 atoms, each of which is optionally substituted with 1-5 $R^{a'}$; $C_2$-$C_{12}$ alkenyloxy; $C_2$-$C_{12}$ alkynyloxy; $C_3$-$C_{16}$ cycloalkyloxy, $C_3$-$C_{16}$ cycloalkenyloxy, heterocyclyloxy including 3-16 atoms, heterocycloalkenyloxy including 3-16 atoms, $C_7$-$C_{20}$ aralkoxy, or heteroaralkoxy including 6-20 atoms, each of which is optionally substituted with 1-5 $R^b$; mercapto; cyano; $C_1$-$C_3$ alkylenedioxy; —C(O)$R^g$, —C(O)O$R^g$; —OC(O)$R^g$; —C(O)S$R^g$; —SC(O)$R^g$; —C(S)S$R^g$; —SC(S)$R^g$; —C(O)N$R^dR^e$; —$NR^hC(O)R^i$; —OC(O)N$R^dR^e$;

$R^m$ is (i) $C_1$-$C_{12}$ alkyl or $C_1$-$C_{12}$ haloalkyl; each of which is optionally substituted with from 1-5 $R^j$; or (ii) $C_7$-$C_{20}$ aralkyl; $C_3$-$C_{16}$ cycloalkyl; heteroaralkyl including 6-20 atoms; $C_3$-$C_{16}$ cycloalkenyl; heterocyclyl including 3-16 atoms; or heterocycloalkenyl including 3-16 atoms; each of which is optionally substituted with from 1-10 $R^b$; or (iii) $C_6$-$C_{16}$ aryl or heteroaryl including 5-16 atoms, each of which is optionally substituted with from 1-10 $R^a$; and provided:
(a) when $R^2$ is substituted pyridyl or pyrimidinyl, then $R^c$ cannot be $C_1$-$C_{12}$ alkoxy optionally substituted with 1-5 $R^f$; $C_1$-$C_{12}$ haloalkoxy; or $SO_2R^m$; and
(b) when one of $Z^1$ and $W^2$ is $CH_3$, and $R^2$ is phenyl substituted with from 1-5 $R^c$, then 1 $R^c$ must be halo; $C_1$-$C_{12}$ haloalkoxy; cyano; or $C_1$-$C_{12}$ haloalkyl, optionally substituted with from 1-5 $R^j$; or a pharmaceutically acceptable salt and/or N-oxide thereof.

2. The compound of claim 1, wherein X is $SO_2$.

3. The compound of claim 1, wherein one or two of $W^1$, $Z^1$, $W^2$, and $Z^2$ are each, independently, $C_1$-$C_4$ alkyl, and the others are hydrogen.

4. The compound of claim 1, wherein $R^1$ is:
(a) phenyl which is monosubstituted at the meta position with $R^a$; or
(b) phenyl which is disubstituted with 2 $R^a$; phenyl which is trisubstituted with 3 $R^a$; phenyl which is tetrasubstituted with 4 $R^a$; or phenyl which is pentasubstituted with 5 $R^a$; or
(c) naphthyl which is optionally substituted with from 1-2 $R^a$.

5. The compound of claim 4, wherein $R^a$ at each occurrence is, independently, halo; $NR^dR^e$; hydroxyl; $C_1$-$C_{12}$ alkyl which is optionally substituted with a hydroxy group; $C_1$-$C_{12}$ haloalkyl, which is optionally substituted with from 1-2 $R^j$; $C_1$-$C_{12}$ alkoxy, optionally substituted with from 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-2 $R^b$; —C(O)OR$^g$; —C(O)NR$^d$R$^e$; or —NR$^h$C(O)R$^i$.

6. The compound of claim 4, wherein $R^1$ has formula (II):

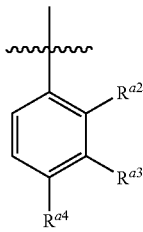

(II)

wherein $R^{a3}$ is halo; $NR^dR^e$; hydroxyl; $C_1$-$C_{12}$ alkyl which is optionally substituted with a hydroxy group; $C_1$-$C_{12}$ haloalkyl, which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)OR$^g$; —C(O)NR$^d$R$^e$; or —NR$^h$C(O)R$^i$; and each of $R^{a2}$ and $R^{a4}$ is hydrogen.

7. The compound of claim 6, wherein $R^{a3}$ is $C_1$-$C_4$ haloalkyl, optionally substituted with from 1-2 $R^j$.

8. The compound of claim 7, wherein $R^{a3}$ is 1,1,1-trifluoro-2-hydroxy-2-propyl.

9. The compound of claim 6, wherein $R^{a3}$ is heterocyclyl including 3-8 atoms, which is optionally substituted with from 1-3 $R^b$.

10. The compound of claim 9, wherein $R^b$ at each occurrence is, independently, halo; $NR^dR^e$; hydroxyl; oxo; $C_1$-$C_{12}$ alkyl or $C_1$-$C_{12}$ haloalkyl, each of which is optionally substituted with from 1-3 $R^j$; $C_1$-$C_{12}$ alkoxy, optionally substituted with 1-2 $R^f$; $C_1$-$C_{12}$ haloalkoxy; heterocyclyl including 3-10 atoms or $C_3$-$C_{10}$ cycloalkyl, each of which is optionally substituted with 1-3 $R^b$; —C(O)R$^g$; —C(O)OR$^g$; —C(O)NR$^d$R$^e$; —OC(O)R$^g$; or —NR$^h$C(O)R$^i$.

11. The compound of claim 9, wherein $R^{a3}$ is piperazinyl, piperidyl, morpholinyl, or pyrrolidinyl, each of which is optionally substituted with 1-3 $R^b$.

12. The compound of claim 6, wherein $R^{a3}$ is $C_1$-$C_{12}$ alkyl, optionally substituted with 1 $R^j$.

13. The compound of claim 12, wherein $R^{a3}$ is 2-hydroxy-2-propyl.

14. The compound of claim 6, wherein $R^{a3}$ is heteroaryl including 5 or 6 atoms, optionally substituted with from 1-2 $R^{a'}$.

15. The compound of claim 4, wherein $R^1$ has formula (II-A):

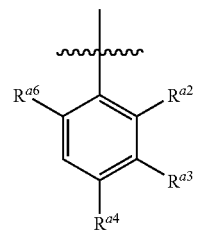

(II-A)

wherein two of $R^{a2}$, $R^{a3}$, $R^{a4}$, and $R^{a6}$ are each, independently, halo; $NR^dR^e$; hydroxyl; $C_1$-$C_{12}$ alkyl which is optionally substituted with a hydroxy group; $C_1$-$C_{12}$ haloalkyl, which is optionally substituted with from 1-2 $R^j$; $C_1$-$C_{12}$ alkoxy, optionally substituted with from 1-2 $R^f$; $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; —C(O)OR$^g$; —C(O)NR$^d$R$^e$; or —NR$^h$C(O)R$^i$; and the others are hydrogen.

16. The compound of claim 15, wherein $R^{a2}$ is halo, and $R^{a4}$ is halo; $NR^dR^e$; hydroxyl; $C_1$-$C_{12}$ alkoxy, optionally substituted with from 1-2 $R^f$; $C_1$-$C_{12}$ haloalkoxy; heterocyclyl including 3-10 atoms, optionally substituted with from 1-3 $R^b$; heteroaryl including 5-12 atoms, optionally substituted with from 1-2 $R^{a'}$; —C(O)OR$^g$; —C(O)NR$^d$R$^e$; or —NR$^h$C(O)R$^i$.

17. The compound of claim 16, wherein $R^{a2}$ is chloro.

18. The compound of claim 17, wherein $R^{a4}$ is heterocyclyl including 5-8 atoms, optionally substituted with from 1-3 $R^b$.

19. The compound of claim 1, wherein $R^1$ is heteroaryl including 5-14 atoms, optionally substituted with from 1-5 $R^a$.

20. The compound of claim 19, wherein $R^1$ is heteroaryl including 5-6 atoms, optionally substituted with from 1-2 $R^a$.

21. The compound of claim 19, wherein $R^1$ has formula (II-B):

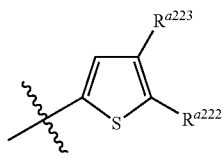

(II-B)

wherein $R^{a222}$ and $R^{a223}$ are each, independently, hydrogen; halo; $NR^dR^e$; $C_1$-$C_{12}$ alkyl which is optionally substituted with a hydroxy group; $C_1$-$C_{12}$ haloalkyl, which is optionally substituted with from 1-2 $R^j$; $C_6$-$C_{10}$ aryl or heteroaryl including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)R$^g$, —C(O)OR$^g$; —C(O)NR$^d$R$^e$; —NR$^h$C(O)R$^i$.

22. The compound of claim 21, wherein $R^{a222}$ is halo; $NR^dR^e$; $C_1$-$C_{12}$ alkyl which is optionally substituted with a hydroxy group; $C_1$-$C_{12}$ haloalkyl, which is optionally substituted with from 1-2 $R^j$; $C_6$-$C_{10}$ aryl or heteroaryl including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)R$^g$; —C(O)OR$^g$; —C(O)NR$^d$R$^e$; or —NR$^h$C(O)R$^i$; and $R^{a223}$ is hydrogen.

23. The compound of claim 22, wherein $R^{a222}$ is heterocyclyl including 3-8 atoms, optionally substituted with from 1-3 $R^b$.

24. The compound of claim 23, wherein $R^{a222}$ is piperazinyl, piperidyl, morpholinyl, or pyrrolidinyl, each of which is optionally substituted with 1-3 $R^b$.

25. The compound of claim 1, wherein $R^2$ is $C_6$-$C_{10}$ aryl, optionally substituted with from 1-3 $R^c$.

26. The compound of claim 25, wherein $R^2$ has formula (IV-A):

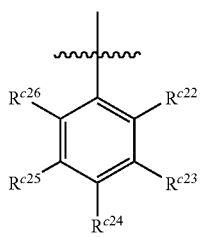

(IV-A)

wherein two of $R^{c22}$, $R^{c23}$, $R^{c24}$, $R^{c25}$, and $R^{c26}$ are each, independently, halo; $C_1$-$C_{12}$ alkyl or $C_1$-$C_{12}$ haloalkyl, each of which is optionally substituted with from 1-3 $R^j$; $C_1$-$C_{12}$ alkoxy; $C_1$-$C_{12}$ haloalkoxy; cyano; nitro; or $C_6$-$C_{10}$ aryl or heteroaryl including 5-12 atoms, each of which is optionally substituted with from 1-2 $R^a$; and the others are hydrogen.

27. The compound of claim 26, wherein two of $R^{c22}$, $R^{c23}$, $R^{c24}$, $R^{c25}$, and $R^{c26}$ are each, independently, halo; $C_1$-$C_4$ haloalkyl, optionally substituted with from 1-3 $R^j$; cyano; or heteroaryl including 5-6 atoms, optionally substituted with from 1-2 $R^a$.

28. The compound of claim 26, wherein $R^{c22}$ is $C_1$-$C_4$ haloalkyl, optionally substituted with from 1-3 $R^j$; and $R^{c24}$ is halo; $C_1$-$C_4$ haloalkyl, optionally substituted with from 1-3 $R^j$; cyano; or heteroaryl including 5-6 atoms, optionally substituted with from 1-2 $R^a$.

29. The compound of claim 28, wherein $R^{c22}$ is $CF_3$.

30. The compound of claim 29, wherein $R^{c24}$ is fluoro.

31. The compound of claim 26, wherein $R^{c22}$ and $R^{c24}$ are each, independently, fluoro or chloro.

32. The compound of claim 31, wherein $R^{c22}$ is chloro, and $R^{c24}$ is fluoro.

33. The compound of claim 3, wherein one or both of $W^1$ and $Z^2$ are each, independently, $C_1$-$C_4$ alkyl; and each of $Z^1$ and $W^2$ is hydrogen.

34. The compound of claim 1, wherein the compound has formula (VI-A):

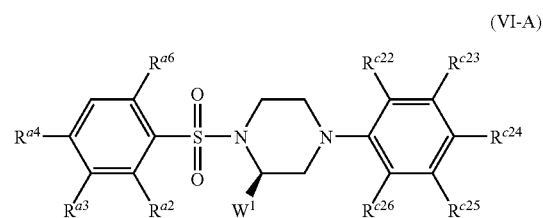

(VI-A)

wherein:
$R^{a3}$ is halo; $NR^dR^e$; hydroxyl; $C_1$-$C_{12}$ alkyl which is optionally substituted with a hydroxy group; $C_1$-$C_{12}$ haloalkyl, which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)OR$^g$; —C(O)NR$^d$R$^e$; or —NR$^h$C(O)R$^i$; and each of $R^{a2}$, $R^{a4}$, and $R^{a6}$ is hydrogen; or two of $R^{a2}$, $R^{a3}$, $R^{a4}$, and $R^{a6}$ are each, independently, halo; $NR^dR^e$; hydroxyl; $C_1$-$C_{12}$ alkyl which is optionally substituted with a hydroxy group; $C_1$-$C_{12}$ haloalkyl, which is optionally substituted with from 1-2 $R^j$; $C_1$-$C_{12}$ alkoxy, optionally substituted with 1-2 $R^f$; $C_1$-$C_{12}$ haloalkoxy; cyano; nitro; $C_6$-$C_{10}$ aryl or heteroaryl including 5-12 atoms, each of which is optionally substituted with from 1-2 $R^{a'}$; $C_6$-$C_{10}$ aryloxy or heteroaryloxy including 5-12 atoms, each of which is optionally substituted with from 1-2 $R^{a'}$; heterocyclyl including 3-10 atoms, $C_3$-$C_{10}$ cycloalkyl, $C_7$-$C_{12}$ aralkoxy or heteroaralkoxy including 6-12 atoms, each of which is optionally substituted with 1-3 $R^b$; —C(O)OR$^g$; —C(O)NR$^d$R$^e$; or —NR$^h$C(O)R$^i$; and the others are hydrogen;

$W^1$ is $C_1$-$C_4$ alkyl; and one or two of $R^{c22}$, $R^{c23}$, $R^{c24}$, $R^{c25}$, and $R^{c26}$ are each, independently, halo; $C_1$-$C_{12}$ alkyl or $C_1$-$C_{12}$ haloalkyl, each of which is optionally substituted with from 1-3 $R^j$; $C_1$-$C_{12}$ alkoxy; $C_1$-$C_{12}$ haloalkoxy; cyano; nitro; or $C_6$-$C_{10}$ aryl or heteroaryl including 5-12 atoms, each of which is optionally substituted with from 1-2 $R^a$; and the others are hydrogen.

35. The compound of claim 34, wherein $W^1$ is $CH_3$.

36. The compound of claim 34, wherein $R^{a3}$ is $C_1$-$C_4$ haloalkyl, optionally substituted with from 1-2 $R^j$.

37. The compound of claim 36, wherein $R^{a3}$ is:

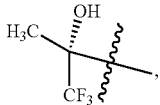

and each of $R^{a2}$, $R^{a4}$, and $R^{a6}$ is hydrogen.

38. The compound of claim 34, wherein $R^{c22}$ is $C_1$-$C_4$ haloalkyl, optionally substituted with from 1-2 $R^j$.

39. The compound of claim 34, wherein $R^{c22}$ is $CF_3$.

40. The compound of claim 34, wherein $R^{c24}$ is fluoro, and each of $R^{c23}$, $R^{c25}$, $R^{c26}$ is hydrogen.

41. A pharmaceutical composition comprising a compound of formula I, or a pharmaceutically acceptable salt and/or N-oxide thereof as claimed in claim 1 and a pharmaceutically acceptable carrier.

42. The compound of claim 1, wherein the compound is selected from:

- (2R)-1,1,1-trifluoro-2-[3-({(2R)-4-[4-fluoro-2-(trifluoromethyl)phenyl]-2-methylpiperazin-1-yl}sulfonyl)phenyl]propan-2-ol;
- (2S)-1,1,1-trifluoro-2-[3-({(2R)-4-[4-fluoro-2-(trifluoromethyl)phenyl]-2-methylpiperazin-1-yl}sulfonyl)phenyl]propan-2-ol;
- 1,1,1-trifluoro-2-[3-({(2R)-4-[4-fluoro-2-(trifluoromethyl)phenyl]-2-methylpiperazin-1-yl}sulfonyl)phenyl]propan-2-ol;
- 3-({(2R)-4-[4-fluoro-2-(trifluoromethyl)phenyl]-2-methylpiperazin-1-yl}sulfonyl)benzoic acid;
- 1,1,1-trifluoro-2-(3-{[(2R)-4-(4-fluoro-2-methylphenyl)-2-methylpiperazin-1-yl]sulfonyl}phenyl)propan-2-ol;
- 2-(3-{[(2R)-4-(2-chloro-4-fluorophenyl)-2-methylpiperazin-1-yl]sulfonyl}phenyl)propan-2-ol;
- 2-[3-({(2R)-4-[4-chloro-2-(trifluoromethyl)phenyl]-2-methylpiperazin-1-yl}sulfonyl)phenyl]-1,1,1-trifluoropropan-2-ol;
- 1,1,1-trifluoro-2-[3-({(2R)-2-methyl-4-[2-(trifluoromethoxy)phenyl]piperazin-1-yl}sulfonyl)phenyl]propan-2-ol;
- 4-((3R)-3-methyl-4-{[3-(2,2,2-trifluoro-1-hydroxy-1-methylethyl)phenyl]sulfonyl}piperazin-1-yl)-3-(trifluoromethyl)benzonitrile;
- 2-(3-{[(2R)-4-(2,4-dichlorophenyl)-2-methylpiperazin-1-yl]sulfonyl}phenyl)-1,1,1-trifluoropropan-2-ol; and
- 2-(3-{[(2R)-4-(2-chloro-4-methylphenyl)-2-methylpiperazin-1-yl]sulfonyl}phenyl)-1,1,1-trifluoropropan-2-ol; or a pharmaceutically acceptable salt and/or N-oxide thereof.

43. The compound of claim 1, wherein the compound is selected from:

- 2-(3-{[(2R)-4-(2,4-difluorophenyl)-2-methylpiperazin-1-yl]sulfonyl}phenyl)-1,1,1-trifluoropropan-2-ol;
- 1,1,1-trifluoro-2-[3-({(2R)-2-methyl-4-[4-(1H-tetrazol-5-yl)-2-(trifluoromethyl)phenyl]piperazin-1-yl}sulfonyl)phenyl]propan-2-ol;
- 1,1,1,3,3,3-hexafluoro-2-[3-({(2R)-4-[4-fluoro-2-(trifluoromethyl)phenyl]-2-methylpiperazin-1-yl}sulfonyl)phenyl]propan-2-amine;
- 3-({(2R)-4-[4-fluoro-2-(trifluoromethyl)phenyl]-2-methylpiperazin-1-yl}sulfonyl)benzamide;
- 5-[(3R)-3-methyl-4-{[3-(2,2,2-trifluoro-1-hydroxy-1-methylethyl)phenyl]sulfonyl}piperazin-1-yl]pyridine-2-carbonitrile;
- 2-(3-{[(2R)-4-{4-[1-amino-2,2,2-trifluoro-1-(trifluoromethyl)ethyl]-2-(trifluoromethyl)phenyl}-2-methylpiperazin-1-yl]sulfonyl}phenyl)-1,1,1-trifluoropropan-2-ol;
- 4-[(3R)-4-{[3-(1-hydroxy-1-methylethyl)phenyl]sulfonyl}-3-methylpiperazin-1-yl]-3-(trifluoromethyl)benzonitrile;
- (2R)-1-[(3-bromophenyl)sulfonyl]-4-(2-chloro-4-fluorophenyl)-2-methylpiperazine;
- 2-(3-{[(2R)-4-(2-chloro-4-fluorophenyl)-2-methylpiperazin-1-yl]sulfonyl}phenyl)propan-2-ol;
- 4-((3R)-3-methyl-4-{[3-(4-methylpiperazin-1-yl)phenyl]sulfonyl}piperazin-1-yl)-3-(trifluoromethyl)benzonitrile;
- 4-{(3R)-4-[(3-bromophenyl)sulfonyl]-3-methylpiperazin-1-yl}-3-(trifluoromethyl)benzonitrile;
- (2R)-1-[(3-bromophenyl)sulfonyl]-4-(2,4-dichlorophenyl)-2-methylpiperazine; and
- (2R)-4-(2,4-dichlorophenyl)-2-methyl-1-{[3-(4-methylpiperazin-1-yl)phenyl]sulfonyl}piperazine; or a pharmaceutically acceptable salt and/or N-oxide thereof.

44. The compound of claim 1, wherein the compound is selected from:

- (2R)-1-[(3-bromophenyl)sulfonyl]-2-methyl-4-(2,4,5-trifluorophenyl)piperazine;
- (2R)-2-methyl-1-{[3-(4-methylpiperazin-1-yl)phenyl]sulfonyl}-4-(2,4,5-trifluorophenyl)piperazine;
- 3-({(2R)-4-[4-fluoro-2-(trifluoromethyl)phenyl]-2-methylpiperazin-1-yl}sulfonyl)phenol;
- 2-[3-({(2R)-4-[4-fluoro-2-(trifluoromethyl)phenyl]-2-methylpiperazin-1-yl}sulfonyl)phenoxy]-N,N-dimethylethanamine;
- 3-[3-({(2R)-4-[4-fluoro-2-(trifluoromethyl)phenyl]-2-methylpiperazin-1-yl}sulfonyl)phenoxy]-N,N-dimethylpropan-1-amine;
- 4-{(3R)-4-[(3-hydroxyphenyl)sulfonyl]-3-methylpiperazin-1-yl}-3-(trifluoromethyl)benzonitrile;
- 4-{(3R)-4-[(3-methoxyphenyl)sulfonyl]-3-methylpiperazin-1-yl}-3-(trifluoromethyl)benzonitrile;
- 4-((3R)-3-methyl-4-{[3-(1H-1,2,4-triazol-1-yl)phenyl]sulfonyl}piperazin-1-yl)-3-(trifluoromethyl)benzonitrile;
- 4-{(3R)-4-[(3-fluorophenyl)sulfonyl]-3-methylpiperazin-1-yl}-3-(trifluoromethyl)benzonitrile;
- 4-((3R)-3-methyl-4-{[3-(4H-1,2,4-triazol-4-yl)phenyl]sulfonyl}piperazin-1-yl)-3-(trifluoromethyl)benzonitrile;
- (2R)-4-(2,4-dichlorophenyl)-2-methyl-1-{[3-(1H-1,2,4-triazol-1-yl)phenyl]sulfonyl}piperazine;
- (2R)-2-methyl-1-{[3-(1H-1,2,4-triazol-1-yl)phenyl]sulfonyl}-4-(2,4,5-trifluorophenyl)piperazine; and
- (2R)-1-[(3-bromophenyl)sulfonyl]-4-[2,5-difluoro-4-(1H-1,2,4-triazol-1-yl)phenyl]-2-methylpiperazine; or a pharmaceutically acceptable salt and/or N-oxide thereof.

45. The compound of claim 1, wherein the compound is selected from:

- 4-[(3R)-3-methyl-4-{[3-(1H-1,2,4-triazol-1-yl)phenyl]sulfonyl}piperazin-1-yl]benzonitrile;
- 5-[(3R)-3-methyl-4-{[3-(1H-1,2,4-triazol-1-yl)phenyl]sulfonyl}piperazin-1-yl]pyridine-2-carbonitrile;
- 2-[3-({(2R)-4-[4-(aminomethyl)-2-(trifluoromethyl)phenyl]-2-methylpiperazin-1-yl}sulfonyl)phenyl]-1,1,1-trifluoropropan-2-ol;

2-[3-({(2R)-4-[4-(aminomethyl)-2-(trifluoromethyl)phenyl]-2-methylpiperazin-1-yl}sulfonyl)phenyl]propan-2-ol;

N-[3-({(2R)-4-[4-fluoro-2-(trifluoromethyl)phenyl]-2-methylpiperazin-1-yl}sulfonyl)phenyl]-N,1-dimethylpyrrolidin-3-amine;

(2R)-4-[4-fluoro-2-(trifluoromethyl)phenyl]-2-methyl-1-{[3-(4-methylpiperazin-1-yl)phenyl]sulfonyl}piperazine;

N-{1-[3-({(2R)-4-[4-fluoro-2-(trifluoromethyl)phenyl]-2-methylpiperazin-1-yl}sulfonyl)phenyl]pyrrolidin-3-yl}-N-methylacetamide;

{(2S)-1-[3-({(2R)-4-[4-fluoro-2-(trifluoromethyl)phenyl]-2-methylpiperazin-1-yl}sulfonyl)phenyl]pyrrolidin-2-yl}methanol;

(3R)-1-[3-({(2R)-4-[4-fluoro-2-(trifluoromethyl)phenyl]-2-methylpiperazin-1-yl}sulfonyl)phenyl]pyrrolidin-3-ol;

{(2R)-1-[3-({(2R)-4-[4-fluoro-2-(trifluoromethyl)phenyl]-2-methylpiperazin-1-yl}sulfonyl)phenyl]pyrrolidin-2-yl}methyl acetate;

(methyl 1-[3-({(2R)-4-[4-fluoro-2-(trifluoromethyl)phenyl]-2-methylpiperazin-1-yl}sulfonyl)phenyl]pyrrolidine-3-carboxylate;

1-[3-({(2R)-4-[4-fluoro-2-(trifluoromethyl)phenyl]-2-methylpiperazin-1-yl}sulfonyl)phenyl]pyrrolidine-3-carboxylic acid; and {(2R)-1-[3-({(2R)-4-[4-fluoro-2-(trifluoromethyl)phenyl]-2-methylpiperazin-1-yl}sulfonyl)phenyl]pyrrolidin-2-yl}methanol; or a pharmaceutically acceptable salt and/or N-oxide thereof.

46. The compound of claim 1, wherein the compound is selected from:

1-[3-({(2R)-4-[4-fluoro-2-(trifluoromethyl)phenyl]-2-methylpiperazin-1-yl}sulfonyl)phenyl]pyrrolidin-3-ol;

1-(3-{[(2R)-4-(2-chloro-4-fluorophenyl)-2-methylpiperazin-1-yl]sulfonyl}phenyl)pyrrolidin-3-ol;

(2R)-4-(2-chloro-4-fluorophenyl)-2-methyl-1-({3-[4-(2-oxo-2-pyrrolidin-1-ylethyl)piperazin-1-yl]phenyl}sulfonyl)piperazine;

(2R)-4-[4-fluoro-2-(trifluoromethyl)phenyl]-1-({3-[(2S)-2-(methoxymethyl)pyrrolidin-1-yl]phenyl}sulfonyl)-2-methylpiperazine;

(2R)-4-[4-fluoro-2-(trifluoromethyl)phenyl]-2-methyl-1-{[3-(4-pyrrolidin-1-ylpiperidin-1-yl)phenyl]sulfonyl}piperazine;

(2R)-4-[4-fluoro-2-(trifluoromethyl)phenyl]-2-methyl-1-({3-[4-(2-oxo-2-pyrrolidin-1-ylethyl)piperazin-1-yl]phenyl}sulfonyl)piperazine;

(3S)-1-[3-({(2R)-4-[4-fluoro-2-(trifluoromethyl)phenyl]-2-methylpiperazin-1-yl}sulfonyl)phenyl]pyrrolidin-3-ol;

(2R)-4-[4-fluoro-2-(trifluoromethyl)phenyl]-2-methyl-1-[(3-pyrrolidin-1-ylphenyl)sulfonyl]piperazine;

1-[3-({(2R)-4-[4-fluoro-2-(trifluoromethyl)phenyl]-2-methylpiperazin-1-yl}sulfonyl)phenyl]pyrrolidin-3-amine;

4-({1-[3-({(2R)-4-[4-fluoro-2-(trifluoromethyl)phenyl]-2-methylpiperazin-1-yl}sulfonyl)phenyl]pyrrolidin-3-yl}carbonyl)morpholine;

N-cyclohexyl-1-[3-({(2R)-4-[4-fluoro-2-(trifluoromethyl)phenyl]-2-methylpiperazin-1-yl}sulfonyl)phenyl]pyrrolidine-3-carboxamide;

N,N-diethyl-1-[3-({(2R)-4-[4-fluoro-2-(trifluoromethyl)phenyl]-2-methylpiperazin-1-yl}sulfonyl)phenyl]pyrrolidine-3-carboxamide; and 1-[3-({(2R)-4-[4-fluoro-2-(trifluoromethyl)phenyl]-2-methylpiperazin-1-yl}sulfonyl)phenyl]pyrrolidine-3-carboxamide; or a pharmaceutically acceptable salt and/or N-oxide thereof.

47. The compound of claim 1, wherein the compound is selected from:

1-[3-({(2R)-4-[4-cyano-2-(trifluoromethyl)phenyl]-2-methylpiperazin-1-yl}sulfonyl)phenyl]prolinamide;

1-(3-((R)-4-(4-fluoro-2-(trifluoromethyl)phenyl)-2-methylpiperazin-1-ylsulfonyl)phenyl)pyrrolidine-2-carboxamide;

1-(3-((R)-4-(4-fluoro-2-(trifluoromethyl)phenyl)-2-methylpiperazin-1-ylsulfonyl)phenyl)pyrrolidine-2-carboxylic acid;

1,1,1-trifluoro-2-(3-((2R,6S)-4-(4-fluoro-2-(trifluoromethyl)phenyl)-2,6-dimethylpiperazin-1-ylsulfonyl)phenyl)propan-2-ol;

(2R)-1-[(3-bromophenyl)sulfonyl]-4-[4-fluoro-2-(trifluoromethyl)phenyl]-2-methylpiperazine;

(2R)-4-[4-fluoro-2-(trifluoromethyl)phenyl]-2-methyl-1-{[3-(4-methylpiperazin-1-yl)phenyl]sulfonyl}piperazine;

(2R)-4-[4-fluoro-2-(trifluoromethyl)phenyl]-2-methyl-1-[(3-piperazin-1-ylphenyl)sulfonyl]piperazine;

(2R)-1-{[3-(4-ethylpiperazin-1-yl)phenyl]sulfonyl}-4-[4-fluoro-2-(trifluoromethyl)phenyl]-2-methylpiperazine;

(2R)-4-[4-fluoro-2-(trifluoromethyl)phenyl]-1-{[3-(4-isopropylpiperazin-1-yl)phenyl]sulfonyl}-2-methylpiperazine;

(2R)-4-[4-fluoro-2-(trifluoromethyl)phenyl]-1-{[3-(4-isobutylpiperazin-1-yl)phenyl]sulfonyl}-2-methylpiperazine;

(2R)-1-{[3-(4-cyclohexylpiperazin-1-yl)phenyl]sulfonyl}-4-[4-fluoro-2-(trifluoromethyl)phenyl]-2-methylpiperazine;

(2R)-4-[4-fluoro-2-(trifluoromethyl)phenyl]-2-methyl-1-({3-[4-(tetrahydro-2H-pyran-4-yl)piperazin-1-yl]phenyl}sulfonyl)piperazine; and (2R)-1-{[3-(4-acetylpiperazin-1-yl)phenyl]sulfonyl}-4-[4-fluoro-2-(trifluoromethyl)phenyl]-2-methylpiperazine; or a pharmaceutically acceptable salt and/or N-oxide thereof.

48. The compound of claim 1, wherein the compound is selected from:

Methyl 4-[3-({(2R)-4-[4-fluoro-2-(trifluoromethyl)phenyl]-2-methylpiperazin-1-yl}sulfonyl)phenyl]piperazine-1-carboxylate;

N-ethyl-4-[3-({(2R)-4-[4-fluoro-2-(trifluoromethyl)phenyl]-2-methylpiperazin-1-yl}sulfonyl)phenyl]piperazine-1-carboxamide;

(2R)-4-[4-fluoro-2-(trifluoromethyl)phenyl]-2-methyl-1-{[3-(5-methyl-2-furyl)phenyl]sulfonyl}piperazine;

4-[(3R)-4-{[3-(2,4-dimethyl-1,3-thiazol-5-yl)phenyl]sulfonyl}-3-methylpiperazin-1-yl]-3-(trifluoromethyl)benzonitrile;

(2R)-4-[4-fluoro-2-(trifluoromethyl)phenyl]-2-methyl-1-{[3-(trifluoromethoxy)phenyl]sulfonyl}piperazine;

(2R)-1-{[3-(difluoromethoxy)phenyl]sulfonyl}-4-[4-fluoro-2-(trifluoromethyl)phenyl]-2-methylpiperazine;

1-[3-({(2R)-4-[4-fluoro-2-(trifluoromethyl)phenyl]-2-methylpiperazin-1-yl}sulfonyl)phenyl]piperidin-4-ol;

4-[3-({(2R)-4-[4-fluoro-2-(trifluoromethyl)phenyl]-2-methylpiperazin-1-yl}sulfonyl)phenyl]-1-methylpiperidin-4-ol;

tert-butyl 4-[3-({(2R)-4-[4-fluoro-2-(trifluoromethyl)phenyl]-2-methylpiperazin-1-yl}sulfonyl)phenyl]piperidine-1-carboxylate;

(2R)-4-[4-fluoro-2-(trifluoromethyl)phenyl]-2-methyl-1-[(3-piperidin-4-ylphenyl)sulfonyl]piperazine;

(2R)-4-[4-fluoro-2-(trifluoromethyl)phenyl]-2-methyl-1-{[3-(1-methylpiperidin-4-yl)phenyl]sulfonyl}piperazine;

(2R)-4-[4-fluoro-2-(trifluoromethyl)phenyl]-1-{[3-(1-isopropylpiperidin-4-yl)phenyl]sulfonyl}-2-methylpiperazine; and (R)-2-(3-(4-(4-fluoro-2-(trifluoromethyl)phenyl)-2-methylpiperazin-1-ylsulfonyl)phenyl)propan-2-ol; or a pharmaceutically acceptable salt and/or N-oxide thereof.

49. The compound of claim 1, wherein the compound is selected from:

(2R)-4-[4-fluoro-2-(trifluoromethyl)phenyl]-2-methyl-1-{[3-(1H-imidazol-1-yl)phenyl]sulfonyl}piperazine;

(2R)-4-[4-fluoro-2-(trifluoromethyl)phenyl]-2-methyl-1-{[3-(1H-pyrazol-1-yl)phenyl]sulfonyl}piperazine;

(2R)-2-methyl-1-{[3-(1H-1,2,4-triazol-1-yl)phenyl]sulfonyl}-4-[4-(1H-1,2,4-triazol-1-yl)-2-(trifluoromethyl)phenyl]piperazine;

(2R)-4-[4-fluoro-2-(trifluoromethyl)phenyl]-2-methyl-1-{[3-(1H-1,2,4-triazol-1-yl)phenyl]sulfonyl}piperazine;

(2S)-3,3,3-trifluoro-2-[3-({(2R)-4-[4-fluoro-2-(trifluoromethyl)phenyl]-2-methylpiperazin-1-yl}sulfonyl)phenyl]propane-1,2-diol;

(2R)-1-[(3-fluorophenyl)sulfonyl]-4-[4-fluoro-2-(trifluoromethyl)phenyl]-2-methylpiperazine;

3-({(2R)-4-[4-fluoro-2-(trifluoromethyl)phenyl]-2-methylpiperazin-1-yl}sulfonyl)aniline;

(2R)-1-{[3-(4,4-difluoropiperidin-1-yl)phenyl]sulfonyl}-4-[4-fluoro-2-(trifluoromethyl)phenyl]-2-methylpiperazine;

(2R)-1-{[3-(4-fluoropiperidin-1-yl)phenyl]sulfonyl}-4-[4-fluoro-2-(trifluoromethyl)phenyl]-2-methylpiperazine;

(2R)-1-{[3-(4,4-difluoropiperidin-1-yl)phenyl]sulfonyl}-4-[4-fluoro-2-(trifluoromethyl)phenyl]-2-methylpiperazine; and ethyl 1-[3-({(2R)-4-[4-fluoro-2-(trifluoromethyl)phenyl]-2-methylpiperazin-1-yl}sulfonyl)phenyl]piperidine-4-carboxylate; or a pharmaceutically acceptable salt and/or N-oxide thereof.

50. The compound of claim 1, wherein the compound is selected from:

1-[3-({(2R)-4-[4-fluoro-2-(trifluoromethyl)phenyl]-2-methylpiperazin-1-yl}sulfonyl)phenyl]-N,N-dimethylpiperidine-4-carboxamide;

(2R)-4-[4-fluoro-2-(trifluoromethyl)phenyl]-2-methyl-1-({3-[4-(pyrrolidin-1-ylcarbonyl)piperidin-1-yl]phenyl}sulfonyl)piperazine;

4-({1-[3-({(2R)-4-[4-fluoro-2-(trifluoromethyl)phenyl]-2-methylpiperazin-1-yl}sulfonyl)phenyl]piperidin-4-yl}carbonyl)morpholine;

N-tert-butyl-1-[3-({(2R)-4-[4-fluoro-2-(trifluoromethyl)phenyl]-2-methylpiperazin-1-yl}sulfonyl)phenyl]piperidine-4-carboxamide;

1-[3-({(2R)-4-[4-fluoro-2-(trifluoromethyl)phenyl]-2-methylpiperazin-1-yl}sulfonyl)phenyl]-N-isobutylpiperidine-4-carboxamide;

(2R)-1-(biphenyl-3-ylsulfonyl)-4-[4-fluoro-2-(trifluoromethyl)phenyl]-2-methylpiperazine;

(2R)-4-[4-fluoro-2-(trifluoromethyl)phenyl]-2-methyl-1-[(3-pyridin-4-ylphenyl)sulfonyl]piperazine;

3'-({(2R)-4-[4-fluoro-2-(trifluoromethyl)phenyl]-2-methylpiperazin-1-yl}sulfonyl)biphenyl-4-carboxylic acid;

(2R)-4-[4-fluoro-2-(trifluoromethyl)phenyl]-2-methyl-1-{[3-(4H-1,2,4-triazol-4-yl)phenyl]sulfonyl}piperazine; and (2R)-4-(2,4-dichlorophenyl)-2-methyl-1-{[3-(4H-1,2,4-triazol-4-yl)phenyl]sulfonyl}piperazine; or a pharmaceutically acceptable salt and/or N-oxide thereof.

51. The compound of claim 1, wherein the compound is selected from:

1-(3-chloropyridin-2-yl)-4-[(3,4-dichlorophenyl)sulfonyl]-trans-2,5-dimethylpiperazine;

4-(3-chloropyridin-2-yl)-1-[(3,4-dichlorophenyl)sulfonyl]-cis-2,6-dimethylpiperazine;

(2R)-1-[(3,4-dichlorophenyl)sulfonyl]-2-methyl-4-[2-(trifluoromethyl)phenyl]piperazine;

(2R)-1-[(5-bromo-2-methoxyphenyl)sulfonyl]-4-[4-fluoro-2-(trifluoromethyl)phenyl]-2-methylpiperazine;

N-[3-chloro-4-({(2R)-4-[4-fluoro-2-(trifluoromethyl)phenyl]-2-methylpiperazin-1-yl}sulfonyl)phenyl]morpholine-4-carboxamide;

4-chloro-2-fluoro-5-({(2R)-4-[4-fluoro-2-(trifluoromethyl)phenyl]-2-methylpiperazin-1-yl}sulfonyl)benzamide;

2-chloro-4-fluoro-5-({(2R)-4-[4-fluoro-2-(trifluoromethyl)phenyl]-2-methylpiperazin-1-yl}sulfonyl)benzoic acid;

3-({(2R)-4-[4-fluoro-2-(trifluoromethyl)phenyl]-2-methylpiperazin-1-yl}sulfonyl)-4-methoxybenzamide;

4-chloro-3-({(2R)-4-[4-fluoro-2-(trifluoromethyl)phenyl]-2-methylpiperazin-1-yl}sulfonyl)benzamide; and 2-fluoro-5-({(2R)-4-[4-fluoro-2-(trifluoromethyl)phenyl]-2-methylpiperazin-1-yl}sulfonyl)benzamide; or a pharmaceutically acceptable salt and/or N-oxide thereof.

52. The compound of claim 1, wherein the compound is selected from:

(2R)-1-{[2-chloro-4-(1H-1,2,4-triazol-1-yl)phenyl]sulfonyl}-4-[4-fluoro-2-(trifluoromethyl)phenyl]-2-methylpiperazine;

(2R)-1-{[3-chloro-4-(1H-1,2,4-triazol-1-yl)phenyl]sulfonyl}-4-[4-fluoro-2-(trifluoromethyl)phenyl]-2-methylpiperazine;

3-chloro-4-({(2R)-4-[4-fluoro-2-(trifluoromethyl)phenyl]-2-methylpiperazin-1-yl}sulfonyl)benzamide;

(2R)-1-[(4-bromo-2-chlorophenyl)sulfonyl]-4-[4-fluoro-2-(trifluoromethyl)phenyl]-2-methylpiperazine;

(2R)-1-[(3-chloro-2-methylphenyl)sulfonyl]-4-[4-fluoro-2-(trifluoromethyl)phenyl]-2-methylpiperazine;

(2R)-1-[(2,3-dichlorophenyl)sulfonyl]-4-[4-fluoro-2-(trifluoromethyl)phenyl]-2-methylpiperazine;

4-{(3R)-4-[(4-bromo-2-chlorophenyl)sulfonyl]-3-methylpiperazin-1-yl}-3-(trifluoromethyl)benzonitrile;

4-{(3R)-4-[(4-bromo-2-fluorophenyl)sulfonyl]-3-methylpiperazin-1-yl}-3-(trifluoromethyl)benzonitrile;

4-[3-chloro-4-({(2R)-4-[4-fluoro-2-(trifluoromethyl)phenyl]-2-methylpiperazin-1-yl}sulfonyl)phenyl]morpholine;

(2R)-1-[(2-chloro-4-piperidin-1-ylphenyl)sulfonyl]-4-[4-fluoro-2-(trifluoromethyl)phenyl]-2-methylpiperazine;

(2R)-1-{[2-chloro-4-(4-methylpiperazin-1-yl)phenyl]sulfonyl}-4-[4-fluoro-2-(trifluoromethyl)phenyl]-2-methylpiperazine;

(2R)-1-[(4-tert-butoxy-2-chlorophenyl)sulfonyl]-4-[4-fluoro-2-(trifluoromethyl)phenyl]-2-methylpiperazine;

(2R)-1-[(4-tert-butoxy-2-fluorophenyl)sulfonyl]-4-[4-fluoro-2-(trifluoromethyl)phenyl]-2-methylpiperazine; or a pharmaceutically acceptable salt and/or N-oxide thereof.

53. The compound of claim 1, wherein the compound is selected from:
- 3-chloro-4-({(2R)-4-[4-fluoro-2-(trifluoromethyl)phenyl]-2-methylpiperazin-1-yl}sulfonyl)-N,N-dimethylaniline;
- (2R)-1-[(2-chloro-4-pyrrolidin-1-ylphenyl)sulfonyl]-4-[4-fluoro-2-(trifluoromethyl)phenyl]-2-methylpiperazine;
- N-tert-butyl-3-chloro-4-({(2R)-4-[4-fluoro-2-(trifluoromethyl)phenyl]-2-methylpiperazin-1-yl}sulfonyl) aniline;
- 3-chloro-4-({(2R)-4-[4-fluoro-2-(trifluoromethyl)phenyl]-2-methylpiperazin-1-yl}sulfonyl)-N-isobutylaniline;
- 1-[3-chloro-4-({(2R)-4-[4-fluoro-2-(trifluoromethyl)phenyl]-2-methylpiperazin-1-yl}sulfonyl)phenyl]piperidin-4-ol;
- (2R)-1-({2-chloro-4-[(3S)-3-methylpiperazin-1-yl]phenyl}sulfonyl)-4-[4-fluoro-2-(trifluoromethyl)phenyl]-2-methylpiperazine;
- 1-[3-chloro-4-({(2R)-4-[4-fluoro-2-(trifluoromethyl)phenyl]-2-methylpiperazin-1-yl}sulfonyl)phenyl]-N,N-dimethylpiperidin-4-amine;
- 4-[3-chloro-4-({(2R)-4-[4-fluoro-2-(trifluoromethyl)phenyl]-2-methylpiperazin-1-yl}sulfonyl)phenyl]thiomorpholine 1,1-dioxide;
- 4-[3-fluoro-4-({(2R)-4-[4-fluoro-2-(trifluoromethyl)phenyl]-2-methylpiperazin-1-yl}sulfonyl)phenyl]morpholine;
- 4-[3-chloro-4-({(2R)-4-[4-fluoro-2-(trifluoromethyl)phenyl]-2-methylpiperazin-1-yl}sulfonyl)phenyl]-2,6-cis-dimethylmorpholine;
- 1-[3-chloro-4-({(2R)-4-[4-fluoro-2-(trifluoromethyl)phenyl]-2-methylpiperazin-1-yl}sulfonyl)phenyl]piperidine-4-carboxylic acid;
- 4-[3-chloro-4-({(2R)-4-[4-fluoro-2-(trifluoromethyl)phenyl]-2-methylpiperazin-1-yl}sulfonyl)phenyl]piperazin-2-one; and
- 1-[3-chloro-4-({(2R)-4-[4-fluoro-2-(trifluoromethyl)phenyl]-2-methylpiperazin-1-yl}sulfonyl)phenyl]piperidine-4-carboxamide; or a pharmaceutically acceptable salt and/or N-oxide thereof.

54. The compound of claim 1, wherein the compound is selected from:
- (2R)-1-({2-chloro-4-[(3R)-3-methylpiperazin-1-yl]phenyl}sulfonyl)-4-[4-fluoro-2-(trifluoromethyl)phenyl]-2-methylpiperazine;
- 1-[3-chloro-4-({(2R)-4-[4-fluoro-2-(trifluoromethyl)phenyl]-2-methylpiperazin-1-yl}sulfonyl)phenyl]piperazin-2-one;
- (2R)-1-{[2-chloro-4-(4-fluoropiperidin-1-yl)phenyl]sulfonyl}-4-[4-fluoro-2-(trifluoromethyl)phenyl]-2-methylpiperazine;
- 4-[3-({(2R)-4-[4-fluoro-2-(trifluoromethyl)phenyl]-2-methylpiperazin-1-yl}sulfonyl)-4-methoxyphenyl]morpholine;
- (2R)-4-[4-fluoro-2-(trifluoromethyl)phenyl]-1-[(2-methoxy-5-piperidin-1-ylphenyl)sulfonyl]-2-methylpiperazine;
- (2R)-4-[4-fluoro-2-(trifluoromethyl)phenyl]-1-{[2-methoxy-5-(4-methylpiperazin-1-yl)phenyl]sulfonyl}-2-methylpiperazine;
- 4-[2-chloro-3-({(2R)-4-[4-fluoro-2-(trifluoromethyl)phenyl]-2-methylpiperazin-1-yl}sulfonyl)phenyl]morpholine;
- (2R)-1-[(2-chloro-3-piperidin-1-ylphenyl)sulfonyl]-4-[4-fluoro-2-(trifluoromethyl)phenyl]-2-methylpiperazine; and
- 4-{(3R)-4-[(4-tert-butoxy-2-chlorophenyl)sulfonyl]-3-methylpiperazin-1-yl}-3-(trifluoromethyl)benzonitrile; or a pharmaceutically acceptable salt and/or N-oxide thereof.

55. The compound of claim 1, wherein the compound is selected from:
- 4-{(3R)-4-[(4-tert-butoxy-2-fluorophenyl)sulfonyl]-3-methylpiperazin-1-yl}-3-(trifluoromethyl)benzonitrile;
- 3-fluoro-4-({(2R)-4-[4-fluoro-2-(trifluoromethyl)phenyl]-2-methylpiperazin-1-yl}sulfonyl)phenol;
- 2-chloro-4-({(2R)-4-[4-fluoro-2-(trifluoromethyl)phenyl]-2-methylpiperazin-1-yl}sulfonyl)phenol;
- (2R)-1-{[2-chloro-4-(2-methoxyethoxy)phenyl]sulfonyl}-4-[4-fluoro-2-(trifluoromethyl)phenyl]-2-methylpiperazine;
- (2R)-1-[(2-chloro-4-ethoxyphenyl)sulfonyl]-4-[4-fluoro-2-(trifluoromethyl)phenyl]-2-methylpiperazine;
- 2-[3-chloro-4-({(2R)-4-[4-fluoro-2-(trifluoromethyl)phenyl]-2-methylpiperazin-1-yl}sulfonyl)phenoxy]-N,N-dimethylethanamine;
- (2R)-1-{[2-chloro-4-(difluoromethoxy)phenyl]sulfonyl}-4-[4-fluoro-2-(trifluoromethyl)phenyl]-2-methylpiperazine;
- 4-[3-chloro-4-({(2R)-2-methyl-4-[4-(1H-1,2,4-triazol-1-yl)-2-(trifluoromethyl)phenyl]piperazin-1-yl}sulfonyl)phenyl]morpholine; and
- 1,1,1-trifluoro-2-[3-({(2R)-4-[4-fluoro-2-(trifluoromethyl)phenyl]-2-methylpiperazin 1-yl}sulfonyl)-4-methoxyphenyl]propan-2-ol; or a pharmaceutically acceptable salt and/or N-oxide thereof.

56. The compound of claim 1, wherein the compound is selected from:
- (2R)-1-[(5-chloro-2-naphthyl)sulfonyl]-2-methyl-4-[2-(trifluoromethyl)phenyl]piperazine;
- (2R)-4-[4-fluoro-2-(trifluoromethyl)phenyl]-2-methyl-1-[(4-piperazin-1-yl-1-naphthyl)sulfonyl]piperazine; and
- (2R)-4-[4-fluoro-2-(trifluoromethyl)phenyl]-2-methyl-1-{[4-(4-methylpiperazin-1-yl)-1-naphthyl]sulfonyl}piperazine; or a pharmaceutically acceptable salt and/or N-oxide thereof.

57. The compound of claim 1, wherein the compound is selected from:
- (2R)-1-[(5-chloro-2-thienyl)sulfonyl]-2-methyl-4-[2-(trifluoromethyl)phenyl]piperazine;
- (2R)-1-[(5-chloro-3-methyl-1-benzothien-2-yl)sulfonyl]-2-methyl-4-[2-(trifluoromethyl)phenyl]piperazine;
- 4-{(3R)-3-methyl-4-[(5-piperazin-1-yl-2-thienyl)sulfonyl]piperazin-1-yl}benzonitrile;
- (2R)-4-[4-fluoro-2-(trifluoromethyl)phenyl]-2-methyl-1-({5-[5-(trifluoromethyl)isoxazol-3-yl]-2-thienyl}sulfonyl)piperazine;
- 4-[5-({(2R)-4-[4-fluoro-2-(trifluoromethyl)phenyl]-2-methylpiperazin-1-yl}sulfonyl)pyridin-2-yl]morpholine;
- (2R)-1-[(5-bromo-2-thienyl)sulfonyl]-4-[4-fluoro-2-(trifluoromethyl)phenyl]-2-methylpiperazine;
- (2R)-4-[4-fluoro-2-(trifluoromethyl)phenyl]-2-methyl-1-[(5-pyridin-2-yl-2-thienyl)sulfonyl]piperazine;
- (2R)-4-[4-fluoro-2-(trifluoromethyl)phenyl]-2-methyl-1-{[5-(1,3-oxazol-5-yl)-2-thienyl]sulfonyl}piperazine; and (2R)-1-[(4-bromo-5-chloro-2-thienyl)sulfonyl]-4-[4-fluoro-2-(trifluoromethyl)phenyl]-2-methylpiperazine; or a pharmaceutically acceptable salt and/or N-oxide thereof.

58. The compound of claim 1, wherein the compound is selected from:
(2R)-1-[(5-chloro-2-thienyl)sulfonyl]-4-[4-fluoro-2-(trifluoromethyl)phenyl]-2-methylpiperazine;
(2R)-4-[4-fluoro-2-(trifluoromethyl)phenyl]-2-methyl-1-{[5-(4-methylpiperazin-1-yl)-2-thienyl]sulfonyl}piperazine;
4-[5-({(2R)-4-[4-fluoro-2-(trifluoromethyl)phenyl]-2-methylpiperazin-1-yl}sulfonyl)-2-thienyl]morpholine;
(2R)-4-[4-fluoro-2-(trifluoromethyl)phenyl]-2-methyl-1-[(5-piperidin-1-yl-2-thienyl)sulfonyl]piperazine;
(2R)-4-[4-fluoro-2-(trifluoromethyl)phenyl]-2-methyl-1-[(5-piperidin-1-yl-2-thienyl)sulfonyl]piperazine;
(2R)-4-[4-fluoro-2-(trifluoromethyl)phenyl]-2-methyl-1-({5-[(3R)-3-methylpiperazin-1-yl]-2-thienyl}sulfonyl)piperazine;
(2R)-4-[4-fluoro-2-(trifluoromethyl)phenyl]-2-methyl-1-({5-[(3S)-3-methylpiperazin-1-yl]-2-thienyl}sulfonyl)piperazine;
1-[5-({(2R)-4-[4-fluoro-2-(trifluoromethyl)phenyl]-2-methylpiperazin-1-yl}sulfonyl)-2-thienyl]-N,N-dimethylpiperidin-4-amine;
4-[5-({(2R)-4-[4-fluoro-2-(trifluoromethyl)phenyl]-2-methylpiperazin-1-yl}sulfonyl)-2-thienyl]-2,6-cis-dimethylmorpholine;
4-[5-({(2R)-4-[4-fluoro-2-(trifluoromethyl)phenyl]-2-methylpiperazin-1-yl}sulfonyl)-2-thienyl]piperazin-2-one;
1-[5-({(2R)-4-[4-fluoro-2-(trifluoromethyl)phenyl]-2-methylpiperazin-1-yl}sulfonyl)-2-thienyl]piperidine-4-carboxamide;
(2R)-1-({5-[3,5-cis-dimethylpiperazin-1-yl]-2-thienyl}sulfonyl)-4-[4-fluoro-2-(trifluoromethyl)phenyl]-2-methylpiperazine;
1-[5-({(2R)-4-[4-fluoro-2-(trifluoromethyl)phenyl]-2-methylpiperazin-1-yl}sulfonyl)-2-thienyl]piperidine-4-carboxylic acid; and
(2R)-1-{[5-(4-acetylpiperazin-1-yl)-2-thienyl]sulfonyl}-4-[4-fluoro-2-(trifluoromethyl)phenyl]-2-methylpiperazine; or a pharmaceutically acceptable salt and/or N-oxide thereof.

59. The compound of claim 1, wherein the compound is selected from:
(2R)-4-[4-fluoro-2-(trifluoromethyl)phenyl]-1-{[5-(4-isobutyrylpiperazin-1-yl)-2-thienyl]sulfonyl}-2-methylpiperazine;
Methyl 4-[5-({(2R)-4-[4-fluoro-2-(trifluoromethyl)phenyl]-2-methylpiperazin-1-yl}sulfonyl)-2-thienyl]piperazine-1-carboxylate;
Isopropyl 4-[5-({(2R)-4-[4-fluoro-2-(trifluoromethyl)phenyl]-2-methylpiperazin-1-yl}sulfonyl)-2-thienyl]piperazine-1-carboxylate;
4-[5-({(2R)-4-[4-fluoro-2-(trifluoromethyl)phenyl]-2-methylpiperazin-1-yl}sulfonyl)-2-thienyl]-N-isopropylpiperazine-1-carboxamide;
(2R)-4-[4-fluoro-2-(trifluoromethyl)phenyl]-1-{[5-(4-isopropylpiperazin-1-yl)-2-thienyl]sulfonyl}-2-methylpiperazine;
(2R)-1-{[5-(4-cyclohexylpiperazin-1-yl)-2-thienyl]sulfonyl}-4-[4-fluoro-2-(trifluoromethyl)phenyl]-2-methylpiperazine;
(2R)-4-[4-fluoro-2-(trifluoromethyl)phenyl]-2-methyl-1-({5-[4-(tetrahydro-2H-pyran-4-yl)piperazin-1-yl]-2-thienyl}sulfonyl)piperazine;
2-{4-[5-({(2R)-4-[4-fluoro-2-(trifluoromethyl)phenyl]-2-methylpiperazin-1-yl}sulfonyl)-2-thienyl]piperazin-1-yl}ethanol;
2,2,2-trifluoro-1-[5-({(2R)-4-[4-fluoro-2-(trifluoromethyl)phenyl]-2-methylpiperazin-1-yl}sulfonyl)-2-thienyl]ethanone;
2-[5-({(2R)-4-[4-fluoro-2-(trifluoromethyl)phenyl]-2-methylpiperazin-1-yl}sulfonyl)-2-thienyl]propan-2-ol;
1,1,1-trifluoro-2-[5-({(2R)-4-[4-fluoro-2-(trifluoromethyl)phenyl]-2-methylpiperazin-1-yl}sulfonyl)-2-thienyl]propan-2-ol;
5-({(2R)-4-[4-fluoro-2-(trifluoromethyl)phenyl]-2-methylpiperazin-1-yl}sulfonyl)thiophene-2-carboxylic acid;
3,3,3-trifluoro-2-[5-({(2R)-4-[4-fluoro-2-(trifluoromethyl)phenyl]-2-methylpiperazin-1-yl}sulfonyl)-2-thienyl]-2-hydroxypropanoic acid; and
(2S)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol; or a pharmaceutically acceptable salt and/or N-oxide thereof.

60. The compound of claim 1, wherein the compound is selected from:
(2R)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol;
5-({(2R)-4-[4-fluoro-2-(trifluoromethyl)phenyl]-2-methylpiperazin-1-yl}sulfonyl)-N,N-dimethylthiophene-2-carboxamide;
5-({(2R)-4-[4-fluoro-2-(trifluoromethyl)phenyl]-2-methylpiperazin-1-yl}sulfonyl)thiophene-2-carboxamide;
(2R)-4-[4-fluoro-2-(trifluoromethyl)phenyl]-2-methyl-1-[(5-piperidin-4-yl-2-thienyl)sulfonyl]piperazine;
1-[5-({(2R)-4-[4-fluoro-2-(trifluoromethyl)phenyl]-2-methylpiperazin-1-yl}sulfonyl)-2-thienyl]piperazin-2-one;
(2R)-1-[(4,5-dichloro-2-thienyl)sulfonyl]-4-[4-fluoro-2-(trifluoromethyl)phenyl]-2-methylpiperazine;
(2R)-4-[4-fluoro-2-(trifluoromethyl)phenyl]2-methyl-1-(2-thienylsulfonyl)piperazine;
1-[5-({(2R)-4-[4-fluoro-2-(trifluoromethyl)phenyl]-2-methylpiperazin-1-yl}sulfonyl)-2-thienyl]piperidin-4-ol;
(2R)-4-[4-fluoro-2-(trifluoromethyl)phenyl]-1-{[5-(4-methoxypiperidin-1-yl)-2-thienyl]sulfonyl}-2-methylpiperazine;
(2R)-4-(2,4-dichlorophenyl)-2-methyl-1-[(5-piperazin-1-yl-2-thienyl)sulfonyl]piperazine;
(2R)-1-{[5-(4-fluoropiperidin-1-yl)-2-thienyl]sulfonyl}-4-[4-fluoro-2-(trifluoromethyl) phenyl]-2-methylpiperazine;
(2R)-1-{[5-(4,4-difluoropiperidin-1-yl)-2-thienyl]sulfonyl}-4-[4-fluoro-2-(trifluoromethyl)phenyl]-2-methylpiperazine;
4-[5-({(2R)-4-[4-fluoro-2-(trifluoromethyl)phenyl]-2-methylpiperazin-1-yl}sulfonyl)-2-thienyl]benzoic acid; and
4-[5-({(2R)-4-[4-fluoro-2-(trifluoromethyl)phenyl]-2-methylpiperazin-1-yl}sulfonyl)-2-thienyl]benzamide; or a pharmaceutically acceptable salt and/or N-oxide thereof.

61. A compound selected from:
(2R)-1,1,1-trifluoro-2-[3-({(2R)-4-[4-fluoro-2-(trifluoromethyl)phenyl]-2-methylpiperazin-1-yl}sulfonyl)phenyl]propan-2-ol;

(2S)-1,1,1-trifluoro-2-[3-({(2R)-4-[4-fluoro-2-(trifluoromethyl)phenyl]-2-methylpiperazin-1-yl}sulfonyl)phenyl]propan-2-ol;

1,1,1-trifluoro-2-[3-({(2R)-4-[4-fluoro-2-(trifluoromethyl)phenyl]-2-methylpiperazin-1-yl}sulfonyl)phenyl]propan-2-ol;

(2S)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol;

3-chloro-4-({(2R)-4-[4-fluoro-2-(trifluoromethyl)phenyl]-2-methylpiperazin-1-yl}sulfonyl)benzamide;

4-[3-chloro-4-({(2R)-4-[4-fluoro-2-(trifluoromethyl)phenyl]-2-methylpiperazin-1-yl}sulfonyl)phenyl]morpholine; and 1-[3-chloro-4-({(2R)-4-[4-fluoro-2-(trifluoromethyl)phenyl]-2-methylpiperazin-1-yl}sulfonyl)phenyl]piperidine-4-carboxylic acid; or a pharmaceutically acceptable salt and/or N-oxide thereof.

62. The compound of claim 61, wherein the compound is (2S)-1,1,1-trifluoro-2-[3-({(2R)-4-[4-fluoro-2-(trifluoromethyl)phenyl]-2-methylpiperazin-1-yl}sulfonyl)phenyl]propan-2-ol; or a pharmaceutically acceptable salt and/or N-oxide thereof.

63. The compound of claim 61, wherein the compound is 1,1,1-trifluoro-2-[3-({(2R)-4-[4-fluoro-2-(trifluoromethyl)phenyl]-2-methylpiperazin-1-yl}sulfonyl)phenyl]propan-2-ol, or a pharmaceutically acceptable salt and/or N-oxide thereof.

64. The compound of claim 61, wherein the compound is (2S)-1,1,1-trifluoro-2-[5-({(2R)-4-[4-fluoro-2-(trifluoromethyl)phenyl]-2-methylpiperazin-1-yl}sulfonyl)-2-thienyl]propan-2-ol, or a pharmaceutically acceptable salt and/or N-oxide thereof.

65. The compound of claim 61, wherein the compound is 3-chloro-4-({(2R)-4-[4-fluoro-2-(trifluoromethyl)phenyl]-2-methylpiperazin-1-yl}sulfonyl)benzamide, or a pharmaceutically acceptable salt and/or N-oxide thereof.

66. The compound of claim 61, wherein the compound is 4-[3-chloro-4-({(2R)-4-[4-fluoro-2-(trifluoromethyl)phenyl]-2-methylpiperazin-1-yl}sulfonyl)phenyl]morpholine, or a pharmaceutically acceptable salt and/or N-oxide thereof.

67. The compound of claim 61, wherein the compound is 1-[3-chloro-4-({(2R)-4-[4-fluoro-2-(trifluoromethyl)phenyl]-2-methylpiperazin-1-yl}sulfonyl)phenyl]piperidine-4-carboxylic acid, or a pharmaceutically acceptable salt and/or N-oxide thereof.

68. A pharmaceutical composition comprising (2R)-1,1,1-trifluoro-2-[3-({(2R)-4-[4-fluoro-2-(trifluoromethyl)phenyl]-2-methylpiperazin-1-yl}sulfonyl)phenyl]propan-2-ol, or a pharmaceutically acceptable salt and/or N-oxide thereof and a pharmaceutically acceptable carrier.

69. The compound of claim 62, wherein the compound is (2R)-1,1,1-trifluoro-2-[3-({(2R)-4-[4-fluoro-2-(trifluoromethyl)phenyl]-2-methylpiperazin-1-yl}sulfonyl)phenyl]propan-2-ol, or a pharmaceutically acceptable salt and/or N-oxide thereof.

* * * * *